US008846031B2

(12) United States Patent
Roy et al.

(10) Patent No.: US 8,846,031 B2
(45) Date of Patent: Sep. 30, 2014

(54) SIMIAN ADENOVIRUS 41 AND USES THEREOF

(75) Inventors: Soumitra Roy, Liederdorp (NL); James M. Wilson, Glen Mills, PA (US); Luc H. Vandenberghe, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 139 days.

(21) Appl. No.: 13/321,985

(22) PCT Filed: May 27, 2010

(86) PCT No.: PCT/US2010/036332
§ 371 (c)(1),
(2), (4) Date: Mar. 7, 2012

(87) PCT Pub. No.: WO2010/138675
PCT Pub. Date: Dec. 2, 2010

(65) Prior Publication Data
US 2012/0189582 A1  Jul. 26, 2012

Related U.S. Application Data

(60) Provisional application No. 61/182,290, filed on May 29, 2009, provisional application No. 61/219,917, filed on Jun. 24, 2009.

(51) Int. Cl.
*C12N 15/861* (2006.01)
*C12N 7/01* (2006.01)
*C07K 14/075* (2006.01)
*C12N 15/33* (2006.01)

(52) U.S. Cl.
USPC ......... 424/93.6; 435/456; 435/69.1; 435/320; 435/91.1; 424/186.1; 424/233.1

(58) Field of Classification Search
CPC ............ C12N 15/8613; C12N 15/861; C12N 2710/10321; C12N 2710/10322; C12N 2710/10343; A61K 2039/5256; C07K 14/075
See application file for complete search history.

(56) References Cited

U.S. PATENT DOCUMENTS

| | | | |
|---|---|---|---|
| 6,083,716 A | 7/2000 | Wilson | |
| 7,247,472 B2 | 7/2007 | Wilson et al. | |
| 7,291,498 B2 | 11/2007 | Roy et al. | |
| 7,491,508 B2 | 2/2009 | Roy et al. | |
| 8,105,574 B2 | 1/2012 | Wilson et al. | |
| 2005/0069866 A1 | 3/2005 | Wilson et al. | |
| 2009/0074810 A1 | 3/2009 | Roy et al. | |
| 2009/0215871 A1 | 8/2009 | Wilson et al. | |
| 2010/0247490 A1 | 9/2010 | Roy et al. | |
| 2010/0254947 A1 | 10/2010 | Roy et al. | |
| 2010/0260799 A1 | 10/2010 | Roy et al. | |
| 2011/0217332 A1* | 9/2011 | Colloca et al. ............. 424/233.1 |

FOREIGN PATENT DOCUMENTS

| | | |
|---|---|---|
| EP | 2012822 | 1/2009 |
| WO | WO 99/29334 | 6/1999 |
| WO | WO 03/000851 | 1/2003 |
| WO | WO 2005/001103 | 1/2005 |
| WO | WO 2005/071093 | 8/2005 |
| WO | WO 2009/073103 | 6/2009 |
| WO | WO 2009/073104 | 8/2009 |
| WO | WO 2009/136977 | 11/2009 |
| WO | WO 2009/105084 | 12/2009 |

OTHER PUBLICATIONS

Thomas et al, Progress and Problems With the Use of Viral Vectors for Gene Therapy, Nature, 346 I May 2003, vol. 4, pp. 346-358.*
Russell, S. J., Replicating Vectors for Gene Therapy of Cancer: Risks, Limitations and Prospects, European J Cancer, 1994, vol. 30A (8), pp. 1165-1171.*
Farina, Replication-Defective Vector Based on a Chimpanzee Adenovirus, Journal of Virology, 75(23):11603-11613, Dec. 1, 2001.
Roy, Characterization of a Family of Chimpanzee Adenoviruses and Development of Molecular Clones for Gene Transfer Vectors, Human Gene Therapy, 15(5):519-530, May 1, 2004.
Roy, Complete Nucleotide Sequences and Genome Organization of Four Chimpanzee Adenoviruses, Virology, 324(2):361-372, Jul. 1, 2004.
Roy, Generation of an Adenoviral Vaccine Vector Based on Simian Adenovirus 21, Journal of General Virology, 87(9):2477-2485, Sep. 2006.
Roy, Isolation and Characterization of Adenoviruses Persistently Shed from the Gastrointestinal Tract of Non-Human Primates, PLOS, Pathogens, 5(7):1-9, Jul. 1, 2009.
Roy, Partial Protection against H5N1 Influenza in Mice with a Single Dose of a Chimpanzee Adenovirus Vector Expressing Nucleoprotein, Vaccine, 25(39-40):6845-6851, Sep. 15, 2007.
Roy, Rescue of Chimeric Adenoviral Vectors to Expand the Serotype Repertoire, Journal of Virological Methods, 141(1):14-21, Feb. 21, 2007.
Russell, W.C., Update on Adenovirus and its Vectors, Journal of General Virology, 81:2573-2604, (Nov. 2000).
Shenk, T., Adenoviridae: The Viruses and Their Replication, Fields Virology, Third Edition, Chapter 67, pp. 2111-2112, (1996).

* cited by examiner

*Primary Examiner* — Maria Marvich
(74) *Attorney, Agent, or Firm* — Howson & Howson LLP

(57) ABSTRACT

Novel simian adenovirus 41 and two isolates thereof are described. Various uses of these isolates, including construction of a recombinant vector which comprises simian adenovirus 41 sequences and a heterologous gene under the control of regulatory sequences are provided. A cell line which expresses simian adenovirus 41 gene(s) is also disclosed. Methods of using the vectors and cell lines are provided.

9 Claims, No Drawings

SIMIAN ADENOVIRUS 41 AND USES THEREOF

CROSS-REFERENCE TO RELATED APPLICATIONS

This application is a national stage of International Patent Application No. PCT/US2010/036332, filed May 27, 2010, which claims the benefit under 35USC 119(e) of U.S. Patent Application Nos. 61/182,290, filed on May 29, 2009 (now expired), and 61/219,917, filed Jun. 24, 2009 (now expired), all of which are incorporated by reference herein.

STATEMENT REGARDING FEDERALLY SPONSORED RESEARCH OR DEVELOPMENT

This invention was made with government support under grant number P30DK47757 awarded by the National Institutes of Health. The government has certain rights in this the invention.

INCORPORATION-BY-REFERENCE OF MATERIAL SUBMITTED IN ELECTRONIC FORM

Applicant hereby incorporates by reference the Sequence Listing material filed in electronic form herewith. These file is labeled "UPN-U4710PCT_ST25.txt".

BACKGROUND OF THE INVENTION

Adenovirus is a double-stranded DNA virus with a genome size of about 36 kilobases (kb), which has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Adenoviruses have a characteristic morphology with an icosahedral capsid consisting of three major proteins, hexon (II), penton base (III) and a knobbed fibre (IV), along with a number of other minor proteins, VI, VIII, IX, IIIa and IVa2 [W. C. Russell, *J. Gen Virol.*, 81:2573-2604 (Nov. 2000)]. The virus genome is a linear, double-stranded DNA with a terminal protein attached covalently to the 5' terminus, which have inverted terminal repeats (ITRs). The virus DNA is intimately associated with the highly basic protein VII and a small peptide pX (formerly termed mu). Another protein, V, is packaged with this DNA-protein complex and provides a structural link to the capsid via protein VI. The virus also contains a virus-encoded protease, which is necessary for processing of some of the structural proteins to produce mature infectious virus.

A classification scheme has been developed for the Mastadenovirus family, which includes human, simian, bovine, equine, porcine, ovine, canine and opossum adenoviruses. This classification scheme was developed based on the differing abilities of the adenovirus sequences in the family to agglutinate red blood cells. The result was six subgroups, now referred to as subgroups A, B, C, D, E and F. See, T. Shenk et al., *Adenoviridae: The Viruses and their Replication*", Ch. 67, in FIELD'S VIROLOGY, 6$^{th}$ Ed., edited by B. N Fields et al, (Lippincott Raven Publishers, Philadelphia, 1996), p. 111-2112.

Recombinant adenoviruses have been described for delivery of heterologous molecules to host cells. See, U.S. Pat. No. 6,083,716, which describes the genome of two chimpanzee adenoviruses. Simian adenoviruses, C5, C6 and C7, have been described in U.S. Pat. No. 7,247,472 as being useful as vaccine vectors. Other chimpanzee adenoviruses are described in WO 2005/1071093 as being useful for making adenovirus vaccine carriers.

Additional adenovirus isolates useful in preparing vectors useful for therapy and/or immunogenic applications are needed.

SUMMARY OF THE INVENTION

Isolated nucleic acid sequences and amino acid sequences of simian adenovirus 41 (SAdV-41) and vectors containing these sequences are provided herein. Also provided are a number of methods for using the vectors and cells of the invention.

The methods described herein involve delivering one or more selected heterologous gene(s) to a mammalian patient by administering a vector of the invention. Use of the compositions described herein for vaccination permits presentation of a selected antigen for the elicitation of protective immune responses. The vectors based on simian adenovirus 41 may also be used for producing heterologous gene products in vitro. Such gene products are themselves useful in a variety for a variety of purposes such as are described herein.

These and other embodiments and advantages of the invention are described in more detail below.

DETAILED DESCRIPTION OF THE INVENTION

Novel nucleic acid and amino acid sequences from simian adenovirus 41, which was isolated from chimpanzee feces, are provided. Also provided are novel adenovirus vectors and packaging cell lines to produce those vectors for use in the in vitro production of recombinant proteins or fragments or other reagents. Further provided are compositions for use in delivering a heterologous molecule for therapeutic or vaccine purposes. Such therapeutic or vaccine compositions contain the adenoviral vectors carrying an inserted heterologous molecule. In addition, the novel SAdV-41 sequences are useful in providing the essential helper functions required for production of recombinant adeno-associated viral (AAV) vectors. Thus, helper constructs, methods and cell lines which use these sequences in such production methods, are provided.

The SAdV-41 sequence has been determined by the inventors to be within the same subgroup as human subgroup B adenoviruses. Human species B adenoviruses have previously been subclassified into B:1 and B:2 subclades based on restriction enzyme digestion patterns and are seen to cluster separately. SAdV-41 clusters with the human B:1 isolates.

In one embodiment, the invention provides a novel adenovirus isolate which is termed SAdV41.1. In another embodiment, the invention provides a novel adenovirus isolate termed SAdV41.2. These two isolates have hexon proteins which are 100% identical at the amino acid level (i.e., SEQ ID NO: 11 and SEQ ID NO: 44 are identical). Except where otherwise specified, the constructs described herein and the uses for the adenoviral sequences and constructs are applicable to both SAdV41 isolates described herein.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 95, 96, 97, 98, 98.5, 99, or 99.5% of the aligned sequences.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95, 96, 97, 98, 98.5, 99, or 99.5% of the aligned sequences. Preferably, the homology is over full-length sequence, or a protein thereof, or a fragment thereof which is at least 8 amino acids, or more desirably, at least 15 amino acids in length. Examples of suitable fragments are described herein.

The term "percent sequence identity" or "identical" in the context of nucleic acid sequences refers to the residues in the two sequences that are the same when aligned for maximum correspondence. The length of sequence identity comparison may be over the full-length of the genome (e.g., about 36 kbp), the full-length of an open reading frame of a gene, protein, subunit, or enzyme [see, e.g., the tables providing the adenoviral coding regions], or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein. In one embodiment, there is amino acid identity in at least about 95, 96, 97, 98, 98.5, 99 or 99.5% of the aligned sequences.

Identity is readily determined using such algorithms and computer programs as are defined herein at default settings. Preferably, such identity is over the full length of the protein, enzyme, subunit, or over a fragment of at least about 8 amino acids in length. However, identity may be based upon shorter regions, where suited to the use to which the identical gene product is being put.

As described herein, alignments are performed using any of a variety of publicly or commercially available Multiple Sequence Alignment Programs, such as "Clustal W", accessible through Web Servers on the internet. Alternatively, Vector NTI® utilities [In Vitrogen] are also used. There are also a number of algorithms known in the art that can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similarly programs are available for performing amino acid alignments. Generally, these programs are used at default settings, although one of skill in the art can alter these settings as needed. Alternatively, one of skill in the art can utilize another algorithm or computer program that provides at least the level of identity or alignment as that provided by the referenced algorithms and programs.

"Recombinant", as applied to a polynucleotide, means that the polynucleotide is the product of various combinations of cloning, restriction or ligation steps, and other procedures that result in a construct that is distinct from a polynucleotide found in nature. A recombinant virus is a viral particle having packaged therein a heterologous polynucleotide (e.g., an expression cassette). In certain embodiments, a viral particle may be generated which does not contain an expression cassette or other heterologous polynucleotide. Such a construct is termed herein an "empty capsid" and may be used, e.g., as described in International Patent Publication No. WO 2008/010864, published 24 Jan. 2008.

The terms respectively include replicates of the original polynucleotide construct and progeny of the original virus construct.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. A site-specific recombination site that has been cloned into a genome of a virus or viral vector, wherein the genome of the virus does not naturally contain it, is a heterologous recombination site. When a polynucleotide with an encoding sequence for a recombinase is used to genetically alter a cell that does not normally express the recombinase, both the polynucleotide and the recombinase are heterologous to the cell.

As used throughout this specification and the claims, the term "comprise" and its variants including, "comprises", "comprising", among other variants, is inclusive of other components, elements, integers, steps and the like. The term "consists of" or "consisting of" are exclusive of other components, elements, integers, steps and the like.

I. The Simian Adenovirus Sequences

The invention provides nucleic acid sequences and amino acid sequences of simian adenovirus 41 (SAdV-41), which is isolated from the other material with which they are associated in nature.

A. Nucleic Acid Sequences

The SAdV-41.1 nucleic acid sequences provided herein include nucleotides 1 to 35100 of SEQ ID NO: 1. See, Sequence Listing, which is incorporated by reference herein. The nucleic acid sequences of SAdV41.2, 1 to 35776, are provided in SEQ ID NO: 34. In one embodiment, the nucleic acid sequences of the invention further encompass the strand which is complementary to the sequences of SEQ ID NO: 1 or SEQ ID NO: 34, as well as the RNA and cDNA sequences corresponding to the sequences of the following sequences and their complementary strands. In another embodiment, the nucleic acid sequences further encompass sequences which are greater than 98.5% identical, and preferably, greater than about 99% identical, to the Sequence Listing. Also included in one embodiment, are natural variants and engineered modifications of the sequences provided in SEQ ID NO: 1 or SEQ ID NO: 34, and its complementary strand. Such modifications include, for example, labels that are known in the art, methylation, and substitution of one or more of the naturally occurring nucleotides with a degenerate nucleotide.

TABLE 1

| Regions | | SAdV-41.1 ORF SEQ ID NO: 1 | SAdV-41.2 ORF SEQ ID NO: 34 |
|---|---|---|---|
| ITR | | 1 ... 112 | 1 ... 132 |
| E1a | 13S | Complement | Complement |
| | 12S | (564 ... 1140, | (573 ... 1149, |
| | 9S | 1229 ... 1434) | 1243 ... 1448) |

TABLE 1-continued

| Regions | | SAdV-41.1 ORF SEQ ID NO: 1 | SAdV-41.2 ORF SEQ ID NO: 34 |
|---|---|---|---|
| E1b | Small T/19K | 1605 ... 2147 | 1619 ... 2161 |
| | Large T/55K | 1910 ... 3394 | 1924 ... 3408 |
| | IX | 3491 ... 3904 | 3503 ... 3916 |
| E2b | pTP | Complement (8447 ... 10402, 13871 ... 13879) | Complement (8459 ... 10435, 13909 ... 13917) |
| | Polymerase | Complement (5076 ... 8645, 13871 ... 13879) | Complement (5088 ... 8657, 13909 ... 13917) |
| | IVa2 | Complement (3973 ... 5303, 5582 ... 5594) | Complement (3985 ... 5315, 5594 ... 5606) |
| L1 | 52/55D | 10883 ... 12049 | 10921 ... 12087 |
| | IIIa | 12077 ... 13837 | 12115 ... 13875 |
| L2 | Penton | 13924 ... 15675 | 13962 ... 15713 |
| | VII | 15683 ... 16258 | 15720 ... 16295 |
| | V | 16304 ... 17353 | 16341 ... 17390 |
| | pX | 17385 ... 17609 | 17422 ... 17646 |
| L3 | VI | 17686 ... 18435 | 17724 ... 18473 |
| | Hexon | 18550 ... 21378 | 18592 ... 21420 |
| | Endo-protease | 21412 ... 22038 | 21296 ... 22081 |
| E2a | DBP | Complement (22133 ... 23689) | Complement (22175 ... 23731) |
| L4 | 100 kD | 23720 ... 26212 | 23762 ... 26254 |
| | 33 kD homolog | Complement (25908 ... 26265, 26434 ... 26793) | Complement (25950 ... 26307, 26477 ... 26832) |
| | 22 kD | 25908 ... 26525 | 25950 ... 26564 |
| | VIII | 26866 ... 27546 | 26905 ... 27585 |
| E3 | 12.5K | 27549 ... 27863 | 27588 ... 27902 |
| | CR1-alpha | 27820 ... 28263 | 27859 ... 28284 |
| | gp19K | 28251 ... 28787 | 28272 ... 28787 |
| | CR1-beta | 28820 ... 29428 | 28819 ... 29421 |
| | CR1-delta | | 30138 ... 30443 |
| | CR1-gamma | 29442 ... 29780 | 29474 ... 30118 |
| | RID-alpha | 29822 ... 30094 | 30476 ... 30748 |
| | RID-beta | 30066 ... 30491 | 30723 ... 31142 |
| | 14.7K | 30487 ... 30891 | 31138 ... 31533 |
| L5 | Fiber | 31118 ... 32080 | 31766 ... 32740 |
| E4 | Orf 6/7 | Complement (32126 ... 32374, 33097 ... 33300) | Complement (32789 ... 33037, 33760 ... 33963) |
| | Orf 6 | Complement (32374 ... 33300) | Complement (33037 ... 33963) |
| | Orf 4 | Complement (33176 ... 33556) | Complement (33839 ... 34219) |
| | Orf 3 | Complement (33569 ... 33919) | Complement (34232 ... 34582) |
| | Orf 2 | Complement (33919 ... 34305) | Complement (34582 ... 34968) |
| | Orf 1 | Complement (34350 ... 34721) | Complement (35018 ... 35389) |
| ITR | | Complement (34989 ... 35100) | Complement (35636 ... 35767) |

In one embodiment, fragments of the sequences of SAdV-41, and their complementary strand, cDNA and RNA complementary thereto are provided. Suitable fragments are at least 15 nucleotides in length, and encompass functional fragments, i.e., fragments which are of biological interest. For example, a functional fragment can express a desired adenoviral product or may be useful in production of recombinant viral vectors. Such fragments include the gene sequences and fragments listed in the tables herein. The tables provide the transcript regions and open reading frames in the SAdV-41 sequences. For certain genes, the transcripts and open reading frames (ORFs) are located on the strand complementary to that presented in SEQ ID NO: 1 and SEQ ID NO: 34. See, e.g., E2b, E4 and Eta. The calculated molecular weights of the encoded proteins are also shown. Note that the Eta open reading frame of SAdV-41 and the E2b open reading frame contain internal splice sites. These splice sites are noted in the table above.

The SAdV-41 adenoviral nucleic acid sequences are useful as therapeutic agents and in construction of a variety of vector systems and host cells. As used herein, a vector includes any suitable nucleic acid molecule including, naked DNA, a plasmid, a virus, a cosmid, or an episome. These sequences and products may be used alone or in combination with other adenoviral sequences or fragments, or in combination with elements from other adenoviral or non-adenoviral sequences. The SAdV-41 sequences are also useful as antisense delivery vectors, gene therapy vectors, or vaccine vectors. Thus, further provided are nucleic acid molecules, gene delivery vectors, and host cells which contain the SAdV-41 sequences.

For example, the invention encompasses a nucleic acid molecule containing simian Ad ITR sequences of the invention. In another example, the invention provides a nucleic acid molecule containing simian Ad sequences of the invention encoding a desired Ad gene product. Still other nucleic acid molecule constructed using the sequences of the invention will be readily apparent to one of skill in the art, in view of the information provided herein.

In one embodiment, the simian Ad gene regions identified herein may be used in a variety of vectors for delivery of a heterologous molecule to a cell. For example, vectors are generated for expression of an adenoviral capsid protein (or fragment thereof) for purposes of generating a viral vector in a packaging host cell. Such vectors may be designed for expression in trans. Alternatively, such vectors are designed to provide cells which stably contain sequences which express desired adenoviral functions, e.g., one or more of E1a, E1b, the terminal repeat sequences, Eta, E2b, E4, E4ORF6 region.

In addition, the adenoviral gene sequences and fragments thereof are useful for providing the helper functions necessary for production of helper-dependent viruses (e.g., adenoviral vectors deleted of essential functions, or adeno-associated viruses (AAV)). For such production methods, the SAdV-41 sequences can be utilized in such a method in a manner similar to those described for the human Ad. However, due to the differences in sequences between the SAdV-41 sequences and those of human Ad, the use of the SAdV-41 sequences greatly minimize or eliminate the possibility of homologous recombination with helper functions in a host cell carrying human Ad E1 functions, e.g., 293 cells, which may produce infectious adenoviral contaminants during rAAV production.

Methods of producing rAAV using adenoviral helper functions have been described at length in the literature with human adenoviral serotypes. See, e.g., U.S. Pat. No. 6,258, 595 and the references cited therein. See, also, U.S. Pat. No. 5,871,982; WO 99/14354; WO 99/15685; WO 99/47691. These methods may also be used in production of non-human serotype AAV, including non-human primate AAV serotypes. The SAdV-41 sequences which provide the necessary helper functions (e.g., E1a, E1b, E2a and/or E4 ORF6) can be particularly useful in providing the necessary adenoviral function while minimizing or eliminating the possibility of recombination with any other adenoviruses present in the rAAV-packaging cell which are typically of human origin. Thus, selected genes or open reading frames of the SAdV-41 sequences may be utilized in these rAAV production methods.

Alternatively, recombinant SAdV-41 vectors may be utilized in these methods. Such recombinant adenoviral simian vectors may include, e.g., a hybrid chimp Ad/AAV in which chimp Ad sequences flank a rAAV expression cassette composed of, e.g., AAV 3' and/or 5' ITRs and a transgene under the control of regulatory sequences which control its expression. One of skill in the art will recognize that still other simian adenoviral vectors and/or SAdV-41 gene sequences will be useful for production of rAAV and other viruses dependent upon adenoviral helper.

In still another embodiment, nucleic acid molecules are designed for delivery and expression of selected adenoviral gene products in a host cell to achieve a desired physiologic effect. For example, a nucleic acid molecule containing sequences encoding an SAdV-41 E1a protein may be delivered to a subject for use as a cancer therapeutic. Optionally, such a molecule is formulated in a lipid-based carrier and preferentially targets cancer cells. Such a formulation may be combined with other cancer therapeutics (e.g., cisplatin, taxol, or the like). Still other uses for the adenoviral sequences provided herein will be readily apparent to one of skill in the art.

In addition, one of skill in the art will readily understand that the SAdV-41 sequences can be readily adapted for use for a variety of viral and non-viral vector systems for in vitro, ex vivo or in vivo delivery of therapeutic and immunogenic molecules. For example, the SAdV-41 simian Ad sequences can be utilized in a variety of rAd and non-rAd vector systems. Such vectors systems may include, e.g., plasmids, lentiviruses, retroviruses, poxviruses, vaccinia viruses, and adeno-associated viral systems, among others. Selection of these vector systems is not a limitation of the present invention.

The invention further provides molecules useful for production of the simian and simian-derived proteins of the invention. Such molecules which carry polynucleotides including the simian Ad DNA sequences of the invention can be in the form of naked DNA, a plasmid, a virus or any other genetic element.

B. SAdV-41 Adenoviral Proteins

Gene products of the SAdV-41 adenovirus, such as proteins, enzymes, and fragments thereof, which are encoded by the adenoviral nucleic acids described herein are provided. Further encompassed are SAdV-41 proteins, enzymes, and fragments thereof, having the amino acid sequences encoded by these nucleic acid sequences which are generated by other methods. Such proteins include those encoded by the open reading frames identified in the table above, the proteins in the Table below (also shown in the Sequence Listing) and fragments thereof of the proteins and polypeptides.

TABLE 2

Simian Ad 41
PROTEIN SEQUENCES

| Regions | | SAdV41.1 SEQ ID NO: | SAdV41.2 SEQ ID NO: |
|---|---|---|---|
| E1a | 13S | 29 | 63 |
| | 12S | | |
| | 9S | | |
| E1b | Small T/19K | 23 | 56 |
| | Large T/55K | 2 | 35 |
| | IX | 3 | 36 |
| L1 | 52/55D | 4 | 37 |
| | IIIa | 5 | 38 |
| L2 | Penton | 6 | 39 |
| | VII | 7 | 40 |
| | V | 8 | 41 |
| | pX | 9 | 42 |
| L3 | VI | 10 | 43 |
| | Hexon | 11 | 44 |
| | Endoprotease | 12 | 58 |
| L4 | 100 kD | 13 | 59 |
| | 33 kD homolog | 31 | 65 |
| | 22 kD | 25 | 45 |
| | VIII | 14 | 46 |

TABLE 2-continued

Simian Ad 41
PROTEIN SEQUENCES

| Regions | | SAdV41.1 SEQ ID NO: | SAdV41.2 SEQ ID NO: |
|---|---|---|---|
| E3 | E3/12.5k | 15 | 47 |
| | CR1-alpha | 26 | 60 |
| | gp19K | 16 | 48 |
| | CR1-beta | 17 | 49 |
| | CR1-gamma | 18 | 50 |
| | CR1-delta | | 51 |
| | RID-alpha | 19 | 52 |
| | RID-beta | 27 | 61 |
| | E3/14.7K | 20 | 53 |
| L5 | Fiber | 21 | 54 |

Thus, in one aspect, unique simian adenoviral 41 proteins which are substantially pure, i.e., are free of other viral and proteinaceous proteins are provided. Preferably, these proteins are at least 10% homogeneous, more preferably 60% homogeneous, and most preferably 95% homogeneous.

In one embodiment, unique simian-derived capsid proteins are provided. As used herein, a simian-derived capsid protein includes any adenoviral capsid protein that contains a SAdV-41 capsid protein or a fragment thereof, as defined above, including, without limitation, chimeric capsid proteins, fusion proteins, artificial capsid proteins, synthetic capsid proteins, and recombinant capsid proteins, without limitation to means of generating these proteins.

Suitably, these simian-derived capsid proteins contain one or more SAdV-41 regions or fragments thereof (e.g., a hexon, penton, fiber, or fragment thereof) in combination with capsid regions or fragments thereof of different adenoviral serotypes, or modified simian capsid proteins or fragments, as described herein. A "modification of a capsid protein associated with altered tropism" as used herein includes an altered capsid protein, i.e, a penton, hexon or fiber protein region, or fragment thereof, such as the knob domain of the fiber region, or a polynucleotide encoding same, such that specificity is altered. The simian-derived capsid may be constructed with one or more of the simian Ad of the invention or another Ad serotype which may be of human or non-human origin. Such Ad may be obtained from a variety of sources including the ATCC, commercial and academic sources, or the sequences of the Ad may be obtained from GenBank or other suitable sources.

The SAdV-41.1 penton protein is provided in SEQ ID NO: 6 and the SAdV41.2 penton protein is provided in SEQ ID NO: 39. Suitably, this penton protein, or unique fragments thereof, may be utilized for a variety of purposes. Examples of suitable fragments include the penton having N-terminal and/or C-terminal truncations of about 50, 100, 150, or 200 amino acids, based upon the amino acid numbering provided above and in SEQ ID NO: 6 and/or 39. Other suitable fragments include shorter internal, C -terminal, or N-terminal fragments. Further, the penton protein may be modified for a variety of purposes known to those of skill in the art.

Also provided are the amino acid sequences of the hexon protein of SAdV-41.1 [SEQ ID NO: 11] and SAdV41.2 [SEQ ID NO: 44] (these two virus have hexons that are 100% identical at the amino acid level). Suitably, this hexon protein, or unique fragments thereof, may be utilized for a variety of purposes. Examples of suitable fragments include the hexon having N-terminal and/or C-terminal truncations of about 50, 100, 150, 200, 300, 400, or 500 amino acids, based upon the amino acid numbering provided above and in SEQ ID NO: 11 or 44. Other suitable fragments include shorter internal, C-terminal, or N-terminal fragments. For example, one suitable fragment the loop region (domain) of the hexon protein, designated DE1 and FG1, or a hypervariable region thereof. Such fragments include the regions spanning amino acid residues about 125 to 443; about 138 to 441, or smaller fragments, such as those spanning about residue 138 to residue 163; about 170 to about 176; about 195 to about 203; about 233 to about 246; about 253 to about 264; about 287 to about 297; and about 404 to about 430 of the simian hexon proteins, with reference to SEQ ID NO: 11 or SEQ ID NO: 44. Other suitable fragments may be readily identified by one of skill in the art. Further, the hexon protein may be modified for a variety of purposes known to those of skill in the art. Because the hexon protein is the determinant for serotype of an adenovirus, such artificial hexon proteins would result in adenoviruses having artificial serotypes. Other artificial capsid proteins can also be constructed using the chimp Ad penton sequences and/or fiber sequences of the invention and/or fragments thereof.

In one embodiment, an adenovirus having an altered hexon protein utilizing the sequences of a SAdV-41 hexon protein may be generated. One suitable method for altering hexon proteins is described in U.S. Pat. No. 5,922,315, which is incorporated by reference. In this method, at least one loop region of the adenovirus hexon is changed with at least one loop region of another adenovirus serotype. Thus, at least one loop region of such an altered adenovirus hexon protein is a simian Ad hexon loop region of SAdV-41. In one embodiment, a loop region of the SAdV-41 hexon protein is replaced by a loop region from another adenovirus serotype. In another embodiment, the loop region of the SAdV-41 hexon is used to replace a loop region from another adenovirus serotype. Suitable adenovirus serotypes may be readily selected from among human and non-human serotypes, as described herein. The selection of a suitable serotype is not a limitation of the present invention. Still other uses for the SAdV-41 hexon protein sequences will be readily apparent to those of skill in the art.

The fiber protein of SAdV-41.1 has the amino acid sequence of SEQ ID NO:21 and the fiber protein of SAdV-41.2 has the amino acid sequence of SEQ ID NO: 54. Suitably, this fiber protein, or unique fragments thereof, may be utilized for a variety of purposes. One suitable fragment is the fiber knob, located within SEQ ID NO: 21 or SEQ ID NO: 54. Examples of other suitable fragments include the fiber having N-terminal and/or C-terminal truncations of about 50, 100, 150, or 200 amino acids, based upon the amino acid numbering provided in SEQ ID NO: 21 or SEQ ID NO: 54. Still other suitable fragments include internal fragments. Further, the fiber protein may be modified using a variety of techniques known to those of skill in the art.

Unique fragments of the proteins of the SAdV-41 are at least 8 amino acids in length. However, fragments of other desired lengths can be readily utilized. In addition, modifications as may be introduced to enhance yield and/or expression of a SAdV41 gene product, e.g., construction of a fusion molecule in which all or a fragment of the SAdV41 gene product is fused (either directly or via a linker) with a fusion partner to enhance are provided herein. Other suitable modifications include, without limitation, truncation of a coding region (e.g., a protein or enzyme) to eliminate a pre- or pro-protein ordinarily cleaved and to provide the mature protein or enzyme and/or mutation of a coding region to provide a secretable gene product. Still other modifications will be readily apparent to one of skill in the art. Further encompassed are proteins having at least about 99% identity to the SAdV41 proteins provided herein.

As described herein, vectors of the invention containing the adenoviral capsid proteins of SAdV-41 are particularly well suited for use in applications in which the neutralizing antibodies diminish the effectiveness of other Ad serotype based vectors, as well as other viral vectors. The rAd vectors are particularly advantageous in readministration for repeat gene therapy or for boosting immune response (vaccine titers).

Under certain circumstances, it may be desirable to use one or more of the SAdV41 gene products (e.g., a capsid protein or a fragment thereof) to generate an antibody. The term "an antibody," as used herein, refers to an immunoglobulin molecule which is able to specifically bind to an epitope. The antibodies may exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE.

Such antibodies may be generated using any of a number of methods know in the art. Suitable antibodies may be generated by well-known conventional techniques, e.g., Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., 1986 *Science*, 233:747-753; Queen et al., 1989 *Proc. Nat'l. Acad. Sci. USA*, 86:10029-10033; PCT Patent Application No. PCT/WO9007861; and Riechmann et al., *Nature*, 332:323-327 (1988); Huse et al, 1988a *Science*, 246:1275-1281]. Alternatively, antibodies can be produced by manipulating the complementarity determining regions of animal or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, *Proc. Natl. Acad. Sci. USA* 85:5879-5883; and Bird et al., 1988, *Science* 242:423-426. Further provided by the present invention are anti-idiotype antibodies (Ab2) and anti-anti-idiotype antibodies (Ab3). See, e.g., M. Wettendorff et al., "Modulation of anti-tumor immunity by anti-idiotypic antibodies." In Idiotypic Network and Diseases, ed. by J. Cerny and J. Hiernaux, 1990 *J. Am. Soc. Microbial.*, Washington D.C.: pp. 203-229]. These anti-idiotype and anti-anti-idiotype antibodies are produced using techniques well known to those of skill in the art. These antibodies may be used for a variety of purposes, including diagnostic and clinical methods and kits.

Under certain circumstances, it may be desirable to introduce a detectable label or a tag onto a SAdV41 gene product, antibody or other construct of the invention. As used herein, a detectable label is a molecule which is capable, alone or upon interaction with another molecule, of providing a detectable signal. Most desirably, the label is detectable visually, e.g. by fluorescence, for ready use in immunohistochemical analyses or immunofluorescent microscopy. For example, suitable labels include fluorescein isothiocyanate (FITC), phyco-erythrin (PE), allophycocyanin (APC), coriphosphine-O (CPO) or tandem dyes, PE-cyanin-5 (PC5), and PE-Texas Red (ECD). All of these fluorescent dyes are commercially available, and their uses known to the art. Other useful labels include a colloidal gold label. Still other useful labels include radioactive compounds or elements. Additionally, labels include a variety of enzyme systems that operate to reveal a colorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP), alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other label systems that are utilized in the methods described herein are detectable by other means, e.g., colored latex microparticles [Bangs Laboratories, Indiana] in which a dye is embedded are used in place of enzymes to form conjugates with the target sequences provide a visual signal indicative of the presence of the resulting complex in applicable assays.

Methods for coupling or associating the label with a desired molecule are similarly conventional and known to those of skill in the art. Known methods of label attachment are described [see, for example, Handbook of Fluorescent probes and Research Chemicals, 6th Ed., R. P. M. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

The sequences, proteins, and fragments of SAdV-41 may be produced by any suitable means, including recombinant production, chemical synthesis, or other synthetic means. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.*, 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

In addition, one of skill in the art will readily understand that the SAdV-41 sequences can be readily adapted for use for a variety of viral and non-viral vector systems for in vitro, ex vivo or in vivo delivery of therapeutic and immunogenic molecules. For example, in one embodiment, the simian Ad capsid proteins and other simian adenovirus proteins described herein are used for non-viral, protein-based delivery of genes, proteins, and other desirable diagnostic, therapeutic and immunogenic molecules. In one such embodiment, a protein of the invention is linked, directly or indirectly, to a molecule for targeting to cells with a receptor for adenoviruses. Preferably, a capsid protein such as a hexon, penton, fiber or a fragment thereof having a ligand for a cell surface receptor is selected for such targeting. Suitable molecules for delivery are selected from among the therapeutic molecules described herein and their gene products. A variety of linkers including, lipids, polyLys, and the like may be utilized as linkers. For example, the simian penton protein may be readily utilized for such a purpose by production of a fusion protein using the simian penton sequences in a manner analogous to that described in Medina-Kauwe L K, et al, *Gene Ther.* 2001 May; 8(10):795-803 and Medina-Kauwe L K, et al, *Gene Ther.* 2001 December; 8(23): 1753-1761. Alternatively, the amino acid sequences of simian Ad protein IX may be utilized for targeting vectors to a cell surface receptor, as described in US Patent Appln 20010047081. Suitable ligands include a CD40 antigen, an RGD-containing or polylysine-containing sequence, and the like. Still other simian Ad proteins, including, e.g., the hexon protein and/or the fiber protein, may be used for used for these and similar purposes.

Still other SAdV-41 adenoviral proteins may be used as alone, or in combination with other adenoviral protein, for a variety of purposes which will be readily apparent to one of skill in the art. In addition, still other uses for the SAdV-41 adenoviral proteins will be readily apparent to one of skill in the art.

II. Recombinant Adenoviral Vectors

The compositions described herein include vectors that deliver a heterologous molecule to cells, either for therapeutic or vaccine purposes. As used herein, a vector may include any genetic element including, without limitation, naked DNA, a phage, transposon, cosmid, episome, plasmid, or a virus. Such vectors contain simian adenovirus DNA of SAdV41 and a minigene. By "minigene" is meant the combination of a selected heterologous gene and the other regulatory elements necessary to drive translation, transcription and/or expression of the gene product in a host cell.

Typically, a SAdV-derived adenoviral vector is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of such as the site of a functional E1 deletion or functional E3 deletion, among others that may be selected. The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed elsewhere in the application.

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5' cis-elements necessary for packaging and replication; i.e., the 5' inverted terminal repeat (ITR) sequences (which function as origins of replication) and the native 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation. Suitably, a recombinant adenovirus contains both 5' and 3' adenoviral cis-elements and the minigene is located between the 5' and 3' adenoviral sequences. A SAdV-41 based adenoviral vector may also contain additional adenoviral sequences.

Suitably, these SAdV-41 based adenoviral vectors contain one or more adenoviral elements derived from the adenoviral genome of the invention. In one embodiment, the vectors contain adenoviral ITRs from SAdV41 and additional adenoviral sequences from the same adenoviral serotype. In another embodiment, the vectors contain adenoviral sequences that are derived from a different adenoviral serotype than that which provides the ITRs.

As defined herein, a pseudotyped adenovirus refers to an adenovirus in which the capsid protein of the adenovirus is from a different adenovirus than the adenovirus which provides the ITRs.

Further, chimeric or hybrid adenoviruses may be constructed using the adenoviruses described herein using techniques known to those of skill in the art. See, e.g., U.S. Pat. No. 7,291,498.

The selection of the adenoviral source of the ITRs and the source of any other adenoviral sequences present in vector is not a limitation of the present embodiment. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Homologous adenovirus vectors prepared from other simian or from human adenoviruses are described in the published literature [see, for example, U.S. Pat. No. 5,240,846]. The DNA sequences of a number of adenovirus types are available from GenBank, including type Ad5 [GenBank Accession No. M73260]. The adenovirus sequences may be obtained from any known adenovirus serotype, such as serotypes 2, 3, 4, 7, 12 and 40, and further including any of the presently identified human types. Similarly adenoviruses known to infect non-human animals (e.g., simians) may also be employed in the vector constructs of this invention. See, e.g., U.S. Pat. No. 6,083,716.

The viral sequences, helper viruses (if needed), and recombinant viral particles, and other vector components and sequences employed in the construction of the vectors described herein are obtained as described above. The DNA sequences of the SAdV41 simian adenovirus sequences of the invention are employed to construct vectors and cell lines useful in the preparation of such vectors.

Modifications of the nucleic acid sequences forming the vectors of this invention, including sequence deletions, insertions, and other mutations may be generated using standard molecular biological techniques and are within the scope of this embodiment.

A. The "Minigene"

The methods employed for the selection of the transgene, the cloning and construction of the "minigene" and its insertion into the viral vector are within the skill in the art given the teachings provided herein.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is GFP or luciferase, the vector carrying the signal may be measured visually by color or light production in a luminometer.

In one embodiment, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a molecule (e.g., a gene product) to induce a T cell and/or a humoral immune response to the molecule. The invention further includes using multiple transgenes, e.g., to correct or ameliorate a condition caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Viral.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this embodiment.

2. Regulatory Elements

In addition to the major elements identified above for the minigene, the vector also includes conventional control elements necessary which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product.

A great number of expression control sequences, including promoters which are native, constitutive, inducible and/or tissue-specific, are known in the art and may be utilized. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the B-actin promoter, the phosphoglycerol kinase (PGK) promoter, and the EF1a promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), see also Harvey et al, *Curr. Opin. Chem. Biol.,* 2:512-518 (1998)]. Other systems include the FK506 dimer, VP16 or p65 using castradiol, diphenol murislerone, the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. The effectiveness of some inducible promoters increases over time. In such cases one can enhance the effectiveness of such systems by inserting multiple repressors in tandem, e.g., TetR linked to a TetR by an IRES. Alternatively, one can wait at least 3 days before screening for the desired function. One can enhance expression of desired proteins by known means to enhance the effectiveness of this system. For example, using the Woodchuck Hepatitis Virus Posttranscriptional Regulatory Element (WPRE).

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al., *Nat. Biotech.,* 17:241-245 (1999)). Examples of promoters that are tissue-specific are known for liver (albumin, Miyatake et al., *J. Virol.,* 71:5124-32 (1997); hepatitis B virus core promoter, Sandig et al., *Gene Ther.,* 3:1002-9 (1996); alpha-fetoprotein (AFP), Arbuthnot et al., *Hum. Gene Ther.,* 7:1503-14 (1996)), bone osteocalcin (Stein et al., *Mol. Biol. Rep.,* 24:185-96 (1997)); bone sialoprotein (Chen et al., *J. Bone Miner. Res.,* 11:654-64 (1996)), lymphocytes (CD2, Hansal et al., *J. Immunol.,* 161:1063-8 (1998); immunoglobulin heavy chain; T cell receptor chain), neuronal such as neuron-specific enolase (NSE) promoter (Andersen et al., *Cell. Mol. Neurobiol.,* 13:503-15 (1993)), neurofilament light-chain gene (Piccioli et al., *Proc. Natl. Acad. Sci. USA,* 88:5611-5 (1991)), and the neuron-specific vgf gene (Piccioli et al., *Neuron,* 15:373-84 (1995)), among others.

Optionally, vectors carrying transgenes encoding therapeutically useful or immunogenic products may also include selectable markers or reporter genes may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication. Selection of these and other promoters and vector elements are conventional and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

III. Production of the Viral Vector

In one embodiment, the simian adenoviral plasmids (or other vectors) are used to produce adenoviral vectors. In one embodiment, the adenoviral vectors are adenoviral particles which are replication-defective. In one embodiment, the adenoviral particles are rendered replication-defective by deletions in the E1a and/or E1b genes. Alternatively, the adenoviruses are rendered replication-defective by another means, optionally while retaining the E1a and/or E1b genes. The adenoviral vectors can also contain other mutations to the adenoviral genome, e.g., temperature-sensitive mutations or deletions in other genes. In other embodiments, it is desirable to retain an intact E1a and/or E1b region in the adenoviral vectors. Such an intact E1 region may be located in its native location in the adenoviral genome or placed in the site of a deletion in the native adenoviral genome (e.g., in the E3 region).

In the construction of useful simian adenovirus vectors for delivery of a gene to the human (or other mammalian) cell, a range of adenovirus nucleic acid sequences can be employed in the vectors. For example, all or a portion of the adenovirus delayed early gene E3 may be eliminated from the simian adenovirus sequence which forms a part of the recombinant virus. The function of simian E3 is believed to be irrelevant to the function and production of the recombinant virus particle. Simian adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the simian adenovirus genome. Similarly, deletions in the intermediate genes IX and IVa$_2$ may be useful for some purposes. Other deletions may be made in the other structural or non-structural adenovirus genes. The above discussed deletions may be used individually, i.e., an adenovirus sequence for use as described herein may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

An adenoviral vector lacking any essential adenoviral sequences (e.g., E1a, E1b, E2a, E2b, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell. See, for example, the techniques described for preparation of a "minimal" human Ad vector in International Patent Application WO96/13597, published May 9, 1996, and incorporated herein by reference.

1. Helper Viruses

Thus, depending upon the simian adenovirus gene content of the viral vectors employed to carry the minigene, a helper adenovirus or non-replicating virus fragment may be necessary to provide sufficient simian adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 264:16985-16987 (1989); K. J. Fisher and J. M. Wilson, *Biochem. J.*, 299:49 (Apr. 1, 1994). Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification.

2. Complementation Cell Lines

To generate recombinant simian adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human E1 can be used to transcomplement the chimp Ad vector. This is particularly advantageous because, due to the diversity between the chimp Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line which expresses the E1 gene products can be utilized for production of an E1-deleted simian adenovirus. Such cell lines have been described. See, e.g., U.S. Pat. No. 6,083,716.

If desired, one may utilize the sequences provided herein to generate a packaging cell or cell line that expresses, at a minimum, the adenovirus E1 gene from SAdV41 under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired SAdV41 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

Such E1-expressing cell lines are useful in the generation of recombinant simian adenovirus E1 deleted vectors. Additionally, or alternatively, cell lines that express one or more simian adenoviral gene products, e.g., E1a, E1b, E2a, and/or E4 ORF6, can be constructed using essentially the same procedures are used in the generation of recombinant simian viral vectors. Such cell lines can be utilized to transcomplement adenovirus vectors deleted in the essential genes that encode those products, or to provide helper functions necessary for packaging of a helper-dependent virus (e.g., adeno-associated virus). The preparation of a host cell involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus genomes, combined with polymerase chain reaction, synthetic methods, and any other suitable methods which provide the desired nucleotide sequence.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, HEK 293 cells or PERC6 (both of which express functional adenoviral E1) [Fallaux, F J et al, (1998), *Hum Gene Ther*, 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

3. Assembly of Viral Particle and Transfection of a Cell Line

Generally, when delivering the vector comprising the minigene by transfection, the vector is delivered in an amount from about 5 μg to about 100 μg DNA, and preferably about 10 to about 50 μg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

The vector may be any vector known in the art or disclosed above, including naked DNA, a plasmid, phage, transposon, cosmids, episomes, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The current method for producing such virus particles is transfection-based. However, the invention is not limited to such methods.

The resulting recombinant simian adenoviruses are useful in transferring a selected transgene to a selected cell. In in vivo experiments with the recombinant virus grown in the packaging cell lines, the E1-deleted recombinant simian adenoviral vectors of the invention demonstrate utility in transferring a transgene to a non-simian, preferably a human, cell.

IV. Use of the Recombinant Adenovirus Vectors

The recombinant simian adenovirus—41 based vectors are useful for gene transfer to a human or non-simian veterinary patient in vitro, ex vivo, and in vivo.

The recombinant adenovirus vectors described herein can be used as expression vectors for the production of the products encoded by the heterologous genes in vitro. For example, the recombinant adenoviruses containing a gene inserted into the location of an E1 deletion may be transfected into an E1 expressing cell line as described above. Alternatively, replication-competent adenoviruses may be used in another selected cell line. The transfected cells are then cultured in the conventional manner, allowing the recombinant adenovirus to express the gene product from the promoter. The gene product may then be recovered from the culture medium by known conventional methods of protein isolation and recovery from culture.

A SAdV41-derived recombinant simian adenoviral vector provides an efficient gene transfer vehicle that can deliver a selected transgene to a selected host cell in vivo or ex vivo even where the organism has neutralizing antibodies to one or more AAV serotypes. In one embodiment, the rAAV and the cells are mixed ex vivo; the infected cells are cultured using conventional methodologies; and the transduced cells are re-infused into the patient. These compositions are particularly well suited to gene delivery for therapeutic purposes and for immunization, including inducing protective immunity.

More commonly, the SAdV41 recombinant adenoviral vectors will be utilized for delivery of therapeutic or immunogenic molecules, as described below. It will be readily understood for both applications, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g., one, two, three, four or more). Thus, a regimen may involve delivery of a rAd with a first simian capsid, delivery with a rAd with a second simian capsid, and delivery with a third simian capsid. A variety of other regimens which use the Ad capsids of the invention alone, in combination with one another, or in combination with other adenoviruses (which are preferably immunologically non-crossreactive) will be apparent to those of skill in the art. Optionally, such a regimen may involve administration of rAd with capsids of other non-human primate adenoviruses, human adenoviruses, or artificial sequences such as are described herein. Each phase of the regimen may involve administration of a series of injections (or other delivery routes) with a single Ad capsid followed by a series with another capsid from a different Ad source. Alternatively, the SAdV-41 vectors may be utilized in regimens involving other non-adenoviral-mediated delivery systems, including other viral systems, non-viral delivery systems, protein, peptides, and other biologically active molecules.

The following sections will focus on exemplary molecules which may be delivered via the adenoviral vectors of the invention.

A. Ad-Mediated Delivery of Therapeutic Molecules

In one embodiment, the above-described recombinant vectors are administered to humans according to published methods for gene therapy. A simian viral vector bearing the selected transgene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The simian adenoviral vectors are administered in sufficient amounts to transduce the target cells and to provide sufficient levels of gene transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the retina and other intraocular delivery methods, intracochlear delivery (to the ear), direct delivery to the liver, inhalation, intranasal, intravenous, intramuscular, intratracheal, subcutaneous, intradermal, rectal, oral and other parenteral routes of administration. Routes of administration may be combined, if desired, or adjusted depending upon the transgene or the condition. The route of administration primarily will depend on the nature of the condition being treated.

Dosages of the viral vector will depend primarily on factors such as the condition being treated, the age, weight and health of the patient, and may thus vary among patients. For example, a therapeutically effective adult human or veterinary dosage of the viral vector is generally in the range of from about 100 µL to about 100 mL of a carrier containing concentrations of from about $1 \times 10^6$ to about $1 \times 10^{15}$ particles, about $1 \times 10^{11}$ to $1 \times 10^{13}$ particles, or about $1 \times 10^9$ to $1 \times 10^{12}$ particles virus. Dosages will range depending upon the size of the animal and the route of administration. For example, a suitable human or veterinary dosage (for about an 80 kg animal) for intramuscular injection is in the range of about $1 \times 10^9$ to about $5 \times 10^{12}$ particles per mL, for a single site. Optionally, multiple sites of administration may be delivered. In another example, a suitable human or veterinary dosage may be in the range of about $1 \times 10^{11}$ to about $1 \times 10^{15}$ particles for an oral formulation. One of skill in the art may adjust these doses, depending the route of administration, and the therapeutic or vaccinal application for which the recombinant vector is employed. The levels of expression of the transgene, or for an immunogen, the level of circulating antibody, can be monitored to determine the frequency of dosage administration. Yet other methods for determining the timing of frequency of administration will be readily apparent to one of skill in the art.

An optional method step involves the co-administration to the patient, either concurrently with, or before or after administration of the viral vector, of a suitable amount of a short acting immune modulator. The selected immune modulator is defined herein as an agent capable of inhibiting the formation of neutralizing antibodies directed against the recombinant vector of this invention or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the vector. A variety of useful immune modulators and dosages for use of same are disclosed, for example, in Yang et al. *J. Virol.*, 70(9) (September, 1996); International Patent Application No. WO96/12406, published May 2, 1996; and International Patent Application No. PCT/US96/03035, all incorporated herein by reference.

1. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor (TGF), platelet-derived growth factor (PDGF), insulin growth factors I and II (IGF-I and IGF-II), any one of the transforming growth factor superfamily, including TGF, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors and, interferons, and, stem cell factor, flk-2/flt3 ligand. Gene products produced by the immune system are also useful in the invention. These include, without limitation, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene are particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce self-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

The simian adenoviral vectors of the invention are particularly well suited for therapeutic regimens in which multiple adenoviral-mediated deliveries of transgenes is desired, e.g., in regimens involving redelivery of the same transgene or in combination regimens involving delivery of other transgenes. Such regimens may involve administration of a SAdV41 simian adenoviral vector, followed by re-administration with a vector from the same serotype adenovirus. Particularly desirable regimens involve administration of a SAdV41 simian adenoviral vector, in which the source of the adenoviral capsid sequences of the vector delivered in the first administration differs from the source of adenoviral capsid sequences of the viral vector utilized in one or more of the subsequent administrations. For example, a therapeutic regimen involves administration of a SAdV41 vector and repeat administration with one or more adenoviral vectors of the same or different serotypes. In another example, a therapeutic regimen involves administration of an adenoviral vector followed by repeat administration with a SAdV41 vector which has a capsid which differs from the source of the capsid in the first delivered adenoviral vector, and optionally further administration with another vector which is the same or, preferably, differs from the source of the adenoviral capsid of the vector in the prior administration steps. These regimens are not limited to delivery of adenoviral vectors constructed using the SAdV41 simian sequences. Rather, these regimens can readily utilize vectors other adenoviral sequences, including, without limitation, other simian adenoviral sequences, (e.g., Pang or C68, C1, etc), other non-human primate adenoviral sequences, or human adenoviral sequences, in combination with one or more of the SAdV41 vectors. Examples of such simian, other non-human primate and human adenoviral serotypes are discussed elsewhere in this document. Further, these therapeutic regimens may involve either simultaneous or sequential delivery of SAdV41 adenoviral vectors in combination with non-adenoviral vectors, non-viral vectors, and/or a variety of other therapeutically useful compounds or molecules. The invention is not limited to these therapeutic regimens, a variety of which will be readily apparent to one of skill in the art.

B. Ad-Mediated Delivery of Immunogenic Transgenes

The recombinant SAdV-41 vectors may also be employed as immunogenic compositions. As used herein, an immunogenic composition is a composition to which a humoral (e.g., antibody) or cellular (e.g., a cytotoxic T cell) response is mounted to a transgene product delivered by the immunogenic composition following delivery to a mammal, and preferably a primate. A recombinant simian Ad can contain in any of its adenovirus sequence deletions a gene encoding a desired immunogen. The simian adenovirus is likely to be better suited for use as a live recombinant virus vaccine in different animal species compared to an adenovirus of human origin, but is not limited to such a use. The recombinant adenoviruses can be used as prophylactic or therapeutic vaccines against any pathogen for which the antigen(s) crucial for induction of an immune response and able to limit the spread of the pathogen has been identified and for which the cDNA is available.

Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a vaccinal composition of the invention may be formulated to contain other components, including, e.g., adjuvants, stabilizers, pH adjusters, preservatives and the like. Such components are well known to those of skill in the vaccine art. Examples of suitable adjuvants include, without limitation, liposomes, alum, monophosphoryl lipid A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming DNA vaccine encoding an antigen to enhance the antigen-specific immune response compared with the immune response generated upon priming with a DNA vaccine encoding the antigen only.

The recombinant adenoviruses are administered in a "an immunogenic amount", that is, an amount of recombinant adenovirus that is effective in a route of administration to transfect the desired cells and provide sufficient levels of expression of the selected gene to induce an immune response. Where protective immunity is provided, the recombinant adenoviruses are considered to be vaccine compositions useful in preventing infection and/or recurrent disease.

Alternatively, or in addition, the vectors of the invention may contain a transgene encoding a peptide, polypeptide or protein which induces an immune response to a selected immunogen. The recombinant SAdV-41 vectors are expected to be highly efficacious at inducing cytolytic T cells and antibodies to the inserted heterologous antigenic protein expressed by the vector.

For example, immunogens may be selected from a variety of viral families. Example of viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies).

Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phiebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FM, equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. Nos. 5,891, 994 and 6,193,981.] See, also, the HIV and SIV proteins described in D. H. Barouch et al, J. Virol., 75(5):2462-2467 (March 2001), and R. R. Amara, et al, *Science,* 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Such combinations are discussed in more detail below.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera *simplexvirus* (HSVI, HSVII), *varicellovirus* (pseudorabies, varicella zoster) and the sub-family betaherpesvirinae, which includes the genera *cytomegalovirus* (HCMV, *muromegalovirus*) and the sub-family gammaherpesvirinae, which includes the genera *lymphocryptovirus,* EBV (Burkitts lymphoma), infectious *rhinotracheitis*, Marek's disease virus, and *rhabinovirus*. The poxvirus family includes the sub-family chordopoxvirinae, which encompasses the genera *orthopoxvirus* (Variola (Smallpox) and Vaccinia (Cowpox)), *parapoxvirus, avipoxvirus, capripoxvirus, leporipoxvirus, suipoxvirus,* and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

Immunogens which are useful to immunize a human or non-human animal against other pathogens include, e.g., bacteria, fungi, parasitic microorganisms or multicellular parasites which infect human and non-human vertebrates, or from a cancer cell or tumor cell. Examples of bacterial pathogens include pathogenic gram-positive cocci include *pneumococci; staphylococci*; and *streptococci*. Pathogenic gram-negative cocci include *meningococcus; gonococcus*. Pathogenic enteric gram-negative bacilli include enterobacteriaceae; *pseudomonas, acinetobacteria* and *eikenella; melioidosis; salmonella; shigella; haemophilus; moraxella; H. ducreyi* (which causes chancroid); *brucella; Franisella tularensis* (which causes tularemia); *yersinia* (pasteurella); *streptobacillus moniliformis* and *spirillum*; Gram-positive bacilli include *listeria monocytogenes; erysipelothrix rhusiopathiae; Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petrielliodiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: *mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); Brucella species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the SAdV-41 vectors to deliver immunogens against the variable region of the T cells are anticipated to elicit an immune response including CTLs to eliminate those T cells. In RA, several specific variable regions of TCRs which are involved in the disease have been characterized. These TCRs include V-3, V-14, V-17 and Va-17. Thus, delivery of a nucleic acid sequence that encodes at least one of these polypeptides will elicit an immune response that will target T cells involved in RA. In MS, several specific variable regions of TCRs which are involved in the disease have been characterized. These TCRs include V-7 and Va-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Va-16, Va-3C, Va-7, Va-14, Va-15, Va-16, Va-28 and Va-12. Thus, delivery of a recombinant simian adenovirus that encodes at least one of these polypeptides will elicit an immune response that will target T cells involved in scleroderma.

C. Ad-Mediated Delivery Methods

The therapeutic levels, or levels of immunity, of the selected gene can be monitored to determine the need, if any, for boosters. Following an assessment of CD8+ T cell response, or optionally, antibody titers, in the serum, optional booster immunizations may be desired. Optionally, the recombinant SAdV-41 vectors may be delivered in a single administration or in various combination regimens, e.g., in combination with a regimen or course of treatment involving other active ingredients or in a prime-boost regimen. A variety of such regimens have been described in the art and may be readily selected.

For example, prime-boost regimens may involve the administration of a DNA (e.g., plasmid) based vector to prime the immune system to second, booster, administration with a traditional antigen, such as a protein or a recombinant virus carrying the sequences encoding such an antigen. See, e.g., WO 00/11140, published Mar. 2, 2000, incorporated by reference. Alternatively, an immunization regimen may involve the administration of a recombinant SAdV-41 vector to boost the immune response to a vector (either viral or DNA-based) carrying an antigen, or a protein. In still another alternative, an immunization regimen involves administration of a protein followed by booster with a vector encoding the antigen.

In one embodiment, a method of priming and boosting an immune response to a selected antigen by delivering a plasmid DNA vector carrying said antigen, followed by boosting with a recombinant SAdV-41 vector is described. In one embodiment, the prime-boost regimen involves the expression of multiproteins from the prime and/or the boost vehicle. See, e.g., R. R. Amara, *Science,* 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered in a recombinant SAdV-41 adenovirus construct. Still other regimens are described in WO 99/16884 and WO 01/54719.

However, the prime-boost regimens are not limited to immunization for HIV or to delivery of these antigens. For example, priming may involve delivering with a first SAdV-41 vector followed by boosting with a second Ad vector, or with a composition containing the antigen itself in protein form. In one example, the prime-boost regimen can provide a protective immune response to the virus, bacteria or other organism from which the antigen is derived. In another embodiment, the prime-boost regimen provides a therapeutic effect that can be measured using convention assays for detection of the presence of the condition for which therapy is being administered.

The priming composition may be administered at various sites in the body in a dose dependent manner, which depends on the antigen to which the desired immune response is being targeted. The amount or situs of injection(s) or to pharmaceutical carrier is not a limitation. Rather, the regimen may involve a priming and/or boosting step, each of which may include a single dose or dosage that is administered hourly, daily, weekly or monthly, or yearly. As an example, the mammals may receive one or two doses containing between about 10 µg to about 50 µg of plasmid in carrier. A desirable amount of a DNA composition ranges between about 1 µg to about 10,000 µg of the DNA vector. Dosages may vary from about 1 µg to 1000 µg DNA per kg of subject body weight. The amount or site of delivery is desirably selected based upon the identity and condition of the mammal.

The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions described herein may be administered to a mammal according to the routes described above, in a sustained release formulation using a biodegradable biocompatible polymer, or by on-site delivery using micelles, gels and liposomes. Optionally, the priming step also includes administering with the priming composition, a suitable amount of an adjuvant, such as are defined herein.

Preferably, a boosting composition is administered about 2 to about 27 weeks after administering the priming composition to the mammalian subject. The administration of the boosting composition is accomplished using an effective amount of a boosting composition containing or capable of delivering the same antigen as administered by the priming DNA vaccine. The boosting composition may be composed of a recombinant viral vector derived from the same viral source (e.g., adenoviral sequences of the invention) or from another source. Alternatively, the "boosting composition" can be a composition containing the same antigen as encoded in the priming DNA vaccine, but in the form of a protein or peptide, which composition induces an immune response in the host. In another embodiment, the boosting composition contains a DNA sequence encoding the antigen under the control of a regulatory sequence directing its expression in a mammalian cell, e.g., vectors such as well-known bacterial or viral vectors. The primary requirements of the boosting composition are that the antigen of the composition is the same antigen, or a cross-reactive antigen, as that encoded by the priming composition.

In another embodiment, the SAdV-41 vectors are also well suited for use in a variety of other immunization and therapeutic regimens. Such regimens may involve delivery of SAdV-41 vectors simultaneously or sequentially with Ad vectors of different serotype capsids, regimens in which SAdV-41 vectors are delivered simultaneously or sequentially with non-Ad vectors, regimens in which the SAdV-41 vectors are delivered simultaneously or sequentially with proteins, peptides, and/or other biologically useful therapeutic or immunogenic compounds. Such uses will be readily apparent to one of skill in the art.

The following examples illustrate the cloning of SAdV-41 and the construction of exemplary recombinant SAdV-41 vectors. These examples are illustrative only, and do not limit the scope of the present invention.

EXAMPLE 1

Isolation of Simian Adenovirus 41 and PCR Analysis

Stool samples from a variety of great apes were obtained from 9 different zoos in the United States. SAdV-41.1 was isolated from a gorilla housed in Buffalo.

Stool samples were recovered from the floors of the facilities that houses the animals and were frozen and sent to University of Pennsylvania. They were thawed and suspended in Hanks' Balanced Salt solution, the particulates pelleted by centrifugation, and sterile filtered through 0.2 micron syringe filters. 100 ml of each filtered sample was inoculated into A549 cells grown in Ham's F12 with 10% FBS, 1% Penn-Strep and 50 mg/ml gentamicin. After about 1 to 2 weeks in culture, visual cytopathic effect (CPE) was obvious in cell cultures with several of the inocula. The presence of adenoviruses in the cultures was confirmed by PCR amplification of an internal 1.9 kb of the hexon—the region encompassing the hypervariable (HVR) regions and that is predominantly responsible for conferring serotype specificity. The primer pair that was utilized for PCR was CAGGAT-GCTTCGGAGTACCTGAG [SEQ ID NO: 32] and TTGGC-NGGDATDGGGTAVAGCATGTT [SEQ ID NO: 33]. The sequence obtained from this region was used to make an initial determination of adenoviral species and novelty of the serotype. The sequence was determined to be a member of species B.

Adenoviral isolates that were determined to be novel were plaque purified on A549 cells, propagated to high titer and purified on cesium chloride gradients using standard procedures. Viral DNAs obtained from purified virus preparations were completely sequenced (Qiagen Genomics Services, Hilden, Germany).

The resulting simian adenovirus 41.1 genomic sequence was subsequently deposited with GenBank under Accession Number FJ025913 pursuant to confidentiality provisions until following the filing of this application.

Using similar methods, simian adenovirus 41.2, complete genome, was isolated from a gorilla housed in Atlanta. This sequence was deposited with GenBank under Accession Number FJ025927, pursuant to confidentiality provisions until following the filing of this application.

EXAMPLE 2

Vector Construction Using SAdV41.1

An E1 deleted vector using the SAdV-41 can be prepared. Because both published reports and the inventors experience with AdC1 have indicated that E1 deletions in subgroup B adenoviruses are not complemented by the Ad5 E1 genes in HEK 293 cells, a hybrid adenovirus based on the strategy using AdC1 [Roy et al., *J. Virol. Methods*. (2007) 141, 14-21; Roy et al., *J Gen Viral*. (2006) 87, 2477-2485], where the left and right ends of a chimeric construct are derived from the chimpanzee adenovirus Pan 5 (a.k.a. Simian adenovirus 22) can be utilized.

The species E adenovirus that was used was SAdV-36, which is described in International Patent Application No. PCT/US09/01344, filed Mar. 3, 2009, which is incorporated by referenced herein. The starting plasmid was a molecular clone of E1-deleted SAdV36-pC36 IP.

A. Construction of Plasmid(p) C36Asc-Not for the Creation of Hybrid Adenovirus Vectors.

C36 fwd—SEQ ID NO: 66] gatcGGCGCGCCACGCGTGCGGCCGCttacaggattcgagcagttatt and C36rev—CTGGCCCTGTGGTTCCGCAG [SEQ ID NO: 67] were used to generate a 763 bp fragment using pC36 IP as template. The PCR fragment harbors the end of E4 orf 6/7 along with a 5' extension encoding the restriction sites for AscI MluI and NotI.

The PCR fragment was digested with AscI and Acc65I and ligated into pC36 IP cut with the same enzymes, to generate pC36Asc-Not. Mini-preps were checked with SmaI to confirm the presence of the expected fragments. The mini-prep was further diagnosed to confirm the presence of the AscI, MluI and NotI sites.

B. Construction of an E1-Deleted Adenovirus Vector Based on SAdV-41.

The primers: C41 fwd—gatcACGCGTtaacgcaggtgtacagctgg [SEQ ID NO: 68] and

C41 rev—[SEQ ID NO: 69]: CATGacgcgtACTGATTTTTCAATAAAAAGTTAAATTTATTTTTGTTGTC (Phusion polymerase, 55° annealing, 2 minute extension, 30 cycles) were used to generate a 4972 bp fragment using SAdV41.1 (clone DP957) as template. The PCR primers contain MluI sites for insertion into the MluI site of pAsc-Not.

The AscI (7936)—BsrGI fragment of SAdV-41.1 was inserted into pC36 Asc-Not, which was prepared as described in part A above. The plasmid pC36/41 IP harbors a chimeric adenovirus genome (chimeric between SAdV-36 and SAdV-41.1) flanked by PacI restriction sites. The left end, extending from the ITR to the AscI site (at by #6047), is derived from SAdV-36. The E1 gene of SAdV-36 has been deleted and in its place, restriction sites for the enzymes I-CeuI and PI-SceI have been inserted for the insertion of transgene cassettes. The right end—extending from the NotI site to the ITR is also derived from SAdV-36. This harbors the E4 genes. The SAdV-41.1 genome is present between the AscI and the NotI sites. The fusion at the AscI site between SAdV-36 and SAdV-41.1 generates a chimeric open reading frame (encoding DNA polymerase).

A transgene cassette designed to express FluA NP was ligated between the I-CeuI and PI-SceI sites of pC36/41 IP. The nucleotide sequence encoding the H1N1 influenza A virus nucleoprotein (NP) (A/Puerto Rico/8/34/Mount Sinai, GenBank accession number AF389119.1) was codon optimized and completely synthesized (Celtek Genes, Nashville, Tenn.). An expression cassette (approximately 2.5 kb) composed of the human cytomegalovirus early promoter, an artificial intron derived from the Promega (Madison, Wis.) plasmid pCI, the codon optimized influenza A NP coding sequence and the bovine growth hormone polyadenylation signal was constructed in a shuttle plasmid.

The resulting plasmid was transfected into HEK293 cells and cytopathic effect was observed indicating the successful rescue of recombinant SAdV-41.1 based adenovirus vector designed to transduce cell to express the FluA antigen. Adenovirus may be was purified by cesium chloride density gradient centrifugation and the particle titer determined by measuring absorbance at 260 and 280 nm.

The protocols contained in Roy, et al. ["Partial protection against H5N1 influenza in mice with a single dose of a chimpanzee adenovirus vector expressing nucleoprotein", *Vaccine* 25:6845-6851 (Aug. 6, 2007)], which is herein incorporated by reference, may be utilized to assess T cell induction by the resulting recombinant adenovirus virus.

All documents recited above, the Sequence Listing, and the entirety of U.S. Provisional Patent Application Nos.: 61/182,290 (filed May 29, 2009) and 61/219,917 (filed Jun. 24, 2009), are incorporated herein by reference. Numerous modifications and variations are included in the scope of the above-identified specification and are expected to be obvious to one of skill in the art. Such modifications and alterations to the compositions and processes, such as selections of different minigenes or selection or dosage of the vectors or immune modulators are believed to be within the scope of the claims appended hereto.

TABLE 3

(Comparison of nucleotide sequences of SAdV-41.2 vs. SAdV-41.1) The table provides an alignment of nucleotide sequences in SEQ ID NOs: 1 (SAdV-41.1) and 34 (SAdV-41.2). Nucleotide (s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 113-122 | CCGGCGCGGG | ---------- |
| 134 | G | T |
| 138 | G | C |
| 213 | C | G |
| 768 | T | G |
| 954 | A | C |
| 990 | T | G |
| 1034 | A | G |
| 1161 | T | C |
| 1165 | G | C |
| 1191 | G | - |
| 1199-1200 | GT | AA |
| 1223 | T | C |
| 1227-1231 | TGCTT | ----- |
| 1384 | G | A |
| 1456 | A | G |
| 1566 | G | A |
| 1653 | A | G |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 1662 | G | A |
| 1902 | A | T |
| 1905 | T | C |
| 2058 | G | A |
| 2079 | A | G |
| 2081 | T | C |
| 2372 | G | A |
| 2465 | A | G |
| 2482 | G | A |
| 2492 | G | A |
| 2523 | T | G |
| 2537 | A | C |
| 2582 | T | C |
| 2612 | T | C |
| 2624 | A | G |
| 2627 | A | C |
| 2639 | T | A |
| 2720 | C | G |
| 2742 | G | T |
| 2744 | A | T |
| 2753 | G | A |
| 2756 | T | C |
| 2760 | G | A |
| 2762 | A | C |
| 2765 | A | G |
| 2768 | C | T |
| 2843 | T | C |
| 2855 | T | C |
| 2876 | C | T |
| 2974 | C | T |
| 2981 | A | G |
| 3245 | T | C |
| 3434 | T | G |
| 3443 | A | G |
| 3487 | G | C |
| 3620 | A | G |
| 3689 | C | T |
| 3773 | T | A |
| 4151 | C | T |
| 4292 | C | T |
| 4454 | G | C |
| 4514 | A | G |
| 4691 | A | G |
| 4757 | C | G |
| 4783 | G | A |
| 5060 | T | G |
| 5063 | T | C |
| 5134 | A | G |
| 5137 | A | G |
| 5209 | C | T |
| 5365 | C | T |
| 6547 | T | C |
| 6652 | G | A |
| 6655 | G | A |
| 7120 | G | T |
| 7225 | G | A |
| 7228 | A | G |
| 7267 | T | C |
| 7315 | A | G |
| 7417 | A | G |
| 7438 | C | T |
| 7624 | C | T |
| 7627 | A | G |
| 7669 | T | G |
| 7720 | C | G |
| 7741 | A | G |
| 7765 | G | A |
| 7786 | G | T |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 7959 | T | A |
| 7978 | G | A |
| 8341 | C | T |
| 8361 | T | A |
| 8472 | A | G |
| 8505 | G | T |
| 8526 | C | T |
| 9066 | T | C |
| 9422 | G | A |
| 9448 | C | T |
| 9624 | T | C |
| 9644-9664 | GGCTAGATGCTCGGTCGGGGT | --------------------- |
| 9703 | G | A |
| 9903 | G | A |
| 9953 | G | A |
| 10044 | T | C |
| 10115 | G | T |
| 10131 | G | T |
| 10254 | T | G |
| 10338 | C | T |
| 10536-10537 | AC | CA |
| 10574 | C | T |
| 10665 | C | - |
| 10680-10681 | TG | CA |
| 10700 | T | C |
| 10716 | C | T |
| 10796 | T | C |
| 10906 | T | G |
| 10909-10912 | GTTT | ---- |
| 10999 | G | T |
| 11053 | A | T |
| 11098 | G | A |
| 11212 | G | C |
| 11230 | T | C |
| 11257 | T | C |
| 11312 | G | A |
| 11353 | A | C |
| 11359 | T | C |
| 11398 | C | T |
| 11506 | C | A |
| 11572 | T | C |
| 11587 | G | A |
| 11605 | G | A |
| 11623 | T | C |
| 11653 | A | G |
| 11662 | C | T |
| 11666 | C | T |
| 11678 | C | G |
| 11692 | T | C |
| 11704 | T | G |
| 11800 | T | C |
| 11809 | T | C |
| 11812 | A | G |
| 11815 | G | T |
| 11827 | C | T |
| 11839 | G | A |
| 11851 | C | T |
| 11941 | C | G |
| 11950 | C | A |
| 11995 | G | A |
| 12106 | A | G |
| 12475 | C | A |
| 12490 | A | C |
| 12589 | T | C |
| 12610 | C | T |
| 12682 | C | T |
| 12736 | G | A |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 12749 | T | C |
| 12766 | T | C |
| 12769 | G | A |
| 12781 | T | C |
| 12805 | C | T |
| 12824 | T | C |
| 12853 | T | C |
| 12916 | A | G |
| 12922 | C | T |
| 12943 | T | C |
| 12967 | C | T |
| 12991 | T | C |
| 13007 | T | C |
| 13082 | T | C |
| 13084 | G | C |
| 13123 | G | A |
| 13162 | G | C |
| 13216 | A | G |
| 13237 | A | G |
| 13243 | T | C |
| 13273 | C | T |
| 13276 | T | C |
| 13387 | T | C |
| 13399 | T | C |
| 13525 | T | C |
| 13657 | T | C |
| 14953 | G | T |
| 15357 | C | T |
| 16036 | C | T |
| 16135 | A | G |
| 16165 | G | A |
| 16180 | A | G |
| 16264 | T | C |
| 16528 | G | A |
| 16545-16546 | GG | AA |
| 16597 | A | G |
| 16699 | A | G |
| 16726 | A | G |
| 16738 | C | A |
| 16765 | G | A |
| 16771 | C | A |
| 16798 | G | A |
| 16819 | C | T |
| 16859 | T | C |
| 17041-17042 | TA | CG |
| 17048 | G | A |
| 17053 | C | T |
| 17074 | A | T |
| 17080 | G | A |
| 17090 | A | G |
| 17099 | G | A |
| 17112-17113 | TT | CC |
| 17153 | A | T |
| 17188 | G | A |
| 17288 | A | G |
| 17410 | A | G |
| 17585 | C | T |
| 17665 | A | - |
| 17926 | G | A |
| 17929 | G | A |
| 18001 | G | A |
| 18054 | A | C |
| 18163 | C | G |
| 18172 | G | A |
| 18193 | A | G |
| 18350 | G | T |
| 18482-18485 | TTAA | ---- |
| 18542 | A | G |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the se-
quences are identical, no information is provided in the Table.

| Nucleotide(s) Alignment Position | SAdV-41.2 | SAdV-41.1 |
|---|---|---|
| 18704 | C | T |
| 21080 | A | G |
| 21254 | T | C |
| 21401 | G | A |
| 21429 | A | - |
| 21543 | G | T |
| 21583 | G | A |
| 21606 | T | C |
| 21633 | T | A |
| 21660 | T | C |
| 21693 | C | T |
| 21705 | T | G |
| 21954 | A | G |
| 22069 | A | G |
| 22071 | T | C |
| 22074 | A | T |
| 22391 | C | T |
| 22478 | A | G |
| 22682 | A | C |
| 22688 | A | G |
| 24112 | C | A |
| 24259 | G | A |
| 24263 | C | A |
| 24266 | C | G |
| 24298 | T | C |
| 24442 | T | A |
| 24448 | A | T |
| 24577 | T | G |
| 24595 | A | C |
| 24616 | G | A |
| 24619 | C | G |
| 24649 | A | C |
| 24661 | C | T |
| 24697 | T | C |
| 24715 | C | A |
| 24813 | G | C |
| 24844 | G | A |
| 24934 | C | T |
| 24967 | T | C |
| 25057 | G | A |
| 25060 | C | T |
| 25064 | T | C |
| 25069 | T | C |
| 25081 | A | G |
| 25093 | C | T |
| 25285 | C | T |
| 25540 | T | C |
| 25549 | G | T |
| 25591 | C | T |
| 25621 | T | C |
| 25702 | T | C |
| 25744 | C | T |
| 25802 | A | G |
| 25988 | G | A |
| 26012 | T | C |
| 26148 | G | A |
| 26162 | G | A |
| 26191 | C | T |
| 26411 | G | A |
| 26486 | C | T |
| 26517 | G | A |
| 26520 | G | A |
| 27372 | A | G |
| 27444 | A | G |
| 27528 | T | C |
| 27918 | C | A |
| 27923 | C | T |
| 27925 | T | A |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 27929-27930 | AC | TT |
| 28000 | A | G |
| 28044 | T | A |
| 28046-28047 | TT | CC |
| 28064-28065 | TT | AA |
| 28079 | A | G |
| 28094 | A | C |
| 28171 | A | G |
| 28236 | A | C |
| 28284 | T | C |
| 28317 | G | T |
| 28320 | C | T |
| 28357-28358 | AT | CG |
| 28361 | C | A |
| 28376 | C | G |
| 28392 | C | G |
| 28394 | C | T |
| 28416 | A | G |
| 28434 | A | C |
| 28500 | C | T |
| 28568 | C | T |
| 28612 | T | C |
| 28634 | T | C |
| 28739 | C | A |
| 28749 | C | A |
| 28753 | T | C |
| 28762-28764 | CTT | TCA |
| 28766 | G | A |
| 28770 | A | G |
| 28772 | T | G |
| 28776 | T | A |
| 28784 | A | G |
| 28787 | T | C |
| 28794-28795 | TT | AC |
| 28800 | C | T |
| 28802 | A | C |
| 28814 | C | T |
| 28826 | A | G |
| 28830 | G | A |
| 28837 | A | G |
| 28839 | T | C |
| 28845-28847 | CCT | TTC |
| 28849 | A | T |
| 28851 | C | G |
| 28856 | T | C |
| 28861 | T | C |
| 28871-28872 | GC | AT |
| 28875 | C | T |
| 28877 | G | A |
| 28880 | G | A |
| 28882-28883 | TG | -A |
| 28885 | T | C |
| 28887-28888 | TA | -- |
| 28897-28898 | AA | TG |
| 28900 | T | - |
| 28901 | A | - |
| 28904 | T | G |
| 28907 | G | T |
| 28912 | T | - |
| 28915-28916 | AT | TA |
| 28920-28921 | GG | CA |
| 28923-28931 | TAAAATTTA | --------- |
| 28935-28936 | AT | GA |
| 28940-28941 | AT | CA |
| 28943 | G | A |
| 28945-28946 | CC | AA |
| 28950 | T | C |
| 28954-28956 | TTC | CGA |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide (s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 28960-28963 | CCAT | TTTC |
| 28967 | C | T |
| 28969-28971 | GCG | AGT |
| 28975 | A | G |
| 28978 | A | T |
| 28980 | T | A |
| 28982-28984 | GGC | --- |
| 28987-28988 | TT | AC |
| 28992-28993 | AA | TT |
| 28996-28997 | AA | CT |
| 29004 | A | T |
| 29009 | T | - |
| 29011 | T | C |
| 29014-29015 | TG | AA |
| 29017-29019 | AGA | C-- |
| 29024-29026 | AGC | CCA |
| 29030 | C | G |
| 29033-29034 | GA | -- |
| 29041-29043 | TTG | GAT |
| 29045-29046 | GA | AC |
| 29049-29051 | ACA | GGT |
| 29054 | A | C |
| 29056 | T | C |
| 29059-29061 | ACA | -TG |
| 29063 | A | G |
| 29065-29067 | CAT | TGG |
| 29069 | C | G |
| 29071-29076 | TACAAA | ------ |
| 29078-29079 | AC | TT |
| 29083-29084 | TA | GT |
| 29088-29092 | GTAAG | AATCT |
| 29094-29096 | CTA | ACC |
| 29100 | A | C |
| 29103-29104 | AT | TC |
| 29107 | C | T |
| 29110 | T | C |
| 29112 | C | A |
| 29114 | G | A |
| 29117 | T | C |
| 29119-29120 | TG | AA |
| 29122-29123 | TT | CC |
| 29127-29128 | TT | CA |
| 29132 | G | A |
| 29134 | T | C |
| 19140 | C | T |
| 29145 | C | A |
| 29147 | A | G |
| 29149-29160 | CTATTCAGGTTT | ------------ |
| 29165 | T | G |
| 29167 | C | A |
| 29173-29174 | TA | AT |
| 29176 | T | C |
| 29178 | T | A |
| 29181 | A | G |
| 29183 | A | G |
| 29187-29188 | TT | -- |
| 29190 | C | A |
| 29193 | A | C |
| 29199-29214 | ATATTCTAGTAAAGTT | ---------------- |
| 29119-29220 | CC | AT |
| 29223 | C | G |
| 29225-29226 | AC | GT |
| 29229-29231 | CTA | TAG |
| 29233 | A | C |
| 29236-29237 | GT | TC |
| 29241-29242 | GC | AG |
| 29245-29271 | GAGTACTATAACCAGCACCACGCTTCC | --------------------------- |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
| --- | --- | --- |
| 29273 | A | T |
| 29275 | T | C |
| 29277 | G | A |
| 29280 | C | G |
| 29284-29310 | AATGTTTCAATTGAACAAAATAGAAAA | --------------------------- |
| 29314 | C | A |
| 29317 | C | T |
| 29320-29323 | TAGC | ---- |
| 29325 | A | G |
| 29331-29336 | CTCTAT | ----GA |
| 29339 | A | C |
| 29342 | G | A |
| 29344 | T | C |
| 29350-29352 | TGT | ATC |
| 29355 | A | T |
| 29358-29359 | GG | CA |
| 29363 | T | C |
| 29366-29373 | ACTACAAT | -------C |
| 29378-29379 | AT | -- |
| 29381 | C | T |
| 29388-29397 | TTGTGGGGTT | C--------- |
| 29399 | A | G |
| 29402-29403 | AT | CA |
| 29408-29409 | AT | CC |
| 29415 | G | A |
| 29418-29468 | TGATAGTCTATACCTGCCGCTACAGAAAACTACACAATAAAGTAGACCCCT | --------------------------------------------------- |
| 29472 | A | G |
| 29474 | A | C |
| 29477-29478 | CC | -- |
| 29481-29482 | AC | GT |
| 29484 | T | A |
| 29486-29487 | GA | CT |
| 29492 | T | A |
| 29495-29530 | CTTTTTTTAAAACACTTTATTTTCAGCCATGATTTC | ------------------------------------ |
| 29539 | C | T |
| 29543 | T | G |
| 29545 | T | - |
| 29549 | T | C |
| 29551 | T | C |
| 29554-29585 | CTGCCATTACTACTGTACAGGGGTTCACAAAC | -------------------------------- |
| 29591-29592 | AA | TG |
| 29595-29596 | AC | GA |
| 29600-29614 | ACATGTGGGATCCAG | --------------- |
| 29616 | T | C |
| 29620-29640 | CACTAGAAGGTTACCAATCCC | --------------------- |
| 29646-29647 | CG | -A |
| 29650-29658 | TTTCTTGGT | --------- |
| 29664 | T | G |
| 29667 | T | C |
| 29669-29670 | CC | TT |
| 29673-29681 | GATCAGCCA | A-------- |
| 29684-29685 | TA | GG |
| 29687-29688 | TA | GG |
| 29691 | C | G |
| 29693-29694 | TT | -- |
| 29696-29697 | CA | GG |
| 29700 | G | T |
| 29705-29706 | TC | AT |
| 29708-29711 | GGAA | ---- |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 29713 | C | T |
| 29716 | C | T |
| 29721 | C | T |
| 29723 | C | T |
| 29725-29726 | CA | TG |
| 29731-29732 | AA | CC |
| 29735-29760 | CAAATGCAATAACAATAATTTAACCC | -------------------------- |
| 29762-29763 | AA | GC |
| 29767 | A | C |
| 29770 | T | C |
| 29776-29785 | CTCAATATGC | ---------- |
| 29787-29791 | GGAAC | AAGTT |
| 29795 | C | T |
| 29800 | G | A |
| 29802-29803 | AC | GA |
| 29807-29820 | TTTTAACATAGGAC | -------------- |
| 29822 | A | G |
| 29825 | C | G |
| 29828-29830 | ATA | CCC |
| 29834-29837 | TACC | CTAA |
| 29841-29845 | ACAGT | TTGAC |
| 29847 | A | T |
| 29852 | C | T |
| 29854 | C | T |
| 29856-29863 | ACTACTCC | -------T |
| 29865 | G | A |
| 29868-29876 | ACAACTACC | G-------- |
| 29879 | A | G |
| 29884-29890 | CTACAAA | ------- |
| 29896-29912 | AAAGCACAAAAACTCAC | GG-------------T |
| 29915 | T | C |
| 29918-29962 | CCCTAGCAGCAAGCCCACCTCAATCTATACAACTTCACTTTTGCA | ----------------------------------------G |
| 29964 | C | T |
| 29967 | C | T |
| 29970-29991 | CAAAAGGCTAACGTTACAGACA | ---------------------- |
| 29993 | T | C |
| 29995-29996 | AT | GC |
| 29998-29999 | CT | GC |
| 30005 | C | T |
| 30007-30009 | CCA | TTT |
| 30013-30021 | TTCCTAGCG | --------- |
| 30024-30026 | GAG | TTA |
| 3028 | T | C |
| 30032 | C | A |
| 30034 | A | C |
| 30036 | T | C |
| 30040-30060 | TGATAGGAATTATTGCTGCTG | C-------------------- |
| 30062 | G | A |
| 30066 | G | A |
| 30068-30088 | GGGAATGCTAATTATAATTCT | A-------------------- |
| 30093-30098 | ATGATT | GCAGAC |
| 30101 | T | C |
| 30103 | A | T |
| 30105 | G | A |
| 30107-30108 | TT | CA |
| 30110-30112 | CTG | TCA |
| 30114 | T | C |
| 30118-30132 | GAAAATATGAACATG | --------------- |
| 30140-30163 | AATAGACCCACTACTGAGCTTTGA | C----------------------- |
| 30166-30167 | TT | CC |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 30169 | A | C |
| 30171 | T | G |
| 30177 | T | C |
| 30180 | G | A |
| 30182-30233 | GCACCATGAAAGGTCCAGTTATCCTATTGTTTATTTCCACTTTTTGGTGTTG | ---------------------------------------------------- |
| 30235 | G | A |
| 30240-30262 | TTTTTCAATTACCACCAATGTGC | ----------------------- |
| 30268-30280 | ACTTTAAATAACA | ------------- |
| 30282 | C | T |
| 30284-30285 | TG | AT |
| 30290 | C | A |
| 30294 | T | C |
| 30298-30315 | ACACAACTTTCACCTCAA | ------------------ |
| 30319 | G | A |
| 30325-30328 | GACA | TTTC |
| 30330-30331 | AA | TC |
| 30336 | A | T |
| 30346-30348 | ATC | GCT |
| 30355 | G | A |
| 30363 | T | A |
| 30369 | T | A |
| 30372 | C | T |
| 30375 | T | A |
| 30378-30379 | TG | AA |
| 30381 | T | C |
| 30384 | C | T |
| 30387 | T | A |
| 30394 | A | G |
| 30405-30406 | TC | CA |
| 30411 | C | A |
| 30420-30423 | AGTT | TCAC |
| 30426-30431 | GAAACC | ACCCAT |
| 30343-30435 | CC | AA |
| 30437-30438 | GA | AG |
| 30444 | C | T |
| 30447 | C | T |
| 30450-30454 | TCGAT | CAACC |
| 30456 | A | C |
| 30459-30460 | AA | CT |
| 30462 | C | A |
| 30466 | A | G |
| 30468 | A | G |
| 30473 | C | A |
| 30476 | A | T |
| 30478 | G | A |
| 30480-30481 | CT | AC |
| 30484-30486 | CTA | TGG |
| 30488-30489 | AT | GG |
| 30495 | T | C |
| 30508 | T | C |
| 30510 | C | T |
| 30512-30513 | CT | TC |
| 30515-30516 | CA | TT |
| 30531 | A | T |
| 30536 | T | C |
| 30554 | C | T |
| 30569 | T | C |
| 30576-30577 | GC | CT |
| 30579 | T | C |
| 30585 | G | A |
| 30590 | T | C |
| 30596-30597 | AT | CC |
| 30599 | C | T |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 30602-30603 | CA | TG |
| 30605 | A | G |
| 30609 | G | A |
| 30611 | C | T |
| 30613-30614 | AT | GC |
| 30617-30618 | GA | CT |
| 30626 | T | C |
| 30629 | T | C |
| 30635-30636 | GG | AG |
| 30644-30645 | TT | CA |
| 30651 | G | T |
| 30653 | A | G |
| 30656 | A | T |
| 30662 | C | A |
| 30665 | C | G |
| 30668 | T | C |
| 30674 | C | T |
| 30680 | C | T |
| 30683-30684 | TT | GA |
| 30691 | T | C |
| 30698 | C | T |
| 29705-29706 | TC | AT |
| 29708-29711 | GGAA | ---- |
| 29703 | C | T |
| 29706 | C | T |
| 29721 | C | T |
| 29723 | C | T |
| 29725-29726 | CA | TG |
| 29731-29732 | AA | CC |
| 29735-29760 | CAAATGCAATAACAATAATTTAACCC | -------------------------- |
| 29762-29763 | AA | GC |
| 29767 | A | C |
| 29770 | T | C |
| 29776-29785 | CTCAATATGC | ---------- |
| 29787-29792 | GGAAC | AAGTT |
| 29795 | C | T |
| 29880 | G | A |
| 29802-29803 | AC | GA |
| 29807-29820 | TTTTAACATAGGAC | -------------- |
| 29822 | A | G |
| 29825 | C | G |
| 29828-29830 | ATA | CCC |
| 29834-29837 | TACC | CTAA |
| 29841-29845 | ACAGT | TTGAC |
| 29847 | A | T |
| 29852 | C | T |
| 29854 | C | T |
| 29856-29863 | ACTACTCC | -------T |
| 29865 | G | A |
| 29868-29876 | ACAACTACC | G-------- |
| 29879 | A | G |
| 29884-29890 | CTACAAA | ------- |
| 29896-29912 | AAGCACAAAAACTCAC | GG-------------T |
| 29915 | T | C |
| 29918-29962 | CCCTAGCAGCAAGCCCACCTCAATCTATACAACTTCACTTTTGCA | ----------------------------------------G |
| 29964 | C | T |
| 29967 | C | T |
| 29970-29991 | CAAAAGGCTAACGTTACAGACA | ---------------------- |
| 29993 | T | C |
| 22995-29996 | AT | GC |
| 29998-30000 | CT | GC |
| 30005 | C | T |
| 30007-30009 | CCA | TTT |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
| --- | --- | --- |
| 30013-30021 | TTCCTAGCG | --------- |
| 30024-30026 | GAG | TTA |
| 30028 | T | C |
| 30032 | C | A |
| 30034 | A | C |
| 30036 | T | C |
| 30040-30060 | TGATAGGAATTATTGCTGCTG | C-------------------- |
| 30062 | G | A |
| 30066 | G | A |
| 30068-30088 | GGGAATGCTAATTATAATTCT | A-------------------- |
| 30093-30098 | ATGATT | GCAGAC |
| 30101 | T | C |
| 30103 | A | T |
| 30105 | G | A |
| 30107-30108 | TT | CA |
| 30110-30112 | CTG | TCA |
| 30114 | T | C |
| 30118-30132 | GAAAATATGAACATG | --------------- |
| 30140-30163 | AATAGACCCACTACTGAGCTTTGA | C----------------------- |
| 30166-30167 | TT | CC |
| 30169 | A | C |
| 30171 | T | G |
| 30177 | T | C |
| 30180 | G | A |
| 30182-30233 | GCACCATGAAAGGTCCAGTTATCCTATTGTTTATTTCCACTTTTTGGTGTTG | ---------------------------------------------------- |
| 30235 | G | A |
| 30240-30262 | TTTTTCAATTACCACCAATGTGC | ----------------------- |
| 30268-30280 | ACTTTAAATAACA | ------------- |
| 30282 | C | T |
| 30284-30285 | TG | AT |
| 30290 | C | A |
| 30294 | T | C |
| 30298-30315 | ACACAACTTTCACCTCAA | ------------------ |
| 30319 | G | A |
| 30325-30328 | GACA | TTTC |
| 30330-30331 | AA | TC |
| 30336 | A | T |
| 30346-30348 | ATC | GCT |
| 30355 | G | A |
| 30363 | T | A |
| 30369 | T | A |
| 30372 | C | T |
| 30375 | T | A |
| 30378-30379 | TG | AA |
| 30381 | T | C |
| 30384 | C | T |
| 30387 | T | A |
| 30394 | A | G |
| 30405-30406 | TC | CA |
| 30408 | A | C |
| 30411 | A | C |
| 30420-30423 | AGTT | TCAC |
| 30426-30431 | GAAACC | ACCCAT |
| 30434-30435 | CC | AA |
| 30437-30438 | GA | AG |
| 30444 | C | T |
| 30447 | C | T |
| 30450-30454 | C | T |
| 30456 | TCGAT | CAACC |
| 30459-30460 | AA | CT |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
| --- | --- | --- |
| 30462 | C | A |
| 30466 | A | G |
| 30468 | A | G |
| 30473 | C | A |
| 30476 | A | T |
| 30478 | G | A |
| 30480-30486 | CT--CTA | ACGGTGG |
| 30488-30489 | AT | GG |
| 30495 | T | C |
| 30500-30505 | ------ | ACATCT |
| 30508 | T | C |
| 30510 | C | T |
| 30512-30513 | CT | TC |
| 30515-30516 | CA | TT |
| 30531 | A | T |
| 30533-30536 | ---T | AAAC |
| 30554 | C | T |
| 30569 | T | C |
| 30576-30577 | GC | CT |
| 30579 | T | C |
| 30585 | G | A |
| 30590 | T | C |
| 30596-30597 | AT | CC |
| 30599 | C | T |
| 30602-30603 | CA | TG |
| 30605 | A | G |
| 30609 | G | A |
| 30611 | C | T |
| 30613-30614 | AT | GC |
| 30617-30618 | GA | CT |
| 30626 | A | T |
| 30629 | T | C |
| 30635-30636 | GG | AC |
| 30644-30645 | TT | CA |
| 30651 | G | T |
| 30653 | A | G |
| 60656 | A | T |
| 30662 | C | A |
| 30665 | C | G |
| 30674 | T | C |
| 30680 | C | T |
| 30683-30684 | TT | GA |
| 30691 | T | C |
| 30698 | C | T |
| 30707 | C | T |
| 30710 | C | T |
| 30713 | C | T |
| 30716 | T | C |
| 30722-30723 | AG | TA |
| 30732 | G | A |
| 30740 | A | G |
| 30755-30757 | ACA | GAG |
| 30761 | T | C |
| 30764 | C | T |
| 30767 | T | A |
| 30782-30783 | AA | TG |
| 30786 | G | A |
| 30791 | A | G |
| 30795 | A | C |
| 30797 | T | A |
| 30800 | C | T |
| 30803 | G | A |
| 30806-30807 | CA | TC |
| 30819 | G | A |
| 30822-30823 | AA | GG |
| 30826 | C | T |
| 30833-30834 | TG | CA |
| 30837 | T | G |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 30840-30841 | GC | AT |
| 30843-30844 | AG | GC |
| 30846-30847 | TA | GC |
| 30851-30852 | AC | TG |
| 30855 | A | C |
| 30860 | C | A |
| 30862 | T | A |
| 30868-30869 | AA | GC |
| 30871 | C | A |
| 30877-30880 | AGCC | CCTA |
| 30883-30884 | AC | CT |
| 30888-30890 | ATT | CCC |
| 30892 | G | A |
| 30897 | A | T |
| 30912 | T | C |
| 30918 | A | G |
| 30927 | A | T |
| 30933-30934 | TG | CA |
| 30936 | T | A |
| 30939 | C | T |
| 30943 | C | A |
| 30952-30953 | TC | AT |
| 30960 | C | T |
| 30963-30964 | CA | AC |
| 30966 | A | C |
| 30969 | C | T |
| 30975 | T | A |
| 30987-30988 | GG | AA |
| 30990-30991 | TG | CC |
| 30997 | C | G |
| 30999 | A | G |
| 31002 | C | A |
| 31004-31005 | CT | GC |
| 31011-31012 | AC | CA |
| 31017-31018 | CT | TG |
| 31020 | T | A |
| 31029 | T | A |
| 31032 | C | T |
| 31034 | A | C |
| 31036 | T | A |
| 31038 | A | G |
| 31050 | A | G |
| 31056-31058 | CTC | TGT |
| 31061 | T | C |
| 31075 | T | C |
| 31090 | G | C |
| 31101 | A | C |
| 31110 | G | A |
| 31116 | A | G |
| 31123 | T | C |
| 31132 | G | A |
| 31189 | T | C |
| 31198 | G | A |
| 31215 | A | T |
| 31234 | T | C |
| 31276 | C | A |
| 31282 | T | C |
| 31321 | A | G |
| 31340 | C | G |
| 31375 | G | A |
| 31387 | C | T |
| 31405 | C | T |
| 31441 | C | G |
| 31462 | C | T |
| 31471 | T | G |
| 31477 | C | T |
| 31576 | T | C |
| 31592 | C | A |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 31594 | T | C |
| 31597 | G | A |
| 31615-31618 | CCCG | AAAC |
| 31620-31623 | CCTT | ATAC |
| 31626-31627 | CT | TC |
| 31629 | A | T |
| 31632 | A | C |
| 31637-31639 | CAA | --- |
| 31643 | G | T |
| 31657-31658 | AA | T- |
| 31680 | T | C |
| 31683 | G | A |
| 31693-31695 | TGC | CAA |
| 31707 | G | T |
| 31735 | T | C |
| 31758 | T | C |
| 31798 | T | C |
| 31804 | C | T |
| 31810 | G | T |
| 31829 | T | C |
| 31831-31833 | ATC | --T |
| 31856 | A | T |
| 31874 | T | C |
| 31895 | C | T |
| 31900 | G | A |
| 31903 | C | G |
| 31905 | A | T |
| 31913 | T | C |
| 31928 | T | C |
| 31930 | C | T |
| 31940 | A | C |
| 31943-31944 | TG | CA |
| 31953 | G | A |
| 31960 | G | A |
| 31962 | C | T |
| 31970 | G | A |
| 31976-31977 | CA | AG |
| 31979 | A | T |
| 31988-31990 | TAT | CGC |
| 31992 | T | G |
| 31994 | C | T |
| 32002-32003 | AT | CC |
| 32006 | T | C |
| 32012 | C | T |
| 32015 | A | T |
| 32018-32019 | AT | TC |
| 32021 | A | T |
| 32024 | A | G |
| 32036-32037 | AG | TA |
| 32039 | A | G |
| 32045 | A | T |
| 32047 | A | C |
| 32049 | G | A |
| 32051 | G | T |
| 32055 | T | A |
| 32060 | A | T |
| 32066-32067 | AT | GA |
| 32069-32070 | TC | AT |
| 32072 | G | A |
| 32078-32079 | AA | GG |
| 32087 | T | C |
| 32089-32092 | CAAC | TCTT |
| 32096 | T | A |
| 32105 | T | A |
| 32112-32113 | AA | GC |
| 32117 | T | C |
| 32120 | T | C |
| 32123-32124 | CA | AG |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 32127 | A | T |
| 32129 | G | A |
| 32131-32133 | TGG | CAT |
| 32135 | A | G |
| 32144 | C | G |
| 32148 | C | G |
| 32150-32154 | TACTG | ATTAA |
| 32159 | A | C |
| 32161 | A | G |
| 32170 | G | A |
| 32173-32174 | CA | TT |
| 32180 | G | A |
| 32184 | C | G |
| 32186 | A | T |
| 32192-32193 | TG | AA |
| 32205-32207 | GGT | AAC |
| 32210 | T | C |
| 32213 | T | A |
| 32217 | A | T |
| 32222 | T | C |
| 32225-32226 | CA | TG |
| 32228 | T | C |
| 32230-32232 | CA | TT |
| 32237-32238 | AC | TT |
| 32246 | A | C |
| 32250 | G | A |
| 32252-32256 | TCCCA | GAATC |
| 32258-32264 | TGAGGCC | GTCCATT |
| 32267 | T | C |
| 32271 | C | A |
| 32273 | T | C |
| 32276-32277 | GC | TA |
| 32279-32280 | AG | GC |
| 32282-32283 | GT | AC |
| 32285-32287 | CAC | --- |
| 32297 | A | T |
| 32301 | T | A |
| 32306 | A | G |
| 32309 | C | A |
| 32312 | A | T |
| 32318-32319 | TC | CT |
| 32321-32323 | TGT | AAC |
| 32335-32336 | CT | GA |
| 32345 | C | T |
| 32347 | G | C |
| 32357-32358 | TC | AT |
| 32360-32361 | TA | GG |
| 32363 | G | A |
| 32366 | T | G |
| 32369-32370 | CA | AT |
| 32375-32379 | CGAAT | TATTG |
| 32381 | T | A |
| 32384-32385 | TG | CT |
| 32387-32388 | TA | AC |
| 32391-32393 | ACC | TTT |
| 32395 | C | A |
| 32397-32402 | GTTAAA | CGGGCC |
| 32404 | T | C |
| 32408-32409 | TC | AA |
| 32411-32412 | AC | TA |
| 32414 | T | C |
| 32417-32424 | TGCTGATA | AATAAGGC |
| 32427-32429 | TAT | AGC |
| 32436 | A | G |
| 32438-32440 | AAA | CTC |
| 32444 | A | C |
| 32447-32448 | GG | TT |
| 32450 | C | A |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
|---|---|---|
| 32453 | T | A |
| 32456-32460 | TGATA | AAGCC |
| 32467 | C | A |
| 32471 | T | A |
| 32477-32479 | AGA | CCC |
| 32481 | T | C |
| 32483 | A | G |
| 32486-32487 | AT | TC |
| 32489 | T | C |
| 32491-32492 | AG | GA |
| 32494 | C | A |
| 32498-32499 | AC | CA |
| 32501-32502 | AA | TG |
| 32504 | T | C |
| 32509-32510 | CA | AC |
| 32513 | A | T |
| 32515-32518 | GTGA | ACAC |
| 32520-32521 | CC | TT |
| 32523 | T | A |
| 32525 | A | T |
| 32528-32529 | CA | TG |
| 32537 | C | T |
| 32540 | C | T |
| 32546 | A | C |
| 32550-32552 | CTA | ACT |
| 32555 | T | A |
| 32558 | A | C |
| 32561 | C | T |
| 32564-32565 | AC | CT |
| 32568-32570 | CGA | --- |
| 32574-32575 | CC | GA |
| 32581-32582 | TT | CA |
| 32584-32592 | AACCAGTTA | --------- |
| 32594 | A | G |
| 32596 | G | A |
| 32600 | T | A |
| 32603-32604 | GG | AA |
| 32622-62623 | AC | TG |
| 32629 | T | A |
| 32632 | G | A |
| 32636 | C | A |
| 32638-32639 | GC | CT |
| 32642 | T | A |
| 32645 | T | C |
| 32648-32649 | TC | AT |
| 32651 | C | G |
| 32653-32654 | TA | AC |
| 32657 | A | G |
| 32663-32699 | TACATAT | AGTTGCC |
| 32672 | T | C |
| 32674-32675 | TG | CA |
| 32681-32688 | TTACAAAC | CAGACGGA |
| 32691-32692 | TC | AG |
| 32695 | A | G |
| 32699-32704 | CCAATG | TGCGT |
| 32706 | G | T |
| 32708 | A | T |
| 32714 | A | T |
| 32718-32721 | CACT | ACTA |
| 32724-32726 | ATG | GCT |
| 32730 | T | A |
| 32732 | A | T |
| 32734-32735 | GG | TA |
| 32737 | A | G |
| 32739 | A | G |
| 32741-32743 | TTC | AAA |
| 32746-32750 | TTAAA | CACCC |
| 32753 | A | T |

TABLE 3-continued (Comparison of nucleotide sequences of SAdV-41.2 vs. SAdV-41.1)
The table provides an alignment of nucleotide sequences in
SEQ ID NOs: 1 (SAdV-41.1) and 34 (SAdV-41.2). Nucleotide (s)
alignment position 1 corresponds to nucleotide 1 of SEQ ID
NOs: 1 and 34. Where one isolate contains no sequences and the
other has an insertion, a dash (-) is used. Where the sequences are identical, no information is provided in the Table.

| Nucleotide(s) Alignment Position | SAdV-41.2 | SAdV-41.1 |
| --- | --- | --- |
| 32757-32759 | GAA | ACT |
| 32762-32766 | AGCCA | CATAG |
| 32768 | T | A |
| 32772 | T | C |
| 32775 | A | G |
| 32778 | G | A |
| 32780 | T | C |
| 32789 | T | C |
| 32792 | C | T |
| 32798 | A | C |
| 32801 | C | T |
| 32811 | G | A |
| 32829-32830 | AA | -- |
| 32835 | G | T |
| 32838 | C | T |
| 32847 | T | - |
| 32851 | A | G |
| 32854 | C | A |
| 32908-32909 | GA | CG |
| 32961 | A | G |
| 33952 | A | C |
| 34040 | G | A |
| 34052 | C | T |
| 34062 | A | G |
| 34068 | T | G |
| 34071 | T | C |
| 34073 | T | G |
| 34080 | T | C |
| 34083 | A | G |
| 34089 | T | C |
| 34107 | A | G |
| 34116-34117 | GA | AT |
| 34149 | C | A |
| 34152 | C | T |
| 34155 | G | A |
| 34158 | T | C |
| 34209 | T | C |
| 34219 | T | A |
| 34221 | G | T |
| 34260 | A | G |
| 34309 | T | G |
| 34334 | C | T |
| 34404 | G | A |
| 34416 | A | C |
| 34644 | T | C |
| 34988 | C | A |
| 35086-35090 | AAAAA | ----- |
| 35196 | A | G |
| 35451 | A | T |
| 35572 | A | G |
| 35600 | C | A |
| 35614 | G | A |
| 35617 | C | G |
| 35622 | T | A |
| 35626 | C | T |
| 35640 | A | T |
| 35661-35662 | GA | AT |
| 35672 | G | A |
| 35677 | C | G |
| 35689-35690 | GC | AT |
| 35703 | T | C |
| 35761 | G | A |

TABLE 4

(Sequence Listing Free Text)
The following information is provided for sequences containing free text under numeric identifier <223>.

| SEQ ID NO: (containing free text) | Free text under <223> |
|---|---|
| 1 | Simian adenovirus 41.1 |
| 2 | Synthetic Construct |
| 3 | Synthetic Construct |
| 4 | Synthetic Construct |
| 5 | Synthetic Construct |
| 6 | Synthetic Construct |
| 7 | Synthetic Construct |
| 8 | Synthetic Construct |
| 9 | Synthetic Construct |
| 10 | Synthetic Construct |
| 11 | Synthetic Construct |
| 12 | Synthetic Construct |
| 13 | Synthetic Construct |
| 14 | Synthetic Construct |
| 15 | Synthetic Construct |
| 16 | Synthetic Construct |
| 17 | Synthetic Construct |
| 18 | Synthetic Construct |
| 19 | Synthetic Construct |
| 20 | Synthetic Construct |
| 21 | Synthetic Construct |
| 22 | Simian adenovirus 41.1 |
| 23 | Synthetic Construct |
| 24 | Simian adenovirus 41.1 |
| 25 | Synthetic Construct |
| 26 | Synthetic Construct |
| 27 | Synthetic Construct |
| 28 | Simian adenovirus 41.1 |
| 29 | Synthetic Construct |
| 30 | Simian adenovirus 41.1 |
| 31 | Synthetic Construct |
| 32 | based on Simian adenovirus 41.1 |
| 33 | based on Simian adenovirus 41.1 |
| 34 | Simian adenovirus 41.2 |
| 35 | Synthetic Construct |
| 36 | Synthetic Construct |
| 37 | Synthetic Construct |
| 38 | Synthetic Construct |
| 39 | Synthetic Construct |
| 40 | Synthetic Construct |
| 41 | Synthetic Construct |
| 42 | Synthetic Construct |
| 43 | Synthetic Construct |
| 44 | Synthetic Construct |
| 45 | Synthetic Construct |
| 46 | Synthetic Construct |
| 47 | Synthetic Construct |
| 48 | Synthetic Construct |
| 49 | Synthetic Construct |
| 50 | Synthetic Construct |
| 51 | Synthetic Construct |
| 52 | Synthetic Construct |
| 53 | Synthetic Construct |
| 54 | Synthetic Construct |
| 55 | Simian adenovirus 41.2 |
| 56 | Synthetic Construct |
| 57 | Simian adenovirus 41.2 |
| 58 | Synthetic Construct |
| 59 | Synthetic Construct |
| 60 | Synthetic Construct |
| 61 | Synthetic Construct |
| 62 | Simian adenovirus 41.2 |
| 63 | Synthetic Construct |
| 64 | Simian adenovirus 41.2 |
| 65 | Synthetic Construct |
| 66 | based on Simian adenovirus 41.2 |
| 67 | Simian adenovirus 41.2 |
| 68 | Simian adenovirus 41.2 |
| 69 | Simian adenovirus 41.2 |

The invention claimed is:

1. A recombinant adenovirus having a capsid comprising a hexon protein, a penton protein, and a fiber protein, said hexon protein is the SAdV-41 hexon protein with the amino acids 1 to 943 of SEQ ID NO: 11 or amino acids 1 to 943 of SEQ ID NO: 44, and said fiber protein is the fiber protein of SAdV-41.1 with the amino acids 1 to 321 of SEQ ID NO: 21 or the fiber protein of SAdV-41.2 of amino acids 1 to 325 of SEQ ID NO: 54,
   said capsid encapsidating a heterologous nucleic acid comprising a gene operably linked to expression control sequences which direct transcription, translation, and/or expression thereof in a host cell.

2. The adenovirus according to claim 1, further comprising a 5' and a 3' adenovirus cis-element necessary for replication and encapsidation.

3. The recombinant adenovirus according to claim 1, wherein said recombinant adenovirus lacks all or a part of the E1 gene.

4. The recombinant adenovirus according to claim 3, wherein said recombinant adenovirus is replication-defective.

5. The recombinant adenovirus according to claim 1, wherein said capsid is a hybrid capsid.

6. A composition comprising the recombinant adenovirus according to claim 1, further comprising one or more simian adenovirus proteins selected from the group consisting of:
   E1a having the amino acid sequence of SEQ ID NO: 29 or SEQ ID NO: 63;
   E1b, small T/19K having the amino acid sequence of SEQ ID NO: 23 or SEQ ID NO: 56;
   E1b, large T/55K having the amino acid sequence of SEQ ID NO: 2 or SEQ ID NO: 35;
   IX, having the amino acid sequence of SEQ ID NO: 3 or SEQ ID NO: 36;
   52/55D, having the amino acid sequence of SEQ ID NO: 4 or SEQ ID NO: 37;
   IIIa, having the amino acid sequence of SEQ ID NO: 5 or SEQ ID NO: 38;
   Penton, having the amino acid sequence of SEQ ID NO: 6 or SEQ ID NO: 39;
   VII, having the amino acid sequence of SEQ ID NO: 7 or SEQ ID NO: 40;
   V, having the amino acid sequence of SEQ ID NO: 8 or SEQ ID NO: 41;
   pX, having the amino acid sequence of SEQ ID NO: 9 or SEQ ID NO: 36;
   VI, having the amino acid sequence of SEQ ID NO: 10 or SEQ ID NO: 43;
   Endoprotease, having the amino acid sequence of SEQ ID NO: 12 or SEQ ID NO: 58;
   100kD, having the amino acid sequence of SEQ ID NO: 13 or SEQ ID NO: 59;
   33kD homolog, having the amino acid sequence of SEQ ID NO: 31 or SEQ ID NO: 65;
   22kD, having the amino acid sequence of SEQ ID NO: 25 or SEQ ID NO: 45;
   VIII, having the amino acid sequence of SEQ ID NO: 14 or SEQ ID NO: 46;
   E3/12.5K, having the amino acid sequence of SEQ ID NO: 15 or SEQ ID NO: 47;
   CR1-alpha, having the amino acid sequence of SEQ ID NO: 26 or SEQ ID NO: 60;
   gp19K, having the amino acid sequence of SEQ ID NO: 16 or SEQ ID NO: 48;
   CR1-beta, having the amino acid sequence of SEQ ID NO: 17 or SEQ ID NO: 49;
   CR1-gamma, having the amino acid sequence of SEQ ID NO: 18 or SEQ ID NO: 50;
   RID-alpha, having the amino acid sequence of SEQ ID NO: 19 or SEQ ID NO: 52;
   RID-beta, having the amino acid sequence of SEQ ID NO: 27 or SEQ ID NO: 61; and
   E3/14.7K, having the amino acid sequence of SEQ ID NO: 20 or SEQ ID NO: 53.

7. A composition comprising the recombinant adenovirus according to claim 1 in a pharmaceutically acceptable carrier.

8. The recombinant adenovirus according to claim 1, wherein said penton protein is the penton protein of SAdV-41.1 with the amino acids 1 to 584 of SEQ ID NO: 6.

9. The recombinant adenovirus according to claim 1, wherein said penton protein is the penton protein of SAdV-41.2 with the amino acids 1 to 584 of SEQ ID NO: 39.

* * * * *

```
                        SEQUENCE LISTING

<160> NUMBER OF SEQ ID NOS: 69

<210> SEQ ID NO 1
<211> LENGTH: 35100
<212> TYPE: DNA
<213> ORGANISM: Unknown
<220> FEATURE:
<223> OTHER INFORMATION: Simian adenovirus 41.1
<220> FEATURE:
<221> NAME/KEY: repeat_region
<222> LOCATION: (1)..(112)
<223> OTHER INFORMATION: ITR
<220> FEATURE:
<221> NAME/KEY: CDS
<222> LOCATION: (1910)..(3394)
<223> OTHER INFORMATION: E1b\55K
<220> FEATURE:
<221> NAME/KEY: CDS
<222> LOCATION: (3491)..(3904)
<223> OTHER INFORMATION: pIX
<220> FEATURE:
<221> NAME/KEY: misc_feature
<222> LOCATION: (3973)..(5594)
<223> OTHER INFORMATION: IVa2    complement (3973..5303,5582..5594)
<220> FEATURE:
<221> NAME/KEY: misc_feature
<222> LOCATION: (5076)..(13879)
<223> OTHER INFORMATION: pol    complement (5076..8645,13871..13879)
<220> FEATURE:
<221> NAME/KEY: misc_feature
<222> LOCATION: (8447)..(13879)
```

```
<223> OTHER INFORMATION: pTP    complement (8447..10402,13871..13879)
<220> FEATURE:
<221> NAME/KEY: CDS
<222> LOCATION: (10883)..(12049)
<223> OTHER INFORMATION: 52K
<220> FEATURE:
<221> NAME/KEY: CDS
<222> LOCATION: (12077)..(13837)
<223> OTHER INFORMATION: pIIIa
<220> FEATURE:
<221> NAME/KEY: CDS
<222> LOCATION: (13924)..(15675)
<223> OTHER INFORMATION: penton
<220> FEATURE:
<221> NAME/KEY: CDS
<222> LOCATION: (15683)..(16258)
<223> OTHER INFORMATION: pVII
<220> FEATURE:
<221> NAME/KEY: CDS
<222> LOCATION: (16304)..(17353)
<223> OTHER INFORMATION: V
<220> FEATURE:
<221> NAME/KEY: CDS
<222> LOCATION: (17385)..(17609)
<223> OTHER INFORMATION: pX
<220> FEATURE:
<221> NAME/KEY: CDS
<222> LOCATION: (17686)..(18435)
<223> OTHER INFORMATION: pVI
<220> FEATURE:
<221> NAME/KEY: CDS
<222> LOCATION: (18550)..(21378)
<223> OTHER INFORMATION: hexon
<220> FEATURE:
<221> NAME/KEY: CDS
<222> LOCATION: (21412)..(22038)
<223> OTHER INFORMATION: protease
<220> FEATURE:
<221> NAME/KEY: misc_feature
<222> LOCATION: (22133)..(23689)
<223> OTHER INFORMATION: DBP    complement (22133..23689)
<220> FEATURE:
<221> NAME/KEY: CDS
<222> LOCATION: (23720)..(26212)
<223> OTHER INFORMATION: 100K
<220> FEATURE:
<221> NAME/KEY: CDS
<222> LOCATION: (26866)..(27546)
<223> OTHER INFORMATION: pVIII
<220> FEATURE:
<221> NAME/KEY: CDS
<222> LOCATION: (27549)..(27863)
<223> OTHER INFORMATION: E3\12.5K
<220> FEATURE:
<221> NAME/KEY: CDS
<222> LOCATION: (28251)..(28787)
<223> OTHER INFORMATION: E3\gp19K
<220> FEATURE:
<221> NAME/KEY: CDS
<222> LOCATION: (28820)..(29428)
<223> OTHER INFORMATION: E3\CR1-beta
<220> FEATURE:
<221> NAME/KEY: CDS
<222> LOCATION: (29442)..(29780)
<223> OTHER INFORMATION: E3\CR1-gamma
<220> FEATURE:
<221> NAME/KEY: CDS
<222> LOCATION: (29822)..(30094)
<223> OTHER INFORMATION: E3\RID\alpha
<220> FEATURE:
<221> NAME/KEY: CDS
<222> LOCATION: (30487)..(30891)
<223> OTHER INFORMATION: E3\14.7K
<220> FEATURE:
<221> NAME/KEY: misc_feature
<222> LOCATION: (30948)..(31105)
<223> OTHER INFORMATION: U\exon    complement (30948..31105)
<220> FEATURE:
<221> NAME/KEY: CDS
```

```
<222> LOCATION: (31118)..(32080)
<223> OTHER INFORMATION: fiber
<220> FEATURE:
<221> NAME/KEY: misc_feature
<222> LOCATION: (32126)..(33300)
<223> OTHER INFORMATION: E4\orf\6/7   complement
      (32126..32374,33097..33300)
<220> FEATURE:
<221> NAME/KEY: misc_feature
<222> LOCATION: (32374)..(33300)
<223> OTHER INFORMATION: E4\orf6  complement (32374..33300)
<220> FEATURE:
<221> NAME/KEY: misc_feature
<222> LOCATION: (33176)..(33556)
<223> OTHER INFORMATION: E4\orf4  complement (33176..33556)
<220> FEATURE:
<221> NAME/KEY: misc_feature
<222> LOCATION: (33569)..(33919)
<223> OTHER INFORMATION: E4\orf3  complement (33569..33919)
<220> FEATURE:
<221> NAME/KEY: misc_feature
<222> LOCATION: (33919)..(34305)
<223> OTHER INFORMATION: E4\orf2  complement (33919..34305)
<220> FEATURE:
<221> NAME/KEY: misc_feature
<222> LOCATION: (34350)..(34721)
<223> OTHER INFORMATION: E4\orf1  complement (34350..34721)
<220> FEATURE:
<221> NAME/KEY: repeat_region
<222> LOCATION: (34989)..(35100)
<223> OTHER INFORMATION: ITR\ (1bp\mismatch   complement (34989..35100)

<400> SEQUENCE: 1
catcatcaat aatatacctt ataaatggaa cggtgccaac atgcaaatga gcttttgaaa      60
atggagggcg aaggggatt ggccagcggg ttcaacggtc aaaagggcg gggaggtgac      120 gtgtttactg tgggaggagt tatgttgcaa gttctcgcgg taaatgtgac gtaaaacgag      180
gtgtggtttg aacacggaag tagacagttt tcccgcgctg actgacagga tatgaggtag      240
ttttgggcgg atgcaagtga aaattctcca ttttcgcgcg aaaactgaat gaggaagtga      300
atttctgagt aatttcgagt ttatgacagg gcggagtatt taccgagggc cgagtagact      360
ttgaccgatt acgtggaggt ttcgattacc gtgttttca cctaaatttc cgcgtacggt      420
gtcaaagtcc tgtgttttta cgtaggcgtc agctgatcgc tagggtattt aaacctgacg      480
agttccgtca agaggccact cttgagtgcc agcgagaaga gatttctcct ccgcgccgcg      540
agtcagatct ccactttgaa aaaatgagac acctgcgatt cctgcctcag gaaatctcca      600
ttgcgaccgg gaatgaaata ctgcagtttg tggtagatgc cctgatggga gacgatccgg      660
agccgcctgc gcagccttc gatcctccta cgcttcatga actgtatgat ttagaggtag      720
acgggccgga ggatcctaac gaggaagctg tgaatgggtt tttcagcgat tctatgctat      780
tagctgctag tgaaggagtg gacttagacc caccttctga gacccttgat accccagggg      840
tggtggtgga aagcggcaga ggtgggaaaa aattgcctga acttggtgct gctgaaatgg      900
atttgcactg ttatgaagag ggctttcctc cgagtgatga tgacgatgag gaaaatgtgc      960
agtcgatcca gaccgcagcg ggtgagggaa tgaaagctgc caatgatggt tttaagttgg      1020
actgcccgga gctgcctgga catggctgta agtcttgtga atttcacagg aatagtactg      1080
gactaaaaga actgttgtgc tcgctttgct atatgagaac gcactgccat ttatttaca      1140 gtaagtgtgt ctaacttaaa tttaaaggga cagtgtagca gtttaatgtc tgttaatgt      1200 gggatttatg tctttgtgat ttttataggt cctgtgtctg atgctgatga atcgccttct      1260
cctgattcaa ctacctcacc tcctgaaatt caggcgccag tccctgcaaa cgtatgcaag      1320
cccattcctg tgaaggctaa gctgggaaaa cgccctgctg tggataaact ggaggacttg      1380
```

```
cttgagggtg gggatggacc tttggacttg agtacccgga aactgccaag gcaatgagtg    1440
ccctgcacct gtgtttattt aatgtgacgt cagtatttat gtgagagtgc catgtaataa    1500
aattatgtca gctgctgagt attttattgc ttcttgggtg gggacttgga tatataagta    1560
ggagcagacc tgtgtggtta gctcacagca gcttgctgcc atccatggag gtttgggcta    1620
tcttggaaga tctcaggcag actagacaac tgctagaaaa cgcctcggac ggagtctcta    1680
gtctttggag attctggttc ggtggtgatc tagctaggct agtctttagg gtaaaacggg    1740
agtatagtga agaatttgaa aagttattgg aagacagtcc aggactttt  gaagccctta    1800 acttgggcca ccaggctcat tttaaggaga aggttttatc agttttagat ttttctaccc    1860
ctggtagaac tgctgctgct gtagctttcc ttactttat attggataaa atg gat ccc    1918
                                                       Met Asp Pro
                                                         1
```

```
aca aac cca ctt cag caa ggg ata cgt ctt gga ttt cat agc agc agc    1966
Thr Asn Pro Leu Gln Gln Gly Ile Arg Leu Gly Phe His Ser Ser Ser
  5                  10                  15 ttt gtg gag aac atg gaa ggc ccg cag gct gag gat aat ctt aga tta    2014
Phe Val Glu Asn Met Glu Gly Pro Gln Ala Glu Asp Asn Leu Arg Leu
 20                  25                  30                  35 ctg gcc agt gca gcc tct ggg cgt agc agc aat cct gag aca ccc acc    2062
Leu Ala Ser Ala Ala Ser Gly Arg Ser Ser Asn Pro Glu Thr Pro Thr
                 40                  45                  50 ggc cat gcc agc ggt ttt gga gga gga gca gca gga gga caa ccc gag    2110
Gly His Ala Ser Gly Phe Gly Gly Gly Ala Ala Gly Gly Gln Pro Glu
             55                  60                  65 agc cgg cct gga ccc tcc ggt gga gga ggc gga gga gta gct gac ctg    2158
Ser Arg Pro Gly Pro Ser Gly Gly Gly Gly Gly Gly Val Ala Asp Leu
         70                  75                  80 ttt cct gaa ctg cga cgg gtg ctt act agg tct acg tcc agt gga cag    2206
Phe Pro Glu Leu Arg Arg Val Leu Thr Arg Ser Thr Ser Ser Gly Gln
     85                  90                  95 gac agg ggc att aag agg gag agg aat gct agt ggg cat aat tca aga    2254
Asp Arg Gly Ile Lys Arg Glu Arg Asn Ala Ser Gly His Asn Ser Arg
100                 105                 110                 115 act gag ttg gct tta agt tta atg agt cgc agc cgc cct gaa act atc    2302
Thr Glu Leu Ala Leu Ser Leu Met Ser Arg Ser Arg Pro Glu Thr Ile
                120                 125                 130 tgg tgg cat gag gtt cag agc gag ggc agg gat gaa gtt tca ata ttg    2350
Trp Trp His Glu Val Gln Ser Glu Gly Arg Asp Glu Val Ser Ile Leu
            135                 140                 145 cag gaa aaa tat tct cta gaa caa att aaa acc tgt tgg ttg gaa cct    2398
Gln Glu Lys Tyr Ser Leu Glu Gln Ile Lys Thr Cys Trp Leu Glu Pro
        150                 155                 160 gag gat gat tgg gag gtg gcc att agg aat tat gct aag ata tct ctg    2446
Glu Asp Asp Trp Glu Val Ala Ile Arg Asn Tyr Ala Lys Ile Ser Leu
    165                 170                 175 agg cct gat aaa cag tat aaa att acc aaa aag att aat atc aga aat    2494
Arg Pro Asp Lys Gln Tyr Lys Ile Thr Lys Lys Ile Asn Ile Arg Asn
180                 185                 190                 195 gca tgc tac ata gca ggg aat ggg gcc gag gtt ata ata gat aca cca    2542
Ala Cys Tyr Ile Ala Gly Asn Gly Ala Glu Val Ile Ile Asp Thr Pro
                200                 205                 210 gat aaa aca gct ttt agg tgt tgc atg atg ggt atg tgg cca ggg gtg    2590
Asp Lys Thr Ala Phe Arg Cys Cys Met Met Gly Met Trp Pro Gly Val
            215                 220                 225 gct ggc atg gag gca gtg acc ctt atg aat ata agg ttt agg gga gat    2638
Ala Gly Met Glu Ala Val Thr Leu Met Asn Ile Arg Phe Arg Gly Asp
```

```
              230                 235                 240
ggg tat aat ggg att gtc ttt atg gct aac act aag ctg att ctg cat    2686
Gly Tyr Asn Gly Ile Val Phe Met Ala Asn Thr Lys Leu Ile Leu His
    245                 250                 255 ggt tgt agc ttt ttt ggg ttt aat aat act tgt gtg gaa tct tgg gga    2734
Gly Cys Ser Phe Phe Gly Phe Asn Asn Thr Cys Val Glu Ser Trp Gly
260                 265                 270                 275 caa gtc agt atc agg ggt tgt agt ttc tat gca tgc tgg att gca cta    2782
Gln Val Ser Ile Arg Gly Cys Ser Phe Tyr Ala Cys Trp Ile Ala Leu
            280                 285                 290 tca ggc aga acc aag agt cag ttg tct gtg aag aaa tgc atg ttc gag    2830
Ser Gly Arg Thr Lys Ser Gln Leu Ser Val Lys Lys Cys Met Phe Glu
                295                 300                 305 aga tgt aac ctg ggc ata ctg aat gaa ggt gaa gca agg gtc cgc cac    2878
Arg Cys Asn Leu Gly Ile Leu Asn Glu Gly Glu Ala Arg Val Arg His
        310                 315                 320 tgt gct gct aca gaa act ggc tgc ttc att cta ata aag gga aat gcc    2926
Cys Ala Ala Thr Glu Thr Gly Cys Phe Ile Leu Ile Lys Gly Asn Ala
    325                 330                 335 agt gtg aag cat aac atg atc tgt gga ccc ttg gat gag agg cct tat    2974
Ser Val Lys His Asn Met Ile Cys Gly Pro Leu Asp Glu Arg Pro Tyr
340                 345                 350                 355 cag atg ctg acc tgt gct gga gga cat tgc aat atg ctg gct act gtg    3022
Gln Met Leu Thr Cys Ala Gly Gly His Cys Asn Met Leu Ala Thr Val
            360                 365                 370 cat att gtt tct cat gca cgc aag aaa tgg cct gtt ttt gaa cat aat    3070
His Ile Val Ser His Ala Arg Lys Lys Trp Pro Val Phe Glu His Asn
                375                 380                 385 gtg atg acc aag tgc acc atg cac gca ggt ggt cgc agg gga atg ttt    3118
Val Met Thr Lys Cys Thr Met His Ala Gly Gly Arg Arg Gly Met Phe
        390                 395                 400 atg cct tac cag tgt aac atg aat cat gtg aag gtg atg ttg gaa cca    3166
Met Pro Tyr Gln Cys Asn Met Asn His Val Lys Val Met Leu Glu Pro
    405                 410                 415 gat gcc ttt tcc aga atg agc tta aca gga atc ttt gat atg aat gtg    3214
Asp Ala Phe Ser Arg Met Ser Leu Thr Gly Ile Phe Asp Met Asn Val
420                 425                 430                 435 caa cta tgg aag atc ctg aga tat gat gag acc aaa tcg agg gtg cgc    3262
Gln Leu Trp Lys Ile Leu Arg Tyr Asp Glu Thr Lys Ser Arg Val Arg
            440                 445                 450 gca tgc gag tgc ggg ggc aag cat gcc agg ttc cag ccg gtg tgt gtg    3310
Ala Cys Glu Cys Gly Gly Lys His Ala Arg Phe Gln Pro Val Cys Val
                455                 460                 465 gat gtg acg gaa gac ctg aga ccc gat cat ttg gtg ctt gcc tgc act    3358
Asp Val Thr Glu Asp Leu Arg Pro Asp His Leu Val Leu Ala Cys Thr
        470                 475                 480 gga gcg gag ttc ggt tct agt ggg gaa gaa act gac taaagtgagt         3404
Gly Ala Glu Phe Gly Ser Ser Gly Glu Glu Thr Asp
    485                 490                 495 agtgggaat gctgtggagg ggggcttcca ggcgggtaag gtgggcagat tgggtaaatt   3464
ctgtttcttt ctgtcttgca gctgcc atg agt gga agc gct tct ttt gag ggg   3517
                               Met Ser Gly Ser Ala Ser Phe Glu Gly
                                                            500 gga gtc ttt agc cct tat ctg acg ggg cga ctc cca ccc tgg gca gga    3565
Gly Val Phe Ser Pro Tyr Leu Thr Gly Arg Leu Pro Pro Trp Ala Gly
505                 510                 515                 520 gtt cgt cag aat gtc atg gga tcc act gtg gat ggg agg ccc gtc cag    3613
Val Arg Gln Asn Val Met Gly Ser Thr Val Asp Gly Arg Pro Val Gln
            525                 530                 535
```

```
ccc gcc aat tcc tca acg ctg acc tat gcc act ttg agc tct tca ccc      3661
Pro Ala Asn Ser Ser Thr Leu Thr Tyr Ala Thr Leu Ser Ser Ser Pro
            540                 545                 550 ttg gat gca gct gca gcc gct gcc gcc tct gct gcc gcc aac act gtc      3709
Leu Asp Ala Ala Ala Ala Ala Ala Ala Ser Ala Ala Ala Asn Thr Val
            555                 560                 565 ctt gga atg ggc tat tat gga agc atc gtt gcc aat tcc agt tcc tca      3757
Leu Gly Met Gly Tyr Tyr Gly Ser Ile Val Ala Asn Ser Ser Ser Ser
            570                 575                 580 aat aac cct tcg acc ctg gct gag gac aag cta ctt gtc ctc ttg gct      3805
Asn Asn Pro Ser Thr Leu Ala Glu Asp Lys Leu Leu Val Leu Leu Ala
585                 590                 595                 600 cag ctc gag gcc ttg acc cag cgc cta ggc gaa ctg tct cag cag gtg      3853
Gln Leu Glu Ala Leu Thr Gln Arg Leu Gly Glu Leu Ser Gln Gln Val
            605                 610                 615 gcc cag ttg cgc gag caa act gag tct gct gtt gcc aca gca aag tct      3901
Ala Gln Leu Arg Glu Gln Thr Glu Ser Ala Val Ala Thr Ala Lys Ser
            620                 625                 630 aaa taaagattcc caaatcaata aataaggag atccttgttg attgtaaaac            3954
Lys aagtgtaatg aatctttatt tgattttttcg cgcgcggtat gccctggacc accggtctcg   4014
atcattgaga actcggtgga tcttttccag gaccctgtag aggtgggatt gaatgtttag    4074
atacatgggc attaggccgt ctcgggggtg gagatagctc cattgaagag cctcatgctc    4134
tggggtagtg ttataaatca cccagtcata acaaggtcgg agtgcatggt gttgcacaat    4194
atcttttagg agcaggctaa ttgcaacggg gaggccctta gtgtaggtgt ttacaaatct    4254
gttgagctgg gacgggtgca ttcggggtga aattatatgc attttggact ggatcttgag    4314
gttggcaatg ttgccgccta gatcccgtct cgggttcata ttgtgcagga ccaccaagac    4374
agtgtatccg gtgcacttgg gaaatttatc atgcagctta gagggaaaag catgaaaaaa    4434
tttcgagacg cctttgtgtc cgcccagatt ctccatgcac tcatccataa tgatagcgat    4494
ggggccgtgg gcggcggcgc gggcaaacac gttccggggg tctgacacat catagttatg    4554
ctcctgagtc aggtcatcat aagccatttt aataaacttg gggcggaggg tgccagattg    4614
ggggatgaaa gttccctcgg gccccggagc atagtttccc tcacatattt gcatttccca    4674
ggctttcagt tcagagggg ggatcatgtc cacctgcggg gctataaaaa ataccgtttc    4734
tggagcgggg gtgattaact gggatgagag caaattcctg agcagctgag acttgccgca    4794
cccagtggga ccgtaaatga ccccgattac gggttgcaga tggtagttta gggagcggca    4854
gctgccgtcc tcccggagca ggggggccac ttcgttcatc atttcccttta catggatatt    4914 ttcccgcacc aagtccgtta ggaggcgctc tcccccagg gatagaagct cctggagcga    4974
ggagaagttt ttcagcggct tcagcccgtc agccatgggc attttggaga gagtctgttg    5034
caagagctcg agccggtccc agagctcggt gatgtgttct atggcatctc gatccagcag    5094
acctcctcgt ttcgcgggtt ggggcggctc ctggagtatg gtatcagacg atgggcgtcc    5154
agcgctgcca gggtccgatc tttccagggt cgcagcgttc gagtcagggt tgtttccgtc    5214
acggtgaagg ggtgcgcgcc tggttgggcg cttgcgaggg tgcgtttcag gctcatcctg    5274
ctggtcgaga accgctgccg atcggcgccc tgcatgtcgg ccaggtagca gtttaccatg    5334
agttcgtagt tgagtgcctc ggccgcgtgg cctttggcgc ggagcttacc tttggaagtt    5394
ttctggcagg cggggcagta cagacacttg agggcataca gtttgggagc gaggaagatg    5454
gattcggggg agtatgcgtc cgcaccgcag gaggcgcaga cggtttcgca ttccacgagc    5514
```

```
caggtcagat ccggctcatc ggggtcaaaa acaagttttc ccccatgttt tttgatgcgt    5574
ttcttacctt tggtctccat gagttcgtgt ccccgctggg tgacaaagag gctgtccgtg    5634
tccccgtaga ccgattttat gggcctgtcc tcgagcggag tgcctcggtc ctcttcgtag    5694
aggaactcgg accactctga tacaaaggcg cgcgtccagg ccagcacaaa agaggccacg    5754
tgggaggggt agcggtcgtt gtcaaccagg gggtccacct tctccacggt atgtaaacac    5814
atgtccccct cctccacatc caagaatgtg attggcttgt aagtgtatgc cacgtgacca    5874
ggggtccccg ccggggggt ataaaggggg gcgggtctct gctcgtcctc actgtcttcc    5934
ggatcgctgt ccaggagcgc cagctgttgg ggtaggtatt ccctctcgaa ggcgggcata    5994
acctctgcac tcaggttgtc agtttctagg aacgaggagg atttgatatt gacagtgcca    6054
gccgagatgc ctttcataag actctcgtcc atttggtcag aaaatacaat cttttgttg     6114 tccagcttgg tggcaaagga tccatagagg gcattggata agagcttggc tatggagcgc    6174
atggtttggt tcttttcctt gtcagcgcgc tccttggcag caatgttgag ctggacatac    6234
tcgcgcgcca gacacttcca ttcagggaag atggttgtca gttcatctgg cacgattctg    6294
actcgccagc ccctgttatg cagggtgatc agatccacac tggtggtcac ttcgcctctg    6354
aggggctcgt tggtccagca gagtcgaccc ccttttctcg aacagaaagg tgggaggggg    6414
tctagcatga gttcatcagg ggggtctgca tccatagtga agattcctgg gagcagatcc    6474
ttgtcaaaat agctgatggg tgtggggtca tccaaagcca tctgccattc tcgagccgcc    6534
agcgcgcgct catagggggtt gagagggtg ccccatggca tggggtgggt gagtgcagag    6594
gcatacatgc cacagatgtc atagacatag aggggctctt caagaatgcc aatgtaggtg    6654
ggataacagc gccccctct gatgcttgct cgcacatagt catagagttc atgcgagggg    6714
gcgagcagac ccgagcccaa attagtgcga ttgggttttt cagccctgta gacgatctgg    6774
cgaaagatgg catgtgaatt tgaagagatg gtgggtctct gaaagatgtt aaaatgggca    6834
tgaggtagac ctacagagtc cctgatgaag tgggcatatg actcttgcag cttggccacc    6894
agctctgcag tgacaaggac atccaaggcg cagtagtcaa gggtctcttg gatgatgtca    6954
taacctggtt ggttttttctt ttcccacagc tcgcggttga aaggtattc ttcgcgatcc    7014 ttccagtact cttcgagggg aaacccgtct ttgtctgcac ggtaagagcc cagcatgtag    7074
aactgattaa ctgctttgta gggacagcat cccttctcca cggggagaga gtatgcttgg    7134
gctgccttgc gcagtgaggt atgagtgagg gcgaaggtgt ccctgaccat gactttgagg    7194
aactggtgct tgaaatcgat gtcatcacag gcccctgtt cccagagttg gaagtccacc     7254
cgcttcttgt aggcggggtt gggcaaagcg aaagtaacat cattgaagag aatcttgccg    7314
gccctgggca tgaaattgcg ggtgatgcgg aaaggctggg gcacctctgc ccggttattg    7374
atcacctgag cggctaggac gatctcgtca aagccattga tgttgtgtcc cacaatgtaa    7434
agttctatga atcgcgggt gccccctgaca tgaggcagct tcttgagttc ttcaaaagtg     7494
aggtctgtag ggtcagagag agcatagtgt tcgagggccc attcgtgcag gtgagggttt    7554
gcattgagga aggaggacca gagatccact gccagtgctg tttgtaactg gtctcggtac    7614
tggcgaaaat gctggccgac tgccatcttt tctggggtga tacagtagaa ggttttgggg    7674
tcttgctgcc agcgatccca cttgagtttg atggcgaggt cgtaggcgat gttgacgagc    7734
cgctcgtccc ccgaaagttt catgaccagc atgaatggga tcagctgctt gccaaaggac    7794
cccatccagg tgtaggtttc cacatcgtag gtgaggaaga gcctttctgt gcgaggatga    7854
```

```
gagccgatcg ggaagaactg gatctcctgc caccagttgg aggaatggct gttgatgtga    7914
tggaagtaga actccctgcg gcgcgccgag cattcatgct tgtgcttata cagacggccg    7974
cagtactcgc agcgcttcac gggatgcacc tcatgaatga gttgtacctg gcttcctttg    8034
acgagaaatt tcagtgggaa gttgaggcct ggcgcttgta cctcgcgctc tactatgtta    8094
tctgcatcgg cctggccatc ttctgtctcg atggtggtca tgctgacgag ccccgcggg    8154
aggcaagtcc agacctcggc gcgggagggg cggagctcga ggacgagagc gcgcaggccg    8214
gagctgtcca gggtcctgag tcgctgcgga gtcaggttag taggtagtgt caggagatta    8274
acttgcatga tcttttcgag ggcatgcggg aggttcagat ggtacttgat ttccacgggt    8334
ccgttggtgg agatgtcgat ggcttgcagg gtcccatgcc ccttgggcgc caccaccgtg    8394
cccttgtttt tccttttggg cggcggtggc tctgttgctt cttgcatgtt cagaagcggt    8454
ggcgagggcg cgcgccgggc ggtaggggcg gctctggccc cggcggcatg gctggtagag    8514
gcacgtcggc gccgcgcgcg ggtaggttct ggtactgcgc cctgagaaga cttgcgtgcg    8574
cgacgacgcg gcggttgacg tcctggatct gacgcctctg ggtgaaagct accggacccg    8634
tgagcttgaa cctgaaagag agttcaacag aatcaatttc ggtatcgttg acggcggctt    8694
gcctcaggat ctcttgcacg tcgcccgagt tgtcctggta ggcgatctcg gccatgaact    8754
gctcgatttc ttcctcctga agatctccgc ggcccgctct ctcgacggtg gccgcgaggt    8814
cgttggagat gcgacccatg agttgagaga atgcattcat gcccgcctcg ttccagacgc    8874
ggctgtagac cacggccccc tcgggatctc tcgcgcgcat gaccacctgg gcgaggttga    8934
gctccacgtg gcgggtgaag accgcatagt tgcataggcg ctggaagagg tagttgagtg    8994
tggtggcgat gtgctcggtg acgaagaaat acatgatcca tcgtctcagc ggcatctcgc    9054
tgacatcgcc cagggcttcc aagcgctcca tggcctcgta gaagtccaca gcgaagttga    9114
aaaactggga gttgcgcgcg gacacggtca actcctcctc cagaagacgg atgagatcgg    9174
cgatggtggc gcgcacctcg cgctcgaagg ccccgggat tcttcctcc tcctcttcta     9234
tctcttcttc cactaacatc tcttcttcct cttcaggcgg gggcggagga ggaggggcg    9294
cgcggcgacg ccgcggcgc acgggcagac ggtcgatgaa tctttcaatg acctctccgc    9354
ggcggcggcg catggtctcg gtgacggcgc ggccgttctc cctgggtctc aaagtgaaga    9414
cgcctccgcg catctccttg aagtggtgac tgggggctc tccgttgggc agggacaggg    9474
cgctgatgat gcattttatc aattgccccg tagggactcc gcgcaaggac ctgatcgtct    9534
gaagatccac gggatctgaa aacctttcga cgaaagcgtc taaccagtcg caatcgcaag    9594
gtaggctgag caccgtttct tgcgggcggg ggttctctct tccttctcct tcctcatcat    9654
ctcgggaggg taagacgatg ctgctggtga tgaaattaaa ataggcagtt ctgagacggc    9714
ggatggtggc gaggagcacc aggtctttgg gtccggcttg ctggatgcgc aggcgatcgg    9774
ccattcccca agcattgtcc tggcatctgg ccagatcttt atagtagtct tgcatgagtc    9834
gctccacggg cacttcttct tcgcccgctc taccatgcat gcgcgtgagc ccgaacccgc    9894
gcatgggctg gacaagtgcc aagtccgcta cgaccctttc ggcgaggatg gcttgctgca    9954
cctgggtgag ggtggcttgg aagtcgtcaa agtccacgaa gcgatggtag gcccggtgt   10014
taatggtgta ggagcagttg gccatgactg accagttgac tgtctggtgc cccgggcgca   10074
cgatctcggt gtacttgagt cgcgagtagg cgcgggtgtc aaagatgtaa tcgttgcagg   10134
tgcgcaccag gtactggtag ccgatgagaa agtgcggcgg tggctggcgg tagagggggcc  10194
atcgctctgt agccgggggct ccgggggcga ggtcttccag catgaggcgg tggtatccgt  10254
```

```
agatgtacct ggacatccag gtgatcccgg aggcggtggt ggacgctcgc gggaactcgc    10314
gcactcggtt ccagatgttg cgcagcggca tgaagtagtt catggtaggc acggtctggc    10374
cagtgaggcg ggcgcagtca ttgatgctct atagacacgg agaaaacgaa agcgatgagc    10434
ggctcgcctc cgtggcctgg aggaacgtga acgggttggg tcgcggtgta ccccggttcg    10494
agaccaaagc caagcgagca caactcgggc cggccggagc cgtggctaac gtggtattgg    10554
cgatcccgtc tcgacccagc cgacgaatat ccaggatacg gagtcgagtc gttttgctgc    10614
ttgttgcttt ttctggacgg gagccagcac cgcgtcaagc tttagaacgc tcagttcacg    10674
gggtcgggag tggctcgcgc ccgtagtctg gagaatcaat cgccagggtt gcgttgcggt    10734
gtgccccggt tcgagcctta gcgcggcccg gatcggccgg tttccgcggc aagcgagggt    10794
ttggcagccc cgtcatttct aagacccgc cagccgactt ctccagttta cgggagcgag    10854
ccctcttttt tttgttttg tcgcccag atg cat ccc gtg ctg cga cag atg       10906
                              Met His Pro Val Leu Arg Gln Met
                                              635             640
```

```
cgc ccc cag caa cag gcc cct tct cag caa cag cag cag cca caa aag    10954
Arg Pro Gln Gln Gln Ala Pro Ser Gln Gln Gln Gln Gln Pro Gln Lys
            645                 650                 655 gct ctt cct gct cct gct ccc gca act act gca gtc gca gcc gtg tgc    11002
Ala Leu Pro Ala Pro Ala Pro Ala Thr Thr Ala Val Ala Ala Val Cys
            660                 665                 670 ggc gcg ggt cag ccc gcc tat gat ctg gac ttg gaa gag ggc gag gga    11050
Gly Ala Gly Gln Pro Ala Tyr Asp Leu Asp Leu Glu Glu Gly Glu Gly
675                 680                 685 ctg gca cgc ctg ggt gca cca tcg ccc gag cgg cac ccg cgg gtg caa    11098
Leu Ala Arg Leu Gly Ala Pro Ser Pro Glu Arg His Pro Arg Val Gln
690             695                 700                 705 ctg aaa aag gac tct cgc gag gcg tac gtg ccc cag cag aac ctg ttc    11146
Leu Lys Lys Asp Ser Arg Glu Ala Tyr Val Pro Gln Gln Asn Leu Phe
                710                 715                 720 agg gac agg agc ggc gag gag ccc gag gag atg cga gcc tcc cgc ttt    11194
Arg Asp Arg Ser Gly Glu Glu Pro Glu Glu Met Arg Ala Ser Arg Phe
            725                 730                 735 aac gcg ggt cgc gag ctg cgc cac ggt ctg gac cga aga cgg gtg ctg    11242
Asn Ala Gly Arg Glu Leu Arg His Gly Leu Asp Arg Arg Arg Val Leu
        740                 745                 750 cgg gac gag gat ttc gag gtc gat gaa atg aca ggg atc agc ccc gct    11290
Arg Asp Glu Asp Phe Glu Val Asp Glu Met Thr Gly Ile Ser Pro Ala
755                 760                 765 agg gca cat gtg gcc gcg gcc aac ctc gtc tcg gcc tac gag cag acc    11338
Arg Ala His Val Ala Ala Ala Asn Leu Val Ser Ala Tyr Glu Gln Thr
770                 775                 780                 785 gtg aag gag gag cgc aat ttc caa aaa tca ttc aac aac cat gtg cgc    11386
Val Lys Glu Glu Arg Asn Phe Gln Lys Ser Phe Asn Asn His Val Arg
            790                 795                 800 acc ctg atc gcc cgt gag gaa gtg acc ctg ggt ctg atg cac ctg tgg    11434
Thr Leu Ile Ala Arg Glu Glu Val Thr Leu Gly Leu Met His Leu Trp
            805                 810                 815 gac ctg atg gaa gct atc acc cag aac cca act agc aaa ccc ctg acc    11482
Asp Leu Met Glu Ala Ile Thr Gln Asn Pro Thr Ser Lys Pro Leu Thr
            820                 825                 830 gct cag ctg ttt ctg gtg gtg caa cac agc agg gac aat gag gca ttc    11530
Ala Gln Leu Phe Leu Val Val Gln His Ser Arg Asp Asn Glu Ala Phe
            835                 840                 845 agg gag gcg ctg cta aac atc acc gag ccc gaa ggg aga tgg ttg tat    11578
Arg Glu Ala Leu Leu Asn Ile Thr Glu Pro Glu Gly Arg Trp Leu Tyr
```

```
                -continued 850             855             860             865 gac ctg atc aat atc ctg cag agt att ata gtg cag gaa cgt agc ttg     11626
Asp Leu Ile Asn Ile Leu Gln Ser Ile Ile Val Gln Glu Arg Ser Leu
            870             875             880 ggt ctg gct gag aaa gtg gca gcc atc aac tac tcg gtc ttg agc ctg     11674
Gly Leu Ala Glu Lys Val Ala Ala Ile Asn Tyr Ser Val Leu Ser Leu
        885             890             895 ggc aag tac tac gct cgc aag atc tac aag acc ccc tac gtg ccc ata     11722
Gly Lys Tyr Tyr Ala Arg Lys Ile Tyr Lys Thr Pro Tyr Val Pro Ile
    900             905             910 gac aag gag gtg aag ata gat ggg ttt tac atg cgc atg act ctc aag     11770
Asp Lys Glu Val Lys Ile Asp Gly Phe Tyr Met Arg Met Thr Leu Lys
915             920             925 gtt ctg act ctc agt gac gat ctg gga gtg tac cgc aat gac agg atg     11818
Val Leu Thr Leu Ser Asp Asp Leu Gly Val Tyr Arg Asn Asp Arg Met
930             935             940             945 cac cgc gcg gtg agc gcc agc agg agg cgc gag ctg agc gac agg gaa     11866
His Arg Ala Val Ser Ala Ser Arg Arg Arg Glu Leu Ser Asp Arg Glu
        950             955             960 ctt atg cac agc ttg caa aga gct ctg acg ggg gca ggg aca gat ggg     11914
Leu Met His Ser Leu Gln Arg Ala Leu Thr Gly Ala Gly Thr Asp Gly
            965             970             975 gag aac tac ttt gac atg ggg gca gac ttg caa tgg caa cct agc cgc     11962
Glu Asn Tyr Phe Asp Met Gly Ala Asp Leu Gln Trp Gln Pro Ser Arg
        980             985             990 cgg gcc ctg gac gcg gca ggg tgt gag ctt cct tac gta gaa gag gtg     12010
Arg Ala Leu Asp Ala Ala Gly Cys Glu Leu Pro Tyr Val Glu Glu Val
    995             1000            1005 gat gaa ggc gag gag gag gag ggc gag tac ctg gaa gac tgatggcgcg     12059
Asp Glu Gly Glu Glu Glu Gly Glu Tyr Leu Glu Asp
1010            1015            1020 acccgtattt ttgctag atg gaa cag cag gca ccg gac ccc gca atg cgg     12109
                    Met Glu Gln Gln Ala Pro Asp Pro Ala Met Arg
                            1025            1030 gcg gcg ctg cag agc cag ccg tcc ggc att aac tcc tcg gac gat          12154
Ala Ala Leu Gln Ser Gln Pro Ser Gly Ile Asn Ser Ser Asp Asp
    1035            1040            1045 tgg acc cag gcc atg caa cgc atc atg gcg ctg acg acc cgc aac          12199
Trp Thr Gln Ala Met Gln Arg Ile Met Ala Leu Thr Thr Arg Asn
    1050            1055            1060 ccc gaa gcc ttt aga cag caa ccc cag gcc aac cgc ctt tcg gcc          12244
Pro Glu Ala Phe Arg Gln Gln Pro Gln Ala Asn Arg Leu Ser Ala
    1065            1070            1075 atc ctg gag gcc gta gtt cct tcc cgc tcc aac ccc acc cac gag          12289
Ile Leu Glu Ala Val Val Pro Ser Arg Ser Asn Pro Thr His Glu
    1080            1085            1090 aag gtc ctg gcc atc gtg aac gcg ctg gtg gag aac aag gcc atc          12334
Lys Val Leu Ala Ile Val Asn Ala Leu Val Glu Asn Lys Ala Ile
    1095            1100            1105 cgt ccc gat gag gcc ggg ctg gta tac aat gcc ctc ttg gag cgc          12379
Arg Pro Asp Glu Ala Gly Leu Val Tyr Asn Ala Leu Leu Glu Arg
    1110            1115            1120 gtg gcc cgc tac aac agc agc aac gtg cag acc aac ctg gac cgg          12424
Val Ala Arg Tyr Asn Ser Ser Asn Val Gln Thr Asn Leu Asp Arg
    1125            1130            1135 atg gtg aca gat gtg cgc gag gcc gtg tct cag cgc gag cgg ttc          12469
Met Val Thr Asp Val Arg Glu Ala Val Ser Gln Arg Glu Arg Phe
    1140            1145            1150 cag cgc gat gcc aac ttg ggg tcg ctg gtg gcg ctg aac gcc ttc          12514
```

-continued

```
                  Gln Arg Asp Ala Asn Leu Gly Ser Leu Val Ala Leu Asn Ala Phe
                      1155                1160                1165 ctc agc acc cag cct gcc aac gtg ccc cgc ggc cag caa gac tat        12559
Leu Ser Thr Gln Pro Ala Asn Val Pro Arg Gly Gln Gln Asp Tyr
    1170                1175                1180 aca aac ttt cta agt gca ctg aga ctc atg gta acc gaa gtc cct        12604
Thr Asn Phe Leu Ser Ala Leu Arg Leu Met Val Thr Glu Val Pro
    1185                1190                1195 cag agc gag gtg tac cag tcc gga cca gac tac ttt ttc cag acc        12649
Gln Ser Glu Val Tyr Gln Ser Gly Pro Asp Tyr Phe Phe Gln Thr
    1200                1205                1210 agc aga cag ggc ttg cag aca gtg aac ctg agc cag gct ttc aaa        12694
Ser Arg Gln Gly Leu Gln Thr Val Asn Leu Ser Gln Ala Phe Lys
    1215                1220                1225 aac ctc aga ggc ctg tgg gga gtg cac gcc cca gta gga gat cgc        12739
Asn Leu Arg Gly Leu Trp Gly Val His Ala Pro Val Gly Asp Arg
    1230                1235                1240 gcg acc gtg tct agc ttg ctg act ccc aac tcc cgc cta ctg ctg        12784
Ala Thr Val Ser Ser Leu Leu Thr Pro Asn Ser Arg Leu Leu Leu
    1245                1250                1255 ctg ctg gta tcc ccc ttc act gac agc ggt agc atc gac cgc aac        12829
Leu Leu Val Ser Pro Phe Thr Asp Ser Gly Ser Ile Asp Arg Asn
    1260                1265                1270 tcc tac ttg ggc tac ctg ctg aac ttg tat cgc gag gcc ata ggg        12874
Ser Tyr Leu Gly Tyr Leu Leu Asn Leu Tyr Arg Glu Ala Ile Gly
    1275                1280                1285 cag agt cag gtg gac gag cag acc tac caa gaa atc acc caa gtg        12919
Gln Ser Gln Val Asp Glu Gln Thr Tyr Gln Glu Ile Thr Gln Val
    1290                1295                1300 agc cgc gcc ctg ggt cag gaa gac acg ggc agc ttg gaa gcc acc        12964
Ser Arg Ala Leu Gly Gln Glu Asp Thr Gly Ser Leu Glu Ala Thr
    1305                1310                1315 ctg aac ttc ttg ctg acc aac cgg tcg cag aag atc cct cct cag        13009
Leu Asn Phe Leu Leu Thr Asn Arg Ser Gln Lys Ile Pro Pro Gln
    1320                1325                1330 tat gcg ctt acc gcg gag gag gag cgg atc ctc aga tat gtg cag        13054
Tyr Ala Leu Thr Ala Glu Glu Glu Arg Ile Leu Arg Tyr Val Gln
    1335                1340                1345 cag agc gtg gga ctg ttc ctg atg caa gag ggg gcg acc cct agt        13099
Gln Ser Val Gly Leu Phe Leu Met Gln Glu Gly Ala Thr Pro Ser
    1350                1355                1360 gcc gcg ctg gac atg aca gcc cga aac atg gag ccc agc atg tat        13144
Ala Ala Leu Asp Met Thr Ala Arg Asn Met Glu Pro Ser Met Tyr
    1365                1370                1375 gcc agt aac cgg cct ttc atc aac aaa ctg ctg gac tac ctg cac        13189
Ala Ser Asn Arg Pro Phe Ile Asn Lys Leu Leu Asp Tyr Leu His
    1380                1385                1390 agg gcg gcc gcc atg aac tct gat tat ttc acc aat gct att ctc        13234
Arg Ala Ala Ala Met Asn Ser Asp Tyr Phe Thr Asn Ala Ile Leu
    1395                1400                1405 aac ccc cac tgg ctg ccc ccg cct gga ttt tac acg ggc gag tac        13279
Asn Pro His Trp Leu Pro Pro Pro Gly Phe Tyr Thr Gly Glu Tyr
    1410                1415                1420 gac atg ccc gac ccc aat gac ggg ttc ctg tgg gac gat gtg gac        13324
Asp Met Pro Asp Pro Asn Asp Gly Phe Leu Trp Asp Asp Val Asp
    1425                1430                1435 agc agc ata ttc tcc ccg ccc cct ggt tat aac act tgg aag aag        13369
Ser Ser Ile Phe Ser Pro Pro Pro Gly Tyr Asn Thr Trp Lys Lys
    1440                1445                1450
```

| | | | | | | | | | | | | | | |
|---|---|---|---|---|---|---|---|---|---|---|---|---|---|---|
| gaa | ggg | ggc | gat | aga | aga | cac | tct | tcc | gtg | tcg | ctg | tcc | ggg | tcg | 13414 |
| Glu | Gly | Gly | Asp | Arg | Arg | His | Ser | Ser | Val | Ser | Leu | Ser | Gly | Ser | |
| | 1455 | | | | | 1460 | | | | | 1465 | | | | |
| agg | ggt | gct | gcc | gcc | gcg | gtg | ccc | gag | gct | gca | agt | cct | ttc | cct | 13459 |
| Arg | Gly | Ala | Ala | Ala | Ala | Val | Pro | Glu | Ala | Ala | Ser | Pro | Phe | Pro | |
| | 1470 | | | | | 1475 | | | | | 1480 | | | | |
| agc | ctg | ccc | ttt | tct | ctg | aac | agc | gtg | cgc | agc | agt | gaa | ctg | ggg | 13504 |
| Ser | Leu | Pro | Phe | Ser | Leu | Asn | Ser | Val | Arg | Ser | Ser | Glu | Leu | Gly | |
| | 1485 | | | | | 1490 | | | | | 1495 | | | | |
| aga | ata | acc | cgc | ccg | cgc | ttg | atg | ggc | gag | gat | gag | tac | ttg | aac | 13549 |
| Arg | Ile | Thr | Arg | Pro | Arg | Leu | Met | Gly | Glu | Asp | Glu | Tyr | Leu | Asn | |
| | 1500 | | | | | 1505 | | | | | 1510 | | | | |
| gac | tcc | ttg | ctt | aga | ccc | gag | agg | gaa | aag | aac | ttc | ccc | aac | aat | 13594 |
| Asp | Ser | Leu | Leu | Arg | Pro | Glu | Arg | Glu | Lys | Asn | Phe | Pro | Asn | Asn | |
| | 1515 | | | | | 1520 | | | | | 1525 | | | | |
| ggt | ata | gag | agc | ctg | gtg | gac | aag | atg | agt | aga | tgg | aag | aca | tat | 13639 |
| Gly | Ile | Glu | Ser | Leu | Val | Asp | Lys | Met | Ser | Arg | Trp | Lys | Thr | Tyr | |
| | 1530 | | | | | 1535 | | | | | 1540 | | | | |
| gca | cag | gat | cac | aaa | gac | gag | cct | agg | atc | ttg | ggg | gct | gcg | agc | 13684 |
| Ala | Gln | Asp | His | Lys | Asp | Glu | Pro | Arg | Ile | Leu | Gly | Ala | Ala | Ser | |
| | 1545 | | | | | 1550 | | | | | 1555 | | | | |
| ggg | acg | acc | cgt | aga | cgc | cag | cgc | cat | gac | aga | cag | agg | ggt | ctt | 13729 |
| Gly | Thr | Thr | Arg | Arg | Arg | Gln | Arg | His | Asp | Arg | Gln | Arg | Gly | Leu | |
| | 1560 | | | | | 1565 | | | | | 1570 | | | | |
| gtg | tgg | gac | gat | gag | gac | tcg | gcc | gat | gac | agc | agc | gtg | ttg | gac | 13774 |
| Val | Trp | Asp | Asp | Glu | Asp | Ser | Ala | Asp | Asp | Ser | Ser | Val | Leu | Asp | |
| | 1575 | | | | | 1580 | | | | | 1585 | | | | |
| ttg | ggt | ggg | aga | gga | ggg | ggc | aac | ccg | ttc | gct | cat | ctg | cgc | ccg | 13819 |
| Leu | Gly | Gly | Arg | Gly | Gly | Gly | Asn | Pro | Phe | Ala | His | Leu | Arg | Pro | |
| | 1590 | | | | | 1595 | | | | | 1600 | | | | |
| cac | ttt | ggg | cgc | atg | ttg | taaaagtgaa | agtaaaataa | aaaggcaact | | | | | | | 13867 |
| His | Phe | Gly | Arg | Met | Leu | | | | | | | | | | |
| | 1605 | | | | | | | | | | | | | | |
| caccaaggcc | atggcgacga | gcgtgcgttc | gttcttttct | gttatctgtg | tctagt | | | | | | | | | | 13923 |
| atg | atg | agg | cga | gcc | gtg | cta | ggc | gga | gcg | gtg | gtg | tat | ccg | gag | 13968 |
| Met | Met | Arg | Arg | Ala | Val | Leu | Gly | Gly | Ala | Val | Val | Tyr | Pro | Glu | |
| 1610 | | | | 1615 | | | | | 1620 | | | | | | |
| ggt | cct | cct | cct | tcg | tac | gag | agc | gtg | atg | cag | cag | cag | gcg | gcg | 14013 |
| Gly | Pro | Pro | Pro | Ser | Tyr | Glu | Ser | Val | Met | Gln | Gln | Gln | Ala | Ala | |
| 1625 | | | | 1630 | | | | | 1635 | | | | | | |
| gcg | gtg | atg | cag | ccc | tcg | ctg | gag | gct | ccc | ttt | gta | ccc | ccg | cgg | 14058 |
| Ala | Val | Met | Gln | Pro | Ser | Leu | Glu | Ala | Pro | Phe | Val | Pro | Pro | Arg | |
| 1640 | | | | 1645 | | | | | 1650 | | | | | | |
| tac | ctg | gcg | cct | aca | gag | ggg | aga | aac | agc | att | cgt | tac | tcg | gag | 14103 |
| Tyr | Leu | Ala | Pro | Thr | Glu | Gly | Arg | Asn | Ser | Ile | Arg | Tyr | Ser | Glu | |
| 1655 | | | | 1660 | | | | | 1665 | | | | | | |
| ctg | gca | ccc | cag | tac | gat | acc | acc | agg | ttg | tat | ctg | gtg | gac | aac | 14148 |
| Leu | Ala | Pro | Gln | Tyr | Asp | Thr | Thr | Arg | Leu | Tyr | Leu | Val | Asp | Asn | |
| 1670 | | | | 1675 | | | | | 1680 | | | | | | |
| aag | tcg | gcg | gac | atc | gcc | tca | ttg | aac | tat | cag | aac | gac | cac | agc | 14193 |
| Lys | Ser | Ala | Asp | Ile | Ala | Ser | Leu | Asn | Tyr | Gln | Asn | Asp | His | Ser | |
| 1685 | | | | 1690 | | | | | 1695 | | | | | | |
| aac | ttc | ctg | acc | acg | gtg | gtg | cag | aac | aat | gac | ttt | acc | ccc | acg | 14238 |
| Asn | Phe | Leu | Thr | Thr | Val | Val | Gln | Asn | Asn | Asp | Phe | Thr | Pro | Thr | |
| 1700 | | | | 1705 | | | | | 1710 | | | | | | |
| gag | gcc | agc | acc | cag | acc | atc | aac | ttt | gac | gag | cgg | tcg | cgg | tgg | 14283 |
| Glu | Ala | Ser | Thr | Gln | Thr | Ile | Asn | Phe | Asp | Glu | Arg | Ser | Arg | Trp | |
| 1715 | | | | 1720 | | | | | 1725 | | | | | | |
| ggc | ggt | cag | ctg | aag | acc | atc | atg | cac | acc | aac | atg | ccc | aac | gtg | 14328 |

```
Gly Gly Gln Leu Lys Thr Ile Met His Thr Asn Met Pro Asn Val
1730         1735             1740 aac gag tac atg ttc agc aac aag ttc aag gcg cgg gtg atg gtg              14373
Asn Glu Tyr Met Phe Ser Asn Lys Phe Lys Ala Arg Val Met Val
1745         1750             1755 tca cgc aag aaa cct gaa ggc tat aca ggg gat aaa aat gat aca              14418
Ser Arg Lys Lys Pro Glu Gly Tyr Thr Gly Asp Lys Asn Asp Thr
1760         1765             1770 agt cag gat att ctg gag tat gag tgg ttt gag ttc act tta cca              14463
Ser Gln Asp Ile Leu Glu Tyr Glu Trp Phe Glu Phe Thr Leu Pro
1775         1780             1785 gaa ggc aac ttc tca gcc acc atg acc atc gac ctg atg aac aat              14508
Glu Gly Asn Phe Ser Ala Thr Met Thr Ile Asp Leu Met Asn Asn
1790         1795             1800 gcc atc att gac aac tac ctg gca gtg ggc aga cag aat gga gtg              14553
Ala Ile Ile Asp Asn Tyr Leu Ala Val Gly Arg Gln Asn Gly Val
1805         1810             1815 ttg gaa agc gac atc ggt gtc aag ttt gat acc agg aac ttc agg              14598
Leu Glu Ser Asp Ile Gly Val Lys Phe Asp Thr Arg Asn Phe Arg
1820         1825             1830 ctg ggc tgg gac ccc ata act aaa ctt gtt atg cca gga gtc tac              14643
Leu Gly Trp Asp Pro Ile Thr Lys Leu Val Met Pro Gly Val Tyr
1835         1840             1845 act tat gaa gcc ttc cat cct gat att gtg cta cta cct ggc tgt              14688
Thr Tyr Glu Ala Phe His Pro Asp Ile Val Leu Leu Pro Gly Cys
1850         1855             1860 ggg gtg gac ttt act gag agc cgc ctt agc aac ttg ctt ggt att              14733
Gly Val Asp Phe Thr Glu Ser Arg Leu Ser Asn Leu Leu Gly Ile
1865         1870             1875 agg aag aga cac cca ttc cag gaa ggt ttt aaa att atg tat gag              14778
Arg Lys Arg His Pro Phe Gln Glu Gly Phe Lys Ile Met Tyr Glu
1880         1885             1890 gat ctt gag ggg ggt aat atc ccc gcc ctt ttg gat gta gat gcc              14823
Asp Leu Glu Gly Gly Asn Ile Pro Ala Leu Leu Asp Val Asp Ala
1895         1900             1905 tat gaa aaa agc aaa aag gaa aac aca gac acc acc acc act acc              14868
Tyr Glu Lys Ser Lys Lys Glu Asn Thr Asp Thr Thr Thr Thr Thr
1910         1915             1920 act gtt act act act gaa gta gca act gtt gca aga cac gtt tct              14913
Thr Val Thr Thr Thr Glu Val Ala Thr Val Ala Arg His Val Ser
1925         1930             1935 gaa gta act act gaa gca gca acg gtt gtt gca gtg gat cct att              14958
Glu Val Thr Thr Glu Ala Ala Thr Val Val Ala Val Asp Pro Ile
1940         1945             1950 gtt gaa gag aac aat aat act gtt aga gga gat aat atc cat act              15003
Val Glu Glu Asn Asn Asn Thr Val Arg Gly Asp Asn Ile His Thr
1955         1960             1965 gcc aat gag atg aaa gca gca gct gat gat aca aca gtt gta gtt              15048
Ala Asn Glu Met Lys Ala Ala Ala Asp Asp Thr Thr Val Val Val
1970         1975             1980 gtg cct ggc gct gta gtg act gaa act gaa acc aaa acc aag aca              15093
Val Pro Gly Ala Val Val Thr Glu Thr Glu Thr Lys Thr Lys Thr
1985         1990             1995 ctc acc att caa cct cta gaa aag gat acc aag gag cgc agt tac              15138
Leu Thr Ile Gln Pro Leu Glu Lys Asp Thr Lys Glu Arg Ser Tyr
2000         2005             2010 aat gtc atc tct ggc acc aat gat act gcc tat cgt agt tgg tac              15183
Asn Val Ile Ser Gly Thr Asn Asp Thr Ala Tyr Arg Ser Trp Tyr
2015         2020             2025
```

```
cta gca tac aac tat ggc gac cct gaa aaa gga gtc cgc tcc tgg      15228
Leu Ala Tyr Asn Tyr Gly Asp Pro Glu Lys Gly Val Arg Ser Trp
2030                2035                2040 acg ctg ctc acc act tca gat gtc acc tgc gga gcg gag caa gta      15273
Thr Leu Leu Thr Thr Ser Asp Val Thr Cys Gly Ala Glu Gln Val
2045                2050                2055 tat tgg tcg ctc cct gac atg atg cag gac ccc gtc acc ttt cga      15318
Tyr Trp Ser Leu Pro Asp Met Met Gln Asp Pro Val Thr Phe Arg
2060                2065                2070 tcc acg aga caa gtc agc aac tac ccc gtg gtg ggt gca gag ctc      15363
Ser Thr Arg Gln Val Ser Asn Tyr Pro Val Val Gly Ala Glu Leu
2075                2080                2085 atg ccc gtc ttc tca aag agt ttc tac aac gag caa gcc gtg tac      15408
Met Pro Val Phe Ser Lys Ser Phe Tyr Asn Glu Gln Ala Val Tyr
2090                2095                2100 tcc cag cag ctc cgc cag acc acc tcg ctt acg cac atc ttc gat      15453
Ser Gln Gln Leu Arg Gln Thr Thr Ser Leu Thr His Ile Phe Asp
2105                2110                2115 cgc ttc cct gag aat cag atc ctc atc cgc ccg gcg ccc acc          15498
Arg Phe Pro Glu Asn Gln Ile Leu Ile Arg Pro Pro Ala Pro Thr
2120                2125                2130 att acc acc gtt agt gaa aac gtt cct gct ctc aca gat cac ggg      15543
Ile Thr Thr Val Ser Glu Asn Val Pro Ala Leu Thr Asp His Gly
2135                2140                2145 acc ctg ccg ttg cgc agc agt atc cgg gga gtc cag cgc gtg acc      15588
Thr Leu Pro Leu Arg Ser Ser Ile Arg Gly Val Gln Arg Val Thr
2150                2155                2160 gtt act gac gcc aga cgc cgc acc tgc ccc tac gtc tac aag gcc      15633
Val Thr Asp Ala Arg Arg Arg Thr Cys Pro Tyr Val Tyr Lys Ala
2165                2170                2175 ctg ggc ata gtc gcg ccg cgc gtc ctt tca agc cgc act ttc          15675
Leu Gly Ile Val Ala Pro Arg Val Leu Ser Ser Arg Thr Phe
2180                2185                2190 taaaaaa atg tcc att ctc atc tca ccc agt aat aac acc ggt tgg      15721
        Met Ser Ile Leu Ile Ser Pro Ser Asn Asn Thr Gly Trp
        2195                2200                2205 ggg ctg cgc aca ccc acc agg atg tac gga ggc gct cgc aaa cgg      15766
Gly Leu Arg Thr Pro Thr Arg Met Tyr Gly Gly Ala Arg Lys Arg
2210                2215                2220 tct acc cag cac cct gtg cgt gtg cgc ggg cat ttc cgc gct ccc      15811
Ser Thr Gln His Pro Val Arg Val Arg Gly His Phe Arg Ala Pro
2225                2230                2235 tgg ggc gcc ctc aag ggc cgt act cgc act cgg acc acc gtc gat      15856
Trp Gly Ala Leu Lys Gly Arg Thr Arg Thr Arg Thr Thr Val Asp
2240                2245                2250 gat gtg atc gac cag gtg gtt gca gat gct cgt aat tat act cct      15901
Asp Val Ile Asp Gln Val Val Ala Asp Ala Arg Asn Tyr Thr Pro
2255                2260                2265 gct gca cct gca tct act gtg gat gca gtt att gac agc gtg gtg      15946
Ala Ala Pro Ala Ser Thr Val Asp Ala Val Ile Asp Ser Val Val
2270                2275                2280 gct gac gct cgc gag tat gct cgc cgg aag agc agg cga aga cgc      15991
Ala Asp Ala Arg Glu Tyr Ala Arg Arg Lys Ser Arg Arg Arg Arg
2285                2290                2295 att gcc agg cgc cac cgg gct acc ccc gct atg cga gct gca aga      16036
Ile Ala Arg Arg His Arg Ala Thr Pro Ala Met Arg Ala Ala Arg
2300                2305                2310 gct ctg ctg cgg aga gcc aaa cgc gtg ggg cga aga gcc atg ctt      16081
Ala Leu Leu Arg Arg Ala Lys Arg Val Gly Arg Arg Ala Met Leu
2315                2320                2325
```

```
aga gcg gcc agg cgc gcg gct tca ggt gcc agc gca ggc aga tcc      16126
Arg Ala Ala Arg Arg Ala Ala Ser Gly Ala Ser Ala Gly Arg Ser
            2330                2335                2340 cgc agg cgc gcg gcc acg gcg gca gca gcg gcc att gcc aac atg      16171
Arg Arg Arg Ala Ala Thr Ala Ala Ala Ala Ala Ile Ala Asn Met
            2345                2350                2355 gcc caa ccg cga aga ggc aat gtg tac tgg gtg cgc gat gcc act      16216
Ala Gln Pro Arg Arg Gly Asn Val Tyr Trp Val Arg Asp Ala Thr
            2360                2365                2370 acc ggc cag cgc gtg ccc gtg cgc acc cgt ccc cct cgc act          16258
Thr Gly Gln Arg Val Pro Val Arg Thr Arg Pro Pro Arg Thr
            2375                2380                2385 tagaagatac tgagcagtct ccgatgttgt gtcccagcgg cgagg atg tcc aag cgc   16315
                                              Met Ser Lys Arg aaa tac aag gaa gag atg ctc cag gtc atc gcg cct gaa atc tac      16360
Lys Tyr Lys Glu Glu Met Leu Gln Val Ile Ala Pro Glu Ile Tyr
2390            2395                2400 ggt cca ccg gtg aag gat gaa aaa aag ccc cgc aaa atc aag cgg      16405
Gly Pro Pro Val Lys Asp Glu Lys Lys Pro Arg Lys Ile Lys Arg
2405            2410                2415 gtc aaa aag gac aaa aag gaa gaa gat ggc gat gat ggg ctg gtg      16450
Val Lys Lys Asp Lys Lys Glu Glu Asp Gly Asp Asp Gly Leu Val
2420            2425                2430 gag ttt gtg cgc gag ttc gct cca agg cgg cgc gta cag tgg cgc      16495
Glu Phe Val Arg Glu Phe Ala Pro Arg Arg Arg Val Gln Trp Arg
2435            2440                2445 ggg cgc aaa gtg cgg ccg gtg ctg aga cca gga acc acg gtg gtc      16540
Gly Arg Lys Val Arg Pro Val Leu Arg Pro Gly Thr Thr Val Val
2450            2455                2460 ttc acg ccc ggc gag cgc tcc agc act act ttt aaa cgc tcc tat      16585
Phe Thr Pro Gly Glu Arg Ser Ser Thr Thr Phe Lys Arg Ser Tyr
2465            2470                2475 gat gag gtg tac ggg gat gat gat att ctg gag cag gcg gcc gac      16630
Asp Glu Val Tyr Gly Asp Asp Asp Ile Leu Glu Gln Ala Ala Asp
2480            2485                2490 cgc ctg ggc gag ttt gct tat ggc aag cgc agc cgc tcc agt ccc      16675
Arg Leu Gly Glu Phe Ala Tyr Gly Lys Arg Ser Arg Ser Ser Pro
2495            2500                2505 aag gat gag gcg gtg tcc ata ccc ttg gat cat gga aat ccc acc      16720
Lys Asp Glu Ala Val Ser Ile Pro Leu Asp His Gly Asn Pro Thr
2510            2515                2520 cca agt cta aaa cca gtc acc ctg cag caa gtg cta ccc gtg cct      16765
Pro Ser Leu Lys Pro Val Thr Leu Gln Gln Val Leu Pro Val Pro
2525            2530                2535 cca cgg aga ggt gtc aag cga gag ggc gag gat ctg tat ccc acc      16810
Pro Arg Arg Gly Val Lys Arg Glu Gly Glu Asp Leu Tyr Pro Thr
2540            2545                2550 atg caa ctg atg gtg ccc aag cgc cag aag ctg gag gac gtg ctg      16855
Met Gln Leu Met Val Pro Lys Arg Gln Lys Leu Glu Asp Val Leu
2555            2560                2565 gag aaa atg aaa gtg gat ccc gat atc cag cct gaa gtt aaa gtc      16900
Glu Lys Met Lys Val Asp Pro Asp Ile Gln Pro Glu Val Lys Val
2570            2575                2580 aga ccc atc aag cag gtg gcg ccc ggt ctg gga gtg caa acc gtg      16945
Arg Pro Ile Lys Gln Val Ala Pro Gly Leu Gly Val Gln Thr Val
2585            2590                2595 gac atc aag att ccc acc gag tcc atg gaa gtc cag act gaa cct      16990
Asp Ile Lys Ile Pro Thr Glu Ser Met Glu Val Gln Thr Glu Pro
2600            2605                2610
```

```
gca  aag  ccc  gca  gcc  acc  tct  att  gag  gtg  cag  acg  gat  cct  tgg     17035
Ala  Lys  Pro  Ala  Ala  Thr  Ser  Ile  Glu  Val  Gln  Thr  Asp  Pro  Trp
2615                2620                     2625 ata  ccc  gcg  ccc  gtt  gca  acc  acc  gcc  agt  acc  gcc  cga  aga  ccc     17080
Ile  Pro  Ala  Pro  Val  Ala  Thr  Thr  Ala  Ser  Thr  Ala  Arg  Arg  Pro
2630                2635                     2640 cgg  cga  aag  tat  ggt  cct  gcg  agt  ctg  ctg  ttg  ccc  aac  tat  gct     17125
Arg  Arg  Lys  Tyr  Gly  Pro  Ala  Ser  Leu  Leu  Leu  Pro  Asn  Tyr  Ala
2645                2650                     2655 ctg  cac  cca  tcc  att  att  cca  act  ccg  ggt  tac  cga  ggc  act  cgc     17170
Leu  His  Pro  Ser  Ile  Ile  Pro  Thr  Pro  Gly  Tyr  Arg  Gly  Thr  Arg
2660                2665                     2670 tac  tac  cgc  agc  cgg  agc  acc  act  tcc  cgc  cgt  cgc  aaa  aca  cct     17215
Tyr  Tyr  Arg  Ser  Arg  Ser  Thr  Thr  Ser  Arg  Arg  Arg  Lys  Thr  Pro
2675                2680                     2685 gca  agc  cgc  agt  cgc  cgt  cgc  cgc  cgc  cgc  gcc  gcc  agc  aaa  ctg     17260
Ala  Ser  Arg  Ser  Arg  Arg  Arg  Arg  Arg  Arg  Ala  Ala  Ser  Lys  Leu
2690                2695                     2700 act  ccc  gcc  gct  ttg  gtg  cgg  agg  gtg  tat  cgc  gat  ggc  cgc  gca     17305
Thr  Pro  Ala  Ala  Leu  Val  Arg  Arg  Val  Tyr  Arg  Asp  Gly  Arg  Ala
2705                2710                     2715 gag  ccc  ctg  atg  ctg  ccg  cgc  gca  cgc  tac  cat  cca  agc  atc  acc     17350
Glu  Pro  Leu  Met  Leu  Pro  Arg  Ala  Arg  Tyr  His  Pro  Ser  Ile  Thr
2720                2725                     2730 act  taatgactgt  tgccgctgcc  tccttgcaga t  atg  gcc  ctc  act  tgc  cgc       17402
Thr                                        Met  Ala  Leu  Thr  Cys  Arg
2735                                                            2740 ctt  cgc  gtc  ccc  att  act  ggc  tac  cga  gga  aga  aac  tcg  cgc  cgt     17447
Leu  Arg  Val  Pro  Ile  Thr  Gly  Tyr  Arg  Gly  Arg  Asn  Ser  Arg  Arg
                    2745                2750                2755 aga  agg  atg  ttg  ggt  agc  ggg  atg  cgt  cgc  cac  agg  cgg  cgg  cgc     17492
Arg  Arg  Met  Leu  Gly  Ser  Gly  Met  Arg  Arg  His  Arg  Arg  Arg  Arg
          2760                2765                     2770 gct  atc  agc  aag  agg  ctg  ggg  ggt  ggc  ttt  ctg  acc  gct  ttg  att     17537
Ala  Ile  Ser  Lys  Arg  Leu  Gly  Gly  Gly  Phe  Leu  Thr  Ala  Leu  Ile
               2775                2780                     2785 ccc  att  atc  gcc  gcg  gcg  atc  ggg  gcg  gta  cca  ggc  ata  gct  tcc     17582
Pro  Ile  Ile  Ala  Ala  Ala  Ile  Gly  Ala  Val  Pro  Gly  Ile  Ala  Ser
               2790                2795                     2800 gtg  gcg  gtt  cag  gcc  tcg  cag  cgc  cac  tgacattgga aaacacttat             17629
Val  Ala  Val  Gln  Ala  Ser  Gln  Arg  His
               2805                2810 aaataaaata gaatggactc tgacgctcct ggtcctgtga ctatgttttt gtagag atg              17688
                                                                Met gaa  gac  atc  aat  ttt  tca  tcc  ctg  gct  ccg  cga  cac  ggc  acg  agg     17733
Glu  Asp  Ile  Asn  Phe  Ser  Ser  Leu  Ala  Pro  Arg  His  Gly  Thr  Arg
                    2815                2820                2825 ccg  tac  atg  ggc  acc  tgg  agc  gac  atc  ggc  acc  agc  caa  ctg  aac     17778
Pro  Tyr  Met  Gly  Thr  Trp  Ser  Asp  Ile  Gly  Thr  Ser  Gln  Leu  Asn
                    2830                2835                2840 ggg  ggc  gcc  ttc  aat  tgg  agc  agt  atc  tgg  agc  ggg  ctt  aaa  aat     17823
Gly  Gly  Ala  Phe  Asn  Trp  Ser  Ser  Ile  Trp  Ser  Gly  Leu  Lys  Asn
                    2845                2850                2855 ttt  ggc  tct  gcc  ata  aaa  acc  tat  ggg  aac  aaa  gct  tgg  aac  agc     17868
Phe  Gly  Ser  Ala  Ile  Lys  Thr  Tyr  Gly  Asn  Lys  Ala  Trp  Asn  Ser
                    2860                2865                2870 agc  aca  ggg  cag  gca  cta  agg  aat  aag  ctt  aaa  gag  cag  aac  ttc     17913
Ser  Thr  Gly  Gln  Ala  Leu  Arg  Asn  Lys  Leu  Lys  Glu  Gln  Asn  Phe
                    2875                2880                2885
```

| | |
|---|---|
| cag cag aag gtg gtc gat ggg atc gcc tct ggc atc aat ggg gta<br>Gln Gln Lys Val Val Asp Gly Ile Ala Ser Gly Ile Asn Gly Val<br>2890                    2895                    2900 | 17958 |
| gtg gat ctg gcc aac cag gcc gtg cag aaa cag ata aac agc cgc<br>Val Asp Leu Ala Asn Gln Ala Val Gln Lys Gln Ile Asn Ser Arg<br>2905                    2910                    2915 | 18003 |
| ctg gac ccg ccg ccc gca gcc cct ggc gaa atg gaa gtg gag gaa<br>Leu Asp Pro Pro Pro Ala Ala Pro Gly Glu Met Glu Val Glu Glu<br>2920                    2925                    2930 | 18048 |
| gag ctc cct ccc ctg gaa aag cgg gga gac aag cgc ccg cgt ccc<br>Glu Leu Pro Pro Leu Glu Lys Arg Gly Asp Lys Arg Pro Arg Pro<br>2935                    2940                    2945 | 18093 |
| gat atg gag gag acg ctg gtg acg cgg gga gac gaa ccg cct cca<br>Asp Met Glu Glu Thr Leu Val Thr Arg Gly Asp Glu Pro Pro Pro<br>2950                    2955                    2960 | 18138 |
| tat gag gag gcg ata aag ctt gga atg ccc act acc agg cct ata<br>Tyr Glu Glu Ala Ile Lys Leu Gly Met Pro Thr Thr Arg Pro Ile<br>2965                    2970                    2975 | 18183 |
| gct ccc atg gcc acc ggg gta atg aaa cct tct cag tcg cat cga<br>Ala Pro Met Ala Thr Gly Val Met Lys Pro Ser Gln Ser His Arg<br>2980                    2985                    2990 | 18228 |
| ccc gcc acc ttg gac ttg cct cct gcc cct gct gct gca gcg ccc<br>Pro Ala Thr Leu Asp Leu Pro Pro Ala Pro Ala Ala Ala Ala Pro<br>2995                    3000                    3005 | 18273 |
| gct cca aag cct gtc gct acc ccg aag ccc acc tcc gta cag ccc<br>Ala Pro Lys Pro Val Ala Thr Pro Lys Pro Thr Ser Val Gln Pro<br>3010                    3015                    3020 | 18318 |
| gtc gcc gta gcc aga ccg cgt cct ggg ggc act ccg cgc ccg aat<br>Val Ala Val Ala Arg Pro Arg Pro Gly Gly Thr Pro Arg Pro Asn<br>3025                    3030                    3035 | 18363 |
| gca aac tgg cag agt act ctg aac agc atc gtg ggt ttg ggc gtg<br>Ala Asn Trp Gln Ser Thr Leu Asn Ser Ile Val Gly Leu Gly Val<br>3040                    3045                    3050 | 18408 |
| cag agt gta aag cgc cgt cgc tgc tat    taaatatgga gtagcgctta<br>Gln Ser Val Lys Arg Arg Arg Cys Tyr<br>3055                    3060 | 18455 |
| acttgcttgt ctgtgtgtat gtgtcatcac cacgccgccg cagcagcaga ggagaaagga | 18515 |
| agaggtcgcg cgccgaggct gagttgcttt caag atg gcc acc cca tcg atg<br>                                                Met Ala Thr Pro Ser Met<br>                                                          3065 | 18567 |
| ctg ccc cag tgg gca tac atg cac atc gcc gga cag gat gct tcg<br>Leu Pro Gln Trp Ala Tyr Met His Ile Ala Gly Gln Asp Ala Ser<br>3070                    3075                    3080 | 18612 |
| gag tac ctg agt ccg ggt ctg gtg cag ttc gcc cgt gcc aca gat<br>Glu Tyr Leu Ser Pro Gly Leu Val Gln Phe Ala Arg Ala Thr Asp<br>3085                    3090                    3095 | 18657 |
| acc tac ttc aat ctg gga aac aag ttt agg aac ccc acc gtg gct<br>Thr Tyr Phe Asn Leu Gly Asn Lys Phe Arg Asn Pro Thr Val Ala<br>3100                    3105                    3110 | 18702 |
| ccc acc cac gat gtg acc acc gac cga agc cag cgg ctg atg ctg<br>Pro Thr His Asp Val Thr Thr Asp Arg Ser Gln Arg Leu Met Leu<br>3115                    3120                    3125 | 18747 |
| cgc ttt gtg ccc gtt gat cgg gag gac aat act tac tct tac aaa<br>Arg Phe Val Pro Val Asp Arg Glu Asp Asn Thr Tyr Ser Tyr Lys<br>3130                    3135                    3140 | 18792 |
| gtt cgc tac aca ctg gct gtg gga gac aac aga gtg ctg gat atg<br>Val Arg Tyr Thr Leu Ala Val Gly Asp Asn Arg Val Leu Asp Met<br>3145                    3150                    3155 | 18837 |

```
gcc agc acc ttc ttt gac atc agg ggg gtg ctt gac aga ggt ccc      18882
Ala Ser Thr Phe Phe Asp Ile Arg Gly Val Leu Asp Arg Gly Pro
            3160            3165                3170 agt ttc aaa ccc tac tct ggg aca gca tac aat tcc ctg gcc cct      18927
Ser Phe Lys Pro Tyr Ser Gly Thr Ala Tyr Asn Ser Leu Ala Pro
        3175            3180                3185 aag gga gct cct aat act agt cag tgg ata gtt aca act aat ggg      18972
Lys Gly Ala Pro Asn Thr Ser Gln Trp Ile Val Thr Thr Asn Gly
    3190            3195                3200 caa gat aat gca gta act acc act aca aac aca ttt ggc att gct      19017
Gln Asp Asn Ala Val Thr Thr Thr Asn Thr Phe Gly Ile Ala
3205                3210                3215 tcc atg aaa gga gac aat att act aaa gaa ggt tta gaa att gga      19062
Ser Met Lys Gly Asp Asn Ile Thr Lys Glu Gly Leu Glu Ile Gly
            3220            3225                3230 aaa gat att act gaa gaa gat aaa ccc atc tat gcc gat aaa aca      19107
Lys Asp Ile Thr Glu Glu Asp Lys Pro Ile Tyr Ala Asp Lys Thr
        3235            3240                3245 tat cag cca gaa cct caa gtt gga gaa gaa tca tgg act gat acc      19152
Tyr Gln Pro Glu Pro Gln Val Gly Glu Glu Ser Trp Thr Asp Thr
    3250            3255                3260 gat gga aca aat gaa aag ttt ggc ggt aga gcg ctt aaa ccc gct      19197
Asp Gly Thr Asn Glu Lys Phe Gly Gly Arg Ala Leu Lys Pro Ala
3265                3270                3275 acc aac atg aaa cca tgc tat ggg tca ttt gca aga cct aca aac      19242
Thr Asn Met Lys Pro Cys Tyr Gly Ser Phe Ala Arg Pro Thr Asn
            3280            3285                3290 ata aaa ggt ggt caa gct aaa aat aga aaa gta aag ccg aca acc      19287
Ile Lys Gly Gly Gln Ala Lys Asn Arg Lys Val Lys Pro Thr Thr
        3295            3300                3305 gag gga ggg gtt gaa act gag gaa ccg gat att gat atg gaa ttt      19332
Glu Gly Gly Val Glu Thr Glu Glu Pro Asp Ile Asp Met Glu Phe
    3310            3315                3320 ttc gat ggt aga gat gct gct gaa gga gct tta tcg cct gaa att      19377
Phe Asp Gly Arg Asp Ala Ala Glu Gly Ala Leu Ser Pro Glu Ile
3325                3330                3335 gtg ctt tac aca gaa aat gta aat ttg gaa act cca gac acc cat      19422
Val Leu Tyr Thr Glu Asn Val Asn Leu Glu Thr Pro Asp Thr His
            3340            3345                3350 gtg gta tac aaa cca gga act tca gat gat aac tct cat gca aat      19467
Val Val Tyr Lys Pro Gly Thr Ser Asp Asp Asn Ser His Ala Asn
        3355            3360                3365 ttg ggt caa caa gct atg ccc aac aga ccc aat tac att ggc ttc      19512
Leu Gly Gln Gln Ala Met Pro Asn Arg Pro Asn Tyr Ile Gly Phe
    3370            3375                3380 aga gac aac ttt gtt gga ctc ttg tac tac aac agc act ggc aac      19557
Arg Asp Asn Phe Val Gly Leu Leu Tyr Tyr Asn Ser Thr Gly Asn
3385                3390                3395 atg gga gtg ttg gca ggt caa gca tca caa cta aat gca gta gtt      19602
Met Gly Val Leu Ala Gly Gln Ala Ser Gln Leu Asn Ala Val Val
            3400            3405                3410 gac ttg cag gac aga aac act gaa ctg tcc tat cag ctt ttg ctt      19647
Asp Leu Gln Asp Arg Asn Thr Glu Leu Ser Tyr Gln Leu Leu Leu
        3415            3420                3425 gat tct ctt ggg gac aga acc aga tac ttc agc atg tgg aat cag      19692
Asp Ser Leu Gly Asp Arg Thr Arg Tyr Phe Ser Met Trp Asn Gln
    3430            3435                3440 gcc gtg gat agt tat gat cct gat gtt cgc att att gaa aat cat      19737
Ala Val Asp Ser Tyr Asp Pro Asp Val Arg Ile Ile Glu Asn His
3445                3450                3455
```

```
ggt atc gag gat gaa cta ccc aac tac tgt ttt cct ctg gat ggc      19782
Gly Ile Glu Asp Glu Leu Pro Asn Tyr Cys Phe Pro Leu Asp Gly
        3460            3465            3470 ata gga cca ggg aac tca tat caa ggc atc aag gct aaa aac ggt      19827
Ile Gly Pro Gly Asn Ser Tyr Gln Gly Ile Lys Ala Lys Asn Gly
        3475            3480            3485 gat aat aat gga tgg gaa aaa gat act aat gct tct act gct aat      19872
Asp Asn Asn Gly Trp Glu Lys Asp Thr Asn Ala Ser Thr Ala Asn
        3490            3495            3500 gaa ata gcc ata gga aac aac ctg gct atg gaa att aat atc cag      19917
Glu Ile Ala Ile Gly Asn Asn Leu Ala Met Glu Ile Asn Ile Gln
        3505            3510            3515 gct aac ctt tgg aga agt ttt ctg tac tcc aac gtg gct ttg tac      19962
Ala Asn Leu Trp Arg Ser Phe Leu Tyr Ser Asn Val Ala Leu Tyr
        3520            3525            3530 ctt cca gac gct tac aag tac acg cca gcc aac att act ttg cct      20007
Leu Pro Asp Ala Tyr Lys Tyr Thr Pro Ala Asn Ile Thr Leu Pro
        3535            3540            3545 gcc aat acc aac acc tat gaa tac atg aac ggg cga gtg gtg gca      20052
Ala Asn Thr Asn Thr Tyr Glu Tyr Met Asn Gly Arg Val Val Ala
        3550            3555            3560 cca tct ttg gtt gat tcg tac atc aac att gga gcc agg tgg tct      20097
Pro Ser Leu Val Asp Ser Tyr Ile Asn Ile Gly Ala Arg Trp Ser
        3565            3570            3575 ctt gac cca atg gac aat gtg aac ccc ttc aat cac cac cga aac      20142
Leu Asp Pro Met Asp Asn Val Asn Pro Phe Asn His His Arg Asn
        3580            3585            3590 gct ggg ctg cgt tac aga tcc atg ctt ctg ggc aat ggt cgc tat      20187
Ala Gly Leu Arg Tyr Arg Ser Met Leu Leu Gly Asn Gly Arg Tyr
        3595            3600            3605 gtg cct ttc cac atc caa gtg cct cag aaa ttc ttt gct atc aag      20232
Val Pro Phe His Ile Gln Val Pro Gln Lys Phe Phe Ala Ile Lys
        3610            3615            3620 aac ctg ctt ctc ctc cca ggc tcc tat acc tat gag tgg aac ttc      20277
Asn Leu Leu Leu Leu Pro Gly Ser Tyr Thr Tyr Glu Trp Asn Phe
        3625            3630            3635 aga aag gat gtg aac atg gtc ctg cag agt tcc ctt ggc aat gat      20322
Arg Lys Asp Val Asn Met Val Leu Gln Ser Ser Leu Gly Asn Asp
        3640            3645            3650 ctc aga act gat gga gcc agc atc agt ttt act agc atc aac ctc      20367
Leu Arg Thr Asp Gly Ala Ser Ile Ser Phe Thr Ser Ile Asn Leu
        3655            3660            3665 tat gcc acc ttc ttc ccc atg gct cac aat act gct tcc acc ctt      20412
Tyr Ala Thr Phe Phe Pro Met Ala His Asn Thr Ala Ser Thr Leu
        3670            3675            3680 gaa gcc atg ctg cgc aat gac aca aat gac cag tca ttc aat gac      20457
Glu Ala Met Leu Arg Asn Asp Thr Asn Asp Gln Ser Phe Asn Asp
        3685            3690            3695 tac ctt tct gca gct aac atg ctc tac cct att cca gcc aat gca      20502
Tyr Leu Ser Ala Ala Asn Met Leu Tyr Pro Ile Pro Ala Asn Ala
        3700            3705            3710 acc aac att ccc att tcc att ccc tct cgc aac tgg gct gcc ttt      20547
Thr Asn Ile Pro Ile Ser Ile Pro Ser Arg Asn Trp Ala Ala Phe
        3715            3720            3725 agg ggt tgg tcc ttc acc aga ctc aaa aca aag gaa aca ccc tct      20592
Arg Gly Trp Ser Phe Thr Arg Leu Lys Thr Lys Glu Thr Pro Ser
        3730            3735            3740 ttg gga tca ggc ttt gat ccc tac ttt gtt tac tct ggc tcc att      20637
Leu Gly Ser Gly Phe Asp Pro Tyr Phe Val Tyr Ser Gly Ser Ile
```

```
                  3745                3750                3755
ccc tac ctg gat  ggc acc ttc tac  ctc aac cac act  ttc aag aag       20682
Pro Tyr Leu Asp  Gly Thr Phe Tyr  Leu Asn His Thr  Phe Lys Lys
        3760                3765                3770 gtg tcc atc atg  ttt gac tcc tca  gtc agc tgg cca  ggc aat gac       20727
Val Ser Ile Met  Phe Asp Ser Ser  Val Ser Trp Pro  Gly Asn Asp
        3775                3780                3785 aga ttg cta act  cca aat gag ttt  gaa atc aag cgc  act gtg gat       20772
Arg Leu Leu Thr  Pro Asn Glu Phe  Glu Ile Lys Arg  Thr Val Asp
        3790                3795                3800 gga gaa ggg tac  aat gtg gct caa  tgc aac atg acc  aag gat tgg       20817
Gly Glu Gly Tyr  Asn Val Ala Gln  Cys Asn Met Thr  Lys Asp Trp
        3805                3810                3815 ttc ctg gtt cag  atg ctt gcc aac  tat aac att ggc  tac cag ggc       20862
Phe Leu Val Gln  Met Leu Ala Asn  Tyr Asn Ile Gly  Tyr Gln Gly
        3820                3825                3830 ttc tac atc cca  gag ggg tac aag  gat cgc atg tac  tcc ttc ttc       20907
Phe Tyr Ile Pro  Glu Gly Tyr Lys  Asp Arg Met Tyr  Ser Phe Phe
        3835                3840                3845 aga aac ttc cag  ccc atg agc aga  cag gtg gtt gat  gag gtg aac       20952
Arg Asn Phe Gln  Pro Met Ser Arg  Gln Val Val Asp  Glu Val Asn
        3850                3855                3860 tac acc gat tac  aaa gcc gtc act  cta gca tac caa  cac aac aac       20997
Tyr Thr Asp Tyr  Lys Ala Val Thr  Leu Ala Tyr Gln  His Asn Asn
        3865                3870                3875 tct ggc ttt gtg  ggt tac ctt gcg  ccc act atg agg  cag gga gaa       21042
Ser Gly Phe Val  Gly Tyr Leu Ala  Pro Thr Met Arg  Gln Gly Glu
        3880                3885                3890 cct tac ccc gct  aac tac cca tac  ccc cta atc gga  acc act gct       21087
Pro Tyr Pro Ala  Asn Tyr Pro Tyr  Pro Leu Ile Gly  Thr Thr Ala
        3895                3900                3905 gtt aag agt gtt  acc cag aaa aag  ttc ctg tgc gac  agg acc atg       21132
Val Lys Ser Val  Thr Gln Lys Lys  Phe Leu Cys Asp  Arg Thr Met
        3910                3915                3920 tgg cgc atc ccc  ttc tcc agc aac  ttc atg tcc atg  ggt gcc ctt       21177
Trp Arg Ile Pro  Phe Ser Ser Asn  Phe Met Ser Met  Gly Ala Leu
        3925                3930                3935 acc gac ctg gga  cag aac atg ctt  tat gcc aac tca  gcc cat gcg       21222
Thr Asp Leu Gly  Gln Asn Met Leu  Tyr Ala Asn Ser  Ala His Ala
        3940                3945                3950 ctg gac atg act  ttt gag gtg gat  ccc atg gat gag  ccc acc ctg       21267
Leu Asp Met Thr  Phe Glu Val Asp  Pro Met Asp Glu  Pro Thr Leu
        3955                3960                3965 ctt tat gtt ctt  ttc gaa gtc ttc  gac gtg gtc aga  gtg cac cag       21312
Leu Tyr Val Leu  Phe Glu Val Phe  Asp Val Val Arg  Val His Gln
        3970                3975                3980 cca cac cgc ggc  gtc atc gag gct  gtc tac ctg cgt  acc cca ttc       21357
Pro His Arg Gly  Val Ile Glu Ala  Val Tyr Leu Arg  Thr Pro Phe
        3985                3990                3995 tca gct ggt aac  gcc acc aca taagaagctt cttgcttct gcaagcagct gcc    21411
Ser Ala Gly Asn  Ala Thr Thr
        4000 atg gcc tgt ggg  tcc ggc aac  gga tcc agc gag  caa gag ctc agg      21456
Met Ala Cys Gly  Ser Gly Asn  Gly Ser Ser Glu  Gln Glu Leu Arg
        4005            4010                4015 gcc att gct aga  gac ctg ggc  tgc gga ccc tat  ttc ctt gga acc      21501
Ala Ile Ala Arg  Asp Leu Gly  Cys Gly Pro Tyr  Phe Leu Gly Thr
        4020            4025                4030 ttt gat aaa cgc  ttc ccg ggg   ttc atg gcc ccc  aac aag ctc gcc    21546
```

|     |     |     |     |     |     |     |     |     |     |     |     |     |     |
| --- | --- | --- | --- | --- | --- | --- | --- | --- | --- | --- | --- | --- | --- |
|     | Phe | Asp | Lys | Arg | Phe | Pro | Gly | Phe | Met | Ala | Pro | Asn | Lys | Leu | Ala |
|     | 4035 |     |     |     | 4040 |     |     |     |     | 4045 |     |     |     |     |

```
tgc gcc att gtc aac acg gcc ggt cgc gag acg ggg gga gag cac         21591
Cys Ala Ile Val Asn Thr Ala Gly Arg Glu Thr Gly Gly Glu His
    4050            4055                4060 tgg ctg gct ttt ggt tgg aac ccg cgc tcc aac acc tgc tac ctt         21636
Trp Leu Ala Phe Gly Trp Asn Pro Arg Ser Asn Thr Cys Tyr Leu
    4065            4070                4075 ttt gat cct ttt ggc ttc tcg gac gag cgc ctc aag caa atc tac         21681
Phe Asp Pro Phe Gly Phe Ser Asp Glu Arg Leu Lys Gln Ile Tyr
    4080            4085                4090 cag ttt gag tat gag ggg ctt ctg cgc cgc agt gcc cta gct acc         21726
Gln Phe Glu Tyr Glu Gly Leu Leu Arg Arg Ser Ala Leu Ala Thr
    4095            4100                4105 aag gac cgc tgt atc acc ctg gaa aag tca acc cag acc gtg cag         21771
Lys Asp Arg Cys Ile Thr Leu Glu Lys Ser Thr Gln Thr Val Gln
    4110            4115                4120 ggc ccg cgc tcc gca gcc tgt gga ctg ttt tgc tgc atg ttc ctc         21816
Gly Pro Arg Ser Ala Ala Cys Gly Leu Phe Cys Cys Met Phe Leu
    4125            4130                4135 cac gct ttt gtg cac tgg cca gac cgc ccc atg gac gga aac ccc         21861
His Ala Phe Val His Trp Pro Asp Arg Pro Met Asp Gly Asn Pro
    4140            4145                4150 acc atg aag ttg ctg act ggg gtg ccc aac agc atg ctc caa tcg         21906
Thr Met Lys Leu Leu Thr Gly Val Pro Asn Ser Met Leu Gln Ser
    4155            4160                4165 ccc caa gtc cag ccc acc ctg cgc cac aac cag gag gcg ctc tac         21951
Pro Gln Val Gln Pro Thr Leu Arg His Asn Gln Glu Ala Leu Tyr
    4170            4175                4180 cgc ttc cta aac tcc cac tca tct tac ttt cgt tct cac cgc gcg         21996
Arg Phe Leu Asn Ser His Ser Ser Tyr Phe Arg Ser His Arg Ala
    4185            4190                4195 cgc atc gaa aag gcc acc gcg ttt gac cgt atg gat atg caa             22038
Arg Ile Glu Lys Ala Thr Ala Phe Asp Arg Met Asp Met Gln
    4200            4205                4210 taataagtca tgtaaaaccg tgttcaaata aacagcactt tattttttac atgcactgtg   22098
gctctgggtt gctcattcat tcatcattca ctcagaagtc gaaggggttc tggcgggaat   22158
cagcgtgacc cgctggcagg gatacgttgc ggaactggaa cctgttctgc cacttgaact   22218
cggggatcac cagcttggga actgggatct cggggaaggt gtcttgccac agctttctgg   22278
ttagttgcag agcaccaagc aggtcaggag cagagatctt gaaatcacag ttggggccag   22338
cattttgggc acgggagttg cggtacactg ggttgcagca ctggacacc atcagggcgg    22398 ggtgtctcac gctcgccagc acggtcgggt cgctgatggt agtcacatcc aagtcttcag   22458
cattggccat tccaaagggg gtcatcttac aggtctgcct gcccatcacg ggagcgcagc   22518
cgggcttgtg gttgcaatcg cagcgaatgg ggatcagcat catcctggcc tggtcggggg   22578
ttatccctgg atacaccgcc ttcataaagg cttcgtactg cttgaaagct tcctgcgcct   22638
tgcttccctc ggtgtagaac atcccacagg acttgctgga aaattgatta gtagcacagt   22698
tggcatcatt cacacagcag cgggcatcgt tgttggccag ctggaccaca ttcctgcccc   22758
agcggttctg ggtgatcttg gctcggtctg ggttctcctt catcgcgcgc tgcccgttct   22818
cgctcgccac atccatctcg atgatgtgat ccttctggat catgatagtg ccatgcaggc   22878
atttcacctt gccttcataa tcggtgcagc catgagccca cagagcgcac ccggtgcact   22938
cccaattgtt gtgggcgatc tcagaataag aatgcaccaa tccctgcatg aatcttccca   22998
```

| | |
|---|---|
| tcatgctggt gagggtctttt atgctggtaa atgtcagcgg gatgccacgg tgctcctcgt | 23058 |
| tcacatactg gtggcagata cgcctgtact gctcgtgctg ctcgggcatc agcttgaaag | 23118 |
| aggttctcag gtcattatcc agcctgtacc tctccattag cacggccatt acttccatgc | 23178 |
| ccttctccca ggcagagacc aagggcaggc tcatgggatt cctaacagca atagcagcag | 23238 |
| acgcagctcc tttagccaga gggtcattct tgtcaatctt ctcaacactt ctcttgccat | 23298 |
| ccttctcagt gatgcgcact gggggtagc tgaagcccac ggccaccagc tccgcctgtt | 23358 |
| ctctttcttc ttcgctgtcc tggctgatgt cttgcaaagg acatgcttg gtcttcctgg | 23418 |
| gcttcttctt gggagggatc ggggagggc tgttgctccg ctccggagac agggaggacc | 23478 |
| gcgaagtttc gctcaccagt accacctggc tctcggtaga agaaccggac cccacgcggc | 23538 |
| ggtaggtgtt cctcttcggg ggcagaggtg gaggcgactg cgatgactg cggtccggcc | 23598 |
| tgggaggcgg atggctggca gagcctcttc cgcgttcggg ggtgtgctcc cggtggcggt | 23658 |
| cgcttgactg atttcctccg cggctggcca ttgtgttctc ctaggcagag aaacaacaga | 23718 |

```
c atg gag act  cag  cca tcg ctg cca  aca ccg ctg caa gcg  cca tca       23764
  Met Glu Thr  Gln  Pro Ser Leu Pro  Thr Pro Leu Gln Ala  Pro Ser
      4215          4220                 4225 cac ctc gcc  ccc agc agc gac gag  gag gag agc tta acc  acc cca           23809
His Leu Ala  Pro Ser Ser Asp Glu  Glu Glu Ser Leu Thr  Thr Pro
      4230                 4235                 4240 cca ccc agt  ccc gcc acc acc acc  tct acc cta gag gat  gag gag           23854
Pro Pro Ser  Pro Ala Thr Thr Thr  Ser Thr Leu Glu Asp  Glu Glu
      4245                 4250                 4255 gag gtc gac  gca ccc cag gag atg  cag gat atg gag gat  gag aaa           23899
Glu Val Asp  Ala Pro Gln Glu Met  Gln Asp Met Glu Asp  Glu Lys
      4260                 4265                 4270 gcg gaa gag  att gag gca gat gtc  gag cag gac ccg ggc  tat gtg           23944
Ala Glu Glu  Ile Glu Ala Asp Val  Glu Gln Asp Pro Gly  Tyr Val
      4275                 4280                 4285 aca ccg gcg  gag cac gag gag gag  ctg aga cgc ttt cta  gac aga           23989
Thr Pro Ala  Glu His Glu Glu Glu  Leu Arg Arg Phe Leu  Asp Arg
      4290                 4295                 4300 gag gat gac  aac cgc cca gag cag  aaa gca gat ggc gat  cac cag           24034
Glu Asp Asp  Asn Arg Pro Glu Gln  Lys Ala Asp Gly Asp  His Gln
      4305                 4310                 4315 gag gct ggg  ctc ggg gat cat gtc  gcc gaa tac ctc acc  ggg ctt           24079
Glu Ala Gly  Leu Gly Asp His Val  Ala Glu Tyr Leu Thr  Gly Leu
      4320                 4325                 4330 ggc ggg gag  gac gtg ctc ctc aaa  cat cta gca agg cag  tcg atc           24124
Gly Gly Glu  Asp Val Leu Leu Lys  His Leu Ala Arg Gln  Ser Ile
      4335                 4340                 4345 ata gtt aaa  gac gca ctg ctc gac  cgc acc gaa gtg ccc  atc agt           24169
Ile Val Lys  Asp Ala Leu Leu Asp  Arg Thr Glu Val Pro  Ile Ser
      4350                 4355                 4360 gtg gaa gag  ctc agc cgc gcc tac  gag ctc aac ctg ttc  tca cct           24214
Val Glu Glu  Leu Ser Arg Ala Tyr  Glu Leu Asn Leu Phe  Ser Pro
      4365                 4370                 4375 agg gtg ccc  ccc aaa cgt cag cca  aac ggc acc tgc gag  ccc aac           24259
Arg Val Pro  Pro Lys Arg Gln Pro  Asn Gly Thr Cys Glu  Pro Asn
      4380                 4385                 4390 cct cgc ctc  aac ttc tat ccg gcc  ttt gct gtc cca gaa  gtg ctt           24304
Pro Arg Leu  Asn Phe Tyr Pro Ala  Phe Ala Val Pro Glu  Val Leu
      4395                 4400                 4405 gct acc tac  cac atc ttt ttc aag  aac caa aag att cca  gtt tcc           24349
Ala Thr Tyr  His Ile Phe Phe Lys  Asn Gln Lys Ile Pro  Val Ser
      4410                 4415                 4420
```

-continued

| | | |
|---|---|---|
| tgc cgt gcc aac cgc acc cgc gcc gat gcc ctg ctc aac ttg gga<br>Cys Arg Ala Asn Arg Thr Arg Ala Asp Ala Leu Leu Asn Leu Gly<br>4425 4430 4435 | 24394 | |
| ccg ggt gct cgc tta cct gat ata gct tcc ttg gaa gag gtt cca<br>Pro Gly Ala Arg Leu Pro Asp Ile Ala Ser Leu Glu Glu Val Pro<br>4440 4445 4450 | 24439 | |
| aag atc ttc gag ggt ctg ggc agt gat gag act cgg gcc gca aat<br>Lys Ile Phe Glu Gly Leu Gly Ser Asp Glu Thr Arg Ala Ala Asn<br>4455 4460 4465 | 24484 | |
| gct ctg caa cag gga gag aat ggc atg gat gaa cat cac agc gcg<br>Ala Leu Gln Gln Gly Glu Asn Gly Met Asp Glu His His Ser Ala<br>4470 4475 4480 | 24529 | |
| ctg gtg gag ttg gag ggc gac aat gcc cgg ctt gca gta ctg aag<br>Leu Val Glu Leu Glu Gly Asp Asn Ala Arg Leu Ala Val Leu Lys<br>4485 4490 4495 | 24574 | |
| cgc agt atc gag gtc acc cat ttt gcc tac ccc gct gtt aac ctg<br>Arg Ser Ile Glu Val Thr His Phe Ala Tyr Pro Ala Val Asn Leu<br>4500 4505 4510 | 24619 | |
| ccc ccc aaa gtc atg agc gct gtc atg gac cag ctg ctc atc aag<br>Pro Pro Lys Val Met Ser Ala Val Met Asp Gln Leu Leu Ile Lys<br>4515 4520 4525 | 24664 | |
| cga gca agc ccc ctt tcc gaa gac cag aac atg cag gat cca gac<br>Arg Ala Ser Pro Leu Ser Glu Asp Gln Asn Met Gln Asp Pro Asp<br>4530 4535 4540 | 24709 | |
| gcc tct gac gag ggc aag ccg gtg gtc agt gac gag cag ctg tct<br>Ala Ser Asp Glu Gly Lys Pro Val Val Ser Asp Glu Gln Leu Ser<br>4545 4550 4555 | 24754 | |
| cgc tgg ctg gcc acc aac tcc ccg cga gac ttg gaa gag aga cgc<br>Arg Trp Leu Ala Thr Asn Ser Pro Arg Asp Leu Glu Glu Arg Arg<br>4560 4565 4570 | 24799 | |
| aag ctt atg atg gct gta gtg cta gtc act gtg gag ctg gag tgt<br>Lys Leu Met Met Ala Val Val Leu Val Thr Val Glu Leu Glu Cys<br>4575 4580 4585 | 24844 | |
| ctc cgc cgc ttt ttc acc gac cct gag acc ctg cgc aag ctt gag<br>Leu Arg Arg Phe Phe Thr Asp Pro Glu Thr Leu Arg Lys Leu Glu<br>4590 4595 4600 | 24889 | |
| gag aac ctg cac tat act ttc aga cat ggc ttc gtg cgc cag gca<br>Glu Asn Leu His Tyr Thr Phe Arg His Gly Phe Val Arg Gln Ala<br>4605 4610 4615 | 24934 | |
| tgc aag atc tcc aac gtg gag ctc acc aac ctg gtc tcc tac atg<br>Cys Lys Ile Ser Asn Val Glu Leu Thr Asn Leu Val Ser Tyr Met<br>4620 4625 4630 | 24979 | |
| ggc att ttg cat gag aac cgc ctg ggg caa agt gtg ctg cac acc<br>Gly Ile Leu His Glu Asn Arg Leu Gly Gln Ser Val Leu His Thr<br>4635 4640 4645 | 25024 | |
| acc ctg aag ggg gag gcc cgt cgc gac tac atc cgc gac tgt gtc<br>Thr Leu Lys Gly Glu Ala Arg Arg Asp Tyr Ile Arg Asp Cys Val<br>4650 4655 4660 | 25069 | |
| tac ctc tac ctc tgc cat acc tgg cag act ggc atg ggt gta tgg<br>Tyr Leu Tyr Leu Cys His Thr Trp Gln Thr Gly Met Gly Val Trp<br>4665 4670 4675 | 25114 | |
| cag cag tgt ttg gaa gag cag aac ctg aaa gag ctg gac aag ctc<br>Gln Gln Cys Leu Glu Glu Gln Asn Leu Lys Glu Leu Asp Lys Leu<br>4680 4685 4690 | 25159 | |
| ttg cag aga tcc ctc aaa gcc ctg tgg aca ggt ttt gac gag cgc<br>Leu Gln Arg Ser Leu Lys Ala Leu Trp Thr Gly Phe Asp Glu Arg<br>4695 4700 4705 | 25204 | |
| acc gtc gcc tca gac ctg gca gac atc atc ttt ccc gag cgt ctc<br>Thr Val Ala Ser Asp Leu Ala Asp Ile Ile Phe Pro Glu Arg Leu | 25249 | |

```
agg gtt act ctg cgc aac ggc ctg cct gac ttc atg agc cag agc      25294
Arg Val Thr Leu Arg Asn Gly Leu Pro Asp Phe Met Ser Gln Ser
        4725            4730            4735 atg ctt aac aac ttt cgc tct ttc atc ctg gaa cgc tcc ggt atc      25339
Met Leu Asn Asn Phe Arg Ser Phe Ile Leu Glu Arg Ser Gly Ile
        4740            4745            4750 ctg ccc gcc acc tgc tgc gcg ctg ccc tcc gac ttt gtg cct ctc      25384
Leu Pro Ala Thr Cys Cys Ala Leu Pro Ser Asp Phe Val Pro Leu
        4755            4760            4765 acc tac cgc gag tgc ccc ccg ccg cta tgg agc cac tgc tac ctg      25429
Thr Tyr Arg Glu Cys Pro Pro Pro Leu Trp Ser His Cys Tyr Leu
        4770            4775            4780 ttc cgc ctg gcc aac tac ctc tcc tac cac tcg gat gtg atc gag      25474
Phe Arg Leu Ala Asn Tyr Leu Ser Tyr His Ser Asp Val Ile Glu
        4785            4790            4795 gat gtg agc gga gac ggc ctg ctg gat tgc cac tgc cgc tgc aat      25519
Asp Val Ser Gly Asp Gly Leu Leu Asp Cys His Cys Arg Cys Asn
        4800            4805            4810 ctt tgc aca ccc cac cgt tcc ctt gcc tgc aac ccc cag ttg ctg      25564
Leu Cys Thr Pro His Arg Ser Leu Ala Cys Asn Pro Gln Leu Leu
        4815            4820            4825 agc gag acc cag atc atc ggc acc ttc gag ttg cag ggt ccc agc      25609
Ser Glu Thr Gln Ile Ile Gly Thr Phe Glu Leu Gln Gly Pro Ser
        4830            4835            4840 agt gaa ggc gag ggg tct tct ccg ggg cag agt ctg aaa ctg acc      25654
Ser Glu Gly Glu Gly Ser Ser Pro Gly Gln Ser Leu Lys Leu Thr
        4845            4850            4855 ccg ggg ctg tgg acc tcc gcc tac ctg cgc aag ttc gcc cct gaa      25699
Pro Gly Leu Trp Thr Ser Ala Tyr Leu Arg Lys Phe Ala Pro Glu
        4860            4865            4870 gac tac cac ccc tat gag atc agg ttc tat gag gac caa tca cag      25744
Asp Tyr His Pro Tyr Glu Ile Arg Phe Tyr Glu Asp Gln Ser Gln
        4875            4880            4885 ccg ccc aaa gcc gag ctc tca gcc tgc gtc atc act cag ggg gca      25789
Pro Pro Lys Ala Glu Leu Ser Ala Cys Val Ile Thr Gln Gly Ala
        4890            4895            4900 att ctc gcc caa ttg caa gcc atc caa aaa tcc cgc caa gaa ttt      25834
Ile Leu Ala Gln Leu Gln Ala Ile Gln Lys Ser Arg Gln Glu Phe
        4905            4910            4915 ctg ctg aaa aag ggg aac ggg gtc tac ctc gac ccc cag acc ggt      25879
Leu Leu Lys Lys Gly Asn Gly Val Tyr Leu Asp Pro Gln Thr Gly
        4920            4925            4930 gag gag ctc aac aca agg ttc cct cag gat gtc cca gcg ccg agg      25924
Glu Glu Leu Asn Thr Arg Phe Pro Gln Asp Val Pro Ala Pro Arg
        4935            4940            4945 aag caa gaa gtt gaa agt gca gct gcc gcc ccc aga gga cat gga      25969
Lys Gln Glu Val Glu Ser Ala Ala Ala Ala Pro Arg Gly His Gly
        4950            4955            4960 gga aga ctg gga cag tca ggc aga gga gga gga gat gga aga ttg      26014
Gly Arg Leu Gly Gln Ser Gly Arg Gly Gly Gly Asp Gly Arg Leu
        4965            4970            4975 gga cag cca ggc aga gga ggc gga cag cct gga gga aga cag ttt      26059
Gly Gln Pro Gly Arg Gly Gly Gly Gln Pro Gly Gly Arg Gln Phe
        4980            4985            4990 gga gga gga aga cga gga ggc aga gga ggt gga aga agc aac cgc      26104
Gly Gly Gly Arg Arg Gly Gly Arg Gly Gly Gly Arg Ser Asn Arg
        4995            5000            5005 cgc caa aca att gtc ctc ggc agc gga gac aag caa ggt ccc aga      26149
```

```
Arg Gln Thr Ile Val Leu Gly Ser     Gly Asp Lys Gln     Pro Arg
        5010            5015                5020 cag cag cag    cag cac ggc tac aat    ctc cgc tcc ggg tcg    ggg ggc       26194
Gln Gln Gln    Gln His Gly Tyr Asn    Leu Arg Ser Gly Ser    Gly Gly
        5025                5030                5035 cca gca gcg    tcc caa cag tagatgggac gagaccgggc gattcccgaa                26242
Pro Ala Ala    Ser Gln Gln
        5040 cccgaccacc gcttccaaga ccggtaagaa ggagcggcag ggatacaagt cctggcgggg          26302 gcataagaat gccatcatct cctgcttgca tgaatgcggg ggcaacatat ccttcacccg          26362 acgctacctg ctcttccacc acggggtgaa cttccccgc aatgtcttgc attactaccg           26422 tcacctccac agcccttact acagccagca agtcccgaca gcctcgacaa agaaagacag          26482 cagcagcagc ggggacctcc agcagaaaac cagcagcagc agttagaaaa tccagtgcag          26542 caggaggagg actgaggatc acagcgaacg agccagcgca gacccgagag ctgagaaaca          26602 ggatctttcc aaccctctat gccatcttcc agcagagtcg ggggcaagag caggaactga         26662 aagtaaaaaa ccgatctctg cgctcgctca cccgaagttg tttgtatcac aagagcgaag          26722 accaacttca gcgcactctc gaggacgccg aggctctctt caacaagtac tgcgcgctga          26782 ctcttaaaga gtagcccgcg cccgcgctcg ctcgaaaaag cgggaattac cgtcacccttt        26842 ggcacctgtc ctttgccctc gtc atg agt    aaa gaa att ccc acg    cct tac       26892
                         Met Ser    Lys Glu Ile Pro Thr    Pro Tyr
                         5045                              5050 atg tgg agc    tat cag ccc caa atg    gga ctg gca gca ggc    gcc tcc       26937
Met Trp Ser    Tyr Gln Pro Gln Met    Gly Leu Ala Ala Gly    Ala Ser
        5055                5060                5065 cag gac tac    tcc acc cgc atg aat    tgg ctc agc gcc ggc    ccc tcg       26982
Gln Asp Tyr    Ser Thr Arg Met Asn    Trp Leu Ser Ala Gly    Pro Ser
        5070                5075                5080 atg atc tca    cgg gtt aat gat ata    cga gct tac cga aac    cag tta       27027
Met Ile Ser    Arg Val Asn Asp Ile    Arg Ala Tyr Arg Asn    Gln Leu
        5085                5090                5095 ctc cta gaa    cag tca gct ctc acc    acc aca ccc cgc caa    cac ctt       27072
Leu Leu Glu    Gln Ser Ala Leu Thr    Thr Thr Pro Arg Gln    His Leu
        5100                5105                5110 aat ccc cgg    aat tgg ccc gcc gcc    ctg gtg tac cag gaa    act ccc       27117
Asn Pro Arg    Asn Trp Pro Ala Ala    Leu Val Tyr Gln Glu    Thr Pro
        5115                5120                5125 gct ccc acc    acc gta cta ctt cct    cga gac gcc cag gcc    gaa gtt       27162
Ala Pro Thr    Thr Val Leu Leu Pro    Arg Asp Ala Gln Ala    Glu Val
        5130                5135                5140 cag atg act    aac gca ggt gta cag    ctg gcg ggc ggt tcc    gcc ctg       27207
Gln Met Thr    Asn Ala Gly Val Gln    Leu Ala Gly Gly Ser    Ala Leu
        5145                5150                5155 tgt cgt cac    cgg cct cag cag agt    ata aaa cgc ctg gtg    atc aga       27252
Cys Arg His    Arg Pro Gln Gln Ser    Ile Lys Arg Leu Val    Ile Arg
        5160                5165                5170 ggc cga ggt    atc cag ctc aac gac    gag tcg gtg agc tct    tcg ctt       27297
Gly Arg Gly    Ile Gln Leu Asn Asp    Glu Ser Val Ser Ser    Ser Leu
        5175                5180                5185 ggt ctg cga    cca gac gga gtc ttc    cag atc gcc ggc tgt    ggg aga       27342
Gly Leu Arg    Pro Asp Gly Val Phe    Gln Ile Ala Gly Cys    Gly Arg
        5190                5195                5200 tct tcc ttc    act cct cgt cag gct    gtc ctg act ttg gag    agt tcg       27387
Ser Ser Phe    Thr Pro Arg Gln Ala    Val Leu Thr Leu Glu    Ser Ser
        5205                5210                5215
```

|  |  |
|---|---|
| tcc tcg cag ccc cgc tcg ggc ggc atc ggg act ctc cag ttt gtg<br>Ser Ser Gln Pro Arg Ser Gly Gly Ile Gly Thr Leu Gln Phe Val<br>    5220                         5225                     5230 | 27432 |
| gag gag ttt act ccc tct gtc tac ttc aac ccc ttc tcc ggc tct<br>Glu Glu Phe Thr Pro Ser Val Tyr Phe Asn Pro Phe Ser Gly Ser<br>    5235                               5240 | 27477 |
| ccc ggc cag tac ccg gac gag ttc ata ccg aac ttc gac gca atc<br>Pro Gly Gln Tyr Pro Asp Glu Phe Ile Pro Asn Phe Asp Ala Ile<br>    5250                              5255 | 27522 |
| agc gag tca gtg gat ggc tat gat tg atg tct ggt ggc gcg gct gag<br>Ser Glu Ser Val Asp Gly Tyr Asp   Met Ser Gly Gly Ala Ala Glu<br>    5265                         5270                           5275 | 27569 |
| tta gct cga ctg cga cat cta gac cac tgc cgc cgc ttt cgc tgt<br>Leu Ala Arg Leu Arg His Leu Asp His Cys Arg Arg Phe Arg Cys<br>    5280                         5285                     5290 | 27614 |
| ttc gcc cgg gaa ctc acc gag ttc atc tac ttc gaa ctc ccc gag<br>Phe Ala Arg Glu Leu Thr Glu Phe Ile Tyr Phe Glu Leu Pro Glu<br>    5295                         5300                     5305 | 27659 |
| gag cac cct cag gga ccg gcc cac gga gtg cgg att acc atc gaa<br>Glu His Pro Gln Gly Pro Ala His Gly Val Arg Ile Thr Ile Glu<br>    5310                         5315                     5320 | 27704 |
| ggg gga ata gac tct cgc ctg cat cgg atc ttc tgc cag cga ccc<br>Gly Gly Ile Asp Ser Arg Leu His Arg Ile Phe Cys Gln Arg Pro<br>    5325                         5330                     5335 | 27749 |
| gtg ctg atc gag cgc gac cag gga act aca aca gtc tcc atc tac<br>Val Leu Ile Glu Arg Asp Gln Gly Thr Thr Thr Val Ser Ile Tyr<br>    5340                         5345                     5350 | 27794 |
| tgc atc tgt aac cac ccc gga ttg cat gaa agc ctt tgc tgt ctt<br>Cys Ile Cys Asn His Pro Gly Leu His Glu Ser Leu Cys Cys Leu<br>    5355                         5360                     5365 | 27839 |
| att tgt gct gag ttt aat aaa aac tgagttaaga ctcacctttg<br>Ile Cys Ala Glu Phe Asn Lys Asn<br>    5370                         5375 | 27883 |
| gactaccgct tcttcaaccc ggactttaca acaccagcca gactctccgt tccagccaga | 27943 |
| agacccaggc ccttcctctg atccaggact ctaattctac ctccccagca ccatccccta | 28003 |
| ctaaccttcc cgaaactaac aacctcggag ctcagctgca accccgcttc tccagaagcc | 28063 |
| tcctttctgc caatactact actcccagaa ccggaggtga gctccgtggt ctccctactg | 28123 |
| acaaccctg ggtggtagcg ggttttgtag cgctaggagt agttgcgggt gggctggtgc | 28183 |
| ttatcctctg ctacctatac acaccttgct gtgcttattt agtagtattg tgctgctggt | 28243 |
| ttaagaa atg ggg gtc gta cta gta tcg ttt gct tta ctt tcg ctt ttg<br>         Met Gly Val Val Leu Val Ser Phe Ala Leu Leu Ser Leu Leu<br>                         5380                           5385 | 28292 |
| ggt ctg ggc tct gct acg cta aga aat cag cct ttg cta tta gat<br>Gly Leu Gly Ser Ala Thr Leu Arg Asn Gln Pro Leu Leu Leu Asp<br>5390                         5395                     5400 | 28337 |
| ccc gat gat gtt gat cca tgt ctg gac ttt gat cca gag aac tgc<br>Pro Asp Asp Val Asp Pro Cys Leu Asp Phe Asp Pro Glu Asn Cys<br>5405                         5410                     5415 | 28382 |
| aca ctc act ttt gca cct gaa aca agt cgc ttc tgt gga gtt gtt<br>Thr Leu Thr Phe Ala Pro Glu Thr Ser Arg Phe Cys Gly Val Val<br>5420                         5425                     5430 | 28427 |
| att agg tgc gga ttt gaa tgc agg tcc att gag att aca cac aat<br>Ile Arg Cys Gly Phe Glu Cys Arg Ser Ile Glu Ile Thr His Asn<br>5435                         5440                     5445 | 28472 |
| aac aaa act tgg aac aat acc tta ttc aca ata tgg caa cca gga<br>Asn Lys Thr Trp Asn Asn Thr Leu Phe Thr Ile Trp Gln Pro Gly<br>5450                         5455                     5460 | 28517 |

```
gat cct cag tgg tat act gtc tct gtc cgg ggt cct gac ggt tcc    28562
Asp Pro Gln Trp Tyr Thr Val Ser Val Arg Gly Pro Asp Gly Ser
5465                5470                5475 gcc cgc atg gct aat aac act ttc att ttt gct gaa atg tgc gat    28607
Ala Arg Met Ala Asn Asn Thr Phe Ile Phe Ala Glu Met Cys Asp
    5480                5485                5490 atg gcc atg ttc atg agc aga cag tat gac cta tgg cct ccc agc    28652
Met Ala Met Phe Met Ser Arg Gln Tyr Asp Leu Trp Pro Pro Ser
5495                5500                5505 aaa gag aac att gtg gca ttc tcc att gct tat tgc tta tgt act    28697
Lys Glu Asn Ile Val Ala Phe Ser Ile Ala Tyr Cys Leu Cys Thr
5510                5515                5520 tgc att acc act gct atc ata tgt gtg tgc ata cac ttg ctc ata    28742
Cys Ile Thr Thr Ala Ile Ile Cys Val Cys Ile His Leu Leu Ile
5525                5530                5535 gca act cgc tcc aaa aac agc aat gag gaa aaa gag aaa atg cct    28787
Ala Thr Arg Ser Lys Asn Ser Asn Glu Glu Lys Glu Lys Met Pro
5540                5545                5550 tgacctttt tcctcgtttt ctgttcacag ct atg att ttt att aca tcc atc    28840
                                  Met Ile Phe Ile Thr Ser Ile
                                  5555                5560 ttt att gtc agc att tca act att gca cat gga caa caa ata aat    28885
Phe Ile Val Ser Ile Ser Thr Ile Ala His Gly Gln Gln Ile Asn
    5565                5570                5575 gca ggc gac aat ttc aca tta gtt ggg cct aaa aaa cca gtt gtc    28930
Ala Gly Asp Asn Phe Thr Leu Val Gly Pro Lys Lys Pro Val Val
5580                5585                5590 tcc tgg ttc tgg act aaa cct gat cca tgg gct aaa act gat tac    28975
Ser Trp Phe Trp Thr Lys Pro Asp Pro Trp Ala Lys Thr Asp Tyr
5595                5600                5605 tgg gtt tca ctt tgt gat ggt gta ttt ctg tat aaa tct aac ctt    29020
Trp Val Ser Leu Cys Asp Gly Val Phe Leu Tyr Lys Ser Asn Leu
    5610                5615                5620 aca ttc aat tgc aat aat caa aac cta aca cta atc aat gtt act    29065
Thr Phe Asn Cys Asn Asn Gln Asn Leu Thr Leu Ile Asn Val Thr
5625                5630                5635 aaa gat tat gaa gga aca tac tat gga gat gga atc tta tat aga    29110
Lys Asp Tyr Glu Gly Thr Tyr Tyr Gly Asp Gly Ile Leu Tyr Arg
5640                5645                5650 att aga gta ata gac act cct aag aga ttc aaa aga gct aca act    29155
Ile Arg Val Ile Asp Thr Pro Lys Arg Phe Lys Arg Ala Thr Thr
    5655                5660                5665 aaa gtt aca gat cca caa cca aaa atc tct agc atc act act atc    29200
Lys Val Thr Asp Pro Gln Pro Lys Ile Ser Ser Ile Thr Thr Ile
5670                5675                5680 ttt act aac agt aca tat acc aat tta caa ttg gct tat gtt aac    29245
Phe Thr Asn Ser Thr Tyr Thr Asn Leu Gln Leu Ala Tyr Val Asn
5685                5690                5695 tca tca aat att aca atc ctg cct aca cca atc aat gaa gaa att    29290
Ser Ser Asn Ile Thr Ile Leu Pro Thr Pro Ile Asn Glu Glu Ile
    5700                5705                5710 cct aaa tca atg att ggg atc att gtg gcg gtg gca gtg gga atg    29335
Pro Lys Ser Met Ile Gly Ile Ile Val Ala Val Ala Val Gly Met
5715                5720                5725 atc ata atc ata ata tgt atg atc acc tat gct tgc tgc tac aga    29380
Ile Ile Ile Ile Ile Cys Met Ile Thr Tyr Ala Cys Cys Tyr Arg
    5730                5735                5740 aag ttt tat tat gaa gaa aaa gga gac ccc cta cta aat ttt gac    29425
Lys Phe Tyr Tyr Glu Glu Lys Gly Asp Pro Leu Leu Asn Phe Asp
```

-continued

```
                  5745                5750                5755
att taattttta tag atg aaa caa  cta ggt atc ttg att  att tac tgc        29474
Ile              Met Lys Gln  Leu Gly Ile Leu Ile  Ile Tyr Cys
                       5760                     5765 agc att aat ctt tct caa tta  aca cca aca cca act  agt aac aat          29519
Ser Ile Asn Leu Ser Gln Leu  Thr Pro Thr Pro Thr  Ser Asn Asn
    5770                5775                 5780 gtg cag act act tta cca gtc  acc ata aac aaa act  acc tca gtt          29564
Val Gln Thr Thr Leu Pro Val  Thr Ile Asn Lys Thr  Thr Ser Val
    5785                5790                 5795 ttt cta aat aat aca gac ttt  aat act aac tcc aac  tct aaa gat          29609
Phe Leu Asn Asn Thr Asp Phe  Asn Thr Asn Ser Asn  Ser Lys Asp
    5800                5805                 5810 ttt ctt caa ctt caa atc act  gct ctt att ata att  gga tta ata          29654
Phe Leu Gln Leu Gln Ile Thr  Ala Leu Ile Ile Ile  Gly Leu Ile
    5815                5820                 5825 att cta gca atc ctt cta tac  ttt gtc ttt tgc cgc  aac atc ccc          29699
Ile Leu Ala Ile Leu Leu Tyr  Phe Val Phe Cys Arg  Asn Ile Pro
    5830                5835                 5840 aat gtt cac aaa ccc att aaa  aag cgt cct att tac  aac ccc atc          29744
Asn Val His Lys Pro Ile Lys  Lys Arg Pro Ile Tyr  Asn Pro Ile
    5845                5850                 5855 tta agc gag cca caa ctt aga  cgg tgg agg gaa atc     taatacatct        29790
Leu Ser Glu Pro Gln Leu Arg  Arg Trp Arg Glu Ile
    5860                5865                 5870 ctcttttctt tcagtatggt gatcatcaaa c atg atc cct aga aat   ttt ttc       29842
                                 Met Ile Pro Arg Asn  Phe Phe
                                                  5875 ttc acc ata ctc atc tgc ctt ctc  aat atc tgc gct acc  ctt gct          29887
Phe Thr Ile Leu Ile Cys Leu Leu  Asn Ile Cys Ala Thr  Leu Ala
    5880                    5885                 5890 gcg gtc act agc gtc tca cca gac  tgc ata gga cca ttt  gcc acc          29932
Ala Val Thr Ser Val Ser Pro Asp  Cys Ile Gly Pro Phe  Ala Thr
    5895                    5900                 5905 tac ttg ctt ttt gca ttg atc acc  tgt atc tgt gtg agt  agc aca          29977
Tyr Leu Leu Phe Ala Leu Ile Thr  Cys Ile Cys Val Ser  Ser Thr
    5910                    5915                 5920 gtc tgt ctg gtt att aat ttt ttc  caa ctt ata gac tgg  att ttt          30022
Val Cys Leu Val Ile Asn Phe Phe  Gln Leu Ile Asp Trp  Ile Phe
    5925                    5930                 5935 gtg cgc att gcc tac ctg aga cac  cat cca gaa tac cgc  aac cat          30067
Val Arg Ile Ala Tyr Leu Arg His  His Pro Glu Tyr Arg  Asn His
    5940                    5945                 5950 gat att gcg gca cta ctc aga ctt  ctt taaaaccata caggctttgc             30114
Asp Ile Ala Ala Leu Leu Arg Leu  Leu
    5955                    5960 taccactgct attgctgcta ctgccctgtg acactatagc caccacacct accctaaacc      30174
caaatcttag aaaatgtaaa ttccaagagc catggaattt cctcaaatgt tataatgaaa      30234
caattgattt tccaccctat tggataacaa tcattggaat ccttaatgtg gtatgctgca     30294
ccatatttgc attccttgta tatcccatgt ttgattttgg gtggaatgtc cccaatgcac     30354
tcactcaccc acaagaacca caggaacata tcccactaca aaacatgcaa ccactagcac    30414
taatagaata tgaaaatgag ccacagcctc cactactccc tgccattagc tacttcaacc   30474
taaccggtag ag atg act gac cca  ctc gcc gca tcc gcc  gct gcc gag       30522
              Met Thr Asp Pro  Leu Ala Ala Ser Ala  Ala Ala Glu
                            5965                 5970 gaa cta ctt gat atg gac ggc  cgt gcc tcc gaa cag  cga ctc gcc          30567
```

```
                Glu Leu Leu Asp Met Asp Gly Arg Ala Ser Glu Gln Arg Leu Ala
                    5975            5980            5985 caa cta cgc att cgc cag cag gaa cgt gcc gcc aag gag ctc              30612
Gln Leu Arg Ile Arg Gln Gln Glu Arg Ala Ala Lys Glu Leu
    5990            5995            6000 agg gat gct att gag att cac cag tgc aaa aaa ggc ata ttc tgc          30657
Arg Asp Ala Ile Glu Ile His Gln Cys Lys Lys Gly Ile Phe Cys
    6005            6010            6015 tta gta aaa caa gct aag atc tcc tac gag att acc gct aac gac          30702
Leu Val Lys Gln Ala Lys Ile Ser Tyr Glu Ile Thr Ala Asn Asp
    6020            6025            6030 cac cgc ctc tca tat gag ctt ggg ccg cag cgt cag aaa ttc act          30747
His Arg Leu Ser Tyr Glu Leu Gly Pro Gln Arg Gln Lys Phe Thr
    6035            6040            6045 tgc atg gtg gga att aac ccc ata gtc atc acc cag caa gct gga          30792
Cys Met Val Gly Ile Asn Pro Ile Val Ile Thr Gln Gln Ala Gly
    6050            6055            6060 gat acc aag ggt tgc atc cat tgt tcc tgt gaa tcc acc gag tgc          30837
Asp Thr Lys Gly Cys Ile His Cys Ser Cys Glu Ser Thr Glu Cys
    6065            6070            6075 atc tac acc ctg ctg aag acc ctc tgc ggc ctt cga gac atc cta          30882
Ile Tyr Thr Leu Leu Lys Thr Leu Cys Gly Leu Arg Asp Ile Leu
    6080            6085            6090 ccc atg aac taatcaacaa accataccct cttcccatta aaatccaatt              30931
Pro Met Asn
    6095 aataaaattc acttacttaa aatcagaaac aaagtttttg tccaagttgt tttcaatcag    30991 cacctcactt ccctcttccc aactctggta ctctaagcct cggcgggcgg catacttcct    31051

ccacactttg aaagggatgt caaatttcag ttcttctttt cccacaatct tcatttctct    31111 tcccag atg gcc aaa cga gct cgt cta agc agc tcc ttc aac ccg gtc       31159
        Met Ala Lys Arg Ala Arg Leu Ser Ser Ser Phe Asn Pro Val
            6100            6105            6110 tac ccc tat gaa gat gaa aac agc tca caa cac ccc ttt ata aac          31204
Tyr Pro Tyr Glu Asp Glu Asn Ser Ser Gln His Pro Phe Ile Asn
    6115            6120            6125 ccc ggt ttc att tcc ccc aat ggg ttt aca caa aat tca gat gga          31249
Pro Gly Phe Ile Ser Pro Asn Gly Phe Thr Gln Asn Ser Asp Gly
    6130            6135            6140 gtt cta gct ctt aaa tgc gca gct cca ctt acc acc aca ggt ggt          31294
Val Leu Ala Leu Lys Cys Ala Ala Pro Leu Thr Thr Thr Gly Gly
    6145            6150            6155 tct ctt cag ctt aaa gtg ggt agg ggg ctt aca att gac act act          31339
Ser Leu Gln Leu Lys Val Gly Arg Gly Leu Thr Ile Asp Thr Thr
    6160            6165            6170 gac ggg aca tta gaa gag gac ata aac atc tta gca cca ctt aca          31384
Asp Gly Thr Leu Glu Glu Asp Ile Asn Ile Leu Ala Pro Leu Thr
    6175            6180            6185 aaa act gcc cac tcc ata ggt tta tca ttg gga aat ggg tta gaa          31429
Lys Thr Ala His Ser Ile Gly Leu Ser Leu Gly Asn Gly Leu Glu
    6190            6195            6200 tta aaa gac agc aaa cta tat gtt aaa cta gga gat ggt cta aaa          31474
Leu Lys Asp Ser Lys Leu Tyr Val Lys Leu Gly Asp Gly Leu Lys
    6205            6210            6215 ttt aac tca aac agc ata tgt tta gac cat gac att aac act tta          31519
Phe Asn Ser Asn Ser Ile Cys Leu Asp His Asp Ile Asn Thr Leu
    6220            6225            6230 tgg acc gga atg aat ccg tcc att aac tgt aac att atg caa caa          31564
Trp Thr Gly Met Asn Pro Ser Ile Asn Cys Asn Ile Met Gln Gln
```

```
                        6235                6240                6245
gat gac aat gac agc  aag cta act cta gtc  tta act aaa aat gga       31609
Asp Asp Asn Asp Ser  Lys Leu Thr Leu Val  Leu Thr Lys Asn Gly
            6250                6255                6260 gga atg gta aat gca  tat gta tca ttg gta  ggg gca tct gat att       31654
Gly Met Val Asn Ala  Tyr Val Ser Leu Val  Gly Ala Ser Asp Ile
            6265                6270                6275 gta aac tca cta ttt  aaa cgg gcc act gca  aat atc aca ata agg       31699
Val Asn Ser Leu Phe  Lys Arg Ala Thr Ala  Asn Ile Thr Ile Arg
            6280                6285                6290 cta agc ttt gat gcc  tct ggc aat tta cta  aca agc cta tca gac       31744
Leu Ser Phe Asp Ala  Ser Gly Asn Leu Leu  Thr Ser Leu Ser Asp
            6295                6300                6305 cta aaa acc cca ctg  aat cac aga tat ggc  aat gac atg gac act       31789
Leu Lys Thr Pro Leu  Asn His Arg Tyr Gly  Asn Asp Met Asp Thr
            6310                6315                6320 gac aca tta act aat  ggc aag agt ttt atg  ccc agc act aca gcc       31834
Asp Thr Leu Thr Asn  Gly Lys Ser Phe Met  Pro Ser Thr Thr Ala
            6325                6330                6335 tat ccc ttt aat gac  act aca agg gat aaa  gaa aac tac ata tat       31879
Tyr Pro Phe Asn Asp  Thr Thr Arg Asp Lys  Glu Asn Tyr Ile Tyr
            6340                6345                6350 ggc acc tgt tat tat  aaa tca act gaa gac  gca ttg tac ccg cta       31924
Gly Thr Cys Tyr Tyr  Lys Ser Thr Glu Asp  Ala Leu Tyr Pro Leu
            6355                6360                6365 gaa gtt gcc gtc aca  ctt aac aga cgg atg  agc agt gct gcc gtt       31969
Glu Val Ala Val Thr  Leu Asn Arg Arg Met  Ser Ser Ala Ala Val
            6370                6375                6380 tct tat gct atg act  att gct tgg act tta  agt gca aac aca ccc       32014
Ser Tyr Ala Met Thr  Ile Ala Trp Thr Leu  Ser Ala Asn Thr Pro
            6385                6390                6395 cct gaa act acc ata  gca acc ctt gtt acc  tcc ccc ttc act ttt       32059
Pro Glu Thr Thr Ile  Ala Thr Leu Val Thr  Ser Pro Phe Thr Phe
            6400                6405                6410 tcc tat att aga gaa  aat gac tgacaacaaa aataaatttt aacttttat        32110
Ser Tyr Ile Arg Glu  Asn Asp
            6415 tgaaaaatca gtttacagga ttcgagtagt tattttgcct cccccttccc atttcatacg   32170 atacaccaat ctctccccac gcacagcttt aaacatttgg attccatttg agatagtcat   32230 ggatttagat tccacattcc acacagtttc agagctagat aatcttggat cagtgataga   32290 tataaatcca tcggggcagt ccttcaaggt gatttcacag tccagttgct gtggctgcgg   32350 ctccggagtc tggatcagag tcatctggaa caagaacgat gggagtcata atccgagaac   32410 gggatcgggc ggttgtgtct catcaaaccc cgaagcagtc gctgtctgcg ccgctccgtg   32470 cgactgctgc tgatgggatc ggggtccaca gtctctcgaa gcatgattct aatagccctc   32530 aacattaaca tcctggtgcg atgcgcacag cagcgcatcc tgatctcact tagctcacag   32590 caataggtac aacacaacac cacaatattg tttaacaggc ataattaaa ggcactccag    32650 ccaaaactca tttcaggaat aatttgccca gcgtgaccat cgtaccaaat cctgatgtaa   32710 atcagatggc gccccctcca gaacacactg cccacataca tgatctcctt aggcatatgc   32770 atattcacaa tctctcggta ccatggacag cgctggttaa tcatgcagcc ccgaataacc   32830 ttccggaacc aaatggccag cactgcgccc ccagcaatac attgaagaga accctgtcga   32890 ttacagtgac aatggagaac ccacttctct cgcccatgga tcacttggga ataaaatata   32950 tctattgtgg cacaacacag acataaatgc atacatcttc tcatcaccct taactcttca   33010
```

```
ggggttaaaa acatatccca gggaatagga agctcttgca aaacagtaaa ggtggcagaa    33070
caaggcagac cgcgaacata acttacactg tgcatggtca aggtattgca atctggtaac    33130
agcggatgct cttcagtcat agaagctctg gtttcacttt cctcacagcg tggtaaaggg    33190
gccctcagtt gaggttccct ggtgtaagga tggtgtctgg cgcacgatgt cgagcgtgca    33250
cgcgacctcg ttgtaatgga gctgcttcct gacattctcg tattttgcat agcagaacct    33310
agtcttggca cagcacacgt cccgtcgcct cctgtcccgc cgcctagcac gttcagtgtg    33370
gtaattatag tacagccatt cccgtagatt ggtcaaaaga tcttcagcct cagttgtcat    33430
aaaaactcca tcatatctta ctgctctgat aaaatcattc actgtagaaa gtgcaatgcc    33490
cagccaggca atgcaattag cttgtgtttc gaccaaagga gggggaggaa gacatggaag    33550
aaccataatt aattttatg ccagacgatc ccgcagtatt tctatatgga gatcacgaag    33610
atggcacctc tcgccccac tgtgttgatg aaaaatgaca gctaggtcaa acataatgcg    33670
attttccagg tgctcaacgg tggcttcaag caaagcctcc aaacgtacat ccaaaaacaa    33730
aagaacagca aaagcaggag cattttctaa ttcctcaatc atcatattac attcctgtac    33790
cattcccaaa taattttcat cttttccatcc ttgaattatt cgtgttattt catctggtaa    33850
atccaatcca cacatgagaa atagctcccg gagggcgccc tccaccggca atctcaagca    33910
taccctcata gtgacaaaat atcgtgctcc tctgtcacct gcagcaaatt gagaatggca    33970
atatcaaacg gaatgccact ggctctaagt tcttctctaa gttccagttg taaaaactct    34030
tgcatatcat cgccaaactg cttagccata ggtcctccag gaataagagc gggggacgct    34090
acagtgcaga acaagcgcat gccgccccaa ttgcctccag caaaagtgag gttgcaatat    34150
gcatactgag aacctccagt gatatcatcc agtgtactgg aaagataatc aggcagagct    34210
tctcgtatgc aattaataat agaaaagtct gccagatgaa catttaaagc ctgtgggatg    34270
cagatgcaat aagttatcgc gctgcgctcc aacattgtta gtatggttag tctgtaaaaa    34330
caaaaacaa aaaaaattac atcacgctag actggcgaac gggtggaaaa atcactctct    34390
ccaacaccag gcaggctaca gggtctccag cgcgaccctc gtaaaacctg tcagtatgat    34450
tgaaaagcat caccgaaagg ggttgttgat ggccagcata tattatttgc gatgaagcat    34510
acaatccaga agtgttagta tcagttaaag aaaaaaatcg gccaagatag catctcggaa    34570
cgattatgct caatctcaaa tgcagcaaag cgacacctcg cggatgcaaa gtaaaatcca    34630
caggagcata aaaaaagtaa ttattcccct cttgcacagg cagcctagct cccggcccct    34690
ccaaaatcac atataatgct tcagcagcca tagcttaccg cgcaaatcag gcacagcagt    34750
cagatagaga aaaagctgtg aactgactgc ccagcctgtg cgcaatatat agagaaccct    34810
tacactgacg taattgggca aagtctaaaa aatcccgcca aaaaaacagc acacgcccaa    34870
aagtgtgaca ctcgctaaaa aaatatttt cacttcctcg ttccgtatat gacgtcaatt    34930
ccgctttccc acgaatcgtc acttccggcc atcttgcaac gtcacctccc cgcgccggcc    34990
cgccccttt gaccgttgaa cccgctagcc aatcccctc cgccctccat tttcaaaagc    35050
tcatttgcat gttggcaccg ttccatttat aaggtatatt attgatgatg             35100
```

<210> SEQ ID NO 2  
<211> LENGTH: 495  
<212> TYPE: PRT  
<213> ORGANISM: Unknown  
<220> FEATURE:  
<223> OTHER INFORMATION: Synthetic Construct

```
<400> SEQUENCE: 2

Met Asp Pro Thr Asn Pro Leu Gln Gln Gly Ile Arg Leu Gly Phe His
1               5                   10                  15

Ser Ser Ser Phe Val Glu Asn Met Glu Gly Pro Gln Ala Glu Asp Asn
            20                  25                  30

Leu Arg Leu Leu Ala Ser Ala Ser Gly Arg Ser Ser Asn Pro Glu
        35                  40                  45

Thr Pro Thr Gly His Ala Ser Gly Phe Gly Gly Ala Ala Gly Gly
    50                  55                  60

Gln Pro Glu Ser Arg Pro Gly Pro Ser Gly Gly Gly Gly Gly Val
65              70                  75                  80

Ala Asp Leu Phe Pro Glu Leu Arg Arg Val Leu Thr Arg Ser Thr Ser
                85                  90                  95

Ser Gly Gln Asp Arg Gly Ile Lys Arg Glu Arg Asn Ala Ser Gly His
            100                 105                 110

Asn Ser Arg Thr Glu Leu Ala Leu Ser Leu Met Ser Arg Ser Arg Pro
        115                 120                 125

Glu Thr Ile Trp Trp His Glu Val Gln Ser Glu Gly Arg Asp Glu Val
    130                 135                 140

Ser Ile Leu Gln Glu Lys Tyr Ser Leu Glu Gln Ile Lys Thr Cys Trp
145                 150                 155                 160

Leu Glu Pro Glu Asp Asp Trp Glu Val Ala Ile Arg Asn Tyr Ala Lys
                165                 170                 175

Ile Ser Leu Arg Pro Asp Lys Gln Tyr Lys Ile Thr Lys Lys Ile Asn
            180                 185                 190

Ile Arg Asn Ala Cys Tyr Ile Ala Gly Asn Gly Ala Glu Val Ile Ile
        195                 200                 205

Asp Thr Pro Asp Lys Thr Ala Phe Arg Cys Cys Met Met Gly Met Trp
    210                 215                 220

Pro Gly Val Ala Gly Met Glu Ala Val Thr Leu Met Asn Ile Arg Phe
225                 230                 235                 240

Arg Gly Asp Gly Tyr Asn Gly Ile Val Phe Met Ala Asn Thr Lys Leu
                245                 250                 255

Ile Leu His Gly Cys Ser Phe Phe Gly Phe Asn Asn Thr Cys Val Glu
            260                 265                 270

Ser Trp Gly Gln Val Ser Ile Arg Gly Cys Ser Phe Tyr Ala Cys Trp
        275                 280                 285

Ile Ala Leu Ser Gly Arg Thr Lys Ser Gln Leu Ser Val Lys Lys Cys
    290                 295                 300

Met Phe Glu Arg Cys Asn Leu Gly Ile Leu Asn Glu Gly Glu Ala Arg
305                 310                 315                 320

Val Arg His Cys Ala Ala Thr Glu Thr Gly Cys Phe Ile Leu Ile Lys
                325                 330                 335

Gly Asn Ala Ser Val Lys His Asn Met Ile Cys Gly Pro Leu Asp Glu
            340                 345                 350

Arg Pro Tyr Gln Met Leu Thr Cys Ala Gly Gly His Cys Asn Met Leu
        355                 360                 365

Ala Thr Val His Ile Val Ser His Ala Arg Lys Lys Trp Pro Val Phe
    370                 375                 380

Glu His Asn Val Met Thr Lys Cys Thr Met His Ala Gly Gly Arg Arg
385                 390                 395                 400

Gly Met Phe Met Pro Tyr Gln Cys Asn Met Asn His Val Lys Val Met
                405                 410                 415
```

```
Leu Glu Pro Asp Ala Phe Ser Arg Met Ser Leu Thr Gly Ile Phe Asp
            420                 425                 430

Met Asn Val Gln Leu Trp Lys Ile Leu Arg Tyr Asp Glu Thr Lys Ser
            435                 440                 445

Arg Val Arg Ala Cys Glu Cys Gly Gly Lys His Ala Arg Phe Gln Pro
        450                 455                 460

Val Cys Val Asp Val Thr Glu Asp Leu Arg Pro Asp His Leu Val Leu
465                 470                 475                 480

Ala Cys Thr Gly Ala Glu Phe Gly Ser Ser Gly Glu Thr Asp
                485                 490                 495

<210> SEQ ID NO 3
<211> LENGTH: 138
<212> TYPE: PRT
<213> ORGANISM: Unknown
<220> FEATURE:
<223> OTHER INFORMATION: Synthetic Construct

<400> SEQUENCE: 3

Met Ser Gly Ser Ala Ser Phe Glu Gly Gly Val Phe Ser Pro Tyr Leu
1               5                   10                  15

Thr Gly Arg Leu Pro Pro Trp Ala Gly Val Arg Gln Asn Val Met Gly
            20                  25                  30

Ser Thr Val Asp Gly Arg Pro Val Gln Pro Ala Asn Ser Ser Thr Leu
        35                  40                  45

Thr Tyr Ala Thr Leu Ser Ser Ser Pro Leu Asp Ala Ala Ala Ala Ala
    50                  55                  60

Ala Ala Ser Ala Ala Ala Asn Thr Val Leu Gly Met Gly Tyr Tyr Gly
65                  70                  75                  80

Ser Ile Val Ala Asn Ser Ser Ser Asn Asn Pro Ser Thr Leu Glu Ala
                85                  90                  95

Glu Asp Lys Leu Leu Val Leu Leu Ala Gln Leu Glu Ala Leu Thr Gln
            100                 105                 110

Arg Leu Gly Glu Leu Ser Gln Gln Val Ala Gln Leu Arg Glu Gln Thr
        115                 120                 125

Glu Ser Ala Val Ala Thr Ala Lys Ser Lys
    130                 135

<210> SEQ ID NO 4
<211> LENGTH: 389
<212> TYPE: PRT
<213> ORGANISM: Unknown
<220> FEATURE:
<223> OTHER INFORMATION: Synthetic Construct

<400> SEQUENCE: 4

Met His Pro Val Leu Arg Gln Met Arg Pro Gln Gln Ala Pro Ser
1               5                   10                  15

Gln Gln Gln Gln Gln Pro Gln Lys Ala Leu Pro Ala Pro Ala Pro Ala
            20                  25                  30

Thr Thr Ala Val Ala Ala Val Cys Gly Ala Gly Gln Pro Ala Tyr Asp
        35                  40                  45

Leu Asp Leu Glu Glu Gly Glu Gly Leu Ala Arg Leu Gly Ala Pro Ser
    50                  55                  60

Pro Glu Arg His Pro Arg Val Gln Leu Lys Lys Asp Ser Arg Glu Ala
65                  70                  75                  80

Tyr Val Pro Gln Gln Asn Leu Phe Arg Asp Arg Ser Gly Glu Glu Pro
```

```
            85                  90                  95
Glu Glu Met Arg Ala Ser Arg Phe Asn Ala Gly Arg Glu Leu Arg His
            100                 105                 110
Gly Leu Asp Arg Arg Val Leu Arg Asp Glu Asp Phe Glu Val Asp
            115                 120                 125
Glu Met Thr Gly Ile Ser Pro Ala Arg Ala His Val Ala Ala Asn
            130                 135                 140
Leu Val Ser Ala Tyr Glu Gln Thr Val Lys Glu Arg Asn Phe Gln
145                 150                 155                 160
Lys Ser Phe Asn Asn His Val Arg Thr Leu Ile Ala Arg Glu Val
                165                 170                 175
Thr Leu Gly Leu Met His Leu Trp Asp Leu Met Glu Ala Ile Thr Gln
                180                 185                 190
Asn Pro Thr Ser Lys Pro Leu Thr Ala Gln Leu Phe Leu Val Val Gln
                195                 200                 205
His Ser Arg Asp Asn Glu Ala Phe Arg Glu Ala Leu Leu Asn Ile Thr
210                 215                 220
Glu Pro Glu Gly Arg Trp Leu Tyr Asp Leu Ile Asn Ile Leu Gln Ser
225                 230                 235                 240
Ile Ile Val Gln Glu Arg Ser Leu Gly Leu Ala Glu Lys Val Ala Ala
                245                 250                 255
Ile Asn Tyr Ser Val Leu Ser Leu Gly Lys Tyr Tyr Ala Arg Lys Ile
                260                 265                 270
Tyr Lys Thr Pro Tyr Val Pro Ile Asp Lys Glu Val Lys Ile Asp Gly
                275                 280                 285
Phe Tyr Met Arg Met Thr Leu Lys Val Leu Thr Leu Ser Asp Asp Leu
                290                 295                 300
Gly Val Tyr Arg Asn Asp Arg Met His Arg Ala Val Ser Ala Ser Arg
305                 310                 315                 320
Arg Arg Glu Leu Ser Asp Arg Glu Leu Met His Ser Leu Gln Arg Ala
                325                 330                 335
Leu Thr Gly Ala Gly Thr Asp Gly Glu Asn Tyr Phe Asp Met Gly Ala
                340                 345                 350
Asp Leu Gln Trp Gln Pro Ser Arg Arg Ala Leu Asp Ala Ala Gly Cys
                355                 360                 365
Glu Leu Pro Tyr Val Glu Val Asp Glu Gly Glu Glu Glu Gly
                370                 375                 380
Glu Tyr Leu Glu Asp
385

<210> SEQ ID NO 5
<211> LENGTH: 587
<212> TYPE: PRT
<213> ORGANISM: Unknown
<220> FEATURE:
<223> OTHER INFORMATION: Synthetic Construct

<400> SEQUENCE: 5

Met Glu Gln Gln Ala Pro Asp Pro Ala Met Arg Ala Ala Leu Gln Ser
1               5                   10                  15
Gln Pro Ser Gly Ile Asn Ser Ser Asp Asp Trp Thr Gln Ala Met Gln
                20                  25                  30
Arg Ile Met Ala Leu Thr Thr Arg Asn Pro Glu Ala Phe Arg Gln Gln
                35                  40                  45
Pro Gln Ala Asn Arg Leu Ser Ala Ile Leu Glu Ala Val Val Pro Ser
```

```
            50                  55                  60
Arg Ser Asn Pro Thr His Glu Lys Val Leu Ala Ile Val Asn Ala Leu
 65                  70                  75                  80

Val Glu Asn Lys Ala Ile Arg Pro Asp Glu Ala Gly Leu Val Tyr Asn
                 85                  90                  95

Ala Leu Leu Glu Arg Val Ala Arg Tyr Asn Ser Ser Asn Val Gln Thr
            100                 105                 110

Asn Leu Asp Arg Met Val Thr Asp Val Arg Glu Ala Val Ser Gln Arg
            115                 120                 125

Glu Arg Phe Gln Arg Asp Ala Asn Leu Gly Ser Leu Val Ala Leu Asn
        130                 135                 140

Ala Phe Leu Ser Thr Gln Pro Ala Asn Val Pro Arg Gly Gln Gln Asp
145                 150                 155                 160

Tyr Thr Asn Phe Leu Ser Ala Leu Arg Leu Met Val Thr Glu Val Pro
                165                 170                 175

Gln Ser Glu Val Tyr Gln Ser Gly Pro Asp Tyr Phe Phe Gln Thr Ser
            180                 185                 190

Arg Gln Gly Leu Gln Thr Val Asn Leu Ser Gln Ala Phe Lys Asn Leu
        195                 200                 205

Arg Gly Leu Trp Gly Val His Ala Pro Val Gly Asp Arg Ala Thr Val
    210                 215                 220

Ser Ser Leu Leu Thr Pro Asn Ser Arg Leu Leu Leu Leu Val Ser
225                 230                 235                 240

Pro Phe Thr Asp Ser Gly Ser Ile Asp Arg Asn Ser Tyr Leu Gly Tyr
                245                 250                 255

Leu Leu Asn Leu Tyr Arg Glu Ala Ile Gly Gln Ser Gln Val Asp Glu
            260                 265                 270

Gln Thr Tyr Gln Glu Ile Thr Gln Val Ser Arg Ala Leu Gly Gln Glu
        275                 280                 285

Asp Thr Gly Ser Leu Glu Ala Thr Leu Asn Phe Leu Leu Thr Asn Arg
    290                 295                 300

Ser Gln Lys Ile Pro Pro Gln Tyr Ala Leu Thr Ala Glu Glu Arg
305                 310                 315                 320

Ile Leu Arg Tyr Val Gln Gln Ser Val Gly Leu Phe Leu Met Gln Glu
                325                 330                 335

Gly Ala Thr Pro Ser Ala Ala Leu Asp Met Thr Ala Arg Asn Met Glu
            340                 345                 350

Pro Ser Met Tyr Ala Ser Asn Arg Pro Phe Ile Asn Lys Leu Leu Asp
        355                 360                 365

Tyr Leu His Arg Ala Ala Ala Met Asn Ser Asp Tyr Phe Thr Asn Ala
    370                 375                 380

Ile Leu Asn Pro His Trp Leu Pro Pro Gly Phe Tyr Thr Gly Glu
385                 390                 395                 400

Tyr Asp Met Pro Asp Pro Asn Asp Gly Phe Leu Trp Asp Asp Val Asp
                405                 410                 415

Ser Ser Ile Phe Ser Pro Pro Gly Tyr Asn Thr Trp Lys Lys Glu
            420                 425                 430

Gly Gly Asp Arg Arg His Ser Val Ser Leu Ser Gly Ser Arg Gly
        435                 440                 445

Ala Ala Ala Ala Val Pro Glu Ala Ala Ser Pro Phe Pro Ser Leu Pro
    450                 455                 460

Phe Ser Leu Asn Ser Val Arg Ser Ser Glu Leu Gly Arg Ile Thr Arg
465                 470                 475                 480
```

-continued

```
Pro Arg Leu Met Gly Glu Asp Glu Tyr Leu Asn Asp Ser Leu Leu Arg
                485                 490                 495

Pro Glu Arg Glu Lys Asn Phe Pro Asn Asn Gly Ile Glu Ser Leu Val
            500                 505                 510

Asp Lys Met Ser Arg Trp Lys Thr Tyr Ala Gln Asp His Lys Asp Glu
        515                 520                 525

Pro Arg Ile Leu Gly Ala Ala Ser Gly Thr Thr Arg Arg Gln Arg
    530                 535                 540

His Asp Arg Gln Arg Gly Leu Val Trp Asp Asp Glu Asp Ser Ala Asp
545                 550                 555                 560

Asp Ser Ser Val Leu Asp Leu Gly Gly Arg Gly Gly Gly Asn Pro Phe
                565                 570                 575

Ala His Leu Arg Pro His Phe Gly Arg Met Leu
            580                 585

<210> SEQ ID NO 6
<211> LENGTH: 584
<212> TYPE: PRT
<213> ORGANISM: Unknown
<220> FEATURE:
<223> OTHER INFORMATION: Synthetic Construct

<400> SEQUENCE: 6

Met Met Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Ala Val
            20                  25                  30

Met Gln Pro Ser Leu Glu Ala Pro Phe Val Pro Pro Arg Tyr Leu Ala
        35                  40                  45

Pro Thr Glu Gly Arg Asn Ser Ile Arg Tyr Ser Glu Leu Ala Pro Gln
    50                  55                  60

Tyr Asp Thr Thr Arg Leu Tyr Leu Val Asp Asn Lys Ser Ala Asp Ile
65                  70                  75                  80

Ala Ser Leu Asn Tyr Gln Asn Asp His Ser Asn Phe Leu Thr Thr Val
                85                  90                  95

Val Gln Asn Asn Asp Phe Thr Pro Thr Glu Ala Ser Thr Gln Thr Ile
            100                 105                 110

Asn Phe Asp Glu Arg Ser Arg Trp Gly Gly Gln Leu Lys Thr Ile Met
        115                 120                 125

His Thr Asn Met Pro Asn Val Asn Glu Tyr Met Phe Ser Asn Lys Phe
    130                 135                 140

Lys Ala Arg Val Met Val Ser Arg Lys Lys Pro Glu Gly Tyr Thr Gly
145                 150                 155                 160

Asp Lys Asn Asp Thr Ser Gln Asp Ile Leu Glu Tyr Glu Trp Phe Glu
                165                 170                 175

Phe Thr Leu Pro Glu Gly Asn Phe Ser Ala Thr Met Thr Ile Asp Leu
            180                 185                 190

Met Asn Asn Ala Ile Ile Asp Asn Tyr Leu Ala Val Gly Arg Gln Asn
        195                 200                 205

Gly Val Leu Glu Ser Asp Ile Gly Val Lys Phe Asp Thr Arg Asn Phe
    210                 215                 220

Arg Leu Gly Trp Asp Pro Ile Thr Lys Leu Val Met Pro Gly Val Tyr
225                 230                 235                 240

Thr Tyr Glu Ala Phe His Pro Asp Ile Val Leu Leu Pro Gly Cys Gly
                245                 250                 255
```

```
Val Asp Phe Thr Glu Ser Arg Leu Ser Asn Leu Leu Gly Ile Arg Lys
            260                 265                 270

Arg His Pro Phe Gln Glu Gly Phe Lys Ile Met Tyr Glu Asp Leu Glu
            275                 280                 285

Gly Gly Asn Ile Pro Ala Leu Leu Asp Val Asp Ala Tyr Glu Lys Ser
            290                 295                 300

Lys Lys Glu Asn Thr Asp Thr Thr Thr Thr Thr Val Thr Thr
305                 310                 315                 320

Glu Val Ala Thr Val Ala Arg His Val Ser Glu Val Thr Thr Glu Ala
                325                 330                 335

Ala Thr Val Val Ala Val Asp Pro Ile Val Glu Asn Asn Thr
            340                 345                 350

Val Arg Gly Asp Asn Ile His Thr Ala Asn Glu Met Lys Ala Ala Ala
            355                 360                 365

Asp Asp Thr Thr Val Val Val Pro Gly Ala Val Val Thr Glu Thr
            370                 375                 380

Glu Thr Lys Thr Lys Thr Leu Thr Ile Gln Pro Leu Glu Lys Asp Thr
385                 390                 395                 400

Lys Glu Arg Ser Tyr Asn Val Ile Ser Gly Thr Asn Asp Thr Ala Tyr
                405                 410                 415

Arg Ser Trp Tyr Leu Ala Tyr Asn Tyr Gly Asp Pro Glu Lys Gly Val
            420                 425                 430

Arg Ser Trp Thr Leu Leu Thr Thr Ser Asp Val Thr Cys Gly Ala Glu
            435                 440                 445

Gln Val Tyr Trp Ser Leu Pro Asp Met Met Gln Asp Pro Val Thr Phe
            450                 455                 460

Arg Ser Thr Arg Gln Val Ser Asn Tyr Pro Val Val Gly Ala Glu Leu
465                 470                 475                 480

Met Pro Val Phe Ser Lys Ser Phe Tyr Asn Glu Gln Ala Val Tyr Ser
                485                 490                 495

Gln Gln Leu Arg Gln Thr Thr Ser Leu Thr His Ile Phe Asp Arg Phe
            500                 505                 510

Pro Glu Asn Gln Ile Leu Ile Arg Pro Pro Ala Pro Thr Ile Thr Thr
            515                 520                 525

Val Ser Glu Asn Val Pro Ala Leu Thr Asp His Gly Thr Leu Pro Leu
            530                 535                 540

Arg Ser Ser Ile Arg Gly Val Gln Arg Val Thr Val Thr Asp Ala Arg
545                 550                 555                 560

Arg Arg Thr Cys Pro Tyr Val Tyr Lys Ala Leu Gly Ile Val Ala Pro
                565                 570                 575

Arg Val Leu Ser Ser Arg Thr Phe
            580

<210> SEQ ID NO 7
<211> LENGTH: 192
<212> TYPE: PRT
<213> ORGANISM: Unknown
<220> FEATURE:
<223> OTHER INFORMATION: Synthetic Construct

<400> SEQUENCE: 7

Met Ser Ile Leu Ile Ser Pro Ser Asn Asn Thr Gly Trp Gly Leu Arg
1               5                   10                  15

Thr Pro Thr Arg Met Tyr Gly Gly Ala Arg Lys Arg Ser Thr Gln His
            20                  25                  30
```

```
Pro Val Arg Val Arg Gly His Phe Arg Ala Pro Trp Gly Ala Leu Lys
         35                  40                  45

Gly Arg Thr Arg Thr Arg Thr Thr Val Asp Asp Val Ile Asp Gln Val
 50                  55                  60

Val Ala Asp Ala Arg Asn Tyr Thr Pro Ala Ala Pro Ala Ser Thr Val
 65                  70                  75                  80

Asp Ala Val Ile Asp Ser Val Val Ala Asp Ala Arg Glu Tyr Ala Arg
                 85                  90                  95

Arg Lys Ser Arg Arg Arg Ile Ala Arg Arg His Arg Ala Thr Pro
                100                 105                 110

Ala Met Arg Ala Ala Arg Ala Leu Leu Arg Arg Ala Lys Arg Val Gly
            115                 120                 125

Arg Arg Ala Met Leu Arg Ala Ala Arg Arg Ala Ala Ser Gly Ala Ser
130                 135                 140

Ala Gly Arg Ser Arg Arg Arg Ala Ala Thr Ala Ala Ala Ala Ile
145                 150                 155                 160

Ala Asn Met Ala Gln Pro Arg Arg Gly Asn Val Tyr Trp Val Arg Asp
                165                 170                 175

Ala Thr Thr Gly Gln Arg Val Pro Val Arg Thr Arg Pro Pro Arg Thr
            180                 185                 190

<210> SEQ ID NO 8
<211> LENGTH: 350
<212> TYPE: PRT
<213> ORGANISM: Unknown
<220> FEATURE:
<223> OTHER INFORMATION: Synthetic Construct

<400> SEQUENCE: 8

Met Ser Lys Arg Lys Tyr Lys Glu Glu Met Leu Gln Val Ile Ala Pro
 1               5                  10                  15

Glu Ile Tyr Gly Pro Pro Val Lys Asp Glu Lys Lys Pro Arg Lys Ile
            20                  25                  30

Lys Arg Val Lys Lys Asp Lys Lys Glu Glu Asp Gly Asp Asp Gly Leu
         35                  40                  45

Val Glu Phe Val Arg Glu Phe Ala Pro Arg Arg Val Gln Trp Arg
 50                  55                  60

Gly Arg Lys Val Arg Pro Val Leu Arg Pro Gly Thr Thr Val Val Phe
 65                  70                  75                  80

Thr Pro Gly Glu Arg Ser Ser Thr Thr Phe Lys Arg Ser Tyr Asp Glu
                 85                  90                  95

Val Tyr Gly Asp Asp Asp Ile Leu Glu Gln Ala Ala Asp Arg Leu Gly
                100                 105                 110

Glu Phe Ala Tyr Gly Lys Arg Ser Arg Ser Ser Pro Lys Asp Glu Ala
            115                 120                 125

Val Ser Ile Pro Leu Asp His Gly Asn Pro Thr Pro Ser Leu Lys Pro
130                 135                 140

Val Thr Leu Gln Gln Val Leu Pro Val Pro Pro Arg Arg Gly Val Lys
145                 150                 155                 160

Arg Glu Gly Glu Asp Leu Tyr Pro Thr Met Gln Leu Met Val Pro Lys
                165                 170                 175

Arg Gln Lys Leu Glu Asp Val Leu Glu Lys Met Lys Val Asp Pro Asp
                180                 185                 190

Ile Gln Pro Glu Val Lys Val Arg Pro Ile Lys Gln Val Ala Pro Gly
            195                 200                 205
```

```
Leu Gly Val Gln Thr Val Asp Ile Lys Ile Pro Thr Glu Ser Met Glu
        210                 215                 220
Val Gln Thr Glu Pro Ala Lys Pro Ala Ala Thr Ser Ile Glu Val Gln
225                 230                 235                 240
Thr Asp Pro Trp Ile Pro Ala Pro Val Ala Thr Thr Ala Ser Thr Ala
                245                 250                 255
Arg Arg Pro Arg Arg Lys Tyr Gly Pro Ala Ser Leu Leu Leu Pro Asn
                260                 265                 270
Tyr Ala Leu His Pro Ser Ile Ile Pro Thr Pro Gly Tyr Arg Gly Thr
        275                 280                 285
Arg Tyr Tyr Arg Ser Arg Ser Thr Thr Ser Arg Arg Lys Thr Pro
290                 295                 300
Ala Ser Arg Ser Arg Arg Arg Arg Arg Ala Ala Ser Lys Leu Thr
305                 310                 315                 320
Pro Ala Ala Leu Val Arg Arg Val Tyr Arg Asp Gly Arg Ala Glu Pro
                325                 330                 335
Leu Met Leu Pro Arg Ala Arg Tyr His Pro Ser Ile Thr Thr
                340                 345                 350

<210> SEQ ID NO 9
<211> LENGTH: 75
<212> TYPE: PRT
<213> ORGANISM: Unknown
<220> FEATURE:
<223> OTHER INFORMATION: Synthetic Construct

<400> SEQUENCE: 9

Met Ala Leu Thr Cys Arg Leu Arg Val Pro Ile Thr Gly Tyr Arg Gly
1               5                   10                  15
Arg Asn Ser Arg Arg Arg Met Leu Gly Ser Gly Met Arg Arg His
            20                  25                  30
Arg Arg Arg Arg Ala Ile Ser Lys Arg Leu Gly Gly Gly Phe Leu Thr
        35                  40                  45
Ala Leu Ile Pro Ile Ile Ala Ala Ile Gly Ala Val Pro Gly Ile
    50                  55                  60
Ala Ser Val Ala Val Gln Ala Ser Gln Arg His
65                  70                  75

<210> SEQ ID NO 10
<211> LENGTH: 250
<212> TYPE: PRT
<213> ORGANISM: Unknown
<220> FEATURE:
<223> OTHER INFORMATION: Synthetic Construct

<400> SEQUENCE: 10

Met Glu Asp Ile Asn Phe Ser Ser Leu Ala Pro Arg His Gly Thr Arg
1               5                   10                  15
Pro Tyr Met Gly Thr Trp Ser Asp Ile Gly Thr Ser Gln Leu Asn Gly
            20                  25                  30
Gly Ala Phe Asn Trp Ser Ser Ile Trp Ser Gly Leu Lys Asn Phe Gly
        35                  40                  45
Ser Ala Ile Lys Thr Tyr Gly Asn Lys Ala Trp Asn Ser Ser Thr Gly
    50                  55                  60
Gln Ala Leu Arg Asn Lys Leu Lys Glu Gln Asn Phe Gln Gln Lys Val
65                  70                  75                  80
Val Asp Gly Ile Ala Ser Gly Ile Asn Gly Val Val Asp Leu Ala Asn
```

```
                        85                  90                  95
Gln Ala Val Gln Lys Gln Ile Asn Ser Arg Leu Asp Pro Pro Ala
                100                 105                 110

Ala Pro Gly Glu Met Glu Val Glu Glu Leu Pro Pro Leu Glu Lys
            115                 120                 125

Arg Gly Asp Lys Arg Pro Arg Pro Asp Met Glu Thr Leu Val Thr
        130                 135                 140

Arg Gly Asp Glu Pro Pro Tyr Glu Ala Ile Lys Leu Gly Met
145                 150                 155                 160

Pro Thr Thr Arg Pro Ile Ala Pro Met Ala Thr Gly Val Met Lys Pro
                165                 170                 175

Ser Gln Ser His Arg Pro Ala Thr Leu Asp Leu Pro Ala Pro Ala
            180                 185                 190

Ala Ala Ala Pro Ala Pro Lys Pro Val Ala Thr Pro Lys Pro Thr Ser
        195                 200                 205

Val Gln Pro Val Ala Val Ala Arg Pro Arg Pro Gly Gly Thr Pro Arg
    210                 215                 220

Pro Asn Ala Asn Trp Gln Ser Thr Leu Asn Ser Ile Val Gly Leu Gly
225                 230                 235                 240

Val Gln Ser Val Lys Arg Arg Arg Cys Tyr
                245                 250

<210> SEQ ID NO 11
<211> LENGTH: 943
<212> TYPE: PRT
<213> ORGANISM: Unknown
<220> FEATURE:
<223> OTHER INFORMATION: Synthetic Construct

<400> SEQUENCE: 11

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Leu Gly Asn Lys Phe Arg Asn Pro
        35                  40                  45

Thr Val Ala Pro Thr His Asp Val Thr Thr Asp Arg Ser Gln Arg Leu
    50                  55                  60

Met Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Phe Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Ile Val Thr Thr Asn Gly Gln Asp Asn
    130                 135                 140

Ala Val Thr Thr Thr Asn Thr Phe Gly Ile Ala Ser Met Lys Gly
145                 150                 155                 160

Asp Asn Ile Thr Lys Glu Gly Leu Glu Ile Gly Lys Asp Ile Thr Glu
                165                 170                 175

Glu Asp Lys Pro Ile Tyr Ala Asp Lys Thr Tyr Gln Pro Glu Pro Gln
            180                 185                 190

Val Gly Glu Glu Ser Trp Thr Asp Thr Asp Gly Thr Asn Glu Lys Phe
```

-continued

```
            195                 200                 205
Gly Gly Arg Ala Leu Lys Pro Ala Thr Asn Met Lys Pro Cys Tyr Gly
210                 215                 220

Ser Phe Ala Arg Pro Thr Asn Ile Lys Gly Gly Gln Ala Lys Asn Arg
225                 230                 235                 240

Lys Val Lys Pro Thr Thr Glu Gly Gly Val Glu Thr Glu Glu Pro Asp
                245                 250                 255

Ile Asp Met Glu Phe Phe Asp Gly Arg Asp Ala Ala Glu Gly Ala Leu
            260                 265                 270

Ser Pro Glu Ile Val Leu Tyr Thr Glu Asn Val Asn Leu Glu Thr Pro
        275                 280                 285

Asp Thr His Val Val Tyr Lys Pro Gly Thr Ser Asp Asn Ser His
    290                 295                 300

Ala Asn Leu Gly Gln Gln Ala Met Pro Asn Arg Pro Asn Tyr Ile Gly
305                 310                 315                 320

Phe Arg Asp Asn Phe Val Gly Leu Leu Tyr Tyr Asn Ser Thr Gly Asn
                325                 330                 335

Met Gly Val Leu Ala Gly Gln Ala Ser Gln Leu Asn Ala Val Val Asp
                340                 345                 350

Leu Gln Asp Arg Asn Thr Glu Leu Ser Tyr Gln Leu Leu Asp Ser
        355                 360                 365

Leu Gly Asp Arg Thr Arg Tyr Phe Ser Met Trp Asn Gln Ala Val Asp
370                 375                 380

Ser Tyr Asp Pro Asp Val Arg Ile Ile Glu Asn His Gly Ile Glu Asp
385                 390                 395                 400

Glu Leu Pro Asn Tyr Cys Phe Pro Leu Asp Gly Ile Gly Pro Gly Asn
                405                 410                 415

Ser Tyr Gln Gly Ile Lys Ala Lys Asn Gly Asp Asn Gly Trp Glu
                420                 425                 430

Lys Asp Thr Asn Ala Ser Thr Ala Asn Glu Ile Ala Ile Gly Asn Asn
            435                 440                 445

Leu Ala Met Glu Ile Asn Ile Gln Ala Asn Leu Trp Arg Ser Phe Leu
450                 455                 460

Tyr Ser Asn Val Ala Leu Tyr Leu Pro Asp Ala Tyr Lys Tyr Thr Pro
465                 470                 475                 480

Ala Asn Ile Thr Leu Pro Ala Asn Thr Asn Thr Tyr Glu Tyr Met Asn
                485                 490                 495

Gly Arg Val Val Ala Pro Ser Leu Val Asp Ser Tyr Ile Asn Ile Gly
                500                 505                 510

Ala Arg Trp Ser Leu Asp Pro Met Asp Asn Val Asn Pro Phe Asn His
            515                 520                 525

His Arg Asn Ala Gly Leu Arg Tyr Arg Ser Met Leu Gly Asn Gly
        530                 535                 540

Arg Tyr Val Pro Phe His Ile Gln Val Pro Gln Lys Phe Phe Ala Ile
545                 550                 555                 560

Lys Asn Leu Leu Leu Leu Pro Gly Ser Tyr Thr Tyr Glu Trp Asn Phe
                565                 570                 575

Arg Lys Asp Val Asn Met Val Leu Gln Ser Ser Leu Gly Asn Asp Leu
            580                 585                 590

Arg Thr Asp Gly Ala Ser Ile Ser Phe Thr Ser Ile Asn Leu Tyr Ala
        595                 600                 605

Thr Phe Phe Pro Met Ala His Asn Thr Ala Ser Thr Leu Glu Ala Met
    610                 615                 620
```

```
Leu Arg Asn Asp Thr Asn Asp Gln Ser Phe Asn Asp Tyr Leu Ser Ala
625                 630                 635                 640

Ala Asn Met Leu Tyr Pro Ile Pro Ala Asn Ala Thr Asn Ile Pro Ile
            645                 650                 655

Ser Ile Pro Ser Arg Asn Trp Ala Ala Phe Arg Gly Trp Ser Phe Thr
        660                 665                 670

Arg Leu Lys Thr Lys Glu Thr Pro Ser Leu Gly Ser Gly Phe Asp Pro
            675                 680                 685

Tyr Phe Val Tyr Ser Gly Ser Ile Pro Tyr Leu Asp Gly Thr Phe Tyr
        690                 695                 700

Leu Asn His Thr Phe Lys Lys Val Ser Ile Met Phe Asp Ser Ser Val
705                 710                 715                 720

Ser Trp Pro Gly Asn Asp Arg Leu Leu Thr Pro Asn Glu Phe Glu Ile
            725                 730                 735

Lys Arg Thr Val Asp Gly Glu Gly Tyr Asn Val Ala Gln Cys Asn Met
            740                 745                 750

Thr Lys Asp Trp Phe Leu Val Gln Met Leu Ala Asn Tyr Asn Ile Gly
        755                 760                 765

Tyr Gln Gly Phe Tyr Ile Pro Glu Gly Tyr Lys Asp Arg Met Tyr Ser
        770                 775                 780

Phe Phe Arg Asn Phe Gln Pro Met Ser Arg Gln Val Val Asp Glu Val
785                 790                 795                 800

Asn Tyr Thr Asp Tyr Lys Ala Val Thr Leu Ala Tyr Gln His Asn Asn
            805                 810                 815

Ser Gly Phe Val Gly Tyr Leu Ala Pro Thr Met Arg Gln Gly Glu Pro
            820                 825                 830

Tyr Pro Ala Asn Tyr Pro Tyr Pro Leu Ile Gly Thr Thr Ala Val Lys
        835                 840                 845

Ser Val Thr Gln Lys Lys Phe Leu Cys Asp Arg Thr Met Trp Arg Ile
850                 855                 860

Pro Phe Ser Ser Asn Phe Met Ser Met Gly Ala Leu Thr Asp Leu Gly
865                 870                 875                 880

Gln Asn Met Leu Tyr Ala Asn Ser Ala His Ala Leu Asp Met Thr Phe
            885                 890                 895

Glu Val Asp Pro Met Asp Glu Pro Thr Leu Leu Tyr Val Leu Phe Glu
            900                 905                 910

Val Phe Asp Val Val Arg Val His Gln Pro His Arg Gly Val Ile Glu
            915                 920                 925

Ala Val Tyr Leu Arg Thr Pro Phe Ser Ala Gly Asn Ala Thr Thr
            930                 935                 940

<210> SEQ ID NO 12
<211> LENGTH: 209
<212> TYPE: PRT
<213> ORGANISM: Unknown
<220> FEATURE:
<223> OTHER INFORMATION: Synthetic Construct

<400> SEQUENCE: 12

Met Ala Cys Gly Ser Gly Asn Gly Ser Ser Glu Gln Glu Leu Arg Ala
1               5                   10                  15

Ile Ala Arg Asp Leu Gly Cys Gly Pro Tyr Phe Leu Gly Thr Phe Asp
            20                  25                  30

Lys Arg Phe Pro Gly Phe Met Ala Pro Asn Lys Leu Ala Cys Ala Ile
        35                  40                  45
```

```
Val Asn Thr Ala Gly Arg Glu Thr Gly Gly Glu His Trp Leu Ala Phe
     50                  55                  60

Gly Trp Asn Pro Arg Ser Asn Thr Cys Tyr Leu Phe Asp Pro Phe Gly
 65                  70                  75                  80

Phe Ser Asp Glu Arg Leu Lys Gln Ile Tyr Gln Phe Glu Tyr Glu Gly
                 85                  90                  95

Leu Leu Arg Arg Ser Ala Leu Ala Thr Lys Asp Arg Cys Ile Thr Leu
             100                 105                 110

Glu Lys Ser Thr Gln Thr Val Gln Gly Pro Arg Ser Ala Ala Cys Gly
             115                 120                 125

Leu Phe Cys Cys Met Phe Leu His Ala Phe Val His Trp Pro Asp Arg
             130                 135                 140

Pro Met Asp Gly Asn Pro Thr Met Lys Leu Leu Thr Gly Val Pro Asn
145                 150                 155                 160

Ser Met Leu Gln Ser Pro Gln Val Gln Pro Thr Leu Arg His Asn Gln
                165                 170                 175

Glu Ala Leu Tyr Arg Phe Leu Asn Ser His Ser Tyr Phe Arg Ser
                180                 185                 190

His Arg Ala Arg Ile Glu Lys Ala Thr Ala Phe Asp Arg Met Asp Met
            195                 200                 205

Gln

<210> SEQ ID NO 13
<211> LENGTH: 831
<212> TYPE: PRT
<213> ORGANISM: Unknown
<220> FEATURE:
<223> OTHER INFORMATION: Synthetic Construct

<400> SEQUENCE: 13

Met Glu Thr Gln Pro Ser Leu Pro Thr Pro Leu Gln Ala Pro Ser His
  1               5                  10                  15

Leu Ala Pro Ser Ser Asp Glu Glu Ser Leu Thr Thr Pro Pro Pro
                 20                  25                  30

Ser Pro Ala Thr Thr Thr Ser Thr Leu Glu Asp Glu Glu Glu Val Asp
             35                  40                  45

Ala Pro Gln Glu Met Gln Asp Met Glu Asp Glu Lys Ala Glu Glu Ile
 50                  55                  60

Glu Ala Asp Val Glu Gln Asp Pro Gly Tyr Val Thr Pro Ala Glu His
 65                  70                  75                  80

Glu Glu Glu Leu Arg Arg Phe Leu Asp Arg Glu Asp Asn Arg Pro
                 85                  90                  95

Glu Gln Lys Ala Asp Gly Asp His Gln Glu Ala Gly Leu Gly Asp His
             100                 105                 110

Val Ala Glu Tyr Leu Thr Gly Leu Gly Gly Glu Asp Val Leu Leu Lys
             115                 120                 125

His Leu Ala Arg Gln Ser Ile Ile Val Lys Asp Ala Leu Leu Asp Arg
             130                 135                 140

Thr Glu Val Pro Ile Ser Val Glu Glu Leu Ser Arg Ala Tyr Glu Leu
145                 150                 155                 160

Asn Leu Phe Ser Pro Arg Val Pro Lys Arg Gln Pro Asn Gly Thr
                165                 170                 175

Cys Glu Pro Asn Pro Arg Leu Asn Phe Tyr Pro Ala Phe Ala Val Pro
             180                 185                 190
```

```
Glu Val Leu Ala Thr Tyr His Ile Phe Phe Lys Asn Gln Lys Ile Pro
            195                 200                 205
Val Ser Cys Arg Ala Asn Arg Thr Arg Ala Asp Ala Leu Leu Asn Leu
210                 215                 220
Gly Pro Gly Ala Arg Leu Pro Asp Ile Ala Ser Leu Glu Val Pro
225                 230                 235                 240
Lys Ile Phe Glu Gly Leu Gly Ser Asp Glu Thr Arg Ala Ala Asn Ala
                245                 250                 255
Leu Gln Gln Gly Glu Asn Gly Met Asp Glu His His Ser Ala Leu Val
            260                 265                 270
Glu Leu Glu Gly Asp Asn Ala Arg Leu Ala Val Leu Lys Arg Ser Ile
        275                 280                 285
Glu Val Thr His Phe Ala Tyr Pro Ala Val Asn Leu Pro Pro Lys Val
    290                 295                 300
Met Ser Ala Val Met Asp Gln Leu Leu Ile Lys Arg Ala Ser Pro Leu
305                 310                 315                 320
Ser Glu Asp Gln Asn Met Gln Asp Pro Asp Ala Ser Asp Glu Gly Lys
                325                 330                 335
Pro Val Val Ser Asp Glu Gln Leu Ser Arg Trp Leu Ala Thr Asn Ser
            340                 345                 350
Pro Arg Asp Leu Glu Glu Arg Lys Leu Met Met Ala Val Val Leu
        355                 360                 365
Val Thr Val Glu Leu Glu Cys Leu Arg Arg Phe Phe Thr Asp Pro Glu
    370                 375                 380
Thr Leu Arg Lys Leu Glu Glu Asn Leu His Tyr Thr Phe Arg His Gly
385                 390                 395                 400
Phe Val Arg Gln Ala Cys Lys Ile Ser Asn Val Glu Leu Thr Asn Leu
                405                 410                 415
Val Ser Tyr Met Gly Ile Leu His Glu Asn Arg Leu Gly Gln Ser Val
            420                 425                 430
Leu His Thr Thr Leu Lys Gly Glu Ala Arg Arg Asp Tyr Ile Arg Asp
        435                 440                 445
Cys Val Tyr Leu Tyr Leu Cys His Thr Trp Gln Thr Gly Met Gly Val
    450                 455                 460
Trp Gln Gln Cys Leu Glu Glu Gln Asn Leu Lys Glu Leu Asp Lys Leu
465                 470                 475                 480
Leu Gln Arg Ser Leu Lys Ala Leu Trp Thr Gly Phe Asp Glu Arg Thr
                485                 490                 495
Val Ala Ser Asp Leu Ala Asp Ile Ile Phe Pro Glu Arg Leu Arg Val
            500                 505                 510
Thr Leu Arg Asn Gly Leu Pro Asp Phe Met Ser Gln Ser Met Leu Asn
        515                 520                 525
Asn Phe Arg Ser Phe Ile Leu Glu Arg Ser Gly Ile Leu Pro Ala Thr
    530                 535                 540
Cys Cys Ala Leu Pro Ser Asp Phe Val Pro Leu Thr Tyr Arg Glu Cys
545                 550                 555                 560
Pro Pro Pro Leu Trp Ser His Cys Tyr Leu Phe Arg Leu Ala Asn Tyr
                565                 570                 575
Leu Ser Tyr His Ser Asp Val Ile Glu Asp Val Ser Gly Asp Gly Leu
            580                 585                 590
Leu Asp Cys His Cys Arg Cys Asn Leu Cys Thr Pro His Arg Ser Leu
        595                 600                 605
Ala Cys Asn Pro Gln Leu Leu Ser Glu Thr Gln Ile Ile Gly Thr Phe
```

```
                    610                 615                 620
Glu Leu Gln Gly Pro Ser Ser Glu Gly Glu Gly Ser Ser Pro Gly Gln
625                 630                 635                 640

Ser Leu Lys Leu Thr Pro Gly Leu Trp Thr Ser Ala Tyr Leu Arg Lys
                    645                 650                 655

Phe Ala Pro Glu Asp Tyr His Pro Tyr Glu Ile Arg Phe Tyr Glu Asp
                    660                 665                 670

Gln Ser Gln Pro Pro Lys Ala Glu Leu Ser Ala Cys Val Ile Thr Gln
                675                 680                 685

Gly Ala Ile Leu Ala Gln Leu Gln Ala Ile Gln Lys Ser Arg Gln Glu
            690                 695                 700

Phe Leu Leu Lys Lys Gly Asn Gly Val Tyr Leu Asp Pro Gln Thr Gly
705                 710                 715                 720

Glu Glu Leu Asn Thr Arg Phe Pro Gln Asp Val Pro Ala Pro Arg Lys
                    725                 730                 735

Gln Glu Val Glu Ser Ala Ala Ala Pro Arg Gly His Gly Gly Arg
                740                 745                 750

Leu Gly Gln Ser Gly Arg Gly Gly Asp Gly Arg Leu Gly Gln Pro
            755                 760                 765

Gly Arg Gly Gly Gly Gln Pro Gly Gly Arg Gln Phe Gly Gly Arg
770                 775                 780

Arg Gly Gly Arg Gly Gly Arg Ser Asn Arg Arg Gln Thr Ile Val
785                 790                 795                 800

Leu Gly Ser Gly Asp Lys Gln Gly Pro Arg Gln Gln Gln Gln His Gly
                    805                 810                 815

Tyr Asn Leu Arg Ser Gly Ser Gly Pro Ala Ala Ser Gln Gln
                    820                 825                 830

<210> SEQ ID NO 14
<211> LENGTH: 227
<212> TYPE: PRT
<213> ORGANISM: Unknown
<220> FEATURE:
<223> OTHER INFORMATION: Synthetic Construct

<400> SEQUENCE: 14

Met Ser Lys Glu Ile Pro Thr Pro Tyr Met Trp Ser Tyr Gln Pro Gln
1               5                   10                  15

Met Gly Leu Ala Ala Gly Ala Ser Gln Asp Tyr Ser Thr Arg Met Asn
                20                  25                  30

Trp Leu Ser Ala Gly Pro Ser Met Ile Ser Arg Val Asn Asp Ile Arg
            35                  40                  45

Ala Tyr Arg Asn Gln Leu Leu Leu Glu Gln Ser Ala Leu Thr Thr Thr
        50                  55                  60

Pro Arg Gln His Leu Asn Pro Arg Asn Trp Pro Ala Ala Leu Val Tyr
65                  70                  75                  80

Gln Glu Thr Pro Ala Pro Thr Thr Val Leu Leu Pro Arg Asp Ala Gln
                85                  90                  95

Ala Glu Val Gln Met Thr Asn Ala Gly Val Gln Leu Ala Gly Gly Ser
                100                 105                 110

Ala Leu Cys Arg His Arg Pro Gln Gln Ser Ile Lys Arg Leu Val Ile
            115                 120                 125

Arg Gly Arg Gly Ile Gln Leu Asn Asp Glu Ser Val Ser Ser Ser Leu
        130                 135                 140

Gly Leu Arg Pro Asp Gly Val Phe Gln Ile Ala Gly Cys Gly Arg Ser
```

-continued

```
                145                 150                 155                 160

Ser Phe Thr Pro Arg Gln Ala Val Leu Thr Leu Glu Ser Ser Ser Ser
                165                 170                 175

Gln Pro Arg Ser Gly Gly Ile Gly Thr Leu Gln Phe Val Glu Glu Phe
                180                 185                 190

Thr Pro Ser Val Tyr Phe Asn Pro Phe Ser Gly Ser Pro Gly Gln Tyr
                195                 200                 205

Pro Asp Glu Phe Ile Pro Asn Phe Asp Ala Ile Ser Glu Ser Val Asp
210                 215                 220

Gly Tyr Asp
225

<210> SEQ ID NO 15
<211> LENGTH: 105
<212> TYPE: PRT
<213> ORGANISM: Unknown
<220> FEATURE:
<223> OTHER INFORMATION: Synthetic Construct

<400> SEQUENCE: 15

Met Ser Gly Gly Ala Ala Glu Leu Ala Arg Leu Arg His Leu Asp His
1               5                   10                  15

Cys Arg Arg Phe Arg Cys Phe Ala Arg Glu Leu Thr Glu Phe Ile Tyr
                20                  25                  30

Phe Glu Leu Pro Glu Glu His Pro Gln Gly Pro Ala His Gly Val Arg
            35                  40                  45

Ile Thr Ile Glu Gly Gly Ile Asp Ser Arg Leu His Arg Ile Phe Cys
    50                  55                  60

Gln Arg Pro Val Leu Ile Glu Arg Asp Gln Gly Thr Thr Thr Val Ser
65                  70                  75                  80

Ile Tyr Cys Ile Cys Asn His Pro Gly Leu His Glu Ser Leu Cys Cys
                85                  90                  95

Leu Ile Cys Ala Glu Phe Asn Lys Asn
                100                 105

<210> SEQ ID NO 16
<211> LENGTH: 179
<212> TYPE: PRT
<213> ORGANISM: Unknown
<220> FEATURE:
<223> OTHER INFORMATION: Synthetic Construct

<400> SEQUENCE: 16

Met Gly Val Val Leu Val Ser Phe Ala Leu Leu Ser Leu Leu Gly Leu
1               5                   10                  15

Gly Ser Ala Thr Leu Arg Asn Gln Pro Leu Leu Leu Asp Pro Asp Asp
                20                  25                  30

Val Asp Pro Cys Leu Asp Phe Asp Pro Glu Asn Cys Thr Leu Thr Phe
            35                  40                  45

Ala Pro Glu Thr Ser Arg Phe Cys Gly Val Val Ile Arg Cys Gly Phe
    50                  55                  60

Glu Cys Arg Ser Ile Glu Ile Thr His Asn Asn Lys Thr Trp Asn Asn
65                  70                  75                  80

Thr Leu Phe Thr Ile Trp Gln Pro Gly Asp Pro Gln Trp Tyr Thr Val
                85                  90                  95

Ser Val Arg Gly Pro Asp Gly Ser Ala Arg Met Ala Asn Asn Thr Phe
                100                 105                 110
```

```
Ile Phe Ala Glu Met Cys Asp Met Ala Met Phe Met Ser Arg Gln Tyr
            115                 120                 125

Asp Leu Trp Pro Pro Ser Lys Glu Asn Ile Val Ala Phe Ser Ile Ala
130                 135                 140

Tyr Cys Leu Cys Thr Cys Ile Thr Thr Ala Ile Ile Cys Val Cys Ile
145                 150                 155                 160

His Leu Leu Ile Ala Thr Arg Ser Lys Asn Ser Asn Glu Glu Lys Glu
                165                 170                 175

Lys Met Pro

<210> SEQ ID NO 17
<211> LENGTH: 203
<212> TYPE: PRT
<213> ORGANISM: Unknown
<220> FEATURE:
<223> OTHER INFORMATION: Synthetic Construct

<400> SEQUENCE: 17

Met Ile Phe Ile Thr Ser Ile Phe Ile Val Ser Ile Ser Thr Ile Ala
1               5                   10                  15

His Gly Gln Gln Ile Asn Ala Gly Asp Asn Phe Thr Leu Val Gly Pro
                20                  25                  30

Lys Lys Pro Val Val Ser Trp Phe Trp Thr Lys Pro Asp Pro Trp Ala
            35                  40                  45

Lys Thr Asp Tyr Trp Val Ser Leu Cys Asp Gly Val Phe Leu Tyr Lys
        50                  55                  60

Ser Asn Leu Thr Phe Asn Cys Asn Asn Gln Asn Leu Thr Leu Ile Asn
65                  70                  75                  80

Val Thr Lys Asp Tyr Glu Gly Thr Tyr Tyr Gly Asp Gly Ile Leu Tyr
                85                  90                  95

Arg Ile Arg Val Ile Asp Thr Pro Lys Arg Phe Lys Arg Ala Thr Thr
            100                 105                 110

Lys Val Thr Asp Pro Gln Pro Lys Ile Ser Ser Ile Thr Thr Ile Phe
        115                 120                 125

Thr Asn Ser Thr Tyr Thr Asn Leu Gln Leu Ala Tyr Val Asn Ser Ser
130                 135                 140

Asn Ile Thr Ile Leu Pro Thr Pro Ile Asn Glu Glu Ile Pro Lys Ser
145                 150                 155                 160

Met Ile Gly Ile Ile Val Ala Val Ala Val Gly Met Ile Ile Ile Ile
                165                 170                 175

Ile Cys Met Ile Thr Tyr Ala Cys Cys Tyr Arg Lys Phe Tyr Tyr Glu
            180                 185                 190

Glu Lys Gly Asp Pro Leu Leu Asn Phe Asp Ile
        195                 200

<210> SEQ ID NO 18
<211> LENGTH: 113
<212> TYPE: PRT
<213> ORGANISM: Unknown
<220> FEATURE:
<223> OTHER INFORMATION: Synthetic Construct

<400> SEQUENCE: 18

Met Lys Gln Leu Gly Ile Leu Ile Tyr Cys Ser Ile Asn Leu Ser
1               5                   10                  15

Gln Leu Thr Pro Thr Pro Thr Ser Asn Asn Val Gln Thr Thr Leu Pro
            20                  25                  30
```

```
Val Thr Ile Asn Lys Thr Thr Ser Val Phe Leu Asn Thr Asp Phe
         35                  40                  45

Asn Thr Asn Ser Asn Ser Lys Asp Phe Leu Gln Leu Gln Ile Thr Ala
 50                  55                  60

Leu Ile Ile Ile Gly Leu Ile Ile Leu Ala Ile Leu Leu Tyr Phe Val
 65                  70                  75                  80

Phe Cys Arg Asn Ile Pro Asn Val His Lys Pro Ile Lys Lys Arg Pro
                 85                  90                  95

Ile Tyr Asn Pro Ile Leu Ser Glu Pro Gln Leu Arg Arg Trp Arg Glu
                100                 105                 110

Ile
```

<210> SEQ ID NO 19
<211> LENGTH: 91
<212> TYPE: PRT
<213> ORGANISM: Unknown
<220> FEATURE:
<223> OTHER INFORMATION: Synthetic Construct

<400> SEQUENCE: 19

```
Met Ile Pro Arg Asn Phe Phe Phe Thr Ile Leu Ile Cys Leu Leu Asn
 1               5                  10                  15

Ile Cys Ala Thr Leu Ala Ala Val Thr Ser Val Ser Pro Asp Cys Ile
             20                  25                  30

Gly Pro Phe Ala Thr Tyr Leu Leu Phe Ala Leu Ile Thr Cys Ile Cys
         35                  40                  45

Val Ser Ser Thr Val Cys Leu Val Ile Asn Phe Phe Gln Leu Ile Asp
 50                  55                  60

Trp Ile Phe Val Arg Ile Ala Tyr Leu Arg His His Pro Glu Tyr Arg
 65                  70                  75                  80

Asn His Asp Ile Ala Ala Leu Leu Arg Leu Leu
             85                  90
```

<210> SEQ ID NO 20
<211> LENGTH: 135
<212> TYPE: PRT
<213> ORGANISM: Unknown
<220> FEATURE:
<223> OTHER INFORMATION: Synthetic Construct

<400> SEQUENCE: 20

```
Met Thr Asp Pro Leu Ala Ala Ser Ala Ala Glu Glu Leu Leu Asp
 1               5                  10                  15

Met Asp Gly Arg Ala Ser Glu Gln Arg Leu Ala Gln Leu Arg Ile Arg
             20                  25                  30

Gln Gln Gln Glu Arg Ala Ala Lys Glu Leu Arg Asp Ala Ile Glu Ile
         35                  40                  45

His Gln Cys Lys Lys Gly Ile Phe Cys Leu Val Lys Gln Ala Lys Ile
 50                  55                  60

Ser Tyr Glu Ile Thr Ala Asn Asp His Arg Leu Ser Tyr Glu Leu Gly
 65                  70                  75                  80

Pro Gln Arg Gln Lys Phe Thr Cys Met Val Gly Ile Asn Pro Ile Val
                 85                  90                  95

Ile Thr Gln Gln Ala Gly Asp Thr Lys Gly Cys Ile His Cys Ser Cys
                100                 105                 110

Glu Ser Thr Glu Cys Ile Tyr Thr Leu Leu Lys Thr Leu Cys Gly Leu
                115                 120                 125
```

Arg Asp Ile Leu Pro Met Asn
    130                 135

<210> SEQ ID NO 21
<211> LENGTH: 321
<212> TYPE: PRT
<213> ORGANISM: Unknown
<220> FEATURE:
<223> OTHER INFORMATION: Synthetic Construct

<400> SEQUENCE: 21

Met Ala Lys Arg Ala Arg Leu Ser Ser Ser Phe Asn Pro Val Tyr Pro
1               5                   10                  15

Tyr Glu Asp Glu Asn Ser Ser Gln His Pro Phe Ile Asn Pro Gly Phe
            20                  25                  30

Ile Ser Pro Asn Gly Phe Thr Gln Asn Ser Asp Gly Val Leu Ala Leu
        35                  40                  45

Lys Cys Ala Ala Pro Leu Thr Thr Thr Gly Gly Ser Leu Gln Leu Lys
    50                  55                  60

Val Gly Arg Gly Leu Thr Ile Asp Thr Thr Asp Gly Thr Leu Glu Glu
65                  70                  75                  80

Asp Ile Asn Ile Leu Ala Pro Leu Thr Lys Thr Ala His Ser Ile Gly
                85                  90                  95

Leu Ser Leu Gly Asn Gly Leu Glu Leu Lys Asp Ser Lys Leu Tyr Val
            100                 105                 110

Lys Leu Gly Asp Gly Leu Lys Phe Asn Ser Asn Ser Ile Cys Leu Asp
        115                 120                 125

His Asp Ile Asn Thr Leu Trp Thr Gly Met Asn Pro Ser Ile Asn Cys
    130                 135                 140

Asn Ile Met Gln Gln Asp Asp Asn Asp Ser Lys Leu Thr Leu Val Leu
145                 150                 155                 160

Thr Lys Asn Gly Gly Met Val Asn Ala Tyr Val Ser Leu Val Gly Ala
                165                 170                 175

Ser Asp Ile Val Asn Ser Leu Phe Lys Arg Ala Thr Ala Asn Ile Thr
            180                 185                 190

Ile Arg Leu Ser Phe Asp Ala Ser Gly Asn Leu Leu Thr Ser Leu Ser
        195                 200                 205

Asp Leu Lys Thr Pro Leu Asn His Arg Tyr Gly Asn Asp Met Asp Thr
    210                 215                 220

Asp Thr Leu Thr Asn Gly Lys Ser Phe Met Pro Ser Thr Thr Ala Tyr
225                 230                 235                 240

Pro Phe Asn Asp Thr Thr Arg Asp Lys Glu Asn Tyr Ile Tyr Gly Thr
                245                 250                 255

Cys Tyr Tyr Lys Ser Thr Glu Asp Ala Leu Tyr Pro Leu Glu Val Ala
            260                 265                 270

Val Thr Leu Asn Arg Arg Met Ser Ser Ala Ala Val Ser Tyr Ala Met
        275                 280                 285

Thr Ile Ala Trp Thr Leu Ser Ala Asn Thr Pro Pro Glu Thr Thr Ile
    290                 295                 300

Ala Thr Leu Val Thr Ser Pro Phe Thr Phe Ser Tyr Ile Arg Glu Asn
305                 310                 315                 320

Asp

<210> SEQ ID NO 22
<211> LENGTH: 560
<212> TYPE: DNA

<213> ORGANISM: Unknown
<220> FEATURE:
<223> OTHER INFORMATION: Simian adenovirus 41.1
<220> FEATURE:
<221> NAME/KEY: CDS
<222> LOCATION: (5)..(547)
<223> OTHER INFORMATION: E1b\19K

<400> SEQUENCE: 22

```
atcc atg gag gtt tgg gct atc ttg gaa gat ctc agg cag act aga caa        49
     Met Glu Val Trp Ala Ile Leu Glu Asp Leu Arg Gln Thr Arg Gln
     1               5                   10                  15 ctg cta gaa aac gcc tcg gac gga gtc tct agt ctt tgg aga ttc tgg         97
Leu Leu Glu Asn Ala Ser Asp Gly Val Ser Ser Leu Trp Arg Phe Trp
                20                  25                  30 ttc ggt ggt gat cta gct agg cta gtc ttt agg gta aaa cgg gag tat        145
Phe Gly Gly Asp Leu Ala Arg Leu Val Phe Arg Val Lys Arg Glu Tyr
            35                  40                  45 agt gaa gaa ttt gaa aag tta ttg gaa gac agt cca gga ctt ttt gaa        193
Ser Glu Glu Phe Glu Lys Leu Leu Glu Asp Ser Pro Gly Leu Phe Glu
        50                  55                  60 gcc ctt aac ttg ggc cac cag gct cat ttt aag gag aag gtt tta tca        241
Ala Leu Asn Leu Gly His Gln Ala His Phe Lys Glu Lys Val Leu Ser
65                  70                  75                  80 gtt tta gat ttt tct acc cct ggt aga act gct gct gct gta gct ttc        289
Val Leu Asp Phe Ser Thr Pro Gly Arg Thr Ala Ala Ala Val Ala Phe
                85                  90                  95 ctt act ttt ata ttg gat aaa tgg atc cca caa acc cac ttc agc aag        337
Leu Thr Phe Ile Leu Asp Lys Trp Ile Pro Gln Thr His Phe Ser Lys
            100                 105                 110 gga tac gtc ttg gat ttc ata gca gca gct ttg tgg aga aca tgg aag        385
Gly Tyr Val Leu Asp Phe Ile Ala Ala Ala Leu Trp Arg Thr Trp Lys
        115                 120                 125 gcc cgc agg ctg agg ata atc tta gat tac tgg cca gtg cag cct ctg        433
Ala Arg Arg Leu Arg Ile Ile Leu Asp Tyr Trp Pro Val Gln Pro Leu
    130                 135                 140 ggc gta gca gca atc ctg aga cac cca ccg gcc atg cca gcg gtt ttg        481
Gly Val Ala Ala Ile Leu Arg His Pro Pro Ala Met Pro Ala Val Leu
145                 150                 155 gag gag gag cag cag gag gac aac ccg aga gcc ggc ctg gac cct ccg        529
Glu Glu Glu Gln Gln Glu Asp Asn Pro Arg Ala Gly Leu Asp Pro Pro
160                 165                 170                 175 gtg gag gag gcg gag gag tagctgacct gtt                                 560
Val Glu Glu Ala Glu Glu
                180
```

<210> SEQ ID NO 23
<211> LENGTH: 181
<212> TYPE: PRT
<213> ORGANISM: Unknown
<220> FEATURE:
<223> OTHER INFORMATION: Synthetic Construct

<400> SEQUENCE: 23

```
Met Glu Val Trp Ala Ile Leu Glu Asp Leu Arg Gln Thr Arg Gln Leu
1               5                   10                  15

Leu Glu Asn Ala Ser Asp Gly Val Ser Ser Leu Trp Arg Phe Trp Phe
            20                  25                  30

Gly Gly Asp Leu Ala Arg Leu Val Phe Arg Val Lys Arg Glu Tyr Ser
        35                  40                  45

Glu Glu Phe Glu Lys Leu Leu Glu Asp Ser Pro Gly Leu Phe Glu Ala
    50                  55                  60
```

```
Leu Asn Leu Gly His Gln Ala His Phe Lys Glu Lys Val Leu Ser Val
 65                  70                  75                  80

Leu Asp Phe Ser Thr Pro Gly Arg Thr Ala Ala Val Ala Phe Leu
             85                  90                  95

Thr Phe Ile Leu Asp Lys Trp Ile Pro Gln Thr His Phe Ser Lys Gly
            100                 105                 110

Tyr Val Leu Asp Phe Ile Ala Ala Leu Trp Arg Thr Trp Lys Ala
            115                 120                 125

Arg Arg Leu Arg Ile Ile Leu Asp Tyr Trp Pro Val Gln Pro Leu Gly
            130                 135                 140

Val Ala Ala Ile Leu Arg His Pro Pro Ala Met Pro Ala Val Leu Glu
145                 150                 155                 160

Glu Glu Gln Gln Glu Asp Asn Pro Arg Ala Gly Leu Asp Pro Val
            165                 170                 175

Glu Glu Ala Glu Glu
            180

<210> SEQ ID NO 24
<211> LENGTH: 4600
<212> TYPE: DNA
<213> ORGANISM: Unknown
<220> FEATURE:
<223> OTHER INFORMATION: Simian adenovirus 41.1
<220> FEATURE:
<221> NAME/KEY: CDS
<222> LOCATION: (8)..(625)
<223> OTHER INFORMATION: 22K
<220> FEATURE:
<221> NAME/KEY: CDS
<222> LOCATION: (1920)..(2363)
<223> OTHER INFORMATION: E3\CR1-alpha
<220> FEATURE:
<221> NAME/KEY: CDS
<222> LOCATION: (4166)..(4591)
<223> OTHER INFORMATION: E3\RID\beta

<400> SEQUENCE: 24 cctcagg atg tcc cag cgc cga gga agc aag aag ttg aaa gtg cag ctg      49
        Met Ser Gln Arg Arg Gly Ser Lys Lys Leu Lys Val Gln Leu
        1               5                   10 ccg ccc cca gag gac atg gag gaa gac tgg gac agt cag gca gag gag      97
Pro Pro Pro Glu Asp Met Glu Glu Asp Trp Asp Ser Gln Ala Glu Glu
15              20                  25                  30 gag gag atg gaa gat tgg gac agc cag gca gag gag gcg gac agc ctg     145
Glu Glu Met Glu Asp Trp Asp Ser Gln Ala Glu Glu Ala Asp Ser Leu
                35                  40                  45 gag gaa gac agt ttg gag gag gaa gac gag gag gca gag gag gtg gaa     193
Glu Glu Asp Ser Leu Glu Glu Glu Asp Glu Glu Ala Glu Glu Val Glu
            50                  55                  60 gaa gca acc gcc gcc aaa caa ttg tcc tcg gca gcg gag aca agc aag     241
Glu Ala Thr Ala Ala Lys Gln Leu Ser Ser Ala Ala Glu Thr Ser Lys
        65                  70                  75 gtc cca gac agc agc agc agc acg gct aca atc tcc gct ccg ggt cgg     289
Val Pro Asp Ser Ser Ser Ser Thr Ala Thr Ile Ser Ala Pro Gly Arg
80                  85                  90 ggg gcc cag cag cgt ccc aac agt aga tgg gac gag acc ggg cga ttc     337
Gly Ala Gln Gln Arg Pro Asn Ser Arg Trp Asp Glu Thr Gly Arg Phe
95                  100                 105                 110 ccg aac ccg acc acc gct tcc aag acc ggt aag aag gag cgg cag gga     385
Pro Asn Pro Thr Thr Ala Ser Lys Thr Gly Lys Lys Glu Arg Gln Gly
                115                 120                 125
```

|  |  |
|---|---:|
| tac aag tcc tgg cgg ggg cat aag aat gcc atc atc tcc tgc ttg cat<br>Tyr Lys Ser Trp Arg Gly His Lys Asn Ala Ile Ile Ser Cys Leu His<br>            130                       135                    140 | 433 |
| gaa tgc ggg ggc aac ata tcc ttc acc cga cgc tac ctg ctc ttc cac<br>Glu Cys Gly Gly Asn Ile Ser Phe Thr Arg Arg Tyr Leu Leu Phe His<br>145                      150                       155 | 481 |
| cac ggg gtg aac ttc ccc cgc aat gtc ttg cat tac tac cgt cac ctc<br>His Gly Val Asn Phe Pro Arg Asn Val Leu His Tyr Tyr Arg His Leu<br>    160                     165                    170 | 529 |
| cac agc cct tac tac agc cag caa gtc ccg aca gcc tcg aca aag aaa<br>His Ser Pro Tyr Tyr Ser Gln Gln Val Pro Thr Ala Ser Thr Lys Lys<br>175                      180                    185                    190 | 577 |
| gac agc agc agc agc ggg gac ctc cag cag aaa acc agc agc agc agt<br>Asp Ser Ser Ser Ser Gly Asp Leu Gln Gln Lys Thr Ser Ser Ser Ser<br>                    195                    200                    205 | 625 |
| tagaaaatcc agtgcagcag gaggaggact gaggatcaca gcgaacgagc cagcgcagac | 685 |
| ccgagagctg agaaacagga tctttccaac cctctatgcc atcttccagc agagtcgggg | 745 |
| gcaagagcag gaactgaaag taaaaaaccg atctctgcgc tcgctcaccc gaagttgttt | 805 |
| gtatcacaag agcgaagacc aacttcagcg cactctcgag gacgccgagg ctctcttcaa | 865 |
| caagtactgc gcgctgactc ttaaagagta gcccgcgccc gcgctcgctc gaaaaaggcg | 925 |
| ggaattacgt caccctggc acctgtcctt tgccctcgtc atgagtaaag aaattcccac | 985 |
| gccttacatg tggagctatc agccccaaat gggactggca gcaggcgcct cccaggacta | 1045 |
| ctccacccgc atgaattggc tcagcgccgg cccctcgatg atctcacggg ttaatgatat | 1105 |
| acgagcttac cgaaaccagt tactcctaga acagtcagct ctcaccacca cacccccgcca | 1165 |
| acaccttaat ccccggaatt ggcccgccgc cctggtgtac caggaaactc ccgctcccac | 1225 |
| caccgtacta cttcctcgag acgcccaggc cgaagttcag atgactaacg caggtgtaca | 1285 |
| gctggcgggc ggttccgccc tgtgtcgtca ccggcctcag cagagtataa aacgcctggt | 1345 |
| gatcagaggc cgaggtatcc agctcaacga cgagtcggtg agctcttcgc ttggtctgcg | 1405 |
| accagacgga gtcttccaga tcgccggctg tgggagatct tccttcactc ctcgtcaggc | 1465 |
| tgtcctgact ttggagagtt cgtcctcgca gccccgctcg gcggcatcg ggactctcca | 1525 |
| gtttgtggag gagtttactc cctctgtcta cttcaacccc ttctccggct ctcccggcca | 1585 |
| gtacccggac gagttcatac cgaacttcga cgcaatcagc gagtcagtgg atggctatga | 1645 |
| ttgatgtctg gtggcgcggc tgagttagct cgactgcgac atctagacca ctgccgccgc | 1705 |
| tttcgctgtt tcgcccggga actcaccgag ttcatctact tcgaactccc cgaggagcac | 1765 |
| cctcagggac cggcccacgg agtgcggatt accatcgaag ggggaataga ctctcgcctg | 1825 |
| catcggatct tctgccagcg acccgtgctg atcgagcgcg accagggaac tacaacagtc | 1885 |
| tccatctact gcatctgtaa ccaccccgga ttgc atg aaa gcc ttt gct gtc tta<br>                                                        Met Lys Ala Phe Ala Val Leu<br>                                                                        210 | 1940 |
| ttt gtg ctg agt tta ata aaa act gag tta aga ctc acc ttt gga cta<br>Phe Val Leu Ser Leu Ile Lys Thr Glu Leu Arg Leu Thr Phe Gly Leu<br>    215                     220                    225 | 1988 |
| ccg ctt ctt caa ccc gga ctt tac aac acc agc cag act ctc cgt tcc<br>Pro Leu Leu Gln Pro Gly Leu Tyr Asn Thr Ser Gln Thr Leu Arg Ser<br>230                      235                    240                    245 | 2036 |
| agc cag aag acc cag gcc ctt cct ctg atc cag gac tct aat tct acc<br>Ser Gln Lys Thr Gln Ala Leu Pro Leu Ile Gln Asp Ser Asn Ser Thr<br>                    250                    255                    260 | 2084 |
| tcc cca gca cca tcc cct act aac ctt ccc gaa act aac aac ctc gga | 2132 |

| | | | | | | | | | | | | | | |
|---|---|---|---|---|---|---|---|---|---|---|---|---|---|---|
|Ser|Pro|Ala|Pro 265|Ser|Pro|Thr|Asn|Leu 270|Pro|Glu|Thr|Asn|Asn 275|Leu|Gly|

| | | | | | | | | | | | | | | |
|---|---|---|---|---|---|---|---|---|---|---|---|---|---|---|
|gct|cag|ctg|caa|ccc|cgc|ttc|tcc|aga|agc|ctc|ctt|tct|gcc|aat|act|
|Ala|Gln|Leu 280|Gln|Pro|Arg|Phe|Ser 285|Arg|Ser|Leu|Leu|Ser 290|Ala|Asn|Thr|

2180

| | | | | | | | | | | | | | | | |
|---|---|---|---|---|---|---|---|---|---|---|---|---|---|---|---|
|act|act|ccc|aga|acc|gga|ggt|gag|ctc|cgt|ggt|ctc|cct|act|gac|aac|
|Thr|Thr 295|Pro|Arg|Thr|Gly|Gly 300|Glu|Leu|Arg|Gly|Leu 305|Pro|Thr|Asp|Asn|

2228

| | | | | | | | | | | | | | | | |
|---|---|---|---|---|---|---|---|---|---|---|---|---|---|---|---|
|ccc|tgg|gtg|gta|gcg|ggt|ttt|gta|gcg|cta|gga|gta|gtt|gcg|ggt|ggg|
|Pro 310|Trp|Val|Val|Ala 315|Gly|Phe|Val|Ala|Leu 320|Gly|Val|Val|Ala|Gly 325|Gly|

2276

| | | | | | | | | | | | | | | | |
|---|---|---|---|---|---|---|---|---|---|---|---|---|---|---|---|
|ctg|gtg|ctt|atc|ctc|tgc|tac|cta|tac|aca|cct|tgc|tgt|gct|tat|tta|
|Leu|Val|Leu|Ile|Leu 330|Cys|Tyr|Leu|Tyr|Thr 335|Pro|Cys|Cys|Ala|Tyr 340|Leu|

2324

| | | | | | | | | | | |
|---|---|---|---|---|---|---|---|---|---|---|
|gta|gta|ttg|tgc|tgc|tgg|ttt|aag|aaa|tgg|ggg|tcg|tac|tagtatcgtt|
|Val|Val|Leu|Cys|Cys 345|Trp|Phe|Lys|Lys 350|Trp|Gly|Ser|Tyr|

2373

| | | |
|---|---|---|
|tgctttactt|tcgcttttgg gtctgggctc tgctacgcta agaaatcagc ctttgctatt|2433|
|agatcccgat|gatgttgatc catgtctgga ctttgatcca gagaactgca cactcacttt|2493|
|tgcacctgaa|acaagtcgct tctgtggagt tgttattagg tgcggatttg aatgcaggtc|2553|
|cattgagatt|acacacaata acaaaacttg gaacaatacc ttattcacaa tatggcaacc|2613|
|aggagatcct|cagtggtata ctgtctctgt ccggggtcct gacggttccg cccgcatggc|2673|
|taataacact|ttcattttg ctgaaatgtg cgatatggcc atgttcatga gcagacagta|2733|
|tgacctatgg|cctcccagca aagagaacat tgtggcattc tccattgctt attgcttatg|2793|
|tacttgcatt|accactgcta tcatatgtgt gtgcatacac ttgctcatag caactcgctc|2853|
|caaaaacagc|aatgaggaaa agagaaaat gccttgacct tttttcctcg ttttctgttc|2913|
|acagctatga|tttttattac atccatcttt attgtcagca tttcaactat tgcacatgga|2973|
|caacaaataa|atgcaggcga caatttcaca ttagttgggc ctaaaaaacc agttgtctcc|3033|
|tggttctgga|ctaaacctga tccatgggct aaaactgatt actgggtttc actttgtgat|3093|
|ggtgtatttc|tgtataaatc taaccttaca ttcaattgca ataatcaaaa cctaacacta|3153|
|atcaatgtta|ctaaagatta tgaaggaaca tactatggag atggaatctt atatagaatt|3213|
|agagtaatag|acactcctaa gagattcaaa agagctacaa ctaaagttac agatccacaa|3273|
|ccaaaaatct|ctagcatcac tactatcttt actaacagta catataccaa tttcaaattg|3333|
|gcttatgtta|actcatcaaa tattacaatc ctgcctacac caatcaatga agaaattcct|3393|
|aaaatcaatga|ttgggatcat tgtggcggtg gcagtgggaa tgatcataat cataatatgt|3453|
|atgatcacct|atgcttgctg ctacagaaag ttttattatg aagaaaaagg agaccccta|3513|
|ctaaattttg|acatttaatt ttttatagat gaaacaacta ggtatcttga ttatttactg|3573|
|cagcattaat|ctttctcaat taacaccaac accaactagt aacaatgtgc agactacttt|3633|
|accagtcacc|ataaacaaaa ctacctcagt ttttctaaat aatacagact ttaatactaa|3693|
|ctccaactct|aaagattttc ttcaacttca aatcactgct cttattataa ttggattaat|3753|
|aattctagca|atccttctat actttgtctt ttgccgcaac atccccaatg ttcacaaacc|3813|
|cattaaaaag|cgtcctattt acaaccccat cttaagcgag ccacaactta gacggtggag|3873|
|ggaaatctaa|tacatctctc ttttctttca gtatggtgat catcaaacat gatccctaga|3933|
|aatttttct|tcaccatact catctgcctt ctcaatatct gcgctaccct tgctgcggtc|3993|
|actagcgtct|caccagactg cataggacca tttgccacct acttgctttt tgcattgatc|4053|

```
acctgtatct gtgtgagtag cacagtctgt ctggttatta attttttcca acttatagac    4113 tggattttg tgcgcattgc ctacctgaga caccatccag aataccgcaa cc atg ata    4171
                                                         Met Ile
                                                         355 ttg cgg cac tac tca gac ttc ttt aaa acc ata cag gct ttg cta cca    4219
Leu Arg His Tyr Ser Asp Phe Phe Lys Thr Ile Gln Ala Leu Leu Pro
    360                 365                 370 ctg cta ttg ctg cta ctg ccc tgt gac act ata gcc acc aca cct acc    4267
Leu Leu Leu Leu Leu Leu Pro Cys Asp Thr Ile Ala Thr Thr Pro Thr
        375                 380                 385 cta aac cca aat ctt aga aaa tgt aaa ttc caa gag cca tgg aat ttc    4315
Leu Asn Pro Asn Leu Arg Lys Cys Lys Phe Gln Glu Pro Trp Asn Phe
390                 395                 400 ctc aaa tgt tat aat gaa aca att gat ttt cca ccc tat tgg ata aca    4363
Leu Lys Cys Tyr Asn Glu Thr Ile Asp Phe Pro Pro Tyr Trp Ile Thr
405                 410                 415                 420 atc att gga atc ctt aat gtg gta tgc tgc acc ata ttt gca ttc ctt    4411
Ile Ile Gly Ile Leu Asn Val Val Cys Cys Thr Ile Phe Ala Phe Leu
                425                 430                 435 gta tat ccc atg ttt gat ttt ggg tgg aat gtc ccc aat gca ctc act    4459
Val Tyr Pro Met Phe Asp Phe Gly Trp Asn Val Pro Asn Ala Leu Thr
            440                 445                 450 cac cca caa gaa cca cag gaa cat atc cca cta caa aac atg caa cca    4507
His Pro Gln Glu Pro Gln Glu His Ile Pro Leu Gln Asn Met Gln Pro
                455                 460                 465 cta gca cta ata gaa tat gaa aat gag cca cag cct cca cta ctc cct    4555
Leu Ala Leu Ile Glu Tyr Glu Asn Glu Pro Gln Pro Pro Leu Leu Pro
470                 475                 480 gcc att agc tac ttc aac cta acc ggt aga gat gac tgaccccact         4600
Ala Ile Ser Tyr Phe Asn Leu Thr Gly Arg Asp Asp
485                 490                 495

<210> SEQ ID NO 25
<211> LENGTH: 206
<212> TYPE: PRT
<213> ORGANISM: Unknown
<220> FEATURE:
<223> OTHER INFORMATION: Synthetic Construct

<400> SEQUENCE: 25

Met Ser Gln Arg Arg Gly Ser Lys Lys Leu Lys Val Gln Leu Pro Pro
1               5                   10                  15

Pro Glu Asp Met Glu Glu Asp Trp Asp Ser Gln Ala Glu Glu Glu Glu
            20                  25                  30

Met Glu Asp Trp Asp Ser Gln Ala Glu Glu Ala Asp Ser Leu Glu Glu
        35                  40                  45

Asp Ser Leu Glu Glu Glu Asp Glu Glu Ala Glu Val Glu Glu Ala
    50                  55                  60

Thr Ala Ala Lys Gln Leu Ser Ser Ala Ala Glu Thr Ser Lys Val Pro
65                  70                  75                  80

Asp Ser Ser Ser Thr Ala Thr Ile Ser Ala Pro Gly Arg Gly Ala
                85                  90                  95

Gln Gln Arg Pro Asn Ser Arg Trp Asp Glu Thr Gly Arg Phe Pro Asn
            100                 105                 110

Pro Thr Thr Ala Ser Lys Thr Gly Lys Lys Glu Arg Gln Gly Tyr Lys
        115                 120                 125

Ser Trp Arg Gly His Lys Asn Ala Ile Ile Ser Cys Leu His Glu Cys
    130                 135                 140
```

```
Gly Gly Asn Ile Ser Phe Thr Arg Arg Tyr Leu Leu Phe His His Gly
145                 150                 155                 160

Val Asn Phe Pro Arg Asn Val Leu His Tyr Tyr Arg His Leu His Ser
                165                 170                 175

Pro Tyr Tyr Ser Gln Gln Val Pro Thr Ala Ser Thr Lys Lys Asp Ser
                180                 185                 190

Ser Ser Ser Gly Asp Leu Gln Gln Lys Thr Ser Ser Ser
                195                 200                 205

<210> SEQ ID NO 26
<211> LENGTH: 148
<212> TYPE: PRT
<213> ORGANISM: Unknown
<220> FEATURE:
<223> OTHER INFORMATION: Synthetic Construct

<400> SEQUENCE: 26

Met Lys Ala Phe Ala Val Leu Phe Val Leu Ser Leu Ile Lys Thr Glu
1               5                   10                  15

Leu Arg Leu Thr Phe Gly Leu Pro Leu Gln Pro Gly Leu Tyr Asn
                20                  25                  30

Thr Ser Gln Thr Leu Arg Ser Ser Gln Lys Thr Gln Ala Leu Pro Leu
                35                  40                  45

Ile Gln Asp Ser Asn Ser Thr Ser Pro Ala Pro Ser Pro Thr Asn Leu
50                  55                  60

Pro Glu Thr Asn Asn Leu Gly Ala Gln Leu Gln Pro Arg Phe Ser Arg
65                  70                  75                  80

Ser Leu Leu Ser Ala Asn Thr Thr Thr Pro Arg Thr Gly Gly Glu Leu
                85                  90                  95

Arg Gly Leu Pro Thr Asp Asn Pro Trp Val Val Ala Gly Phe Val Ala
                100                 105                 110

Leu Gly Val Val Ala Gly Gly Leu Val Leu Ile Leu Cys Tyr Leu Tyr
                115                 120                 125

Thr Pro Cys Cys Ala Tyr Leu Val Val Leu Cys Cys Trp Phe Lys Lys
                130                 135                 140

Trp Gly Ser Tyr
145

<210> SEQ ID NO 27
<211> LENGTH: 142
<212> TYPE: PRT
<213> ORGANISM: Unknown
<220> FEATURE:
<223> OTHER INFORMATION: Synthetic Construct

<400> SEQUENCE: 27

Met Ile Leu Arg His Tyr Ser Asp Phe Phe Lys Thr Ile Gln Ala Leu
1               5                   10                  15

Leu Pro Leu Leu Leu Leu Leu Pro Cys Asp Thr Ile Ala Thr Thr
                20                  25                  30

Pro Thr Leu Asn Pro Asn Leu Arg Lys Cys Lys Phe Gln Glu Pro Trp
                35                  40                  45

Asn Phe Leu Lys Cys Tyr Asn Glu Thr Ile Asp Phe Pro Pro Tyr Trp
                50                  55                  60

Ile Thr Ile Ile Gly Ile Leu Asn Val Val Cys Cys Thr Ile Phe Ala
65                  70                  75                  80

Phe Leu Val Tyr Pro Met Phe Asp Phe Gly Trp Asn Val Pro Asn Ala
                85                  90                  95
```

```
Leu Thr His Pro Gln Glu Pro Gln His Ile Pro Leu Gln Asn Met
            100                 105                 110

Gln Pro Leu Ala Leu Ile Glu Tyr Glu Asn Glu Pro Gln Pro Pro Leu
            115                 120                 125

Leu Pro Ala Ile Ser Tyr Phe Asn Leu Thr Gly Arg Asp Asp
            130                 135                 140

<210> SEQ ID NO 28
<211> LENGTH: 880
<212> TYPE: DNA
<213> ORGANISM: Unknown
<220> FEATURE:
<223> OTHER INFORMATION: Simian adenovirus 41.1
<220> FEATURE:
<221> NAME/KEY: CDS
<222> LOCATION: (4)..(580)
<223> OTHER INFORMATION: E1a
<220> FEATURE:
<221> NAME/KEY: CDS
<222> LOCATION: (669)..(874)
<223> OTHER INFORMATION: E1a

<400> SEQUENCE: 28 aaa atg aga cac ctg cga ttc ctg cct cag gaa atc tcc att gcg acc      48
    Met Arg His Leu Arg Phe Leu Pro Gln Glu Ile Ser Ile Ala Thr
    1               5                   10                  15 ggg aat gaa ata ctg cag ttt gtg gta gat gcc ctg atg gga gac gat      96
Gly Asn Glu Ile Leu Gln Phe Val Val Asp Ala Leu Met Gly Asp Asp
                20                  25                  30 ccg gag ccg cct gcg cag cct ttc gat cct cct acg ctt cat gaa ctg     144
Pro Glu Pro Pro Ala Gln Pro Phe Asp Pro Pro Thr Leu His Glu Leu
            35                  40                  45 tat gat tta gag gta gac ggg ccg gag gat cct aac gag gaa gct gtg     192
Tyr Asp Leu Glu Val Asp Gly Pro Glu Asp Pro Asn Glu Glu Ala Val
        50                  55                  60 aat ggg ttt ttc agc gat tct atg cta tta gct gct agt gaa gga gtg     240
Asn Gly Phe Phe Ser Asp Ser Met Leu Leu Ala Ala Ser Glu Gly Val
    65                  70                  75 gac tta gac cca cct tct gag acc ctt gat acc cca ggg gtg gtg gtg     288
Asp Leu Asp Pro Pro Ser Glu Thr Leu Asp Thr Pro Gly Val Val Val
80                  85                  90                  95 gaa agc ggc aga ggt ggg aaa aaa ttg cct gaa ctt ggt gct gct gaa     336
Glu Ser Gly Arg Gly Gly Lys Lys Leu Pro Glu Leu Gly Ala Ala Glu
                100                 105                 110 atg gat ttg cac tgt tat gaa gag ggc ttt cct ccg agt gat gat gac     384
Met Asp Leu His Cys Tyr Glu Glu Gly Phe Pro Pro Ser Asp Asp Asp
            115                 120                 125 gat gag gaa aat gtg cag tcg atc cag acc gca gcg ggt gag gga atg     432
Asp Glu Glu Asn Val Gln Ser Ile Gln Thr Ala Ala Gly Glu Gly Met
        130                 135                 140 aaa gct gcc aat gat ggt ttt aag ttg gac tgc ccg gag ctg cct gga     480
Lys Ala Ala Asn Asp Gly Phe Lys Leu Asp Cys Pro Glu Leu Pro Gly
    145                 150                 155 cat ggc tgt aag tct tgt gaa ttt cac agg aat agt act gga cta aaa     528
His Gly Cys Lys Ser Cys Glu Phe His Arg Asn Ser Thr Gly Leu Lys
160                 165                 170                 175 gaa ctg ttg tgc tcg ctt tgc tat atg aga acg cac tgc cat ttt att     576
Glu Leu Leu Cys Ser Leu Cys Tyr Met Arg Thr His Cys His Phe Ile
                180                 185                 190 tac a gtaagtgtgt ctaacttaaa tttaaaggga cagtgtagca gtttaatgtc        630
Tyr
```

```
tgttgaatgt gggatttatg tctttgtgat ttttatag gt  cct gtg tct gat gct    685
                                               Ser Pro Val Ser Asp Ala
                                                   195 gat gaa tcg cct tct cct gat tca act acc tca cct cct gaa att cag    733
Asp Glu Ser Pro Ser Pro Asp Ser Thr Thr Ser Pro Pro Glu Ile Gln
    200                 205                 210 gcg cca gtc cct gca aac gta tgc aag ccc att cct gtg aag gct aag    781
Ala Pro Val Pro Ala Asn Val Cys Lys Pro Ile Pro Val Lys Ala Lys
215                 220                 225                 230 cct ggg aaa cgc cct gct gtg gat aaa ctg gag gac ttg ctt gag ggt    829
Pro Gly Lys Arg Pro Ala Val Asp Lys Leu Glu Asp Leu Leu Glu Gly
                235                 240                 245 ggg gat gga cct ttg gac ttg agt acc cgg aaa ctg cca agg caa        874
Gly Asp Gly Pro Leu Asp Leu Ser Thr Arg Lys Leu Pro Arg Gln
            250                 255                 260 tgagtg                                                              880
```

<210> SEQ ID NO 29
<211> LENGTH: 261
<212> TYPE: PRT
<213> ORGANISM: Unknown
<220> FEATURE:
<223> OTHER INFORMATION: Synthetic Construct

<400> SEQUENCE: 29

```
Met Arg His Leu Arg Phe Leu Pro Gln Glu Ile Ser Ile Ala Thr Gly
1               5                   10                  15

Asn Glu Ile Leu Gln Phe Val Val Asp Ala Leu Met Gly Asp Asp Pro
            20                  25                  30

Glu Pro Pro Ala Gln Pro Phe Asp Pro Pro Thr Leu His Glu Leu Tyr
        35                  40                  45

Asp Leu Glu Val Asp Gly Pro Glu Asp Pro Asn Glu Ala Val Asn
50                  55                  60

Gly Phe Phe Ser Asp Ser Met Leu Leu Ala Ala Ser Glu Gly Val Asp
65                  70                  75                  80

Leu Asp Pro Pro Ser Glu Thr Leu Asp Thr Pro Gly Val Val Glu
                85                  90                  95

Ser Gly Arg Gly Gly Lys Lys Leu Pro Glu Leu Gly Ala Ala Glu Met
            100                 105                 110

Asp Leu His Cys Tyr Glu Glu Gly Phe Pro Pro Ser Asp Asp Asp
        115                 120                 125

Glu Glu Asn Val Gln Ser Ile Gln Thr Ala Ala Gly Glu Gly Met Lys
130                 135                 140

Ala Ala Asn Asp Gly Phe Lys Leu Asp Cys Pro Glu Leu Pro Gly His
145                 150                 155                 160

Gly Cys Lys Ser Cys Glu Phe His Arg Asn Ser Thr Gly Leu Lys Glu
                165                 170                 175

Leu Leu Cys Ser Leu Cys Tyr Met Arg Thr His Cys His Phe Ile Tyr
            180                 185                 190

Ser Pro Val Ser Asp Ala Asp Glu Ser Pro Ser Pro Asp Ser Thr Thr
        195                 200                 205

Ser Pro Pro Glu Ile Gln Ala Pro Val Pro Ala Asn Val Cys Lys Pro
210                 215                 220

Ile Pro Val Lys Ala Lys Pro Gly Lys Arg Pro Ala Val Asp Lys Leu
225                 230                 235                 240

Glu Asp Leu Leu Glu Gly Gly Asp Gly Pro Leu Asp Leu Ser Thr Arg
                245                 250                 255
```

```
Lys Leu Pro Arg Gln
        260

<210> SEQ ID NO 30
<211> LENGTH: 900
<212> TYPE: DNA
<213> ORGANISM: Unknown
<220> FEATURE:
<223> OTHER INFORMATION: Simian adenovirus 41.1
<220> FEATURE:
<221> NAME/KEY: CDS
<222> LOCATION: (8)..(365)
<223> OTHER INFORMATION: 33K
<220> FEATURE:
<221> NAME/KEY: CDS
<222> LOCATION: (535)..(893)
<223> OTHER INFORMATION: 33K

<400> SEQUENCE: 30 cctcagg atg tcc cag cgc cga gga agc aag aag ttg aaa gtg cag ctg     49
        Met Ser Gln Arg Arg Gly Ser Lys Lys Leu Lys Val Gln Leu
        1               5                  10 ccg ccc cca gag gac atg gag gaa gac tgg gac agt cag gca gag gag     97
Pro Pro Pro Glu Asp Met Glu Glu Asp Trp Asp Ser Gln Ala Glu Glu
15              20                  25                  30 gag gag atg gaa gat tgg gac agc cag gca gag gag gcg gac agc ctg    145
Glu Glu Met Glu Asp Trp Asp Ser Gln Ala Glu Glu Ala Asp Ser Leu
                35                  40                  45 gag gaa gac agt ttg gag gag gaa gac gag gag gca gag gag gtg gaa    193
Glu Glu Asp Ser Leu Glu Glu Glu Asp Glu Glu Ala Glu Glu Val Glu
            50                  55                  60 gaa gca acc gcc gcc aaa caa ttg tcc tcg gca gcg gag aca agc aag    241
Glu Ala Thr Ala Ala Lys Gln Leu Ser Ser Ala Ala Glu Thr Ser Lys
        65                  70                  75 gtc cca gac agc agc agc agc acg gct aca atc tcc gct ccg ggt cgg    289
Val Pro Asp Ser Ser Ser Ser Thr Ala Thr Ile Ser Ala Pro Gly Arg
    80                  85                  90 ggg gcc cag cag cgt ccc aac agt aga tgg gac gag acc ggg cga ttc    337
Gly Ala Gln Gln Arg Pro Asn Ser Arg Trp Asp Glu Thr Gly Arg Phe
95                  100                 105                 110 ccg aac ccg acc acc gct tcc aag acc g gtaagaagga gcggcaggga        385
Pro Asn Pro Thr Thr Ala Ser Lys Thr
                115 tacaagtcct ggcgggggca taagaatgcc atcatctcct gcttgcatga atgcggggc    445 aacatatcct tcacccgacg ctacctgctc ttccaccacg gggtgaactt ccccgcaat    505 gtcttgcatt actaccgtca cctccacag cc ctt act aca gcc agc aag tcc     557
                                   Ala Leu Thr Thr Ala Ser Lys Ser
                                                            125 cga cag cct cga caa aga aag aca gca gca gca gcg ggg acc tcc agc    605
Arg Gln Pro Arg Gln Arg Lys Thr Ala Ala Ala Ala Gly Thr Ser Ser
        130                 135                 140 aga aaa cca gca gca gca gtt aga aaa tcc agt gca gca gga gga gga    653
Arg Lys Pro Ala Ala Ala Val Arg Lys Ser Ser Ala Ala Gly Gly Gly
    145                 150                 155 ctg agg atc aca gcg aac gag cca gcg cag acc cga gag ctg aga aac    701
Leu Arg Ile Thr Ala Asn Glu Pro Ala Gln Thr Arg Glu Leu Arg Asn
160                 165                 170                 175 agg atc ttt cca acc ctc tat gcc atc ttc cag cag agt cgg ggg caa    749
Arg Ile Phe Pro Thr Leu Tyr Ala Ile Phe Gln Gln Ser Arg Gly Gln
                180                 185                 190 gag cag gaa ctg aaa gta aaa aac cga tct ctg cgc tcg ctc acc cga    797
Glu Gln Glu Leu Lys Val Lys Asn Arg Ser Leu Arg Ser Leu Thr Arg
```

```
Glu Gln Glu Leu Lys Val Lys Asn Arg Ser Leu Arg Ser Leu Thr Arg
                195                 200                 205 agt tgt ttg tat cac aag agc gaa gac caa ctt cag cgc act ctc gag       845
Ser Cys Leu Tyr His Lys Ser Glu Asp Gln Leu Gln Arg Thr Leu Glu
            210                 215                 220 gac gcc gag gct ctc ttc aac aag tac tgc gcg ctg act ctt aaa gag       893
Asp Ala Glu Ala Leu Phe Asn Lys Tyr Cys Ala Leu Thr Leu Lys Glu
    225                 230                 235 tagcccg                                                                900

<210> SEQ ID NO 31
<211> LENGTH: 239
<212> TYPE: PRT
<213> ORGANISM: Unknown
<220> FEATURE:
<223> OTHER INFORMATION: Synthetic Construct

<400> SEQUENCE: 31

Met Ser Gln Arg Arg Gly Ser Lys Lys Leu Lys Val Gln Leu Pro Pro
1               5                   10                  15

Pro Glu Asp Met Glu Glu Asp Trp Asp Ser Gln Ala Glu Glu Glu Glu
                20                  25                  30

Met Glu Asp Trp Asp Ser Gln Ala Glu Glu Ala Asp Ser Leu Glu Glu
            35                  40                  45

Asp Ser Leu Glu Glu Glu Asp Glu Glu Ala Glu Val Glu Glu Ala
50                  55                  60

Thr Ala Ala Lys Gln Leu Ser Ser Ala Ala Glu Thr Ser Lys Val Pro
65                  70                  75                  80

Asp Ser Ser Ser Thr Ala Thr Ile Ser Ala Pro Gly Arg Gly Ala
                85                  90                  95

Gln Gln Arg Pro Asn Ser Arg Trp Asp Glu Thr Gly Arg Phe Pro Asn
                100                 105                 110

Pro Thr Thr Ala Ser Lys Thr Ala Leu Thr Thr Ala Ser Lys Ser Arg
            115                 120                 125

Gln Pro Arg Gln Arg Lys Thr Ala Ala Ala Gly Thr Ser Ser Arg
130                 135                 140

Lys Pro Ala Ala Ala Val Arg Lys Ser Ser Ala Ala Gly Gly Gly Leu
145                 150                 155                 160

Arg Ile Thr Ala Asn Glu Pro Ala Gln Thr Arg Glu Leu Arg Asn Arg
                165                 170                 175

Ile Phe Pro Thr Leu Tyr Ala Ile Phe Gln Gln Ser Arg Gly Gln Glu
            180                 185                 190

Gln Glu Leu Lys Val Lys Asn Arg Ser Leu Arg Ser Leu Thr Arg Ser
                195                 200                 205

Cys Leu Tyr His Lys Ser Glu Asp Gln Leu Gln Arg Thr Leu Glu Asp
        210                 215                 220

Ala Glu Ala Leu Phe Asn Lys Tyr Cys Ala Leu Thr Leu Lys Glu
225                 230                 235

<210> SEQ ID NO 32
<211> LENGTH: 23
<212> TYPE: DNA
<213> ORGANISM: Artificial
<220> FEATURE:
<223> OTHER INFORMATION: based on Simian adenovirus 41.1

<400> SEQUENCE: 32
caggatgctt cggagtacct gag                                              23
```

<210> SEQ ID NO 33
<211> LENGTH: 26
<212> TYPE: DNA
<213> ORGANISM: Artificial
<220> FEATURE:
<223> OTHER INFORMATION: based on Simian adenovirus 41.1
<220> FEATURE:
<221> NAME/KEY: misc_feature
<222> LOCATION: (6)..(6)
<223> OTHER INFORMATION: n is a, c, g, or t

<400> SEQUENCE: 33
ttggcnggda tdgggtavag catgtt                                      26

<210> SEQ ID NO 34
<211> LENGTH: 35767
<212> TYPE: DNA
<213> ORGANISM: Unknown
<220> FEATURE:
<223> OTHER INFORMATION: Simian adenovirus 41.2
<220> FEATURE:
<221> NAME/KEY: repeat_region
<222> LOCATION: (1)..(132)
<223> OTHER INFORMATION: ITR
<220> FEATURE:
<221> NAME/KEY: CDS
<222> LOCATION: (1924)..(3408)
<223> OTHER INFORMATION: E1b/55K
<220> FEATURE:
<221> NAME/KEY: CDS
<222> LOCATION: (3503)..(3916)
<223> OTHER INFORMATION: pIX
<220> FEATURE:
<221> NAME/KEY: misc_feature
<222> LOCATION: (3985)..(5606)
<223> OTHER INFORMATION: IVa2  complement (3985..5315,5594..5606)
<220> FEATURE:
<221> NAME/KEY: misc_feature
<222> LOCATION: (5088)..(13917)
<223> OTHER INFORMATION: pol  complement (5088..8657,13909..13917)
<220> FEATURE:
<221> NAME/KEY: misc_feature
<222> LOCATION: (8459)..(13917)
<223> OTHER INFORMATION: pTP  complement (8459..10435,13909..13917)
<220> FEATURE:
<221> NAME/KEY: CDS
<222> LOCATION: (10921)..(12087)
<223> OTHER INFORMATION: 52K
<220> FEATURE:
<221> NAME/KEY: CDS
<222> LOCATION: (12115)..(13875)
<223> OTHER INFORMATION: pIIIa
<220> FEATURE:
<221> NAME/KEY: CDS
<222> LOCATION: (13962)..(15713)
<223> OTHER INFORMATION: penton
<220> FEATURE:
<221> NAME/KEY: CDS
<222> LOCATION: (15720)..(16295)
<223> OTHER INFORMATION: pVII
<220> FEATURE:
<221> NAME/KEY: CDS
<222> LOCATION: (16341)..(17390)
<223> OTHER INFORMATION: V
<220> FEATURE:
<221> NAME/KEY: CDS
<222> LOCATION: (17422)..(17646)
<223> OTHER INFORMATION: pX
<220> FEATURE:
<221> NAME/KEY: CDS
<222> LOCATION: (17724)..(18473)
<223> OTHER INFORMATION: pVI
<220> FEATURE:
<221> NAME/KEY: CDS
<222> LOCATION: (18592)..(21420)

```
<223> OTHER INFORMATION: hexon
<220> FEATURE:
<221> NAME/KEY: misc_feature
<222> LOCATION: (22175)..(23731)
<223> OTHER INFORMATION: DBP  complement (22175..23731)
<220> FEATURE:
<221> NAME/KEY: CDS
<222> LOCATION: (25950)..(26564)
<223> OTHER INFORMATION: 22K
<220> FEATURE:
<221> NAME/KEY: CDS
<222> LOCATION: (26905)..(27585)
<223> OTHER INFORMATION: pVIII
<220> FEATURE:
<221> NAME/KEY: CDS
<222> LOCATION: (27588)..(27902)
<223> OTHER INFORMATION: E3\12.5K
<220> FEATURE:
<221> NAME/KEY: CDS
<222> LOCATION: (28272)..(28787)
<223> OTHER INFORMATION: E3\gp19K
<220> FEATURE:
<221> NAME/KEY: CDS
<222> LOCATION: (28819)..(29421)
<223> OTHER INFORMATION: E3\CR1\beta
<220> FEATURE:
<221> NAME/KEY: CDS
<222> LOCATION: (29474)..(30118)
<223> OTHER INFORMATION: E3\CR1\gamma
<220> FEATURE:
<221> NAME/KEY: CDS
<222> LOCATION: (30138)..(30443)
<223> OTHER INFORMATION: E3\CR1\delta
<220> FEATURE:
<221> NAME/KEY: CDS
<222> LOCATION: (30476)..(30748)
<223> OTHER INFORMATION: E3\RID\alpha
<220> FEATURE:
<221> NAME/KEY: CDS
<222> LOCATION: (31138)..(31533)
<223> OTHER INFORMATION: E3\14.7K
<220> FEATURE:
<221> NAME/KEY: misc_feature
<222> LOCATION: (31594)..(31751)
<223> OTHER INFORMATION: U\exon  complement (31594..31751)
<220> FEATURE:
<221> NAME/KEY: CDS
<222> LOCATION: (31766)..(32740)
<223> OTHER INFORMATION: fiber
<220> FEATURE:
<221> NAME/KEY: misc_feature
<222> LOCATION: (32789)..(33963)
<223> OTHER INFORMATION: E4\orf6/7  complement
      (32789..33037,33760..33963)
<220> FEATURE:
<221> NAME/KEY: misc_feature
<222> LOCATION: (33037)..(33963)
<223> OTHER INFORMATION: E4\orf6  complement (33037..33963)
<220> FEATURE:
<221> NAME/KEY: misc_feature
<222> LOCATION: (33839)..(34219)
<223> OTHER INFORMATION: E4\orf4  complement (33839..34219)
<220> FEATURE:
<221> NAME/KEY: misc_feature
<222> LOCATION: (34232)..(34582)
<223> OTHER INFORMATION: E4\orf3  complement (34232..34582)
<220> FEATURE:
<221> NAME/KEY: misc_feature
<222> LOCATION: (34582)..(34968)
<223> OTHER INFORMATION: E4\orf2  complement (34582..34968)
<220> FEATURE:
<221> NAME/KEY: misc_feature
<222> LOCATION: (35018)..(35389)
<223> OTHER INFORMATION: E4\orf1  complement (35018..35389)
<220> FEATURE:
<221> NAME/KEY: repeat_region
<222> LOCATION: (35636)..(35767)
<223> OTHER INFORMATION: ITR  complement (35636..35767)
```

<400> SEQUENCE: 34

```
catcatcaat aatatacctt ataaatggaa cggtgccaac atgcaaatga gcttttgaaa    60
atggagggcg aaggggatt ggccagcggg ttcaacggtc aaaaggggcg ggccggcgcg   120
gggaggtgac gtggttagtg tgggaggagt tatgttgcaa gttctcgcgg taaatgtgac   180
gtaaaacgag gtgtggtttg aacacggaag tacacagttt cccgcgctg actgacagga   240
tatgaggtag ttttgggcgg atgcaagtga aaattctcca ttttcgcgcg aaaactgaat   300
gaggaagtga atttctgagt aatttcgagt ttatgacagg gcggagtatt taccgagggc   360
cgagtagact ttgaccgatt acgtggaggt ttcgattacc gtgttttca cctaaatttc   420
cgcgtacggt gtcaaagtcc tgtgttttta cgtaggcgtc agctgatcgc tagggtattt   480
aaacctgacg agttccgtca agaggccact cttgagtgcc agcgagaaga gatttctcct   540
ccgcgccgcg agtcagatct ccactttgaa aaatgagaca cctgcgattc ctgcctcagg   600
aaatctccat tgcgaccggg aatgaaatac tgcagtttgt ggtagatgcc ctgatgggag   660
acgatccgga gccgctgcg cagcctttcg atcctcctac gcttcatgaa ctgtatgatt   720
tagaggtaga cgggccggag gatcctaacg aggaagctgt gaatggtttt ttcagcgatt   780
ctatgctatt agctgctagt gaaggagtgg acttagaccc accttctgag acccttgata   840
ccccaggggt ggtggtggaa agcggcagag gtgggaaaaa attgcctgaa cttggtgctg   900
ctgaaatgga tttgcactgt tatgaagagg ctttcctcc gagtgatgat gaagatgagg   960
aaaatgtgca gtcgatccag accgcagctg gtgagggaat gaaagctgcc aatgatggtt  1020
ttaagttgga ctacccggag ctgcctggac atggctgtaa gtcttgtgaa tttcacagga  1080
atagtactgg actaaaagaa ctgttgtgct cgctttgcta tatgagaacg cactgccatt  1140
ttatttacag taagtgtgtt taagttaaat ttaaagggac agtgtagcag tgttaataac  1200
tgtgaatgtg ggatttatgt ttttgcttg tgatttttat aggtcctgtg tctgatgctg  1260
atgaatcgcc ttctcctgat tcaactacct cacctcctga aattcaggcg ccagtccctg  1320
caaacgtatg caagcccatt cctgtgaagg ctaagcctgg gaaacgccct gctgtggata  1380
agctggagga cttgcttgag ggtgggatg gacctttgga cttgagtacc cggaaactgc  1440
caaggcaatg agtaccctgc acctgtgttt atttaatgtg acgtcagtat ttatgtgaga  1500
gtgccatgta ataaaattat gtcagctgct gagtatttta ttgcttcttg ggtgggact  1560
tgggtatata agtaggagca gacctgtgtg gttagctcac agcagcttgc tgccatccat  1620
ggaggtttgg gctatcttgg aagatctcag acagactagg caactgctag aaaacgcctc  1680
ggacggagtc tctagtcttt ggagattctg gttcggtggt gatctagcta ggctagtctt  1740
tagggtaaaa cgggagtata gtgaagaatt tgaaaagtta ttggaagaca gtccaggact  1800
ttttgaagcc cttaacttgg gccaccaggc tcattttaag gagaaggttt tatcagtttt  1860
agatttttct accctggta gaactgctgc tgctgtagca tttcttactt ttatattgga  1920
```

| | | | | | | | | | | | | | | | | |
|---|---|---|---|---|---|---|---|---|---|---|---|---|---|---|---|---|
| taa | atg | gat | ccc | aca | aac | cca | ctt | cag | caa | ggg | ata | cgt | ctt | gga | ttt | 1968 |
| | Met | Asp | Pro | Thr | Asn | Pro | Leu | Gln | Gln | Gly | Ile | Arg | Leu | Gly | Phe | |
| | 1 | | | 5 | | | | | 10 | | | | | 15 | | |

| | | | | | | | | | | | | | | | | |
|---|---|---|---|---|---|---|---|---|---|---|---|---|---|---|---|---|
| cat | agc | agc | agc | ttt | gtg | gag | aac | atg | gaa | ggc | ccg | cag | gct | gag | gat | 2016 |
| His | Ser | Ser | Ser | Phe | Val | Glu | Asn | Met | Glu | Gly | Pro | Gln | Ala | Glu | Asp | |
| | | | 20 | | | | 25 | | | | | 30 | | | | |

| | | | | | | | | | | | | | | | | |
|---|---|---|---|---|---|---|---|---|---|---|---|---|---|---|---|---|
| aat | ctt | aga | tta | ctg | gcc | agt | gca | gcc | tct | ggg | cgt | agc | ggc | aat | cct | 2064 |
| Asn | Leu | Arg | Leu | Leu | Ala | Ser | Ala | Ala | Ser | Gly | Arg | Ser | Gly | Asn | Pro | |
| | | 35 | | | | | 40 | | | | | 45 | | | | |

| | | | | | | | | | | | | | | |
|---|---|---|---|---|---|---|---|---|---|---|---|---|---|---|
| gag | aca | ccc | acc | agt | cat | gcc | agc | ggt | ttt | gga | gga | gga | gca | gca | gga | 2112 |

|  |  |  |  |  |  |  |  |  |  |  |  |  |  |
|---|---|---|---|---|---|---|---|---|---|---|---|---|---|
| Glu | Thr | Pro<br>50 | Thr | Ser | His | Ala | Ser<br>55 | Gly | Phe | Gly | Gly<br>60 | Ala | Ala | Gly |

```
gga caa ccc gag agc cgg cct gga ccc tcc ggt gga ggc gga gga      2160
Gly Gln Pro Glu Ser Arg Pro Gly Pro Ser Gly Gly Gly Gly Gly
 65                  70                  75 gta gct gac ctg ttt cct gaa ctg cga cgg gtg ctt act agg tct acg  2208
Val Ala Asp Leu Phe Pro Glu Leu Arg Arg Val Leu Thr Arg Ser Thr
 80                  85                  90                  95 tcc agt gga cag gac agg ggc att aag agg gag agg aat gct agt ggg  2256
Ser Ser Gly Gln Asp Arg Gly Ile Lys Arg Glu Arg Asn Ala Ser Gly
                100                 105                 110 cat aat tca aga act gag ttg gct tta agt tta atg agt cgc agc cgc  2304
His Asn Ser Arg Thr Glu Leu Ala Leu Ser Leu Met Ser Arg Ser Arg
            115                 120                 125 cct gaa act atc tgg tgg cat gag gtt cag agc gag ggc agg gat gaa  2352
Pro Glu Thr Ile Trp Trp His Glu Val Gln Ser Glu Gly Arg Asp Glu
        130                 135                 140 gtt tca ata ttg cag gag aaa tat tct cta gaa caa att aaa acc tgt  2400
Val Ser Ile Leu Gln Glu Lys Tyr Ser Leu Glu Gln Ile Lys Thr Cys
145                 150                 155 tgg ttg gaa cct gag gat gat tgg gag gtg gcc att agg aat tat gct  2448
Trp Leu Glu Pro Glu Asp Asp Trp Glu Val Ala Ile Arg Asn Tyr Ala
160                 165                 170                 175 aag ata tct ctg aga cct gat aaa cag tat aga att acc aag aag att  2496
Lys Ile Ser Leu Arg Pro Asp Lys Gln Tyr Arg Ile Thr Lys Lys Ile
                180                 185                 190 aat atc aga aat gca tgc tac ata tca ggg aat ggg gca gag gtt ata  2544
Asn Ile Arg Asn Ala Cys Tyr Ile Ser Gly Asn Gly Ala Glu Val Ile
            195                 200                 205 ata gat aca cca gat aaa aca gct ttt agg tgt tgt atg atg ggt atg  2592
Ile Asp Thr Pro Asp Lys Thr Ala Phe Arg Cys Cys Met Met Gly Met
        210                 215                 220 tgg cca ggg gtg gct ggt atg gag gca gta aca ctt atg aat att agg  2640
Trp Pro Gly Val Ala Gly Met Glu Ala Val Thr Leu Met Asn Ile Arg
225                 230                 235 ttt agg gga gat ggg tat aat ggg att gtc ttt atg gct aac act aag  2688
Phe Arg Gly Asp Gly Tyr Asn Gly Ile Val Phe Met Ala Asn Thr Lys
240                 245                 250                 255 ctg att ctg cat ggt tgt agc ttt ttt ggc ttt aat aat act tgt gtg  2736
Leu Ile Leu His Gly Cys Ser Phe Phe Gly Phe Asn Asn Thr Cys Val
                260                 265                 270 gaa gca tgg gga cag gtt agt gta aga ggc tgt agt ttc tat gca tgc  2784
Glu Ala Trp Gly Gln Val Ser Val Arg Gly Cys Ser Phe Tyr Ala Cys
            275                 280                 285 tgg att gca cta tca ggc aga acc aag agt cag ttg tct gtg aag aaa  2832
Trp Ile Ala Leu Ser Gly Arg Thr Lys Ser Gln Leu Ser Val Lys Lys
        290                 295                 300 tgc atg ttt gag aga tgt aat ctg ggc ata ctg aat gaa ggc gaa gca  2880
Cys Met Phe Glu Arg Cys Asn Leu Gly Ile Leu Asn Glu Gly Glu Ala
305                 310                 315 agg gtc cgc cac tgt gct gct aca gaa act ggc tgc ttc att cta ata  2928
Arg Val Arg His Cys Ala Ala Thr Glu Thr Gly Cys Phe Ile Leu Ile
320                 325                 330                 335 aag gga aat gcc agt gtg aag cat aac atg atc tgt gga ccc tcg gat  2976
Lys Gly Asn Ala Ser Val Lys His Asn Met Ile Cys Gly Pro Ser Asp
                340                 345                 350 gaa agg cct tat cag atg ctg acc tgt gct gga gga cat tgc aat atg  3024
Glu Arg Pro Tyr Gln Met Leu Thr Cys Ala Gly Gly His Cys Asn Met
            355                 360                 365
```

```
ctg gct act gtg cat att gtt tct cat gca cgc aag aaa tgg cct gtt      3072
Leu Ala Thr Val His Ile Val Ser His Ala Arg Lys Lys Trp Pro Val
        370                 375                 380 ttt gaa cat aat gtg atg acc aag tgc acc atg cac gca ggt ggt cgc      3120
Phe Glu His Asn Val Met Thr Lys Cys Thr Met His Ala Gly Gly Arg
    385                 390                 395 agg gga atg ttt atg cct tac cag tgt aac atg aat cat gtg aag gtg      3168
Arg Gly Met Phe Met Pro Tyr Gln Cys Asn Met Asn His Val Lys Val
400                 405                 410                 415 atg ttg gaa cca gat gcc ttt tcc aga atg agc tta aca gga atc ttt      3216
Met Leu Glu Pro Asp Ala Phe Ser Arg Met Ser Leu Thr Gly Ile Phe
                420                 425                 430 gat atg aat gtg caa cta tgg aag att ctg aga tat gat gag acc aaa      3264
Asp Met Asn Val Gln Leu Trp Lys Ile Leu Arg Tyr Asp Glu Thr Lys
            435                 440                 445 tcg agg gtg cgc gca tgc gag tgc ggg ggc aag cat gcc agg ttc cag      3312
Ser Arg Val Arg Ala Cys Glu Cys Gly Gly Lys His Ala Arg Phe Gln
        450                 455                 460 ccg gtg tgt gtg gat gtg acg gaa gac ctg aga ccc gat cat ttg gtg      3360
Pro Val Cys Val Asp Val Thr Glu Asp Leu Arg Pro Asp His Leu Val
465                 470                 475 ctt gcc tgc act gga gcg gag ttc ggt tct agt ggg gaa gaa act gac      3408
Leu Ala Cys Thr Gly Ala Glu Phe Gly Ser Ser Gly Glu Glu Thr Asp
480                 485                 490                 495 taaagtgagt agtggggaat gctttggagg ggattccagg cgggtaaggt gggcagattg      3468
ggtaaattct gtttgtttct gtcttgcagc tgcc atg agt gga agc gct tct ttt      3523
                                     Met Ser Gly Ser Ala Ser Phe
                                                         500 gag ggg gga gtc ttt agc cct tat ctg acg ggg cga ctc cca ccc tgg      3571
Glu Gly Gly Val Phe Ser Pro Tyr Leu Thr Gly Arg Leu Pro Pro Trp
            505                 510                 515 gca gga gtt cgt cag aat gtc atg gga tcc act gtg gat ggg aga ccc      3619
Ala Gly Val Arg Gln Asn Val Met Gly Ser Thr Val Asp Gly Arg Pro
    520                 525                 530 gtc cag ccc gcc aat tcc tca acg ctg acc tat gcc act ttg agc tct      3667
Val Gln Pro Ala Asn Ser Ser Thr Leu Thr Tyr Ala Thr Leu Ser Ser
535                 540                 545                 550 tca ccc ttg gat gca gcc gca gcc gct gcc gcc tct gct gcc gcc aac      3715
Ser Pro Leu Asp Ala Ala Ala Ala Ala Ala Ser Ala Ala Ala Asn
                555                 560                 565 act gtc ctt gga atg ggc tat tat gga agc atc gtt gcc aat tcc agt      3763
Thr Val Leu Gly Met Gly Tyr Tyr Gly Ser Ile Val Ala Asn Ser Ser
            570                 575                 580 tcc tct aat aac cct tcg acc ctg gct gag gac aag cta ctt gtc ctc      3811
Ser Ser Asn Asn Pro Ser Thr Leu Ala Glu Asp Lys Leu Leu Val Leu
        585                 590                 595 ttg gct cag ctc gag gcc ttg acc cag cgc cta ggc gaa ctg tct cag      3859
Leu Ala Gln Leu Glu Ala Leu Thr Gln Arg Leu Gly Glu Leu Ser Gln
    600                 605                 610 cag gtg gcc cag ttg cgc gag caa act gag tct gct gtt gcc aca gca      3907
Gln Val Ala Gln Leu Arg Glu Gln Thr Glu Ser Ala Val Ala Thr Ala
615                 620                 625                 630 aag tct aaa taaagattcc caaatcaata aataaggag atccttgttg               3956
Lys Ser Lys attgtaaaac aagtgtaatg aatctttatt tgattttttcg cgcgcggtat gccctggacc      4016
accggtctcg atcattgaga actcggtgga tcttttccag gaccctgtag aggtgggatt      4076
gaatgtttag atacatgggc attaggccgt ctcgggggtg gagatagctc cattgaagag      4136
```

```
cctcatgctc cggggtagtg ttataaatca cccagtcata acaaggtcgg agtgcatggt    4196
gttgcacaat atcttttagg agcaggctaa ttgcaacggg gaggcccta gtgtaggtgt     4256
ttacaaatct gttgagctgg gacgggtgca tccggggtga aattatatgc attttggact   4316
ggatcttgag gttggcaatg ttgccgccta gatcccgtct cggggttcata ttgtgcagga   4376
ccaccaagac agtgtatccg gtgcacttgg gaaatttatc atgcagctta gagggaaaag   4436
catgaaaaaa tttggagacg cctttgtgtc cgcccagatt ctccatgcac tcatccataa   4496
tgatagcgat gggaccgtgg gcggcggcgc gggcaaacac gttccggggg tctgacacat   4556
catagttatg ctcctgagtc aggtcatcat aagccatttt aataaacttg ggcggaggg    4616
tgccagattg ggggatgaaa gttccctcgg gccccggagc atagtttccc tcacatattt   4676
gcatttccca agctttcagt tcagaggggg ggatcatgtc cacctgcggg gctataaaaa   4736
ataccgtttc tggagccggg gtgattaact gggatgagag cagattcctg agcagctgag   4796
acttgccgca cccagtggga ccgtaaatga ccccgattac gggttgcaga tggtagttta    4856
gggagcggca gctgccgtcc tcccggagca ggggggccac ttcgttcatc atttcctta    4916
catggatatt ttcccgcacc aagtccgtta ggaggcgctc tcccccagg gatagaagct    4976
cctgagcga ggagaagttt ttcagcggct tcagcccgtc agccatgggc attttggaga    5036
gagtctgttg caagagctct agtcggtccc agagctcggt gatgtgttct atggcatctc   5096
gatccagcag acctcctcgt ttcgcgggtt ggacgactc ctggagtatg gtatcagacg    5156
atgggcgtcc agcgctgcca gggtccgatc tttccagggt cgcagcgtcc gagtcagggt    5216
tgtttccgtc acggtgaagg ggtgcgcgcc tggttgggcg cttgcgaggg tgcgtttcag   5276
gctcatcctg ctggtcgaga accgctgccg atcggcgccc tgcatgtcgg ccaggtagca   5336
gtttaccatg agttcgtagt tgagcgcctc ggccgcgtgg cctttggcgc ggagcttacc   5396
tttggaagtt ttctggcagg cggggcagta cagacacttg agggcataca gtttgggagc   5456
gaggaagatg gattcggggg agtatgcgtc cgcaccgcag gaggcgcaga cggtttcgca   5516
ttccacgagc caggtcagat ccggctcatc ggggtcaaaa acaagttttc cccatgtttt   5576
tttgatgcgt tcttacctt tggtctccat gagttcgtgt ccccgctggg tgacaaagag   5636
gctgtccgtg tccccgtaga ccgatttttat gggcctgtcc tcgagcggag tgcctcggtc  5696
ctcttcgtag aggaactcgg accactctga tacaaaggcg cgcgtccagg ccagcacaaa   5756
agaggccacg tgggaggggt agcggtcgtt gtcaaccagg gggtccacct tctccacggt   5816
atgtaaacac atgtccccct cctccacatc aagaatgtg attggcttgt aagtgtatgc    5876
cacgtgacca ggggtccccg ccgggggggt ataaaggggg gcgggtctct gctcgtcctc   5936
actgtcttcc ggatcgctgt ccaggagcgc cagctgttgg ggtaggtatt ccctctcgaa   5996
ggcgggcata acctctgcac tcaggttgtc agtttctagg aacgaggagg atttgatatt   6056
gacagtgcca gccgagatgc ctttcataag actctcgtcc atttggtcag aaaatacaat   6116
cttttttgttg tccagcttgg tggcaaagga tccatagagg cattggata agagcttggc   6176
tatggagcgc atggtttggt tcttttcctt gtcagcgcgc tccttggcag caatgttgag   6236
ctggacatac tcgcgcgcca gacacttcca ttcaggaag atggttgtca gttcatctgg    6296
cacgattctg actcgccagc ccctgttatg cagggtgatc agatccacac tggtggtcac   6356
ttcgcctctg aggggctcgt tggtccagca gagtcgaccc ccttttctcg aacagaaagg   6416
tgggaggggg tctagcatga gttcatcagg ggggtctgca tccatagtga agattcctgg   6476
gagcagatcc ttgtcaaaat agctgatggg tgtggggtca tccaaagcca tctgccattc   6536
```

```
tcgagctgcc agcgcgcgct catagggggtt gagaggggtg ccccatggca tggggtgggt      6596
gagtgcagag gcatacatgc cacagatgtc atagacatag aggggctctt cgaggatgcc      6656
aatgtaggtg ggataacagc gccccctct gatgcttgct cgcacatagt catagagttc       6716
atgcgagggg gcgagcagac ccgagcccaa attagtgcga ttgggttttt cagccctgta      6776
gacgatctgg cgaaagatgg catgtgaatt tgaagagatg gtgggtctct gaaagatgtt      6836
aaaatgggca tgaggtagac ctacagagtc cctgatgaag tgggcatatg actcttgcag      6896
cttggccacc agctctgcag tgacaaggac atccaaggcg cagtagtcaa gggtctcttg      6956
gatgatgtca taacctggtt ggttttttctt ttcccacagc tcgcggttga gaaggtattc     7016
ttcgcgatcc ttccagtact cttcgagggg aaacccgtct tgtctgcac ggtaagagcc       7076
cagcatgtag aactgattaa ctgctttgta gggacagcag cccttctcca cggggagaga      7136
gtatgcttgg gctgccttgc gcagtgaggt atgagtgagg gcgaaggtgt ccctgaccat      7196
gactttgagg aactggtgct tgaagtcaat gtcatcacag gccccctgtt cccagagttg      7256
gaagtctacc cgcttcttgt aggcggggtt gggcaaagcg aaagtaacat cattaaagag      7316
aatcttgccg gccctgggca tgaaattgcg ggtgatgcgg aaaggctggg gcacctctgc      7376
ccggttattg atcacctgag cggctaggac gatctcatca aagccattga tgttgtgccc      7436
cacaatgtaa agttctatga atcgcggggt gcccctgaca tgaggcagct tcttgagttc      7496
ttcaaaagtg aggtctgtag ggtcagagag agcatagtgt tcgagggccc attcgtgcag      7556
gtgagggttt gcattgagga aggaggacca gagatccact gccagtgctg tttgtaactg      7616
gtcccgatac tggcgaaaat gctggccgac tgccatcttt tctggggtta tacagtagaa      7676
ggttttgggg tcttgctgcc agcgatccca cttgagtttc atggcgaggt cgtaggcgat      7736
attgacgagc cgctcgtccc ccgagagttt catgaccagc atgaagggga tcagctgctt      7796
gccaaaggac cccatccagg tgtaggtttc cacatcgtag gtgaggaaga gcctttctgt      7856
gcgaggatga gagccgatcg ggaagaactg gatctcctgc caccagttgg aggaatggct      7916
gttgatgtga tggaagtaga actccctgcg gcgcgccgtg cattcatgct tgtgcttgta      7976
cagacggccg cagtactcgc agcgcttcac gggatgcacc tcatgaatga gttgtacctg      8036
gcttcctttg acgagaaatt tcagtgggaa gttgaggcct ggcgcttgta cctcgcgctc      8096
tactatgtta tctgcatcgg cctggccatc ttctgtctcg atggtggtca tgctgacgag      8156
cccccgcggg aggcaagtcc agacctcggc gcgggagggg cggagctcga ggacgagagc      8216
gcgcaggccg gagctgtcca gggtcctgag tcgctgcgga gtcaggttag taggtagtgt      8276
caggagatta acttgcatga tcttttcgag ggcatgcggg aggttcagat ggtacttgat      8336
ctccacgggt ccgttggtgg tgatgtcgat ggcttgcagg gtcccatgcc ccttgggcgc      8396
caccaccgtg cccttgtttt tccttttggg cggcggtggc tctgttgctt cttgcatgtt      8456
cagaagcggt gacgagggcg cgcgccggc ggtaggggcg gctcgggccc cggcggcatg       8516
gctggcagag gcacgtcggc gccgcgcgcg ggtaggttct ggtactgcgc cctgagaaga      8576
cttgcgtgcg cgacgacgcg gcggttgacg tcctggatct gacgcctctg ggtgaaagct      8636
accggacccg tgagcttgaa cctgaaagag agttcaacag aatcaatttc ggtatcgttg      8696
acggcggctt gcctcaggat ctcttgcacg tcgcccgagt tgtcctggta ggcgatctcg      8756
gccatgaact gctcgatttc ttcctcctga agatctccgc ggcccgctct ctcgacggtg      8816
gccgcgaggt cgttggagat gcgacccatg agttgagaga atgcattcat gcccgcctcg      8876
```

```
ttccagacgc ggctgtagac cacggccccc tcgggatctc tcgcgcgcat gaccacctgg    8936
gcgaggttga gctccacgtg gcgggtgaag accgcatagt tgcataggcg ctggaagagg    8996
tagttgagtg tggtggcgat gtgctcggtg acgaagaaat acatgatcca tcgtctcagc    9056
ggcatttcgc tgacatcgcc cagggcttcc aagcgctcca tggcctcgta gaagtccaca    9116
gcgaagttga aaaactggga gttgcgcgcg acacggtca actcctcctc cagaagacgg     9176
atgagatcgg cgatggtggc gcgcacctcg cgctcgaagg ccccgggat tcttcctcc      9236
tcctcttcta tctcttcttc cactaacatc tcttcttcct cttcaggcgg gggcggagga   9296
ggaggggggcg cgcggcgacg ccggcggcgc acgggcagac ggtcgatgaa tctttcaatg  9356
acctctccgc ggcggcggcg catggtctcg gtgacggcgc ggccgttctc cctgggtctc   9416
agagtgaaga cgcctccgcg catctccctg aagtggtgac tggggggctc tccgttgggc   9476
agggacaggg cgctgatgat gcattttatc aattgccccg tagggactcc gcgcaaggac   9536
ctgatcgtct gaagatccac gggatctgaa aacctttcga cgaaagcgtc taaccagtcg   9596
caatcgcaag gtaggctgag cactgttttct tgcgggcggg ggtggctaga tgctcggtcg  9656
gggttctctc ttccttctcc ttcctcatca tctcgggagg gtgagacgat gctgctggtg   9716
atgaaattaa aataggcagt tctgagacgg cggatggtgg cgaggagcac caggtctttg   9776
ggtccggctt gctggatgcg caggcgatcg gccattcccc aagcattgtc ctggcatctg   9836
gccagatctt tatagtagtc ttgcatgagt cgctccacgg gcacttcttc ttcgcccgct   9896
ctgccatgca tgcgcgtgag cccgaacccg cgcatgggct ggacaagtgc caggtccgct   9956
acgacccttt cggcgaggat ggcttgctgc acctgggtga gggtggcttg gaagtcgtca  10016
aagtccacga agcgatggta ggctccggtg ttaatggtgt aggagcagtt ggccatgact  10076
gaccagttga ctgtctggtg ccccgggcgc acgagctcgg tgtacttgag gcgcgagtag  10136
gcgcgggtgt caaagatgta atcgttgcag gtgcgcacca ggtactggta gccgatgaga  10196
aagtgcggcg gtgctggcg gtagagggggc catcgctctg tagccggggc tcctggggcg   10256
aggtcttcca gcatgaggcg gtggtatccg tagatgtacc tggacatcca ggtgatcccg  10316
gaggcggtgg tggacgcccg cgggaactcg cgcactcggt tccagatgtt gcgcagcggc  10376
atgaagtagt tcatggtagg cacggtctgg ccagtgaggc gggcgcagtc attgatgctc  10436
tatagacacg gagaaaacga aagcgatgag cggctcgcct ccgtggcctg gaggaacgtg  10496
aacgggttgg gtcgcggtgt accccggttc gagacacaag ccaagcgagc acaactcggg  10556
ccggccggag ccgcggctaa cgtggtattg gcgatcccgt ctcgacccag ccgacgaata  10616
tccaggatac ggagtcgagt cgttttgctg cttgttgctt tttcctggac gggagccagt  10676
gccgcgtcaa gctttagaat gctcagttca cggggccggg agtggctcgc gcccgtagtc  10736
tggagaatca atcgccaggg ttgcgttgcg gtgtgccccg gttcgagcct tagcgtggcc  10796
cggatcggcc ggtttccgcg gcaagcgagg gtttggcagc ccgtcatttt ctaagacccc  10856
gccagccgac ttctccagtt tacgggagcg agccctcttt tttttttgt ttttgtcgc    10916 ccag atg cat ccc gtg ctg cga cag atg cgc ccc cag caa cag gcc cct     10965
     Met His Pro Val Leu Arg Gln Met Arg Pro Gln Gln Gln Ala Pro
         635                 640                 645 tct cag caa cag cag cag cca caa aag gcg ctt cct gct cct gct ccc     11013
Ser Gln Gln Gln Gln Gln Pro Gln Lys Ala Leu Pro Ala Pro Ala Pro
    650                 655                 660 gca act act gca gtc gca gcc gtg tgc ggc gcg gga cag ccc gcc tat     11061
Ala Thr Thr Ala Val Ala Ala Val Cys Gly Ala Gly Gln Pro Ala Tyr
665                 670                 675                 680
```

```
gat ctg gac ttg gaa gag ggc gag gga ctg gcg cgc ctg ggt gca cca    11109
Asp Leu Asp Leu Glu Glu Gly Glu Gly Leu Ala Arg Leu Gly Ala Pro
            685                 690                 695 tcg ccc gag cgg cac ccg cgg gtg caa ctg aaa aag gac tct cgc gag    11157
Ser Pro Glu Arg His Pro Arg Val Gln Leu Lys Lys Asp Ser Arg Glu
        700                 705                 710 gcg tac gtg ccc cag cag aac ctg ttc agg gac agg agc ggc gag gag    11205
Ala Tyr Val Pro Gln Gln Asn Leu Phe Arg Asp Arg Ser Gly Glu Glu
                715                 720                 725 ccg gag gag atg cga gcc tct cgc ttt aac gcg ggt cgc gag ctg cgt    11253
Pro Glu Glu Met Arg Ala Ser Arg Phe Asn Ala Gly Arg Glu Leu Arg
    730                 735                 740 cac ggt ctg gac cga aga cgg gtg ctg cgg gac gag gat ttc gag gtc    11301
His Gly Leu Asp Arg Arg Arg Val Leu Arg Asp Glu Asp Phe Glu Val
745                 750                 755                 760 gat gaa gtg aca ggg atc agc ccc gct agg gca cat gtg gcc gcg gca    11349
Asp Glu Val Thr Gly Ile Ser Pro Ala Arg Ala His Val Ala Ala Ala
                765                 770                 775 aac ctt gtc tcg gcc tac gag cag acc gtg aag gag gag cgc aac ttc    11397
Asn Leu Val Ser Ala Tyr Glu Gln Thr Val Lys Glu Glu Arg Asn Phe
            780                 785                 790 caa aaa tca ttc aac aac cat gtg cgc acc ctg atc gcc cgt gag gaa    11445
Gln Lys Ser Phe Asn Asn His Val Arg Thr Leu Ile Ala Arg Glu Glu
        795                 800                 805 gtg acc ctg ggt ctg atg cac ctg tgg gac ctg atg gaa gct atc acc    11493
Val Thr Leu Gly Leu Met His Leu Trp Asp Leu Met Glu Ala Ile Thr
    810                 815                 820 cag aac ccc act agc aaa ccc ctg acc gct cag ctg ttt ctg gtg gtg    11541
Gln Asn Pro Thr Ser Lys Pro Leu Thr Ala Gln Leu Phe Leu Val Val
825                 830                 835                 840 caa cac agc agg gac aat gag gca ttt agg gag gcg ctg ctg aac atc    11589
Gln His Ser Arg Asp Asn Glu Ala Phe Arg Glu Ala Leu Leu Asn Ile
                845                 850                 855 acc gag ccc gag ggg aga tgg ttg tat gat ctg atc aat atc ctg cag    11637
Thr Glu Pro Glu Gly Arg Trp Leu Tyr Asp Leu Ile Asn Ile Leu Gln
            860                 865                 870 agt att ata gta cag gaa cgc agc ctg ggt ctg gcc gag aaa gtg gca    11685
Ser Ile Ile Val Gln Glu Arg Ser Leu Gly Leu Ala Glu Lys Val Ala
        875                 880                 885 gct atc aac tac tct gtc ttg agc ctg ggc aag tac tac gct cgc aag    11733
Ala Ile Asn Tyr Ser Val Leu Ser Leu Gly Lys Tyr Tyr Ala Arg Lys
    890                 895                 900 atc tac aag acc ccc tac gtg ccc ata gac aag gag gtg aag ata gat    11781
Ile Tyr Lys Thr Pro Tyr Val Pro Ile Asp Lys Glu Val Lys Ile Asp
905                 910                 915                 920 ggg ttt tac atg cgt atg act ctt aaa gtg ctg act ctc agc gac gat    11829
Gly Phe Tyr Met Arg Met Thr Leu Lys Val Leu Thr Leu Ser Asp Asp
                925                 930                 935 ctg ggg gtg tac cgc aac gac agg atg cac cgc gcg gtg agc gcc agc    11877
Leu Gly Val Tyr Arg Asn Asp Arg Met His Arg Ala Val Ser Ala Ser
            940                 945                 950 agg agg cgc gag ctg agc gac agg gaa ctt atg cac agc ttg caa aga    11925
Arg Arg Arg Glu Leu Ser Asp Arg Glu Leu Met His Ser Leu Gln Arg
        955                 960                 965 gct ctg acg ggc gca ggg acc gat ggg gag aac tac ttt gac atg ggg    11973
Ala Leu Thr Gly Ala Gly Thr Asp Gly Glu Asn Tyr Phe Asp Met Gly
    970                 975                 980 gca gac ttg caa tgg cag cct agc cgc cgg gcc ctg gac gcg gca ggg    12021
Ala Asp Leu Gln Trp Gln Pro Ser Arg Arg Ala Leu Asp Ala Ala Gly
```

```
                                                  -continued
    985              990              995             1000
tgt gag ctt cct tac gta gaa gag gtg gat  gaa ggc gag gag gag         12066
Cys Glu Leu Pro Tyr Val Glu Glu Val Asp  Glu Gly Glu Glu Glu
                1005              1010                 1015 gag ggc gag tac ctg gaa gac tgatggcgcg acccatattt ttgctag atg        12117
Glu Gly Glu Tyr Leu Glu Asp                                 Met
                1020 gaa cag cag gca ccg gac ccc gca atg cgg gcg gcg ctg cag agc         12162
Glu Gln Gln Ala Pro Asp Pro Ala Met Arg Ala Ala Leu Gln Ser
           1025              1030                  1035 cag ccg tcc ggc att aac tcc tcg gac gat tgg acc cag gcc atg         12207
Gln Pro Ser Gly Ile Asn Ser Ser Asp Asp Trp Thr Gln Ala Met
        1040                 1045                 1050 caa cgc atc atg gcg ctg acg acc cgc aac ccc gaa gcc ttt aga         12252
Gln Arg Ile Met Ala Leu Thr Thr Arg Asn Pro Glu Ala Phe Arg
    1055                 1060                  1065 cag caa ccc cag gcc aac cgc ctt tcg gcc atc ctg gag gcc gta         12297
Gln Gln Pro Gln Ala Asn Arg Leu Ser Ala Ile Leu Glu Ala Val
        1070                1075                 1080 gtt cct tcc cgc tcc aac ccc acc cac gag aag gtc ctg gcc atc         12342
Val Pro Ser Arg Ser Asn Pro Thr His Glu Lys Val Leu Ala Ile
    1085                 1090                 1095 gtg aac gcg ctg gtg gag aac aag gcc atc cgt ccc gat gag gcc         12387
Val Asn Ala Leu Val Glu Asn Lys Ala Ile Arg Pro Asp Glu Ala
        1100                1105                 1110 ggg ctg gta tac aat gcc ctc ttg gag cgc gtg gcc cgc tac aac         12432
Gly Leu Val Tyr Asn Ala Leu Leu Glu Arg Val Ala Arg Tyr Asn
    1115                 1120                 1125 agc agc aac gtg cag acc aac ctg gac cgg atg gtg acc gat gtg         12477
Ser Ser Asn Val Gln Thr Asn Leu Asp Arg Met Val Thr Asp Val
        1130                1135                 1140 cgc gag gca gtg tct cag cgc gag cgg ttc cag cgc gat gcc aac         12522
Arg Glu Ala Val Ser Gln Arg Glu Arg Phe Gln Arg Asp Ala Asn
    1145                 1150                 1155 ttg ggg tcg ctg gtg gcg ctg aac gcc ttc ctc agc acc cag cct         12567
Leu Gly Ser Leu Val Ala Leu Asn Ala Phe Leu Ser Thr Gln Pro
        1160                1165                 1170 gcc aac gtg ccc cgc ggt cag caa gac tat aca aac ttc cta agt         12612
Ala Asn Val Pro Arg Gly Gln Gln Asp Tyr Thr Asn Phe Leu Ser
    1175                 1180                 1185 gca ctg aga ctc atg gta acc gaa gtc cct cag agc gag gtg tac         12657
Ala Leu Arg Leu Met Val Thr Glu Val Pro Gln Ser Glu Val Tyr
        1190                1195                 1200 cag tcc gga cca gac tac ttc ttc cag acc agc aga cag ggc ttg         12702
Gln Ser Gly Pro Asp Tyr Phe Phe Gln Thr Ser Arg Gln Gly Leu
    1205                 1210                 1215 cag aca gtg aac ctg agc cag gct ttc aag aac ctc aga ggc ttg         12747
Gln Thr Val Asn Leu Ser Gln Ala Phe Lys Asn Leu Arg Gly Leu
        1220                1225                 1230 tgg gga gtg cac gct ccg gta gga gat cgt gcg acc gtg tct agc         12792
Trp Gly Val His Ala Pro Val Gly Asp Arg Ala Thr Val Ser Ser
    1235                 1240                 1245 ttg ctg acc ccc aac tcc cgc cta ctg ttg ctg cta gta tcc ccc         12837
Leu Leu Thr Pro Asn Ser Arg Leu Leu Leu Leu Leu Val Ser Pro
        1250                1255                 1260 ttc act gac agt ggt agc atc gac cgc aac tcc tac ttg ggc tac         12882
Phe Thr Asp Ser Gly Ser Ile Asp Arg Asn Ser Tyr Leu Gly Tyr
    1265                 1270                 1275 ctg ctg aac ttg tat cgc gag gcc ata gga cag agc cag gtg gac         12927
```

```
              Leu Leu Asn Leu Tyr Arg Glu Ala Ile Gly Gln Ser Gln Val Asp
                  1280            1285                1290 gag cag acc tat caa gaa atc acc caa gtg agc cgt gcc ctg ggt           12972
Glu Gln Thr Tyr Gln Glu Ile Thr Gln Val Ser Arg Ala Leu Gly
1295                1300                1305 cag gaa gac acg ggt agc ttg gaa gcc acc ttg aac ttc ttg ctg           13017
Gln Glu Asp Thr Gly Ser Leu Glu Ala Thr Leu Asn Phe Leu Leu
1310                1315                1320 acc aac cgg tcg cag aag atc cct cct cag tat gcg ctt acc gcg           13062
Thr Asn Arg Ser Gln Lys Ile Pro Pro Gln Tyr Ala Leu Thr Ala
1325                1330                1335 gag gag gag cgg atc ttg aga tat gtg cag cag agc gtg gga ctg           13107
Glu Glu Glu Arg Ile Leu Arg Tyr Val Gln Gln Ser Val Gly Leu
1340                1345                1350 ttc ctg atg cag gag ggg gcg acc cct agt gcc gcg ctg gac atg           13152
Phe Leu Met Gln Glu Gly Ala Thr Pro Ser Ala Ala Leu Asp Met
1355                1360                1365 aca gcg cga aac atg gag ccc agc atg tat gcc atg aac cgg cct           13197
Thr Ala Arg Asn Met Glu Pro Ser Met Tyr Ala Met Asn Arg Pro
1370                1375                1380 ttc atc aac aaa cta ctg gac tac ctg cac agg gca gcc gct atg           13242
Phe Ile Asn Lys Leu Leu Asp Tyr Leu His Arg Ala Ala Ala Met
1385                1390                1395 aac tct gat tat ttc acc aat gct atc ctt aac ccc cac tgg ctg           13287
Asn Ser Asp Tyr Phe Thr Asn Ala Ile Leu Asn Pro His Trp Leu
1400                1405                1410 ccc ccg cct gga ttt tac acg ggc gag tac gac atg ccc gac ccc           13332
Pro Pro Pro Gly Phe Tyr Thr Gly Glu Tyr Asp Met Pro Asp Pro
1415                1420                1425 aat gac ggg ttc ctg tgg gac gat gtg gac agc agc ata ttc tcc           13377
Asn Asp Gly Phe Leu Trp Asp Asp Val Asp Ser Ser Ile Phe Ser
1430                1435                1440 ccg cct cct ggt tat aat act tgg aag aag gaa ggg ggc gat aga           13422
Pro Pro Pro Gly Tyr Asn Thr Trp Lys Lys Glu Gly Gly Asp Arg
1445                1450                1455 aga cac tct tcc gtg tcg ctg tcc ggg tcg agg ggt gct gcc gcc           13467
Arg His Ser Ser Val Ser Leu Ser Gly Ser Arg Gly Ala Ala Ala
1460                1465                1470 gcg gtg ccc gag gct gca agt cct ttc cct agc ctg ccc ttt tct           13512
Ala Val Pro Glu Ala Ala Ser Pro Phe Pro Ser Leu Pro Phe Ser
1475                1480                1485 ctg aac agt gtg cgc agc agt gaa ctg ggg aga ata acc cgc ccg           13557
Leu Asn Ser Val Arg Ser Ser Glu Leu Gly Arg Ile Thr Arg Pro
1490                1495                1500 cgc ttg atg ggc gag gat gag tac ttg aac gac tcc ttg ctt aga           13602
Arg Leu Met Gly Glu Asp Glu Tyr Leu Asn Asp Ser Leu Leu Arg
1505                1510                1515 ccc gag agg gaa aag aac ttc ccc aac aat ggt ata gag agc ctg           13647
Pro Glu Arg Glu Lys Asn Phe Pro Asn Asn Gly Ile Glu Ser Leu
1520                1525                1530 gtg gat aag atg agt aga tgg aag aca tat gca cag gat cac aaa           13692
Val Asp Lys Met Ser Arg Trp Lys Thr Tyr Ala Gln Asp His Lys
1535                1540                1545 gac gag cct agg atc ttg ggg gct gcg agc ggg acg acc cgt aga           13737
Asp Glu Pro Arg Ile Leu Gly Ala Ala Ser Gly Thr Thr Arg Arg
1550                1555                1560 cgc cag cgc cat gac aga cag agg ggt ctt gtg tgg gac gat gag           13782
Arg Gln Arg His Asp Arg Gln Arg Gly Leu Val Trp Asp Asp Glu
1565                1570                1575
```

| | | | | | | | | | | | | | | |
|---|---|---|---|---|---|---|---|---|---|---|---|---|---|---|
| gac | tcg | gcc | gat | gac | agc | agc | gtg | ttg | gac | ttg | ggt | ggg | aga | gga | 13827 |
| Asp | Ser | Ala | Asp | Asp | Ser | Ser | Val | Leu | Asp | Leu | Gly | Gly | Arg | Gly |
| 1580 | | | | 1585 | | | | | 1590 | | | | | |

```
gac tcg gcc gat gac agc agc gtg ttg gac ttg ggt ggg aga gga     13827
Asp Ser Ala Asp Asp Ser Ser Val Leu Asp Leu Gly Gly Arg Gly
1580                1585                1590 ggg ggc aac ccg ttc gct cat ctg cgc ccg cac ttt ggg cgc atg     13872
Gly Gly Asn Pro Phe Ala His Leu Arg Pro His Phe Gly Arg Met
1595                1600                1605 ttg taaaagtgaa agtaaaataa aaaggcaact caccaaggcc atggcgacga     13925
Leu gcgtgcgttc gttcttttct gttatctgtg tctagt atg  atg agg cga gcc gtg    13979
                                    Met  Met Arg Arg Ala Val
                                    1610             1615 cta ggc gga gcg gtg gtg tat ccg gag ggt cct cct cct tcg tac     14024
Leu Gly Gly Ala Val Val Tyr Pro Glu Gly Pro Pro Pro Ser Tyr
    1620                1625                1630 gag agc gtg atg cag cag cag gcg gcg gcg gtg atg cag ccc tcg     14069
Glu Ser Val Met Gln Gln Gln Ala Ala Ala Val Met Gln Pro Ser
        1635                1640                1645 ctg gag gct ccc ttt gta ccc ccg cgg tac ctg gcg cct aca gag     14114
Leu Glu Ala Pro Phe Val Pro Pro Arg Tyr Leu Ala Pro Thr Glu
            1650                1655                1660 ggg aga aac agc att cgt tac tcg gag ctg gca ccc cag tac gat     14159
Gly Arg Asn Ser Ile Arg Tyr Ser Glu Leu Ala Pro Gln Tyr Asp
                1665                1670                1675 acc acc agg ttg tat ctg gtg gac aac aag tcg gcg gac atc gcc     14204
Thr Thr Arg Leu Tyr Leu Val Asp Asn Lys Ser Ala Asp Ile Ala
                    1680                1685                1690 tca ttg aac tat cag aac gac cac agc aac ttc ctg acc acg gtg     14249
Ser Leu Asn Tyr Gln Asn Asp His Ser Asn Phe Leu Thr Thr Val
                        1695                1700                1705 gtg cag aac aat gac ttt acc ccc acg gag gcc agc acc cag acc     14294
Val Gln Asn Asn Asp Phe Thr Pro Thr Glu Ala Ser Thr Gln Thr
                            1710                1715                1720 atc aac ttt gac gag cgg tcg cgg tgg ggc ggt cag ctg aag acc     14339
Ile Asn Phe Asp Glu Arg Ser Arg Trp Gly Gly Gln Leu Lys Thr
                                1725                1730                1735 atc atg cac acc aac atg ccc aac gtg aac gag tac atg ttc agc     14384
Ile Met His Thr Asn Met Pro Asn Val Asn Glu Tyr Met Phe Ser
                                    1740                1745                1750 aac aag ttc aag gcg cgg gtg atg gtg tca cgc aag aaa cct gaa     14429
Asn Lys Phe Lys Ala Arg Val Met Val Ser Arg Lys Lys Pro Glu
                                        1755                1760                1765 ggc tat aca ggg gat aaa aat gat aca agt cag gat att ctg gag     14474
Gly Tyr Thr Gly Asp Lys Asn Asp Thr Ser Gln Asp Ile Leu Glu
                                            1770                1775                1780 tat gag tgg ttt gag ttc act tta cca gaa ggc aac ttc tca gcc     14519
Tyr Glu Trp Phe Glu Phe Thr Leu Pro Glu Gly Asn Phe Ser Ala
                                                1785                1790                1795 acc atg acc atc gac ctg atg aac aat gcc atc att gac aac tac     14564
Thr Met Thr Ile Asp Leu Met Asn Asn Ala Ile Ile Asp Asn Tyr
                                                    1800                1805                1810 ctg gca gtg ggc aga cag aat gga gtg ttg gaa agc gac atc ggt     14609
Leu Ala Val Gly Arg Gln Asn Gly Val Leu Glu Ser Asp Ile Gly
                                                        1815                1820                1825 gtc aag ttt gat acc agg aac ttc agg ctg ggc tgg gac ccc ata     14654
Val Lys Phe Asp Thr Arg Asn Phe Arg Leu Gly Trp Asp Pro Ile
                                                            1830                1835                1840 act aaa ctt gtt atg cca gga gtc tac act tat gaa gcc ttc cat     14699
Thr Lys Leu Val Met Pro Gly Val Tyr Thr Tyr Glu Ala Phe His
                                                                1845                1850                1855
```

| | | |
|---|---|---|
| cct gat att gtg cta cta cct ggc tgt ggg gtg gac ttt act gag<br>Pro Asp Ile Val Leu Leu Pro Gly Cys Gly Val Asp Phe Thr Glu<br>1860                       1865                      1870 | | 14744 |
| agc cgc ctt agc aac ttg ctt ggt att agg aag aga cac cca ttc<br>Ser Arg Leu Ser Asn Leu Leu Gly Ile Arg Lys Arg His Pro Phe<br>             1875                      1880                      1885 | | 14789 |
| cag gaa ggt ttt aaa att atg tat gag gat ctt gag ggg ggt aat<br>Gln Glu Gly Phe Lys Ile Met Tyr Glu Asp Leu Glu Gly Gly Asn<br>             1890                      1895                      1900 | | 14834 |
| atc ccc gcc ctt ttg gat gta gat gcc tat gaa aaa agc aaa aag<br>Ile Pro Ala Leu Leu Asp Val Asp Ala Tyr Glu Lys Ser Lys Lys<br>1905                       1910                      1915 | | 14879 |
| gaa aac aca gac acc acc act acc act gtt act act act gaa<br>Glu Asn Thr Asp Thr Thr Thr Thr Thr Val Thr Thr Thr Glu<br>1920                       1925                      1930 | | 14924 |
| gta gca act gtt gca aga cac gtt gct gaa gta act act gaa gca<br>Val Ala Thr Val Ala Arg His Val Ala Glu Val Thr Thr Glu Ala<br>             1935                      1940                      1945 | | 14969 |
| gca acg gtt gtt gca gtg gat cct att gtt gaa gag aac aat aat<br>Ala Thr Val Val Ala Val Asp Pro Ile Val Glu Glu Asn Asn Asn<br>             1950                      1955                      1960 | | 15014 |
| act gtt aga gga gat aat atc cat act gcc aat gag atg aaa gca<br>Thr Val Arg Gly Asp Asn Ile His Thr Ala Asn Glu Met Lys Ala<br>1965                       1970                      1975 | | 15059 |
| gca gct gat gat aca aca gtt gta gtt gtg cct ggc gct gta gtg<br>Ala Ala Asp Asp Thr Thr Val Val Val Val Pro Gly Ala Val Val<br>             1980                      1985                      1990 | | 15104 |
| act gaa act gaa acc aaa acc aag aca ctc acc att caa cct cta<br>Thr Glu Thr Glu Thr Lys Thr Lys Thr Leu Thr Ile Gln Pro Leu<br>1995                       2000                      2005 | | 15149 |
| gaa aag gat acc aag gag cgc agt tac aat gtc atc tct ggc acc<br>Glu Lys Asp Thr Lys Glu Arg Ser Tyr Asn Val Ile Ser Gly Thr<br>             2010                      2015                      2020 | | 15194 |
| aat gat act gcc tat cgt agt tgg tac cta gca tac aac tat ggc<br>Asn Asp Thr Ala Tyr Arg Ser Trp Tyr Leu Ala Tyr Asn Tyr Gly<br>2025                       2030                      2035 | | 15239 |
| gac cct gaa aaa gga gtc cgc tcc tgg acg ctg ctc acc act tca<br>Asp Pro Glu Lys Gly Val Arg Ser Trp Thr Leu Leu Thr Thr Ser<br>             2040                      2045                      2050 | | 15284 |
| gat gtc acc tgc gga gcg gag caa gta tat tgg tcg ctc cct gac<br>Asp Val Thr Cys Gly Ala Glu Gln Val Tyr Trp Ser Leu Pro Asp<br>2055                       2060                      2065 | | 15329 |
| atg atg cag gac ccc gtc acc ttc cga tcc acg aga caa gtc agc<br>Met Met Gln Asp Pro Val Thr Phe Arg Ser Thr Arg Gln Val Ser<br>             2070                      2075                      2080 | | 15374 |
| aac tac ccc gtg gtg ggt gca gag ctc atg ccc gtc ttc tca aag<br>Asn Tyr Pro Val Val Gly Ala Glu Leu Met Pro Val Phe Ser Lys<br>2085                       2090                      2095 | | 15419 |
| agt ttc tac aac gag caa gcc gtg tac tcc cag cag ctc cgc cag<br>Ser Phe Tyr Asn Glu Gln Ala Val Tyr Ser Gln Gln Leu Arg Gln<br>             2100                      2105                      2110 | | 15464 |
| acc acc tcg ctt acg cac atc ttc gat cgc ttc cct gag aat cag<br>Thr Thr Ser Leu Thr His Ile Phe Asp Arg Phe Pro Glu Asn Gln<br>2115                       2120                      2125 | | 15509 |
| atc ctc atc cgc ccg gcg ccc acc att acc acc gtt agt gaa<br>Ile Leu Ile Arg Pro Pro Ala Pro Thr Ile Thr Thr Val Ser Glu<br>             2130                      2135                      2140 | | 15554 |
| aac gtt cct gct ctc aca gat cac ggg acc ctg ccg ttg cgc agc<br>Asn Val Pro Ala Leu Thr Asp His Gly Thr Leu Pro Leu Arg Ser<br>2145                       2150                      2155 | | 15599 |

| | | |
|---|---|---|
| agt atc cgg gga gtc cag cgc gtg acc gtt act gac gcc aga cgc<br>Ser Ile Arg Gly Val Gln Arg Val Thr Val Thr Asp Ala Arg Arg<br>                2160                        2165                  2170 | | 15644 |
| cgc acc tgc ccc tac gtc tac aag gcc ctg ggc ata gtc gcg ccg<br>Arg Thr Cys Pro Tyr Val Tyr Lys Ala Leu Gly Ile Val Ala Pro<br>            2175                        2180                  2185 | | 15689 |
| cgc gtc ctt tca agc cgc act ttc taaaaa atg tcc att ctc atc tca<br>Arg Val Leu Ser Ser Arg Thr Phe         Met Ser Ile Leu Ile Ser<br>            2190                                    2195 | | 15737 |
| ccc agt aat aac acc ggt tgg ggg ctg cgc aca ccc acc agg atg<br>Pro Ser Asn Asn Thr Gly Trp Gly Leu Arg Thr Pro Thr Arg Met<br>2200                      2205                        2210 | | 15782 |
| tac gga ggc gct cgc aaa cgg tct acc cag cac cct gtg cgt gtg<br>Tyr Gly Gly Ala Arg Lys Arg Ser Thr Gln His Pro Val Arg Val<br>2215                      2220                        2225 | | 15827 |
| cgc ggg cat ttc cgc gct ccc tgg ggc gcc ctc aag ggc cgt act<br>Arg Gly His Phe Arg Ala Pro Trp Gly Ala Leu Lys Gly Arg Thr<br>2230                      2235                        2240 | | 15872 |
| cgc act cgg acc acc gtc gat gat gtg atc gac cag gtg gtt gca<br>Arg Thr Arg Thr Thr Val Asp Asp Val Ile Asp Gln Val Val Ala<br>2245                      2250                        2255 | | 15917 |
| gat gct cgt aat tat act cct gct gca cct gca tct act gtg gat<br>Asp Ala Arg Asn Tyr Thr Pro Ala Ala Pro Ala Ser Thr Val Asp<br>2260                      2265                        2270 | | 15962 |
| gca gtt att gac agc gtg gtg gct gac gct cgc gag tat gct cgc<br>Ala Val Ile Asp Ser Val Val Ala Asp Ala Arg Glu Tyr Ala Arg<br>2275                      2280                        2285 | | 16007 |
| cgg aag agc agg cga aga cgc atc gcc agg cgc cac cgg gct acc<br>Arg Lys Ser Arg Arg Arg Arg Ile Ala Arg Arg His Arg Ala Thr<br>2290                      2295                        2300 | | 16052 |
| ccc gct atg cga gct gca aga gct ctg ctg cgg aga gcc aaa cgc<br>Pro Ala Met Arg Ala Ala Arg Ala Leu Leu Arg Arg Ala Lys Arg<br>2305                      2310                        2315 | | 16097 |
| gtg ggg cga aga gcc atg ctt aga gcg gcc aga cgc gcg gct tca<br>Val Gly Arg Arg Ala Met Leu Arg Ala Ala Arg Ala Ala Ser<br>2320                      2325                        2330 | | 16142 |
| ggt gcc agc gca ggc agg tcc cgc agg cgc gca gcc acg gcg gca<br>Gly Ala Ser Ala Gly Arg Ser Arg Arg Ala Ala Thr Ala Ala<br>2335                      2340                        2345 | | 16187 |
| gca gcg gcc att gcc aac atg gcc caa ccg cga aga ggc aat gtg<br>Ala Ala Ala Ile Ala Asn Met Ala Gln Pro Arg Arg Gly Asn Val<br>2350                      2355                        2360 | | 16232 |
| tac tgg gtg cgc gat gcc act acc ggt cag cgc gtg ccc gtg cgc<br>Tyr Trp Val Arg Asp Ala Thr Thr Gly Gln Arg Val Pro Val Arg<br>2365                      2370                        2375 | | 16277 |
| acc cgt ccc cct cgc act tagaagatac tgagcagtct ccgatgttgt<br>Thr Arg Pro Pro Arg Thr<br>2380                      2385 | | 16325 |
| gtcccagcgg cgagg atg tcc aag cgc aaa tac aag gaa gag atg ctc<br>                    Met Ser Lys Arg Lys Tyr Lys Glu Glu Met Leu<br>                                      2390                        2395 | | 16373 |
| cag gtc atc gcg cct gaa atc tac ggt cca ccg gtg aag gat gaa<br>Gln Val Ile Ala Pro Glu Ile Tyr Gly Pro Pro Val Lys Asp Glu<br>            2400                        2405                  2410 | | 16418 |
| aaa aag ccc cgc aaa atc aag cgg gtc aaa aag gac aaa aag gaa<br>Lys Lys Pro Arg Lys Ile Lys Arg Val Lys Lys Asp Lys Lys Glu<br>            2415                        2420                  2425 | | 16463 |
| gaa gat ggc gat gat ggg ctg gtg gag ttt gtg cgc gag ttc gct<br>Glu Asp Gly Asp Asp Gly Leu Val Glu Phe Val Arg Glu Phe Ala | | 16508 |

| | | | | | | | | | | |
|---|---|---|---|---|---|---|---|---|---|---|
| | | 2430 | | | 2435 | | | 2440 | | |
| cca | agg | cgg | cgc | gtg | cag | tgg | cgc | ggg | cgc | agg | gtg | cgg | ccg | gtg | 16553 |
| Pro | Arg | Arg | Arg | Val | Gln | Trp | Arg | Gly | Arg | Arg | Val | Arg | Pro | Val | |
| | | 2445 | | | 2450 | | | | 2455 | | |
| ctg | aga | cca | gga | acc | acg | gtg | gtc | ttc | acg | ccc | ggc | gaa | cgc | tcc | 16598 |
| Leu | Arg | Pro | Gly | Thr | Thr | Val | Val | Phe | Thr | Pro | Gly | Glu | Arg | Ser | |
| | | 2460 | | | 2465 | | | | 2470 | | |
| agc | act | act | ttt | aaa | cgc | tcc | tat | gat | gag | gtg | tac | ggg | gat | gat | 16643 |
| Ser | Thr | Thr | Phe | Lys | Arg | Ser | Tyr | Asp | Glu | Val | Tyr | Gly | Asp | Asp | |
| | 2475 | | | | 2480 | | | | 2485 | | |
| gat | att | ctg | gag | cag | gcg | gcc | gac | cgc | ctg | ggc | gag | ttt | gct | tat | 16688 |
| Asp | Ile | Leu | Glu | Gln | Ala | Ala | Asp | Arg | Leu | Gly | Glu | Phe | Ala | Tyr | |
| | | 2490 | | | 2495 | | | | 2500 | | |
| ggc | aaa | cgc | agc | cgc | tcc | agt | ccc | aag | gat | gaa | gcg | gtg | tcc | atc | 16733 |
| Gly | Lys | Arg | Ser | Arg | Ser | Ser | Pro | Lys | Asp | Glu | Ala | Val | Ser | Ile | |
| | | 2505 | | | 2510 | | | | 2515 | | |
| ccc | ttg | gat | cat | gga | aat | ccc | acc | ccg | agt | ctc | aaa | cca | gtc | acc | 16778 |
| Pro | Leu | Asp | His | Gly | Asn | Pro | Thr | Pro | Ser | Leu | Lys | Pro | Val | Thr | |
| | | 2520 | | | 2525 | | | | 2530 | | |
| ctg | cag | caa | gtg | ctg | ccc | gtg | cct | cca | cgg | aga | ggc | gtc | aag | cga | 16823 |
| Leu | Gln | Gln | Val | Leu | Pro | Val | Pro | Pro | Arg | Arg | Gly | Val | Lys | Arg | |
| | | 2535 | | | 2540 | | | | 2545 | | |
| gag | ggc | gag | gat | ctg | tat | ccc | acc | atg | caa | ttg | atg | gtg | ccc | aag | 16868 |
| Glu | Gly | Glu | Asp | Leu | Tyr | Pro | Thr | Met | Gln | Leu | Met | Val | Pro | Lys | |
| | | 2550 | | | 2555 | | | | 2560 | | |
| cgc | cag | aag | ctg | gag | gac | gtg | ctg | gag | aaa | atg | aaa | gtg | gat | ccc | 16913 |
| Arg | Gln | Lys | Leu | Glu | Asp | Val | Leu | Glu | Lys | Met | Lys | Val | Asp | Pro | |
| | | 2565 | | | 2570 | | | | 2575 | | |
| gat | atc | cag | cct | gaa | gtt | aaa | gtc | aga | ccc | atc | aag | cag | gtg | gcg | 16958 |
| Asp | Ile | Gln | Pro | Glu | Val | Lys | Val | Arg | Pro | Ile | Lys | Gln | Val | Ala | |
| | | 2580 | | | 2585 | | | | 2590 | | |
| ccc | ggt | ctg | gga | gtg | caa | acc | gtg | gac | atc | aag | att | ccc | acc | gag | 17003 |
| Pro | Gly | Leu | Gly | Val | Gln | Thr | Val | Asp | Ile | Lys | Ile | Pro | Thr | Glu | |
| | | 2595 | | | 2600 | | | | 2605 | | |
| tcc | atg | gaa | gtc | cag | act | gaa | cct | gca | aag | cct | aca | gcc | gcc | tcc | 17048 |
| Ser | Met | Glu | Val | Gln | Thr | Glu | Pro | Ala | Lys | Pro | Thr | Ala | Ala | Ser | |
| | | 2610 | | | 2615 | | | | 2620 | | |
| att | gag | gtg | cag | acg | gat | cca | tgg | atg | ccc | gcg | ccc | att | gca | acc | 17093 |
| Ile | Glu | Val | Gln | Thr | Asp | Pro | Trp | Met | Pro | Ala | Pro | Ile | Ala | Thr | |
| | | 2625 | | | 2630 | | | | 2635 | | |
| gcc | gcc | agt | acc | gtt | cga | aga | ccc | cgg | cga | aag | tat | ggt | cct | gcg | 17138 |
| Ala | Ala | Ser | Thr | Val | Arg | Arg | Pro | Arg | Arg | Lys | Tyr | Gly | Pro | Ala | |
| | | 2640 | | | 2645 | | | | 2650 | | |
| agt | ctg | ctg | atg | ccc | aac | tat | gct | ctg | cac | cca | tcc | att | att | ccg | 17183 |
| Ser | Leu | Leu | Met | Pro | Asn | Tyr | Ala | Leu | His | Pro | Ser | Ile | Ile | Pro | |
| | | 2655 | | | 2660 | | | | 2665 | | |
| act | ccg | ggt | tac | cga | ggc | act | cgc | tac | tac | cgc | agc | cgg | agc | acc | 17228 |
| Thr | Pro | Gly | Tyr | Arg | Gly | Thr | Arg | Tyr | Tyr | Arg | Ser | Arg | Ser | Thr | |
| | | 2670 | | | 2675 | | | | 2680 | | |
| act | tcc | cgc | cgt | cgc | aaa | aca | cct | gca | agc | cgc | agt | cgc | cgt | cgc | 17273 |
| Thr | Ser | Arg | Arg | Arg | Lys | Thr | Pro | Ala | Ser | Arg | Ser | Arg | Arg | Arg | |
| | | 2685 | | | 2690 | | | | 2695 | | |
| cgc | cgc | cgc | acc | gcc | agc | aaa | ctg | act | ccc | gcc | gct | ttg | gtg | cgg | 17318 |
| Arg | Arg | Arg | Thr | Ala | Ser | Lys | Leu | Thr | Pro | Ala | Ala | Leu | Val | Arg | |
| | | 2700 | | | 2705 | | | | 2710 | | |
| agg | gtg | tat | cgc | gat | ggc | cgc | gca | gag | ccc | ctg | atg | ctg | ccg | cgc | 17363 |
| Arg | Val | Tyr | Arg | Asp | Gly | Arg | Ala | Glu | Pro | Leu | Met | Leu | Pro | Arg | |
| | | 2715 | | | 2720 | | | | 2725 | | |
| gca | cgc | tac | cat | cca | agc | atc | acc | act | taatgactgt | tgccactgcc | 17410 |
| Ala | Arg | Tyr | His | Pro | Ser | Ile | Thr | Thr | | |

```
                Ala Arg Tyr His  Pro Ser Ile Thr Thr
                             2730                2735 tccttgcaga t atg gcc ctc act tgc cgc ctt cgc gtc ccc att act            17457
             Met Ala Leu Thr Cys Arg Leu Arg Val Pro Ile Thr
                 2740                    2745 ggc tac cga gga aga aac tcg cgc cgt aga agg atg ttg ggt agc             17502
Gly Tyr Arg Gly Arg Asn Ser Arg Arg Arg Arg Met Leu Gly Ser
            2750                    2755                2760 ggg atg cgt cgc cac agg cgg cgg cgc gct atc agc aag agg ctg             17547
Gly Met Arg Arg His Arg Arg Arg Arg Ala Ile Ser Lys Arg Leu
            2765                    2770                2775 ggg ggt ggc ttt ctg acc gct ttg att ccc atc atc gcc gcg gcg             17592
Gly Gly Gly Phe Leu Thr Ala Leu Ile Pro Ile Ile Ala Ala Ala
            2780                    2785                2790 atc ggg gcg gta cca ggc ata gct tcc gtg gcg gtt cag gcc tcg             17637
Ile Gly Ala Val Pro Gly Ile Ala Ser Val Ala Val Gln Ala Ser
            2795                    2800                2805 cag cgc cac tgacattgga aaaacactta taaataaaat agaatggact                 17686
Gln Arg His
        2810 ctgacgctcc tggtcctgtg actatgtttt tgtagag atg gaa gac atc aat ttt        17741
                                        Met Glu Asp Ile Asn Phe
                                                            2815 tca tcc ctg gct ccg cga cac ggc acg agg ccg tac atg ggc acc             17786
Ser Ser Leu Ala Pro Arg His Gly Thr Arg Pro Tyr Met Gly Thr
            2820                    2825                2830 tgg agc gac atc ggc acc agc caa ctg aac ggg ggc gcc ttc aat             17831
Trp Ser Asp Ile Gly Thr Ser Gln Leu Asn Gly Gly Ala Phe Asn
            2835                    2840                2845 tgg agc agt atc tgg agc ggg ctt aaa aat ttt ggc tct gcc ata             17876
Trp Ser Ser Ile Trp Ser Gly Leu Lys Asn Phe Gly Ser Ala Ile
            2850                    2855                2860 aaa acc tat ggg aac aaa gct tgg aac agc agc aca ggg cag gcg             17921
Lys Thr Tyr Gly Asn Lys Ala Trp Asn Ser Ser Thr Gly Gln Ala
            2865                    2870                2875 ctg agg aat aag ctt aaa gag cag aac ttc cag cag aag gtg gtc             17966
Leu Arg Asn Lys Leu Lys Glu Gln Asn Phe Gln Gln Lys Val Val
            2880                    2885                2890 gat ggg atc gcc tct ggc atc aat ggg gtg gtg gat ctg gcc aac             18011
Asp Gly Ile Ala Ser Gly Ile Asn Gly Val Val Asp Leu Ala Asn
            2895                    2900                2905 cag gcc gtg cag aaa cag ata aac agc cgc ctg gac cag ccg ccc             18056
Gln Ala Val Gln Lys Gln Ile Asn Ser Arg Leu Asp Gln Pro Pro
            2910                    2915                2920 gca gcc cct ggc gaa atg gaa gtg gag gaa gag ctc cct ccc ctg             18101
Ala Ala Pro Gly Glu Met Glu Val Glu Glu Glu Leu Pro Pro Leu
            2925                    2930                2935 gaa aag cgg gga gac aag cgc ccg cgt ccc gat atg gag gag acg             18146
Glu Lys Arg Gly Asp Lys Arg Pro Arg Pro Asp Met Glu Glu Thr
            2940                    2945                2950 ctg gtg acg cgc gga gac gag ccg cct cca tat gag gag gca ata             18191
Leu Val Thr Arg Gly Asp Glu Pro Pro Pro Tyr Glu Glu Ala Ile
            2955                    2960                2965 aag ctt gga atg ccc act acc agg cct ata gct ccc atg gcc acc             18236
Lys Leu Gly Met Pro Thr Thr Arg Pro Ile Ala Pro Met Ala Thr
            2970                    2975                2980 ggg gta atg aaa cct tct cag tcg cat cga ccc gcc acc ttg gac             18281
Gly Val Met Lys Pro Ser Gln Ser His Arg Pro Ala Thr Leu Asp
            2985                    2990                2995
```

| | | | | | | | | | | | | |
|---|---|---|---|---|---|---|---|---|---|---|---|---|
|ttg|cct|cct|gcc|cct|gct|gct|gca|gcg|ccc|gct|cca|aag|cct|gtc|18326|
|Leu|Pro|Pro|Ala|Pro|Ala|Ala|Ala|Ala|Pro|Ala|Pro|Lys|Pro|Val| |
| | | |3000| | | |3005| | | |3010| | | | |

```
ttg cct cct gcc cct gct gct gca gcg ccc gct cca aag cct gtc    18326
Leu Pro Pro Ala Pro Ala Ala Ala Ala Pro Ala Pro Lys Pro Val
            3000            3005            3010 gct acc ccg aag ccc acc gcc gta cag ccc gtc gcc gta gcc aga    18371
Ala Thr Pro Lys Pro Thr Ala Val Gln Pro Val Ala Val Ala Arg
            3015            3020            3025 ccg cgt cct ggg ggc act ccg cgc ccg aat gca aac tgg cag agt    18416
Pro Arg Pro Gly Gly Thr Pro Arg Pro Asn Ala Asn Trp Gln Ser
            3030            3035            3040 act ctg aac agc atc gtg ggt ttg ggc gtg cag agt gta aag cgc    18461
Thr Leu Asn Ser Ile Val Gly Leu Gly Val Gln Ser Val Lys Arg
            3045            3050            3055 cgt cgc tgc tat  taattaaata tggagtagcg cttaacttgc ttgtctgtgt   18513
Arg Arg Cys Tyr
            3060 gtatgtgtca tcaccacgcc gccacagcag cagaggagaa aggaagaggt cgcgcgccga   18573 ggctgagttg ctttcaag atg gcc acc cca tcg atg ctg ccc cag tgg  gca   18624
                    Met Ala Thr Pro Ser Met Leu Pro Gln Trp Ala
                                    3065            3070 tac atg cac atc gcc gga cag gat gct tcg gag tac ctg agt ccg        18669
Tyr Met His Ile Ala Gly Gln Asp Ala Ser Glu Tyr Leu Ser Pro
            3075            3080            3085 ggt ctg gtg cag ttc gcc cgt gcc aca gac acc tac ttc aat ctg        18714
Gly Leu Val Gln Phe Ala Arg Ala Thr Asp Thr Tyr Phe Asn Leu
            3090            3095            3100 gga aac aag ttt agg aac ccc acc gtg gct ccc acc cac gat gtg        18759
Gly Asn Lys Phe Arg Asn Pro Thr Val Ala Pro Thr His Asp Val
            3105            3110            3115 acc acc gac cga agc cag cgg ctg atg ctg cgc ttt gtg ccc gtt        18804
Thr Thr Asp Arg Ser Gln Arg Leu Met Leu Arg Phe Val Pro Val
            3120            3125            3130 gat cgg gag gac aat act tac tct tac aaa gtt cgc tac aca ctg        18849
Asp Arg Glu Asp Asn Thr Tyr Ser Tyr Lys Val Arg Tyr Thr Leu
            3135            3140            3145 gct gtg gga gac aac aga gtg ctg gat atg gcc agc acc ttc ttt        18894
Ala Val Gly Asp Asn Arg Val Leu Asp Met Ala Ser Thr Phe Phe
            3150            3155            3160 gac atc agg ggg gtg ctt gac aga ggt ccc agt ttc aaa ccc tac        18939
Asp Ile Arg Gly Val Leu Asp Arg Gly Pro Ser Phe Lys Pro Tyr
            3165            3170            3175 tct ggg aca gca tac aat tcc ctg gcc cct aag gga gct cct aat        18984
Ser Gly Thr Ala Tyr Asn Ser Leu Ala Pro Lys Gly Ala Pro Asn
            3180            3185            3190 act agt cag tgg ata gtt aca act aat ggg caa gat aat gca gta        19029
Thr Ser Gln Trp Ile Val Thr Thr Asn Gly Gln Asp Asn Ala Val
            3195            3200            3205 act acc act aca aac aca ttt ggc att gct tcc atg aaa gga gac        19074
Thr Thr Thr Thr Asn Thr Phe Gly Ile Ala Ser Met Lys Gly Asp
            3210            3215            3220 aat att act aaa gaa ggt tta gaa att gga aaa gat att act gaa        19119
Asn Ile Thr Lys Glu Gly Leu Glu Ile Gly Lys Asp Ile Thr Glu
            3225            3230            3235 gaa gat aaa ccc atc tat gcc gat aaa aca tat cag cca gaa cct        19164
Glu Asp Lys Pro Ile Tyr Ala Asp Lys Thr Tyr Gln Pro Glu Pro
            3240            3245            3250 caa gtt gga gaa gaa tca tgg act gat acc gat gga aca aat gaa        19209
Gln Val Gly Glu Glu Ser Trp Thr Asp Thr Asp Gly Thr Asn Glu
            3255            3260            3265 aag ttt ggc ggt aga gcg ctt aaa ccc gct acc aac atg aaa cca        19254
```

```
Lys Phe Gly Gly Arg Ala Leu Lys Pro Ala Thr Asn Met Lys Pro
            3270                3275                3280 tgc tat ggg tca ttt gca aga cct aca aac ata aaa ggt ggt caa      19299
Cys Tyr Gly Ser Phe Ala Arg Pro Thr Asn Ile Lys Gly Gly Gln
            3285                3290                3295 gct aaa aat aga aaa gta aag ccg aca acc gag gga ggg gtt gaa      19344
Ala Lys Asn Arg Lys Val Lys Pro Thr Thr Glu Gly Gly Val Glu
            3300                3305                3310 act gag gaa ccg gat att gat atg gaa ttt ttc gat ggt aga gat      19389
Thr Glu Glu Pro Asp Ile Asp Met Glu Phe Phe Asp Gly Arg Asp
            3315                3320                3325 gct gct gaa gga gct tta tcg cct gaa att gtg ctt tac aca gaa      19434
Ala Ala Glu Gly Ala Leu Ser Pro Glu Ile Val Leu Tyr Thr Glu
            3330                3335                3340 aat gta aat ttg gaa act cca gac acc cat gtg gta tac aaa cca      19479
Asn Val Asn Leu Glu Thr Pro Asp Thr His Val Val Tyr Lys Pro
            3345                3350                3355 gga act tca gat gat aac tct cat gca aat ttg ggt caa caa gct      19524
Gly Thr Ser Asp Asp Asn Ser His Ala Asn Leu Gly Gln Gln Ala
            3360                3365                3370 atg ccc aac aga ccc aat tac att ggc ttc aga gac aac ttt gtt      19569
Met Pro Asn Arg Pro Asn Tyr Ile Gly Phe Arg Asp Asn Phe Val
            3375                3380                3385 gga ctc ttg tac tac aac agc act ggc aac atg gga gtg ttg gca      19614
Gly Leu Leu Tyr Tyr Asn Ser Thr Gly Asn Met Gly Val Leu Ala
            3390                3395                3400 ggt caa gca tca caa cta aat gca gta gtt gac ttg cag gac aga      19659
Gly Gln Ala Ser Gln Leu Asn Ala Val Val Asp Leu Gln Asp Arg
            3405                3410                3415 aac act gaa ctg tcc tat cag ctt ttg ctt gat tct ctt ggg gac      19704
Asn Thr Glu Leu Ser Tyr Gln Leu Leu Leu Asp Ser Leu Gly Asp
            3420                3425                3430 aga acc aga tac ttc agc atg tgg aat cag gcc gtg gat agt tat      19749
Arg Thr Arg Tyr Phe Ser Met Trp Asn Gln Ala Val Asp Ser Tyr
            3435                3440                3445 gat cct gat gtt cgc att att gaa aat cat ggt atc gag gat gaa      19794
Asp Pro Asp Val Arg Ile Ile Glu Asn His Gly Ile Glu Asp Glu
            3450                3455                3460 cta ccc aac tac tgt ttt cct ctg gat ggc ata gga cca ggg aac      19839
Leu Pro Asn Tyr Cys Phe Pro Leu Asp Gly Ile Gly Pro Gly Asn
            3465                3470                3475 tca tat caa ggc atc aag gct aaa aac ggt gat aat aat gga tgg      19884
Ser Tyr Gln Gly Ile Lys Ala Lys Asn Gly Asp Asn Asn Gly Trp
            3480                3485                3490 gaa aaa gat act aat gct tct act gct aat gaa ata gcc ata gga      19929
Glu Lys Asp Thr Asn Ala Ser Thr Ala Asn Glu Ile Ala Ile Gly
            3495                3500                3505 aac aac ctg gct atg gaa att aat atc cag gct aac ctt tgg aga      19974
Asn Asn Leu Ala Met Glu Ile Asn Ile Gln Ala Asn Leu Trp Arg
            3510                3515                3520 agt ttt ctg tac tcc aac gtg gct ttg tac ctt cca gac gct tac      20019
Ser Phe Leu Tyr Ser Asn Val Ala Leu Tyr Leu Pro Asp Ala Tyr
            3525                3530                3535 aag tac acg cca gcc aac att act cct gcc aat acc aac acc         20064
Lys Tyr Thr Pro Ala Asn Ile Thr Leu Pro Ala Asn Thr Asn Thr
            3540                3545                3550 tat gaa tac atg aac ggg cga gtg gtg gca cca tct ttg gtt gat      20109
Tyr Glu Tyr Met Asn Gly Arg Val Val Ala Pro Ser Leu Val Asp
            3555                3560                3565
```

```
tcg tac atc aac att gga gcc agg tgg tct ctt gac cca atg gac    20154
Ser Tyr Ile Asn Ile Gly Ala Arg Trp Ser Leu Asp Pro Met Asp
        3570                3575                3580 aat gtg aac ccc ttc aat cac cac cga aac gct ggg ctg cgt tac    20199
Asn Val Asn Pro Phe Asn His His Arg Asn Ala Gly Leu Arg Tyr
        3585                3590                3595 aga tcc atg ctt ctg ggc aat ggt cgc tat gtg cct ttc cac atc    20244
Arg Ser Met Leu Leu Gly Asn Gly Arg Tyr Val Pro Phe His Ile
        3600                3605                3610 caa gtg cct cag aaa ttc ttt gct atc aag aac ctg ctt ctc ctc    20289
Gln Val Pro Gln Lys Phe Phe Ala Ile Lys Asn Leu Leu Leu Leu
        3615                3620                3625 cca ggc tcc tat acc tat gag tgg aac ttc aga aag gat gtg aac    20334
Pro Gly Ser Tyr Thr Tyr Glu Trp Asn Phe Arg Lys Asp Val Asn
        3630                3635                3640 atg gtc ctg cag agt tcc ctt ggc aat gat ctc aga act gat gga    20379
Met Val Leu Gln Ser Ser Leu Gly Asn Asp Leu Arg Thr Asp Gly
        3645                3650                3655 gcc agc atc agt ttt act agc atc aac ctc tat gcc acc ttc ttc    20424
Ala Ser Ile Ser Phe Thr Ser Ile Asn Leu Tyr Ala Thr Phe Phe
        3660                3665                3670 ccc atg gct cac aat act gct tcc acc ctt gaa gcc atg ctg cgc    20469
Pro Met Ala His Asn Thr Ala Ser Thr Leu Glu Ala Met Leu Arg
        3675                3680                3685 aat gac aca aat gac cag tca ttc aat gac tac ctt tct gca gct    20514
Asn Asp Thr Asn Asp Gln Ser Phe Asn Asp Tyr Leu Ser Ala Ala
        3690                3695                3700 aac atg ctc tac cct att cca gcc aat gca acc aac att ccc att    20559
Asn Met Leu Tyr Pro Ile Pro Ala Asn Ala Thr Asn Ile Pro Ile
        3705                3710                3715 tcc att ccc tct cgc aac tgg gct gcc ttt agg ggt tgg tcc ttc    20604
Ser Ile Pro Ser Arg Asn Trp Ala Ala Phe Arg Gly Trp Ser Phe
        3720                3725                3730 acc aga ctc aaa aca aag gaa aca ccc tct ttg gga tca ggc ttt    20649
Thr Arg Leu Lys Thr Lys Glu Thr Pro Ser Leu Gly Ser Gly Phe
        3735                3740                3745 gat ccc tac ttt gtt tac tct ggc tcc att ccc tac ctg gat ggc    20694
Asp Pro Tyr Phe Val Tyr Ser Gly Ser Ile Pro Tyr Leu Asp Gly
        3750                3755                3760 acc ttc tac ctc aac cac act ttc aag aag gtg tcc atc atg ttt    20739
Thr Phe Tyr Leu Asn His Thr Phe Lys Lys Val Ser Ile Met Phe
        3765                3770                3775 gac tcc tca gtc agc tgg cca ggc aat gac aga ttg cta act cca    20784
Asp Ser Ser Val Ser Trp Pro Gly Asn Asp Arg Leu Leu Thr Pro
        3780                3785                3790 aat gag ttt gaa atc aag cgc act gtg gat gga gaa ggg tac aat    20829
Asn Glu Phe Glu Ile Lys Arg Thr Val Asp Gly Glu Gly Tyr Asn
        3795                3800                3805 gtg gct caa tgc aac atg acc aag gat tgg ttc ctg gtt cag atg    20874
Val Ala Gln Cys Asn Met Thr Lys Asp Trp Phe Leu Val Gln Met
        3810                3815                3820 ctt gcc aac tat aac att ggc tac cag ggc ttc tac atc cca gag    20919
Leu Ala Asn Tyr Asn Ile Gly Tyr Gln Gly Phe Tyr Ile Pro Glu
        3825                3830                3835 ggg tac aag gat cgc atg tac tcc ttc ttc aga aac ttc cag ccc    20964
Gly Tyr Lys Asp Arg Met Tyr Ser Phe Phe Arg Asn Phe Gln Pro
        3840                3845                3850 atg agc aga cag gtg gtt gat gag gtg aac tac acc gat tac aaa    21009
Met Ser Arg Gln Val Val Asp Glu Val Asn Tyr Thr Asp Tyr Lys
        3855                3860                3865
```

| | | | | | | | | | | | | |
|---|---|---|---|---|---|---|---|---|---|---|---|---|
| gcc | gtc | act | cta | gca | tac | caa | cac | aac | aac | tct | ggc | ttt | gtg | ggt | 21054 |
| Ala | Val | Thr | Leu | Ala | Tyr | Gln | His | Asn | Asn | Ser | Gly | Phe | Val | Gly | |
| | | 3870 | | | | 3875 | | | | 3880 | | | | | |
| tac | ctt | gcg | ccc | act | atg | aga | cag | gga | gaa | cct | tac | ccc | gct | aac | 21099 |
| Tyr | Leu | Ala | Pro | Thr | Met | Arg | Gln | Gly | Glu | Pro | Tyr | Pro | Ala | Asn | |
| | | 3885 | | | | 3890 | | | | 3895 | | | | | |
| tac | cca | tac | ccc | cta | atc | gga | acc | act | gct | gtt | aag | agt | gtt | acc | 21144 |
| Tyr | Pro | Tyr | Pro | Leu | Ile | Gly | Thr | Thr | Ala | Val | Lys | Ser | Val | Thr | |
| | | 3900 | | | | 3905 | | | | 3910 | | | | | |
| cag | aaa | aag | ttc | ctg | tgc | gac | agg | acc | atg | tgg | cgc | atc | ccc | ttc | 21189 |
| Gln | Lys | Lys | Phe | Leu | Cys | Asp | Arg | Thr | Met | Trp | Arg | Ile | Pro | Phe | |
| | | 3915 | | | | 3920 | | | | 3925 | | | | | |
| tcc | agc | aac | ttc | atg | tcc | atg | ggt | gcc | ctt | acc | gac | ctg | gga | cag | 21234 |
| Ser | Ser | Asn | Phe | Met | Ser | Met | Gly | Ala | Leu | Thr | Asp | Leu | Gly | Gln | |
| | | 3930 | | | | 3935 | | | | 3940 | | | | | |
| aac | atg | ctt | tat | gct | aac | tca | gcc | cat | gcg | ctg | gac | atg | act | ttt | 21279 |
| Asn | Met | Leu | Tyr | Ala | Asn | Ser | Ala | His | Ala | Leu | Asp | Met | Thr | Phe | |
| | | 3945 | | | | 3950 | | | | 3955 | | | | | |
| gag | gtg | gat | ccc | atg | gat | gag | ccc | acc | ctg | ctt | tat | gtt | ctt | ttc | 21324 |
| Glu | Val | Asp | Pro | Met | Asp | Glu | Pro | Thr | Leu | Leu | Tyr | Val | Leu | Phe | |
| | | 3960 | | | | 3965 | | | | 3970 | | | | | |
| gaa | gtc | ttc | gac | gtg | gtc | aga | gtg | cac | cag | cca | cac | cgc | ggc | gtc | 21369 |
| Glu | Val | Phe | Asp | Val | Val | Arg | Val | His | Gln | Pro | His | Arg | Gly | Val | |
| | | 3975 | | | | 3980 | | | | 3985 | | | | | |
| atc | gag | gct | gtc | tac | ctg | cgt | acc | ccg | ttc | tca | gct | ggt | aac | gcc | 21414 |
| Ile | Glu | Ala | Val | Tyr | Leu | Arg | Thr | Pro | Phe | Ser | Ala | Gly | Asn | Ala | |
| | | 3990 | | | | 3995 | | | | 4000 | | | | | |

| | | |
|---|---|---|
| acc aca taaagaagct tcttgcttct tgcaagcagc tgccatggcc tgtgggtccg | | 21470 |
| Thr Thr | | |
| gcaacggatc cagcgagcaa gagctcaggg ccattgctag agacctgggc tgcggaccct | | 21530 |
| atttcctggg aacctttgat aaacgcttcc cggggttcat ggcccccgac aagctcgcct | | 21590 |
| gcgccattgt taacacggcc ggtcgcgaga cgggggtga gcactggctg gcttttggtt | | 21650 |
| ggaatccgcg ctccaacacc tgctaccttt ttgatccctt tggcttctct gacgagcgcc | | 21710 |
| tcaagcaaat ctaccagttt gagtatgagg ggcttctgcg ccgcagtgcc ctagctacca | | 21770 |
| aggaccgctg tatcaccctg gaaaagtcaa cccagaccgt gcagggcccg cgctccgcag | | 21830 |
| cctgtggact gttttgctgc atgttcctcc acgcttttgt gcactggcca gaccgcccca | | 21890 |
| tggacggaaa ccccaccatg aagttgctga ctggggtgcc caacagcatg ctccaatcac | | 21950 |
| cccaagtcca gcccacccctg cgccacaacc aggaggcgct ctaccgcttc ctaaactccc | | 22010 |
| actcatctta ctttcgttct caccgcgcgc gcatcgaaaa ggccaccgcg tttaatcgaa | | 22070 |
| tggatatgca ataataagtc atgtaaaccg tgttcaaata aacagcactt tattttttac | | 22130 |
| atgcactgtg gctctgggtt gctcattcat tcatcattca ctcagaagtc gaaggggttc | | 22190 |
| tggcgggaat cagcgtgacc cgctggcagg gatacgttgc ggaactggaa cctgttctgc | | 22250 |
| cacttgaact cggggatcac cagcttggga actgggatct cggggaaggt gtcttgccac | | 22310 |
| agctttctgg ttagttgcag agcaccaagc aggtcaggag cagagatctt gaaatcacag | | 22370 |
| ttggggccag cattctgggc acgggagttg cggtacactg ggttgcagca ctggaacacc | | 22430 |
| atcagggcgg ggtgtctcac gctcgccagc acggtcgggt cactgatggt agtcacatcc | | 22490 |
| aagtcttcag cattggccat tccaaagggg gtcatcttac aggtctgcct gccatcacg | | 22550 |
| ggagcgcagc cgggcttgtg gttgcaatcg cagcgaatgg ggatcagcat catcctggcc | | 22610 |
| tggtcggggg ttatccctgg atacaccgcc ttcataaagg cttcgtactg cttgaaagct | | 22670 |

```
tcctgagcct tacttccctc ggtgtagaac atcccacagg acttgctgga aaattgatta    22730
gtagcacagt tggcatcatt cacacagcag cgggcatcgt tgttggccag ctggaccaca    22790
ttcctgcccc agcggttctg ggtgatcttg gctcggtctg ggttctcctt catcgcgcgc    22850
tgcccgttct cgctcgccac atccatctcg atgatgtgat ccttctggat catgatagtg    22910
ccatgcaggc atttcacctt gccttcataa tcggtgcagc catgagccca cagagcgcac    22970
ccggtgcact cccaattgtt gtgggcgatc tcagaataag aatgcaccaa tccctgcatg    23030
aatcttccca tcatgctggt gagggtcttt atgctggtaa atgtcagcgg gatgccacgg    23090
tgctcctcgt tcacatactg gtggcagata cgcctgtact gctcgtgctg ctcgggcatc    23150
agcttgaaag aggttctcag gtcattatcc agcctgtacc tctccattag cacggccatt    23210
acttccatgc ccttctccca ggcagagacc aagggcaggc tcatgggatt cctaacagca    23270
atagcagcag acgcagctcc tttagccaga gggtcattct tgtcaatctt ctcaacactt    23330
ctcttgccat cctctcagt gatgcgcact gggggtagc tgaagcccac ggccaccagc     23390
tccgcctgtt ctctttcttc ttcgctgtcc tggctgatgt cttgcaaagg acatgcttg    23450 gtcttcctgg gcttcttctt gggagggatc ggggagggc tgttgctccg ctccggagac    23510
agggaggacc gcgaagtttc gctcaccagt accacctggc tctcggtaga agaaccggac    23570
cccacgcggc ggtaggtgtt cctcttcggg ggcagaggtg gaggcgactg cgatggactg    23630
cggtccggcc tgggaggcgg atggctggca gagcctcttc cgcgttcggg ggtgtgctcc    23690
cggtggcggt cgcttgactg atttcctccg cggctggcca ttgtgttctc ctaggcagag    23750
aaacaacaga catggagact cagccatcgc tgccaacacc gctgcaagcg ccatcacacc    23810
tcgcccccag cagcgacgag gaggagagct taaccacccc accacccagt cccgccacca    23870
ccacctctac cctagaggat gaggaggagg tcgacgcacc ccaggagatg caggatatgg    23930
aggatgagaa agcggaagag attgaggcag atgtcgagca ggacccgggc tatgtgacac    23990
cggcggagca cgaggaggag ctgagacgct ttctagacag agaggatgac aaccgcccag    24050
agcagaaagc agatggcgat caccaggagg ctgggctcgg ggatcatgtc gccgactacc    24110
tcaccgggct tggcggggag gacgtgctcc tcaaacatct agcaaggcag tcgatcatag    24170
ttaaagacgc actgctcgac cgcaccgaag tgcccatcag tgtggaagag ctcagccgcg    24230
cctacgagct caacctgttc tcgcctcggc tgccccccaa acgtcagcca acggcacct     24290 gtgagcccaa ccctcgcctc aacttctatc cggcctttgc tgtcccagaa gtgcttgcta    24350
cctaccacat cttttcaag aaccaaaaga ttccagtttc ctgccgtgcc aaccgcaccc     24410
gcgccgatgc cctgctcaac ttgggtccgg gagctcgctt acctgatata gcttccttgg    24470
aagaggttcc aaagatcttc gagggtctgg gcagtgatga gactcgggcc gcaaatgctc    24530
tgcaacaggg agagaatggc atggatgaac atcacagcgc tctggtggag ttggagggag    24590
acaatgcccg gcttgcagtg ctcaagcgca gtatcgaggt cacccatttt gcataccccg    24650
ctgtcaacct gccccccaaa gtcatgagcg ctgtcatgga tcagctgctc atcaagcgcg    24710
caagccccct ttccgaagac cagaacatgc aggatccaga cgcctctgac gagggcaagc    24770
cggtggtcag tgacgagcag ctgtctcgct ggctgggcac caactcccg cgagacttgg     24830 aagagaggcg caagcttatg atggctgtag tgctagtcac tgtggagctg gagtgtctcc    24890
gccgcttttt caccgaccct gagacccctgc gcaagctcga ggagaacctg cactatactt   24950
tcagacatgg tttcgtgcgc caggcatgca agatctccaa cgtggagctc accaacctgg    25010
```

```
tctcctacat gggcattttg catgagaacc gcctggggca gagcgtgttg cataccaccc    25070
tgaaagggga ggcccgccgc gactacatcc gcgactgtgt ctacctctac ctctgccata    25130
cctggcagac tggcatgggt gtatggcagc agtgtttgga agagcagaac ctgaaagagc    25190
tggacaagct cttgcagaga tccctcaaag ccctgtggac aggttttgac gagcgcaccg    25250
tcgcctcaga cctggcagac atcatcttcc ccgagcgtct cagggttact ctgcgcaacg    25310
gcctgcctga cttcatgagc cagagcatgc ttaacaactt cgctctttc atcctggaac    25370 gctccggtat cctgcccgcc acctgctgcg cgctgccctc cgactttgtg cctctcacct    25430
accgcgagtg ccccccgccg ctatggagcc actgctacct gttccgcctg gccaactacc    25490
tctcctacca ctcggatgtg atcgaggatg tgagcggaga cggtctgctg gagtgccact    25550
gccgctgcaa tctttgcaca ccccaccgtt ccctcgcctg caaccccag ttgctgagcg    25610 agactcagat catcggcacc ttcgagttgc agggtcccag cagtgaaggc gagggtctt    25670 ctccggggca gagtctgaaa ctgactccgg ggctatggac ctccgcctac ctgcgcaagt    25730
tcgcccccga agactaccac ccctatgaga tcaggttcta tgaggaccaa tcacagccgc    25790
ccaaaaccga gctctcagcc tgcgtcatca ctcaggggc aattctcgcc caattgcaag    25850
ccatccaaaa atcccgccaa gaatttctgc tgaaaaaggg gaacggggtc tacctcgacc    25910
cccagaccgg tgaggagctc aacacaaggt tccctcagg atg tcc cag cgc cga       25964
                                            Met Ser Gln Arg Arg
                                                4005 gga  agc  aag  aag  ttg  aag  gtg  cag  ctg  ccg  ccc  cca  gag  gat  atg    26009
Gly  Ser  Lys  Lys  Leu  Lys  Val  Gln  Leu  Pro  Pro  Pro  Glu  Asp  Met
     4010                4015                     4020 gag  gaa  gac  tgg  gac  agt  cag  gca  gag  gag  gag  atg  gaa  gat           26054
Glu  Glu  Asp  Trp  Asp  Ser  Gln  Ala  Glu  Glu  Glu  Met  Glu  Asp
     4025                4030                     4035 tgg  gac  agc  cag  gca  gag  gag  gcg  gac  agc  ctg  gag  gaa  gac  agt    26099
Trp  Asp  Ser  Gln  Ala  Glu  Glu  Ala  Asp  Ser  Leu  Glu  Glu  Asp  Ser
     4040                4045                     4050 ttg  gag  gag  gaa  gac  gag  gag  gca  gag  gag  gtg  gaa  gaa  gca  gcc    26144
Leu  Glu  Glu  Glu  Asp  Glu  Glu  Ala  Glu  Glu  Val  Glu  Glu  Ala  Ala
     4055                4060                     4065 gcc  gcc  aaa  cag  ttg  tcc  tcg  gca  gcg  gag  aca  agc  aag  gcc  cca    26189
Ala  Ala  Lys  Gln  Leu  Ser  Ser  Ala  Ala  Glu  Thr  Ser  Lys  Ala  Pro
     4070                4075                     4080 gac  agc  agc  agc  agc  acg  gct  aca  atc  tcc  gct  ccg  ggt  cgg  ggg    26234
Asp  Ser  Ser  Ser  Ser  Thr  Ala  Thr  Ile  Ser  Ala  Pro  Gly  Arg  Gly
     4085                4090                     4095 gcc  cag  cag  cgt  ccc  aac  agt  aga  tgg  gac  gag  acc  ggg  cga  ttc    26279
Ala  Gln  Gln  Arg  Pro  Asn  Ser  Arg  Trp  Asp  Glu  Thr  Gly  Arg  Phe
     4100                4105                     4110 ccg  aac  ccg  acc  acc  gct  tcc  aag  acc  ggt  aag  aag  gag  cgg  cag    26324
Pro  Asn  Pro  Thr  Thr  Ala  Ser  Lys  Thr  Gly  Lys  Lys  Glu  Arg  Gln
     4115                4120                     4125 gga  tac  aag  tcc  tgg  cgg  ggg  cat  aag  aat  gcc  atc  atc  tcc  tgc    26369
Gly  Tyr  Lys  Ser  Trp  Arg  Gly  His  Lys  Asn  Ala  Ile  Ile  Ser  Cys
     4130                4135                     4140 ttg  cat  gaa  tgc  ggg  ggc  aac  ata  tcc  ttc  acc  cgg  cgc  tac  ctg    26414
Leu  His  Glu  Cys  Gly  Gly  Asn  Ile  Ser  Phe  Thr  Arg  Arg  Tyr  Leu
     4145                4150                     4155 ctc  ttc  cac  cac  ggg  gtg  aac  ttc  ccc  cgc  aat  gtc  ttg  cat  tac    26459
Leu  Phe  His  His  Gly  Val  Asn  Phe  Pro  Arg  Asn  Val  Leu  His  Tyr
     4160                4165                     4170 tac  cgt  cac  ctc  cac  agc  ccc  tac  tac  agc  cag  caa  gtc  ccg  aca    26504
```

|  |  |  |  |  |  |  |  |  |  |  |  |  |  |
|---|---|---|---|---|---|---|---|---|---|---|---|---|---|
| Tyr | Arg | His | Leu | His | Ser | Pro | Tyr | Tyr | Ser | Gln | Gln | Val | Pro | Thr |
|  | 4175 |  |  |  | 4180 |  |  |  | 4185 |  |  |  |  |  |

```
gcc tcg gca gag aaa gac agc agc agc ggg gac ctc cag cag aaa      26549
Ala Ser Ala Glu Lys Asp Ser Ser Ser Gly Asp Leu Gln Gln Lys
    4190            4195                4200 acc agc agc agc agt tagaaaatcc agtgcagcag gaggaggact gaggatcaca  26604
Thr Ser Ser Ser Ser
    4205 gcgaacgagc cagcgcagac ccgagagctg agaaacagga tctttccaac cctctatgcc 26664 atcttccagc agagtcgggg gcaagagcag gaactgaaag taaaaaaccg atctctgcgc 26724 tcgctcaccc gaagttgttt gtatcacaag agcgaagacc aacttcagcg cactctcgag 26784 gacgccgagg ctctcttcaa caagtactgc gcgctgactc ttaaagagta gcccgcgccc 26844 gcgctcgctc gaaaaaggcg ggaattacgt caccccttggc acctgtcctt tgccctcgtc 26904 atg agt aaa gaa att ccc acg cct tac atg tgg agc tat cag ccc      26949
Met Ser Lys Glu Ile Pro Thr Pro Tyr Met Trp Ser Tyr Gln Pro
    4210            4215                4220 caa atg gga ctg gca gca ggc gcc tcc cag gac tac tcc acc cgc      26994
Gln Met Gly Leu Ala Ala Gly Ala Ser Gln Asp Tyr Ser Thr Arg
    4225            4230                4235 atg aat tgg ctc agc gcc ggc ccc tcg atg atc tca cgg gtt aat      27039
Met Asn Trp Leu Ser Ala Gly Pro Ser Met Ile Ser Arg Val Asn
    4240            4245                4250 gat ata cga gct tac cga aac cag tta ctc cta gaa cag tca gct      27084
Asp Ile Arg Ala Tyr Arg Asn Gln Leu Leu Leu Glu Gln Ser Ala
    4255            4260                4265 ctc acc acc aca ccc cgc caa cac ctt aat ccc cgg aat tgg ccc      27129
Leu Thr Thr Thr Pro Arg Gln His Leu Asn Pro Arg Asn Trp Pro
    4270            4275                4280 gcc gcc ctg gtg tac cag gaa act ccc gct ccc acc acc gta cta      27174
Ala Ala Leu Val Tyr Gln Glu Thr Pro Ala Pro Thr Thr Val Leu
    4285            4290                4295 ctt cct cga gac gcc cag gcc gaa gtt cag atg act aac gca ggt      27219
Leu Pro Arg Asp Ala Gln Ala Glu Val Gln Met Thr Asn Ala Gly
    4300            4305                4310 gta cag ctg gcg ggc ggt tcc gcc ctg tgt cgt cac cgg cct cag      27264
Val Gln Leu Ala Gly Gly Ser Ala Leu Cys Arg His Arg Pro Gln
    4315            4320                4325 cag agt ata aaa cgc ctg gtg atc aga ggc cga ggt atc cag ctc      27309
Gln Ser Ile Lys Arg Leu Val Ile Arg Gly Arg Gly Ile Gln Leu
    4330            4335                4340 aac gac gag tcg gtg agc tct tcg ctt ggt ctg cga cca gac gga      27354
Asn Asp Glu Ser Val Ser Ser Leu Gly Leu Arg Pro Asp Gly
    4345            4350                4355 gtc ttc caa atc gcc ggc tgt ggg aga tct tcc ttc act cct cgt      27399
Val Phe Gln Ile Ala Gly Cys Gly Arg Ser Ser Phe Thr Pro Arg
    4360            4365                4370 cag gct gtc ctg act ttg gag agt tcg tcc tcg caa ccc cgc tcg      27444
Gln Ala Val Leu Thr Leu Glu Ser Ser Ser Ser Gln Pro Arg Ser
    4375            4380                4385 ggc ggc atc ggg act ctc cag ttt gtg gag gag ttt act ccc tct      27489
Gly Gly Ile Gly Thr Leu Gln Phe Val Glu Glu Phe Thr Pro Ser
    4390            4395                4400 gtc tac ttc aac ccc ttc tcc ggc tct cct ggc cag tac ccg gac      27534
Val Tyr Phe Asn Pro Phe Ser Gly Ser Pro Gly Gln Tyr Pro Asp
    4405            4410                4415 gag ttc ata ccg aac ttc gac gca atc agc gag tca gtg gat ggc      27579
Glu Phe Ile Pro Asn Phe Asp Ala Ile Ser Glu Ser Val Asp Gly
```

```
         4420                4425                4430
tat gat tg  atg tct ggt ggc gcg gct gag tta gct cga ctg cga cat    27626
Tyr Asp     Met Ser Gly Gly Ala Ala Glu Leu Ala Arg Leu Arg His
         4435                4440                4445 cta gac cac tgc cgc cgc ttt cgc tgt ttc gcc cgg gaa ctc acc        27671
Leu Asp His Cys Arg Arg Phe Arg Cys Phe Ala Arg Glu Leu Thr
    4450                4455                4460 gag ttc atc tac ttc gaa ctc ccc gag gag cac cct cag gga ccg        27716
Glu Phe Ile Tyr Phe Glu Leu Pro Glu Glu His Pro Gln Gly Pro
    4465                4470                4475 gcc cac gga gtg cgg att acc atc gaa ggg gga ata gac tct cgc        27761
Ala His Gly Val Arg Ile Thr Ile Glu Gly Gly Ile Asp Ser Arg
    4480                4485                4490 ctg cat cgg atc ttc tgc cag cga ccc gtg ctg atc gag cgc gac        27806
Leu His Arg Ile Phe Cys Gln Arg Pro Val Leu Ile Glu Arg Asp
    4495                4500                4505 cag gga act aca aca gtc tcc atc tac tgc atc tgt aac cac ccc        27851
Gln Gly Thr Thr Thr Val Ser Ile Tyr Cys Ile Cys Asn His Pro
    4510                4515                4520 gga ttg cat gaa agc ctt tgc tgt ctt att tgt gct gag ttt aat        27896
Gly Leu His Glu Ser Leu Cys Cys Leu Ile Cys Ala Glu Phe Asn
    4525                4530                4535 aaa aac tgagttcaga ccctcctacg gactaccgct tcttcaaccc ggactttaca     27952
Lys Asn
    4540 acaccagcca gaagacccag acccttcctc tgatccagga ctctaattct acctccccag  28012 cacctttttcc tactaacctt cccgttacta acaacctcga agctcagctg caacaccgct 28072 tctccagaag cctcctttct gccaatacta ctactcccag aaccggaggt gagctccgtg  28132 gtctccctac taacaacccc tgggtggtag cgggttttgt agcgctagga gtagttgcgg  28192 gtgggctggt gcttatactc tgctacctat acacaccttg ctgtgcttat ttagtagtat  28252 tgtgttgctg gtttaagaa atg ggg gtc gta cta gta gcg ctt gct tta       28301
                    Met Gly Val Val Leu Val Ala Leu Ala Leu
                                    4545                4550 ctt tcg ctt ttg ggt ctg ggc tct gct aat ctc att cct ccc gat        28346
Leu Ser Leu Leu Gly Leu Gly Ser Ala Asn Leu Ile Pro Pro Asp
    4555                4560                4565 cac gat cca tgt ctg gac ttt aat cca gag aac tgc aca atc act        28391
His Asp Pro Cys Leu Asp Phe Asn Pro Glu Asn Cys Thr Ile Thr
    4570                4575                4580 ttt gca cct gaa aca agt cgc ttc tgt gga gtt gtt att agg tgc        28436
Phe Ala Pro Glu Thr Ser Arg Phe Cys Gly Val Val Ile Arg Cys
    4585                4590                4595 gga ttt gaa tgc agg ccc att gag att aca cac aat aac aaa act        28481
Gly Phe Glu Cys Arg Pro Ile Glu Ile Thr His Asn Asn Lys Thr
    4600                4605                4610 tgg aac aat acc tta ttc aca ata tgg caa cca gga gac cct cag        28526
Trp Asn Asn Thr Leu Phe Thr Ile Trp Gln Pro Gly Asp Pro Gln
    4615                4620                4625 tgg tat act gtc tct gtc cgg ggt cct gac ggt tcc gtc cgc atg        28571
Trp Tyr Thr Val Ser Val Arg Gly Pro Asp Gly Ser Val Arg Met
    4630                4635                4640 gct aat aac act ttt att ttt gct gaa atg tgc gat atg gcc atg        28616
Ala Asn Asn Thr Phe Ile Phe Ala Glu Met Cys Asp Met Ala Met
    4645                4650                4655 ttc atg agc aga cag tat gac cta tgg cct ccc agc aaa gag aac        28661
Phe Met Ser Arg Gln Tyr Asp Leu Trp Pro Pro Ser Lys Glu Asn
    4660                4665                4670
```

```
att gtg gca ttc tcc att gct tat tgc ttc tgt act tgc ctt atc    28706
Ile Val Ala Phe Ser Ile Ala Tyr Cys Phe Cys Thr Cys Leu Ile
            4675            4680            4685 act gct act ttg tgt att tgc tta cac tta ctt ata gca ttt cgc    28751
Thr Ala Thr Leu Cys Ile Cys Leu His Leu Leu Ile Ala Phe Arg
            4690            4695            4700 cca aaa aac agc aac gag gaa aaa gaa aaa gtg cct taatcttttc     28797
Pro Lys Asn Ser Asn Glu Glu Lys Glu Lys Val Pro
            4705            4710 ctcacctttt ttgtttacag c atg gct tct gtt gct gtt cta atc ttt ata   28848
                        Met Ala Ser Val Ala Val Leu Ile Phe Ile
                            4715                4720 att aca tca gtt cat aca ttt ggg cta aaa ttt aat gat caa ata    28893
Ile Thr Ser Val His Thr Phe Gly Leu Lys Phe Asn Asp Gln Ile
            4725            4730            4735 gtc cat gta ggt tcc aac cat aca ctg cgt gga cca ata ggc aat    28938
Val His Val Gly Ser Asn His Thr Leu Arg Gly Pro Ile Gly Asn
            4740            4745            4750 tca gaa gta acc tgg tac tgg tat tat gca gat gat agc tgg cct    28983
Ser Glu Val Thr Trp Tyr Trp Tyr Tyr Ala Asp Asp Ser Trp Pro
            4755            4760            4765 gaa aaa ctt tgt gat gac att aat tta cat aac att ctt aca aaa    29028
Glu Lys Leu Cys Asp Asp Ile Asn Leu His Asn Ile Leu Thr Lys
            4770            4775            4780 act ctt aat agt aag act att aaa tat aac tgt act gat tat gat    29073
Thr Leu Asn Ser Lys Thr Ile Lys Tyr Asn Cys Thr Asp Tyr Asp
            4785            4790            4795 tta att cta gtt aat gtc act aca aac tat tca ggt ttt tat tac    29118
Leu Ile Leu Val Asn Val Thr Thr Asn Tyr Ser Gly Phe Tyr Tyr
            4800            4805            4810 gga act aat ttt gaa aat gtt gca tat tat aat att cta gta aag    29163
Gly Thr Asn Phe Glu Asn Val Ala Tyr Tyr Asn Ile Leu Val Lys
            4815            4820            4825 ttt aga cct aca aca act aaa acg tct agc agc agt act ata acc    29208
Phe Arg Pro Thr Thr Thr Lys Thr Ser Ser Ser Ser Thr Ile Thr
            4830            4835            4840 agc acc acg ctt cca att aga aca gca atg ttt caa ttg aac aaa    29253
Ser Thr Thr Leu Pro Ile Arg Thr Ala Met Phe Gln Leu Asn Lys
            4845            4850            4855 ata gaa aat acc acc aat agc aat tac act cta ttc aac gat caa    29298
Ile Glu Asn Thr Thr Asn Ser Asn Tyr Thr Leu Phe Asn Asp Gln
            4860            4865            4870 aat gtt caa ggg tca tta act aca att atc att cta cta att gtg    29343
Asn Val Gln Gly Ser Leu Thr Thr Ile Ile Ile Leu Leu Ile Val
            4875            4880            4885 ggg tta ata att ata ata att tgc atg ata gtc tat acc tgc cgc    29388
Gly Leu Ile Ile Ile Ile Ile Cys Met Ile Val Tyr Thr Cys Arg
            4890            4895            4900 tac aga aaa cta cac aat aaa gta gac ccc tat tagattccat         29431
Tyr Arg Lys Leu His Asn Lys Val Asp Pro Tyr
            4905            4910 acttagacat ctaactttt ttaaaacact ttattttcag cc atg att tct att    29485
                                              Met Ile Ser Ile
                                                     4915 aca acc ctt ctc tat atc act gcc att act act gta cag ggg ttc    29530
Thr Thr Leu Leu Tyr Ile Thr Ala Ile Thr Thr Val Gln Gly Phe
            4920            4925            4930 aca aac atc aaa aaa aca ata cat gtg gga tcc agt tct aca cta    29575
Thr Asn Ile Lys Lys Thr Ile His Val Gly Ser Ser Ser Thr Leu
```

```
           4935              4940              4945 gaa ggt tac caa tcc caa tca cgt gtt tct tgg tat tgg tat tac    29620
Glu Gly Tyr Gln Ser Gln Ser Arg Val Ser Trp Tyr Trp Tyr Tyr
        4950              4955              4960 cgt aat cag cca gct att aca ctt tgc aaa gga tct cag gaa acc    29665
Arg Asn Gln Pro Ala Ile Thr Leu Cys Lys Gly Ser Gln Glu Thr
        4965              4970              4975 aca ata cgc aca atc aaa tac aaa tgc aat aac aat aat tta acc    29710
Thr Ile Arg Thr Ile Lys Tyr Lys Cys Asn Asn Asn Asn Leu Thr
        4980              4985              4990 cta att gat gtt aca gct caa tat gca gga act tac tat gga aca    29755
Leu Ile Asp Val Thr Ala Gln Tyr Ala Gly Thr Tyr Tyr Gly Thr
        4995              5000              5005 aat ttt aac ata gga caa gac aca tac tat acc att aca gta att    29800
Asn Phe Asn Ile Gly Gln Asp Thr Tyr Tyr Thr Ile Thr Val Ile
        5010              5015              5020 aac tct act act cct gta aca act acc ata aaa cct aca aaa act    29845
Asn Ser Thr Thr Pro Val Thr Thr Thr Ile Lys Pro Thr Lys Thr
        5025              5030              5035 aaa agc aca aaa act cac att ttc cct agc agc aag ccc acc tca    29890
Lys Ser Thr Lys Thr His Ile Phe Pro Ser Ser Lys Pro Thr Ser
        5040              5045              5050 atc tat aca act tca ctt ttg caa cta ctt caa aag gct aac gtt    29935
Ile Tyr Thr Thr Ser Leu Leu Gln Leu Leu Gln Lys Ala Asn Val
        5055              5060              5065 aca gac aat tat act att aac ccc act ctt cct agc gaa gag ata    29980
Thr Asp Asn Tyr Thr Ile Asn Pro Thr Leu Pro Ser Glu Glu Ile
        5070              5075              5080 ccc aaa tca atg ata gga att att gct gct gtg gta gcg gga atg    30025
Pro Lys Ser Met Ile Gly Ile Ile Ala Ala Val Val Ala Gly Met
        5085              5090              5095 cta att ata att cta tgt atg att tat tat gct tgc tgc tat aga    30070
Leu Ile Ile Ile Leu Cys Met Ile Tyr Tyr Ala Cys Cys Tyr Arg
        5100              5105              5110 aaa tat gaa cat gaa caa aaa ata gac cca cta ctg agc ttt gat    30115
Lys Tyr Glu His Glu Gln Lys Ile Asp Pro Leu Leu Ser Phe Asp
        5115              5120              5125 att taatttttt tagagcacc atg aaa ggt cca gtt atc cta ttg ttt    30164
Ile                     Met Lys Gly Pro Val Ile Leu Leu Phe
                            5130              5135 att tcc act ttt tgg tgt tgt gat act ttt tca att acc acc aat    30209
Ile Ser Thr Phe Trp Cys Cys Asp Thr Phe Ser Ile Thr Thr Asn
        5140              5145              5150 gtg cag act act tta aat aac atc atg act acc tct aac aca caa    30254
Val Gln Thr Thr Leu Asn Asn Ile Met Thr Thr Ser Asn Thr Gln
        5155              5160              5165 ctt tca cct caa tct gaa gat gac ata aaa cta caa atc act atc    30299
Leu Ser Pro Gln Ser Glu Asp Asp Ile Lys Leu Gln Ile Thr Ile
        5170              5175              5180 ctt att gta att ggt tta att atc ctt gct gtt ctc ctt tac ttt    30344
Leu Ile Val Ile Gly Leu Ile Ile Leu Ala Val Leu Leu Tyr Phe
        5185              5190              5195 atc ttt tgc cgt caa ata ccc aat gta gtt aag aaa cct acc aga    30389
Ile Phe Cys Arg Gln Ile Pro Asn Val Val Lys Lys Pro Thr Arg
        5200              5205              5210 cgt ccc atc tat cga tca ata atc agc aaa ccc cac atg gct cta    30434
Arg Pro Ile Tyr Arg Ser Ile Ile Ser Lys Pro His Met Ala Leu
        5215              5220              5225 aat gaa att taatctttct cttcacagta tggtgatcaa ct atg atc cct aga  30487
Asn Glu Ile
```

-continued

```
                                                              Met Ile Pro Arg
Asn Glu Ile
    5230
aat ttc ttc ttc acc ata ctt atc tgc gct ttc aat gtc tgt gct     30532
Asn Phe Phe Phe Thr Ile Leu Ile Cys Ala Phe Asn Val Cys Ala
5235                5240                5245 aca ttc gcc aca gtc gcc aat gtg aca cca gat tgt ata ggg gca     30577
Thr Phe Ala Thr Val Ala Asn Val Thr Pro Asp Cys Ile Gly Ala
5250                5255                5260 ttt gct tcc tac gta cta ttt gcc ttc att acc tgc atc tgc gtt     30622
Phe Ala Ser Tyr Val Leu Phe Ala Phe Ile Thr Cys Ile Cys Val
5265                5270                5275 tgt agc ata gtc tgc ctg gtt atc aac ttc ttt caa cta gta gac     30667
Cys Ser Ile Val Cys Leu Val Ile Asn Phe Phe Gln Leu Val Asp
5280                5285                5290 tgg gtt ttt gta cgc att gcc tac cta caa cat cac cct gaa tac     30712
Trp Val Phe Val Arg Ile Ala Tyr Leu Gln His His Pro Glu Tyr
5295                5300                5305 cgc aac caa aat gtt gca gca att ctt agg ctc att taaaaccatg     30758
Arg Asn Gln Asn Val Ala Ala Ile Leu Arg Leu Ile
5310                5315                5320 caaactctgc tactgcttct gctagttata cacccatgtg cctcaaaccc cacaagcccc   30818
acaaaattag atctaagaaa atgtaaattt caagaaccat ggaaattcct tgattgctat   30878
catgaaacat ctgatttccc cacatactgg attacaatca ttggggttgt taatctagtc   30938
tcttgcacac tattctcttt ccttgtttac cacttatttg atttggatg gaactccctc    30998 aatgcactca cttacccaca agaaccagag gaacatatac cactacagaa catcaaacca   31058
ttagcactag tagaatatga aaatgagcca cagcctccac tactccctgc cattagctac   31118
ttcaacttaa ccggtggag atg act gac cca cac gcc gct gct gag gaa       31167
                    Met Thr Asp Pro His Ala Ala Ala Glu Glu
                                5325                5330 cta ctt gat atg gac ggc cgt gcc tcc gaa cag cgc ctc gct caa     31212
Leu Leu Asp Met Asp Gly Arg Ala Ser Glu Gln Arg Leu Ala Gln
                5335                5340                5345 cta cgc att cgc cag cag cag gaa cgt gcc gcc aaa gag ctc agg     31257
Leu Arg Ile Arg Gln Gln Gln Glu Arg Ala Ala Lys Glu Leu Arg
                5350                5355                5360 gat gct att cag att cac cag tgc aaa aaa ggc ata ttc tgc ttg     31302
Asp Ala Ile Gln Ile His Gln Cys Lys Lys Gly Ile Phe Cys Leu
                5365                5370                5375 gta aaa caa gcc aag atc tcc tac gag atc acc gct aac gac cac     31347
Val Lys Gln Ala Lys Ile Ser Tyr Glu Ile Thr Ala Asn Asp His
                5380                5385                5390 cgc ctc tca tat gag ctt ggc ccg cag cgt cag aaa ttc acc tgc     31392
Arg Leu Ser Tyr Glu Leu Gly Pro Gln Arg Gln Lys Phe Thr Cys
                5395                5400                5405 atg gtt gga atc aac ccc ata gtc atc acc cag caa gct gga gat     31437
Met Val Gly Ile Asn Pro Ile Val Ile Thr Gln Gln Ala Gly Asp
                5410                5415                5420 acc aag ggt tgc atc cat tgt tcc tgt gaa tcc acc gag tgc atc     31482
Thr Lys Gly Cys Ile His Cys Ser Cys Glu Ser Thr Glu Cys Ile
                5425                5430                5435 tac acc ctg ctg aag acc ctt tgc ggc ctt cga gac ctt ctg ccc     31527
Tyr Thr Leu Leu Lys Thr Leu Cys Gly Leu Arg Asp Leu Leu Pro
                5440                5445                5450 atg aac taatcaaccc cgcccttccc ttaccaatta caaaaagcca attaataaaa      31583
Met Asn aatcacttac ttaaaatcag aaataaggtt tttgtctgcg ttgttttcaa gcagcacctc   31643
```

```
                                                             -continued acttccctct tcccaacttt ggtactctaa gcctcggcgg gtggcatact tcctccacac    31703
tttgaaaggg atgtcaaatt ttagttcctc tttgcccaca atcttcattt ctttatcccc    31763 ag atg gcc  aaa cga gct  cga cta  agc agc tcc  ttc aat  ccg gtc tac  31810
   Met Ala  Lys Arg Ala  Arg Leu  Ser Ser Ser  Phe Asn  Pro Val Tyr
       5455              5460                  5465 ccc tat  gaa gac gaa  agc acc  aca cat ccc  ttt ata  aac cct ggc     31855
Pro Tyr  Glu Asp Glu  Ser Thr  Thr His Pro  Phe Ile  Asn Pro Gly
         5470                  5475                  5480 ttc att  tca cct gat  ggg ttt  gca caa agt  cca gat  ggg gtt ctc     31900
Phe Ile  Ser Pro Asp  Gly Phe  Ala Gln Ser  Pro Asp  Gly Val Leu
         5485                  5490                  5495 aca ctt  aaa tgt ata  tcc cca  ctt aat act  aca ggc  gga tca tta     31945
Thr Leu  Lys Cys Ile  Ser Pro  Leu Asn Thr  Thr Gly  Gly Ser Leu
         5500                  5505                  5510 caa ctt  aaa gtg gga  gga ggg  cta aaa gtg  gac tct  aca gac gga     31990
Gln Leu  Lys Val Gly  Gly Gly  Leu Lys Val  Asp Ser  Thr Asp Gly
         5515                  5520                  5525 tct ctg  gaa gaa aac  ata aat  aca aca gct  cca ctt  act aaa act     32035
Ser Leu  Glu Glu Asn  Ile Asn  Thr Thr Ala  Pro Leu  Thr Lys Thr
         5530                  5535                  5540 aac cat  tct atc agt  atg ttg  gta gga aat  ggc tta  cat act gaa     32080
Asn His  Ser Ile Ser  Met Leu  Val Gly Asn  Gly Leu  His Thr Glu
         5545                  5550                  5555 gaa aac  aaa cta tgt  gca aaa  ctg gga caa  ggt ctt  gaa ttt aac     32125
Glu Asn  Lys Leu Cys  Ala Lys  Leu Gly Gln  Gly Leu  Glu Phe Asn
         5560                  5565                  5570 tca ggt  agt att tgt  ata gat  cac aat aca  aac aca  cta tgg aca     32170
Ser Gly  Ser Ile Cys  Ile Asp  His Asn Thr  Asn Thr  Leu Trp Thr
         5575                  5580                  5585 gga gtt  ccc act gag  gcc aat  tgt cat atg  cta gag  tac aca gat     32215
Gly Val  Pro Thr Glu  Ala Asn  Cys His Met  Leu Glu  Tyr Thr Asp
         5590                  5595                  5600 gac aaa  gac tgc aaa  ctc aca  cta gtt ctt  gtt aaa  aat gga gct     32260
Asp Lys  Asp Cys Lys  Leu Thr  Leu Val Leu  Val Lys  Asn Gly Ala
         5605                  5610                  5615 atg gta  aac gga tat  gta tct  ctt atg ggt  gcc act  gac gaa ttt     32305
Met Val  Asn Gly Tyr  Val Ser  Leu Met Gly  Ala Thr  Asp Glu Phe
         5620                  5625                  5630 aat gct  ata acc aca  gtt aaa  att gct caa  ctt act  gct gat ata     32350
Asn Ala  Ile Thr Thr  Val Lys  Ile Ala Gln  Leu Thr  Ala Asp Ile
         5635                  5640                  5645 tat ttt  gat aca aat  gga aag  gtc ctt act  gat ata  tca gcc ctt     32395
Tyr Phe  Asp Thr Asn  Gly Lys  Val Leu Thr  Asp Ile  Ser Ala Leu
         5650                  5655                  5660 aaa aca  gaa tta aaa  tat aag  tct gga caa  aat atg  gca aca ggt     32440
Lys Thr  Glu Leu Lys  Tyr Lys  Ser Gly Gln  Asn Met  Ala Thr Gly
         5665                  5670                  5675 gaa cca  tca aac agc  aag agc  ttc atg cca  agc cta  act gca tac     32485
Glu Pro  Ser Asn Ser  Lys Ser  Phe Met Pro  Ser Leu  Thr Ala Tyr
         5680                  5685                  5690 cca ctt  cga aat ccc  act att  aaa cca gtt  aga ggt  aat gag gac     32530
Pro Leu  Arg Asn Pro  Thr Ile  Lys Pro Val  Arg Gly  Asn Glu Asp
         5695                  5700                  5705 tac ata  tat ggc acc  act tat  ttt aga tcc  agc gat  gat gct ctc     32575
Tyr Ile  Tyr Gly Thr  Thr Tyr  Phe Arg Ser  Ser Asp  Asp Ala Leu
         5710                  5715                  5720 tta cca  cta gat aca  tat gtt  atg ctt aat  tac aaa  ctg tcc aat     32620
Leu Pro  Leu Asp Thr  Tyr Val  Met Leu Asn  Tyr Lys  Leu Ser Asn
```

```
                  5725                5730                5735
gcc  caa  tgt  gca  tat  gca  atg  cac  ttt  atg  tgg  tca  tgg  aat  act     32665
Ala  Gln  Cys  Ala  Tyr  Ala  Met  His  Phe  Met  Trp  Ser  Trp  Asn  Thr
     5740                5745                          5750 tcc  att  aaa  cca  gaa  gaa  aca  gcc  act  acc  ttt  att  gct  tcc  ccc     32710
Ser  Ile  Lys  Pro  Glu  Glu  Thr  Ala  Thr  Thr  Phe  Ile  Ala  Ser  Pro
     5755                     5760                          5765 ttt  acc  ttt  tca  tac  att  aga  gaa  gat  gac  tgacaacaaa aaaataaagt        32760
Phe  Thr  Phe  Ser  Tyr  Ile  Arg  Glu  Asp  Asp
     5770                5775 tcaactttt   tattaaacaa  tcagtttaca  ggattcgagt  agttattttg  cctccccctt       32820
cccatttcat  agaatacacc  aatctctccc  cacgcacagc  tttaaacatt  tggattccat       32880
ttgaaatagt  catggattta  gattccacat  tccacacagt  ttcagagcta  gataatcttg       32940
gatcagtgat  agatataaat  ccatcggggc  agtccttcaa  ggtgatttca  cagtccagtt       33000
gctgtggctg  cggctccgga  gtctggatca  gagtcatctg  gaacaagaac  gatgggagtc       33060
ataatccgag  aacgggatcg  gcggttgtg   tctcatcaaa  ccccgaagca  gtcgctgtct       33120
gcgccgctcc  gtgcgactgc  tgctgatggg  atcgggtcc   acagtctctc  gaagcatgat       33180
tctaatagcc  ctcaacatta  acatcctggt  gcgatgcgca  cagcagcgca  tcctgatctc       33240
acttagctca  cagcaatagg  tacaacacaa  caccacaata  ttgtttaaca  ggccataatt       33300
aaaggcactc  cagccaaaac  tcatttcagg  aataatttgc  ccagcgtgac  catcgtacca       33360
aatcctgatg  taaatcagat  ggcgcccct   ccagaacaca  ctgcccacat  acatgatctc       33420
cttaggcata  tgcatattca  caatctctcg  gtaccatgga  cagcgctggt  taatcatgca       33480
gccccgaata  accttccgga  accaaatggc  cagcaatgcg  ccccagcaa   tacattgaag       33540 agaaccctgt  cgattacagt  gacaatggag  aacccacttc  tctcgcccat  ggatcacttg       33600
ggaataaaat  atatctattg  tggcacaaca  cagacataaa  tgcatacatc  ttctcatcac       33660
ccttaactct  tcaggggtta  aaaacatatc  ccagggaata  ggaagctctt  gcaaaacagt       33720
aaaggtggca  gaacaaggca  gaccgcgaac  ataacttaca  ctgtgcatgg  tcaaggtatt       33780
gcaatctggt  aacagcggat  gctcttcagt  catagaagct  ctggtttcac  tttcctcaca       33840
gcgtggtaaa  ggggccctca  gttgaggttc  cctggtgtaa  ggatggtgtc  tggcgcacga       33900
tgtcgagcgt  gcacgcgacc  tcgttgtaat  ggagctgctt  cctgacattc  tcgtatttg        33960 catggcagaa  cctagccttg  gcacaacaca  cttctcttcg  ccttctatcc  cgtcgcctag       34020
cacgttcagt  atggtaattg  aagtacagcc  attcccgtag  attggtcaaa  agctcctcgg       34080
cttcagttgt  cataaaaact  ccatcatatc  ttactgctct  gataaaatca  tttactgtag       34140
aatgggcaat  gcccagccag  gcaatgcaat  tagcttgtgt  ttcaaccaaa  ggaggggag        34200 gaagacatgg  aagaaccata  attaattttt  attccagacg  atcccgcagt  atttctacat       34260
ggagatcacg  aagatggcac  ctctcgcccc  cactgtgttg  atgaaaaatg  acagctaggt       34320
caaacatgat  gcgattttca  aggtgctcaa  cggtggcttc  aagcaaagcc  tccaaacgta       34380
catccaaaaa  caaagaaca   gcaaaagcag  gagcattttc  taattcctca  atcatcatat       34440
tacattcctg  taccattccc  aaataatttt  catctttcca  tccttgaatt  attcgtgtta       34500
tttcatctgg  taaatccaat  ccacacatga  gaaatagctc  ccggagggcg  ccctccaccg       34560
gcaatcttaa  gcatacccttc  atagtgacaa  aatatcgtgc  tcctctgtca  cctgcagcaa       34620
attgagaatg  gcaatatcaa  acggaatgcc  actggctcta  agttcttctc  taagttccag       34680
ttgtaaaaac  tcttgcatat  catcgccaaa  ctgcttagcc  ataggtcctc  caggaataag       34740
```

-continued

```
agcggggac  gctacagtgc  agaacaagcg  catgccgccc  caattgcctc  cagcaaaagt    34800
gaggttgcaa  tatgcatact  gagaacctcc  agtgatatca  tccagtgtac  tggaaagata    34860
atcaggcaga  gcttctcgta  tgcaattaat  aatagaaaag  tctgccagat  gcacatttaa    34920
agcctgtggg  atgcagatgc  aataagttat  cgcgctgcgc  tccaacattg  ttagtatggt    34980
tagtctgtaa  aaacaaaaaa  caaaaaaaaa  aaaattacat  cacgctagac  tggcgaacgg    35040
gtggaaaaat  cactctctcc  aacaccaggc  aggctacagg  gtctccagcg  cgaccctcgt    35100
aaaacctgtc  agtatgatta  aaaagcatca  ccgaaagggg  ttgttgatgg  ccagcatata    35160
ttatttgcga  tgaagcatac  aatccagaag  tgttagtatc  agttaaagaa  aaaaatcggc    35220
caagatagca  tctcggaacg  attatgctca  atctcaaatg  cagcaaagcg  acacctcgcg    35280
gatgcaaagt  aaaatccaca  ggagcataaa  aaaagtaatt  attcccctct  tgcacaggca    35340
gcctagctcc  cggcccctcc  aaaatcacat  ataaagcttc  agcagccata  gcttaccgcg    35400
caaatcaggc  acagcagtca  gatagagaaa  aagctgtgaa  ctgactgccc  agcctgtgcg    35460
caatatatag  agaacccta   cactgacgta  attggacaaa  gtctaaaaaa  tcccgccaaa    35520
aaaccagcac  acgcccagaa  ctgtgtcacc  cgctaaaaaa  taattttcac  ttcctcgttc    35580
cgtgaatgac  gtcagttccc  cttcccacg   agccgtcact  tccggtcatc  ttgcaacgtc    35640
acctccccgc  gccggcccgc  cccttttgac  cgttgaaccc  gctggccaat  ccccttccgc    35700
cctccatttt  caaaagctca  tttgcatgtt  ggcaccgttc  catttataag  gtatattatt    35760
gatgatg                                                                   35767
```

<210> SEQ ID NO 35
<211> LENGTH: 495
<212> TYPE: PRT
<213> ORGANISM: Unknown
<220> FEATURE:
<223> OTHER INFORMATION: Synthetic Construct

<400> SEQUENCE: 35

Met Asp Pro Thr Asn Pro Leu Gln Gln Gly Ile Arg Leu Gly Phe His
1               5                   10                  15

Ser Ser Ser Phe Val Glu Asn Met Glu Gly Pro Gln Ala Glu Asp Asn
                20                  25                  30

Leu Arg Leu Leu Ala Ser Ala Ala Ser Gly Arg Ser Gly Asn Pro Glu
            35                  40                  45

Thr Pro Thr Ser His Ala Ser Gly Phe Gly Gly Gly Ala Ala Gly Gly
        50                  55                  60

Gln Pro Glu Ser Arg Pro Gly Pro Ser Gly Gly Gly Gly Gly Gly Val
65                  70                  75                  80

Ala Asp Leu Phe Pro Glu Leu Arg Arg Val Leu Thr Arg Ser Thr Ser
                85                  90                  95

Ser Gly Gln Asp Arg Gly Ile Lys Arg Glu Arg Asn Ala Ser Gly His
            100                 105                 110

Asn Ser Arg Thr Glu Leu Ala Leu Ser Leu Met Ser Arg Ser Arg Pro
        115                 120                 125

Glu Thr Ile Trp Trp His Glu Val Gln Ser Gly Arg Asp Glu Val
    130                 135                 140

Ser Ile Leu Gln Glu Lys Tyr Ser Leu Glu Gln Ile Lys Thr Cys Trp
145                 150                 155                 160

Leu Glu Pro Glu Asp Asp Trp Glu Val Ala Ile Arg Asn Tyr Ala Lys
                165                 170                 175

```
Ile Ser Leu Arg Pro Asp Lys Gln Tyr Arg Ile Thr Lys Lys Ile Asn
            180                 185                 190

Ile Arg Asn Ala Cys Tyr Ile Ser Gly Asn Gly Ala Glu Val Ile Ile
        195                 200                 205

Asp Thr Pro Asp Lys Thr Ala Phe Arg Cys Cys Met Met Gly Met Trp
210                 215                 220

Pro Gly Val Ala Gly Met Glu Ala Val Thr Leu Met Asn Ile Arg Phe
225                 230                 235                 240

Arg Gly Asp Gly Tyr Asn Gly Ile Val Phe Met Ala Asn Thr Lys Leu
                245                 250                 255

Ile Leu His Gly Cys Ser Phe Phe Gly Phe Asn Asn Thr Cys Val Glu
            260                 265                 270

Ala Trp Gly Gln Val Ser Val Arg Gly Cys Ser Phe Tyr Ala Cys Trp
        275                 280                 285

Ile Ala Leu Ser Gly Arg Thr Lys Ser Gln Leu Ser Val Lys Lys Cys
290                 295                 300

Met Phe Glu Arg Cys Asn Leu Gly Ile Leu Asn Gly Glu Ala Arg
305                 310                 315                 320

Val Arg His Cys Ala Ala Thr Glu Thr Gly Cys Phe Ile Leu Ile Lys
                325                 330                 335

Gly Asn Ala Ser Val Lys His Asn Met Ile Cys Gly Pro Ser Asp Glu
            340                 345                 350

Arg Pro Tyr Gln Met Leu Thr Cys Ala Gly Gly His Cys Asn Met Leu
        355                 360                 365

Ala Thr Val His Ile Val Ser His Ala Arg Lys Lys Trp Pro Val Phe
370                 375                 380

Glu His Asn Val Met Thr Lys Cys Thr Met His Ala Gly Gly Arg Arg
385                 390                 395                 400

Gly Met Phe Met Pro Tyr Gln Cys Asn Met Asn His Val Lys Val Met
                405                 410                 415

Leu Glu Pro Asp Ala Phe Ser Arg Met Ser Leu Thr Gly Ile Phe Asp
            420                 425                 430

Met Asn Val Gln Leu Trp Lys Ile Leu Arg Tyr Asp Glu Thr Lys Ser
        435                 440                 445

Arg Val Arg Ala Cys Glu Cys Gly Lys His Ala Arg Phe Gln Pro
450                 455                 460

Val Cys Val Asp Val Thr Glu Asp Leu Arg Pro Asp His Leu Val Leu
465                 470                 475                 480

Ala Cys Thr Gly Ala Glu Phe Gly Ser Ser Gly Glu Glu Thr Asp
                485                 490                 495

<210> SEQ ID NO 36
<211> LENGTH: 138
<212> TYPE: PRT
<213> ORGANISM: Unknown
<220> FEATURE:
<223> OTHER INFORMATION: Synthetic Construct

<400> SEQUENCE: 36

Met Ser Gly Ser Ala Ser Phe Glu Gly Gly Val Phe Ser Pro Tyr Leu
1               5                   10                  15

Thr Gly Arg Leu Pro Pro Trp Ala Gly Val Arg Gln Asn Val Met Gly
            20                  25                  30

Ser Thr Val Asp Gly Arg Pro Val Gln Pro Ala Asn Ser Ser Thr Leu
        35                  40                  45
```

```
Thr Tyr Ala Thr Leu Ser Ser Pro Leu Asp Ala Ala Ala Ala
         50              55              60

Ala Ala Ser Ala Ala Ala Asn Thr Val Leu Gly Met Gly Tyr Tyr Gly
 65              70              75              80

Ser Ile Val Ala Asn Ser Ser Ser Asn Asn Pro Ser Thr Leu Ala
                 85              90              95

Glu Asp Lys Leu Leu Val Leu Leu Ala Gln Leu Glu Ala Leu Thr Gln
                100             105             110

Arg Leu Gly Glu Leu Ser Gln Gln Val Ala Gln Leu Arg Glu Gln Thr
            115             120             125

Glu Ser Ala Val Ala Thr Ala Lys Ser Lys
130             135
```

<210> SEQ ID NO 37
<211> LENGTH: 389
<212> TYPE: PRT
<213> ORGANISM: Unknown
<220> FEATURE:
<223> OTHER INFORMATION: Synthetic Construct

<400> SEQUENCE: 37

```
Met His Pro Val Leu Arg Gln Met Arg Pro Gln Gln Gln Ala Pro Ser
 1               5                  10                  15

Gln Gln Gln Gln Gln Pro Gln Lys Ala Leu Pro Ala Pro Ala Pro Ala
                20                  25                  30

Thr Thr Ala Val Ala Ala Val Cys Gly Ala Gly Gln Pro Ala Tyr Asp
            35                  40                  45

Leu Asp Leu Glu Glu Gly Gly Leu Ala Arg Leu Gly Ala Pro Ser
 50                  55                  60

Pro Glu Arg His Pro Arg Val Gln Leu Lys Lys Asp Ser Arg Glu Ala
 65                  70                  75                  80

Tyr Val Pro Gln Gln Asn Leu Phe Arg Asp Arg Ser Gly Glu Glu Pro
                 85                  90                  95

Glu Glu Met Arg Ala Ser Arg Phe Asn Ala Gly Arg Glu Leu Arg His
                100                 105                 110

Gly Leu Asp Arg Arg Val Leu Arg Asp Glu Asp Phe Glu Val Asp
            115                 120                 125

Glu Val Thr Gly Ile Ser Pro Ala Arg Ala His Val Ala Ala Ala Asn
130                 135                 140

Leu Val Ser Ala Tyr Glu Gln Thr Val Lys Glu Glu Arg Asn Phe Gln
145                 150                 155                 160

Lys Ser Phe Asn Asn His Val Arg Thr Leu Ile Ala Arg Glu Glu Val
                165                 170                 175

Thr Leu Gly Leu Met His Leu Trp Asp Leu Met Glu Ala Ile Thr Gln
                180                 185                 190

Asn Pro Thr Ser Lys Pro Leu Thr Ala Gln Leu Phe Leu Val Val Gln
            195                 200                 205

His Ser Arg Asp Asn Glu Ala Phe Arg Glu Ala Leu Leu Asn Ile Thr
210                 215                 220

Glu Pro Glu Gly Arg Trp Leu Tyr Asp Leu Ile Asn Ile Leu Gln Ser
225                 230                 235                 240

Ile Ile Val Gln Glu Arg Ser Leu Gly Leu Ala Glu Lys Val Ala Ala
                245                 250                 255

Ile Asn Tyr Ser Val Leu Ser Leu Gly Lys Tyr Tyr Ala Arg Lys Ile
                260                 265                 270
```

```
Tyr Lys Thr Pro Tyr Val Pro Ile Asp Lys Glu Val Lys Ile Asp Gly
            275                 280                 285

Phe Tyr Met Arg Met Thr Leu Lys Val Leu Thr Leu Ser Asp Asp Leu
290                 295                 300

Gly Val Tyr Arg Asn Asp Arg Met His Arg Ala Val Ser Ala Ser Arg
305                 310                 315                 320

Arg Arg Glu Leu Ser Asp Arg Glu Leu Met His Ser Leu Gln Arg Ala
                325                 330                 335

Leu Thr Gly Ala Gly Thr Asp Gly Glu Asn Tyr Phe Asp Met Gly Ala
            340                 345                 350

Asp Leu Gln Trp Gln Pro Ser Arg Arg Ala Leu Asp Ala Ala Gly Cys
                355                 360                 365

Glu Leu Pro Tyr Val Glu Val Asp Glu Gly Glu Glu Glu Gly
370                 375                 380

Glu Tyr Leu Glu Asp
385

<210> SEQ ID NO 38
<211> LENGTH: 587
<212> TYPE: PRT
<213> ORGANISM: Unknown
<220> FEATURE:
<223> OTHER INFORMATION: Synthetic Construct

<400> SEQUENCE: 38

Met Glu Gln Gln Ala Pro Asp Pro Ala Met Arg Ala Ala Leu Gln Ser
1               5                   10                  15

Gln Pro Ser Gly Ile Asn Ser Ser Asp Asp Trp Thr Gln Ala Met Gln
            20                  25                  30

Arg Ile Met Ala Leu Thr Thr Arg Asn Pro Glu Ala Phe Arg Gln Gln
        35                  40                  45

Pro Gln Ala Asn Arg Leu Ser Ala Ile Leu Glu Ala Val Val Pro Ser
    50                  55                  60

Arg Ser Asn Pro Thr His Glu Lys Val Leu Ala Ile Val Asn Ala Leu
65                  70                  75                  80

Val Glu Asn Lys Ala Ile Arg Pro Asp Glu Ala Gly Leu Val Tyr Asn
                85                  90                  95

Ala Leu Leu Glu Arg Val Ala Arg Tyr Asn Ser Ser Asn Val Gln Thr
            100                 105                 110

Asn Leu Asp Arg Met Val Thr Asp Val Arg Glu Ala Val Ser Gln Arg
        115                 120                 125

Glu Arg Phe Gln Arg Asp Ala Asn Leu Gly Ser Leu Val Ala Leu Asn
    130                 135                 140

Ala Phe Leu Ser Thr Gln Pro Ala Asn Val Pro Arg Gly Gln Gln Asp
145                 150                 155                 160

Tyr Thr Asn Phe Leu Ser Ala Leu Arg Leu Met Val Thr Glu Val Pro
                165                 170                 175

Gln Ser Glu Val Tyr Gln Ser Gly Pro Asp Tyr Phe Gln Thr Ser
            180                 185                 190

Arg Gln Gly Leu Gln Thr Val Asn Leu Ser Gln Ala Phe Lys Asn Leu
        195                 200                 205

Arg Gly Leu Trp Gly Val His Ala Pro Val Gly Asp Arg Ala Thr Val
    210                 215                 220

Ser Ser Leu Leu Thr Pro Asn Ser Arg Leu Leu Leu Leu Val Ser
225                 230                 235                 240
```

```
Pro Phe Thr Asp Ser Gly Ser Ile Asp Arg Asn Ser Tyr Leu Gly Tyr
            245                 250                 255

Leu Leu Asn Leu Tyr Arg Glu Ala Ile Gly Gln Ser Gln Val Asp Glu
            260                 265                 270

Gln Thr Tyr Gln Glu Ile Thr Gln Val Ser Arg Ala Leu Gly Gln Glu
            275                 280                 285

Asp Thr Gly Ser Leu Glu Ala Thr Leu Asn Phe Leu Leu Thr Asn Arg
        290                 295                 300

Ser Gln Lys Ile Pro Pro Gln Tyr Ala Leu Thr Ala Glu Glu Glu Arg
305                 310                 315                 320

Ile Leu Arg Tyr Val Gln Gln Ser Val Gly Leu Phe Leu Met Gln Glu
                325                 330                 335

Gly Ala Thr Pro Ser Ala Ala Leu Asp Met Thr Ala Arg Asn Met Glu
                340                 345                 350

Pro Ser Met Tyr Ala Met Asn Arg Pro Phe Ile Asn Lys Leu Leu Asp
            355                 360                 365

Tyr Leu His Arg Ala Ala Ala Met Asn Ser Asp Tyr Phe Thr Asn Ala
        370                 375                 380

Ile Leu Asn Pro His Trp Leu Pro Pro Gly Phe Tyr Thr Gly Glu
385                 390                 395                 400

Tyr Asp Met Pro Asp Pro Asn Asp Gly Phe Leu Trp Asp Val Asp
                405                 410                 415

Ser Ser Ile Phe Ser Pro Pro Gly Tyr Asn Thr Trp Lys Lys Glu
            420                 425                 430

Gly Gly Asp Arg Arg His Ser Val Ser Leu Ser Gly Ser Arg Gly
            435                 440                 445

Ala Ala Ala Ala Val Pro Glu Ala Ala Ser Pro Phe Pro Ser Leu Pro
450                 455                 460

Phe Ser Leu Asn Ser Val Arg Ser Ser Glu Leu Gly Arg Ile Thr Arg
465                 470                 475                 480

Pro Arg Leu Met Gly Glu Asp Glu Tyr Leu Asn Asp Ser Leu Leu Arg
                485                 490                 495

Pro Glu Arg Glu Lys Asn Phe Pro Asn Asn Gly Ile Glu Ser Leu Val
            500                 505                 510

Asp Lys Met Ser Arg Trp Lys Thr Tyr Ala Gln Asp His Lys Asp Glu
            515                 520                 525

Pro Arg Ile Leu Gly Ala Ala Ser Gly Thr Thr Arg Arg Arg Gln Arg
530                 535                 540

His Asp Arg Gln Arg Gly Leu Val Trp Asp Glu Asp Ser Ala Asp
545                 550                 555                 560

Asp Ser Ser Val Leu Asp Leu Gly Gly Arg Gly Gly Asn Pro Phe
            565                 570                 575

Ala His Leu Arg Pro His Phe Gly Arg Met Leu
            580                 585
```

<210> SEQ ID NO 39
<211> LENGTH: 584
<212> TYPE: PRT
<213> ORGANISM: Unknown
<220> FEATURE:
<223> OTHER INFORMATION: Synthetic Construct

<400> SEQUENCE: 39

```
Met Met Arg Arg Ala Val Leu Gly Gly Ala Val Val Tyr Pro Glu Gly
1               5                   10                  15
```

```
Pro Pro Pro Ser Tyr Glu Ser Val Met Gln Gln Ala Ala Ala Val
            20              25              30

Met Gln Pro Ser Leu Glu Ala Pro Phe Val Pro Arg Tyr Leu Ala
        35              40              45

Pro Thr Glu Gly Arg Asn Ser Ile Arg Tyr Ser Glu Leu Ala Pro Gln
    50              55              60

Tyr Asp Thr Thr Arg Leu Tyr Leu Val Asp Asn Lys Ser Ala Asp Ile
65              70              75              80

Ala Ser Leu Asn Tyr Gln Asn Asp His Ser Asn Phe Leu Thr Thr Val
                85              90              95

Val Gln Asn Asn Asp Phe Thr Pro Thr Glu Ala Ser Thr Gln Thr Ile
            100             105             110

Asn Phe Asp Glu Arg Ser Arg Trp Gly Gly Gln Leu Lys Thr Ile Met
        115             120             125

His Thr Asn Met Pro Asn Val Asn Glu Tyr Met Phe Ser Asn Lys Phe
    130             135             140

Lys Ala Arg Val Met Val Ser Arg Lys Lys Pro Glu Gly Tyr Thr Gly
145             150             155             160

Asp Lys Asn Asp Thr Ser Gln Asp Ile Leu Glu Tyr Glu Trp Phe Glu
                165             170             175

Phe Thr Leu Pro Glu Gly Asn Phe Ser Ala Thr Met Thr Ile Asp Leu
            180             185             190

Met Asn Asn Ala Ile Ile Asp Asn Tyr Leu Ala Val Gly Arg Gln Asn
        195             200             205

Gly Val Leu Glu Ser Asp Ile Gly Val Lys Phe Asp Thr Arg Asn Phe
    210             215             220

Arg Leu Gly Trp Asp Pro Ile Thr Lys Leu Val Met Pro Gly Val Tyr
225             230             235             240

Thr Tyr Glu Ala Phe His Pro Asp Ile Val Leu Leu Pro Gly Cys Gly
                245             250             255

Val Asp Phe Thr Glu Ser Arg Leu Ser Asn Leu Leu Gly Ile Arg Lys
            260             265             270

Arg His Pro Phe Gln Glu Gly Phe Lys Ile Met Tyr Glu Asp Leu Glu
        275             280             285

Gly Gly Asn Ile Pro Ala Leu Leu Asp Val Asp Ala Tyr Glu Lys Ser
    290             295             300

Lys Lys Glu Asn Thr Asp Thr Thr Thr Thr Thr Val Thr Thr Thr
305             310             315             320

Glu Val Ala Thr Val Ala Arg His Val Ala Glu Val Thr Thr Glu Ala
                325             330             335

Ala Thr Val Val Ala Val Asp Pro Ile Val Glu Glu Asn Asn Asn Thr
            340             345             350

Val Arg Gly Asp Asn Ile His Thr Ala Asn Glu Met Lys Ala Ala Ala
        355             360             365

Asp Asp Thr Thr Val Val Val Pro Gly Ala Val Val Thr Glu Thr
    370             375             380

Glu Thr Lys Thr Lys Thr Leu Thr Ile Gln Pro Leu Glu Lys Asp Thr
385             390             395             400

Lys Glu Arg Ser Tyr Asn Val Ile Ser Gly Thr Asn Asp Thr Ala Tyr
                405             410             415

Arg Ser Trp Tyr Leu Ala Tyr Asn Tyr Gly Asp Pro Glu Lys Gly Val
            420             425             430
```

Arg Ser Trp Thr Leu Leu Thr Thr Ser Asp Val Thr Cys Gly Ala Glu
            435                 440                 445

Gln Val Tyr Trp Ser Leu Pro Asp Met Met Gln Asp Pro Val Thr Phe
    450                 455                 460

Arg Ser Thr Arg Gln Val Ser Asn Tyr Pro Val Val Gly Ala Glu Leu
465                 470                 475                 480

Met Pro Val Phe Ser Lys Ser Phe Tyr Asn Glu Gln Ala Val Tyr Ser
                485                 490                 495

Gln Gln Leu Arg Gln Thr Thr Ser Leu Thr His Ile Phe Asp Arg Phe
                500                 505                 510

Pro Glu Asn Gln Ile Leu Ile Arg Pro Pro Ala Pro Thr Ile Thr Thr
            515                 520                 525

Val Ser Glu Asn Val Pro Ala Leu Thr Asp His Gly Thr Leu Pro Leu
    530                 535                 540

Arg Ser Ser Ile Arg Gly Val Gln Arg Val Thr Val Thr Asp Ala Arg
545                 550                 555                 560

Arg Arg Thr Cys Pro Tyr Val Tyr Lys Ala Leu Gly Ile Val Ala Pro
                565                 570                 575

Arg Val Leu Ser Ser Arg Thr Phe
                580

<210> SEQ ID NO 40
<211> LENGTH: 192
<212> TYPE: PRT
<213> ORGANISM: Unknown
<220> FEATURE:
<223> OTHER INFORMATION: Synthetic Construct

<400> SEQUENCE: 40

Met Ser Ile Leu Ile Ser Pro Ser Asn Asn Thr Gly Trp Gly Leu Arg
1               5                   10                  15

Thr Pro Thr Arg Met Tyr Gly Gly Ala Arg Lys Arg Ser Thr Gln His
            20                  25                  30

Pro Val Arg Val Arg Gly His Phe Arg Ala Pro Trp Gly Ala Leu Lys
        35                  40                  45

Gly Arg Thr Arg Thr Arg Thr Thr Val Asp Asp Val Ile Asp Gln Val
    50                  55                  60

Val Ala Asp Ala Arg Asn Tyr Thr Pro Ala Ala Pro Ala Ser Thr Val
65                  70                  75                  80

Asp Ala Val Ile Asp Ser Val Val Ala Asp Ala Arg Glu Tyr Ala Arg
                85                  90                  95

Arg Lys Ser Arg Arg Arg Ile Ala Arg Arg His Arg Ala Thr Pro
                100                 105                 110

Ala Met Arg Ala Ala Arg Ala Leu Leu Arg Arg Ala Lys Arg Val Gly
            115                 120                 125

Arg Arg Ala Met Leu Arg Ala Ala Arg Ala Ala Ser Gly Ala Ser
130                 135                 140

Ala Gly Arg Ser Arg Arg Ala Ala Thr Ala Ala Ala Ala Ile
145                 150                 155                 160

Ala Asn Met Ala Gln Pro Arg Arg Gly Asn Val Tyr Trp Val Arg Asp
                165                 170                 175

Ala Thr Thr Gly Gln Arg Val Pro Val Arg Thr Arg Pro Arg Thr
            180                 185                 190

<210> SEQ ID NO 41
<211> LENGTH: 350

<212> TYPE: PRT
<213> ORGANISM: Unknown
<220> FEATURE:
<223> OTHER INFORMATION: Synthetic Construct

<400> SEQUENCE: 41

```
Met Ser Lys Arg Lys Tyr Lys Glu Glu Met Leu Gln Val Ile Ala Pro
1               5                   10                  15

Glu Ile Tyr Gly Pro Pro Val Lys Asp Glu Lys Lys Pro Arg Lys Ile
            20                  25                  30

Lys Arg Val Lys Lys Asp Lys Lys Glu Glu Asp Gly Asp Asp Gly Leu
        35                  40                  45

Val Glu Phe Val Arg Glu Phe Ala Pro Arg Arg Val Gln Trp Arg
    50                  55                  60

Gly Arg Arg Val Arg Pro Val Leu Arg Pro Gly Thr Thr Val Val Phe
65                  70                  75                  80

Thr Pro Gly Glu Arg Ser Ser Thr Thr Phe Lys Arg Ser Tyr Asp Glu
                85                  90                  95

Val Tyr Gly Asp Asp Asp Ile Leu Glu Gln Ala Ala Asp Arg Leu Gly
                100                 105                 110

Glu Phe Ala Tyr Gly Lys Arg Ser Arg Ser Pro Lys Asp Glu Ala
    115                 120                 125

Val Ser Ile Pro Leu Asp His Gly Asn Pro Thr Pro Ser Leu Lys Pro
130                 135                 140

Val Thr Leu Gln Gln Val Leu Pro Val Pro Pro Arg Arg Gly Val Lys
145                 150                 155                 160

Arg Glu Gly Glu Asp Leu Tyr Pro Thr Met Gln Leu Met Val Pro Lys
                165                 170                 175

Arg Gln Lys Leu Glu Asp Val Leu Glu Lys Met Lys Val Asp Pro Asp
            180                 185                 190

Ile Gln Pro Glu Val Lys Val Arg Pro Ile Lys Gln Val Ala Pro Gly
        195                 200                 205

Leu Gly Val Gln Thr Val Asp Ile Lys Ile Pro Thr Glu Ser Met Glu
210                 215                 220

Val Gln Thr Glu Pro Ala Lys Pro Thr Ala Ala Ser Ile Glu Val Gln
225                 230                 235                 240

Thr Asp Pro Trp Met Pro Ala Pro Ile Ala Thr Ala Ala Ser Thr Val
                245                 250                 255

Arg Arg Pro Arg Arg Lys Tyr Gly Pro Ala Ser Leu Leu Met Pro Asn
            260                 265                 270

Tyr Ala Leu His Pro Ser Ile Ile Pro Thr Pro Gly Tyr Arg Gly Thr
        275                 280                 285

Arg Tyr Tyr Arg Ser Arg Ser Thr Thr Ser Arg Arg Lys Thr Pro
    290                 295                 300

Ala Ser Arg Ser Arg Arg Arg Arg Thr Ala Ser Lys Leu Thr
305                 310                 315                 320

Pro Ala Ala Leu Val Arg Arg Val Tyr Arg Asp Gly Arg Ala Glu Pro
                325                 330                 335

Leu Met Leu Pro Arg Ala Arg Tyr His Pro Ser Ile Thr Thr
            340                 345                 350
```

<210> SEQ ID NO 42
<211> LENGTH: 75
<212> TYPE: PRT
<213> ORGANISM: Unknown
<220> FEATURE:

<223> OTHER INFORMATION: Synthetic Construct

<400> SEQUENCE: 42

```
Met Ala Leu Thr Cys Arg Leu Arg Val Pro Ile Thr Gly Tyr Arg Gly
1               5                   10                  15

Arg Asn Ser Arg Arg Arg Met Leu Gly Ser Gly Met Arg Arg His
            20                  25                  30

Arg Arg Arg Arg Ala Ile Ser Lys Arg Leu Gly Gly Phe Leu Thr
        35                  40                  45

Ala Leu Ile Pro Ile Ile Ala Ala Ile Gly Ala Val Pro Gly Ile
    50                  55                  60

Ala Ser Val Ala Val Gln Ala Ser Gln Arg His
65                  70                  75
```

<210> SEQ ID NO 43
<211> LENGTH: 250
<212> TYPE: PRT
<213> ORGANISM: Unknown
<220> FEATURE:
<223> OTHER INFORMATION: Synthetic Construct

<400> SEQUENCE: 43

```
Met Glu Asp Ile Asn Phe Ser Ser Leu Ala Pro Arg His Gly Thr Arg
1               5                   10                  15

Pro Tyr Met Gly Thr Trp Ser Asp Ile Gly Thr Ser Gln Leu Asn Gly
            20                  25                  30

Gly Ala Phe Asn Trp Ser Ser Ile Trp Ser Gly Leu Lys Asn Phe Gly
        35                  40                  45

Ser Ala Ile Lys Thr Tyr Gly Asn Lys Ala Trp Asn Ser Ser Thr Gly
    50                  55                  60

Gln Ala Leu Arg Asn Lys Leu Lys Glu Gln Asn Phe Gln Gln Lys Val
65                  70                  75                  80

Val Asp Gly Ile Ala Ser Gly Ile Asn Gly Val Val Asp Leu Ala Asn
                85                  90                  95

Gln Ala Val Gln Lys Gln Ile Asn Ser Arg Leu Asp Gln Pro Pro Ala
            100                 105                 110

Ala Pro Gly Glu Met Glu Val Glu Glu Leu Pro Pro Leu Glu Lys
        115                 120                 125

Arg Gly Asp Lys Arg Pro Arg Pro Asp Met Glu Glu Thr Leu Val Thr
    130                 135                 140

Arg Gly Asp Glu Pro Pro Tyr Glu Glu Ala Ile Lys Leu Gly Met
145                 150                 155                 160

Pro Thr Thr Arg Pro Ile Ala Pro Met Ala Thr Gly Val Met Lys Pro
                165                 170                 175

Ser Gln Ser His Arg Pro Ala Thr Leu Asp Leu Pro Pro Ala Pro Ala
            180                 185                 190

Ala Ala Ala Pro Ala Pro Lys Pro Val Ala Thr Pro Lys Pro Thr Ala
        195                 200                 205

Val Gln Pro Val Ala Val Ala Arg Pro Arg Pro Gly Gly Thr Pro Arg
    210                 215                 220

Pro Asn Ala Asn Trp Gln Ser Thr Leu Asn Ser Ile Val Gly Leu Gly
225                 230                 235                 240

Val Gln Ser Val Lys Arg Arg Arg Cys Tyr
                245                 250
```

<210> SEQ ID NO 44

```
<211> LENGTH: 943
<212> TYPE: PRT
<213> ORGANISM: Unknown
<220> FEATURE:
<223> OTHER INFORMATION: Synthetic Construct

<400> SEQUENCE: 44

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Leu Gly Asn Lys Phe Arg Asn Pro
        35                  40                  45

Thr Val Ala Pro Thr His Asp Val Thr Thr Asp Arg Ser Gln Arg Leu
    50                  55                  60

Met Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Phe Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Ile Val Thr Thr Asn Gly Gln Asp Asn
    130                 135                 140

Ala Val Thr Thr Thr Thr Asn Thr Phe Gly Ile Ala Ser Met Lys Gly
145                 150                 155                 160

Asp Asn Ile Thr Lys Glu Gly Leu Glu Ile Gly Lys Asp Ile Thr Glu
                165                 170                 175

Glu Asp Lys Pro Ile Tyr Ala Asp Lys Thr Tyr Gln Pro Glu Pro Gln
            180                 185                 190

Val Gly Glu Glu Ser Trp Thr Asp Thr Asp Gly Thr Asn Glu Lys Phe
        195                 200                 205

Gly Gly Arg Ala Leu Lys Pro Ala Thr Asn Met Lys Pro Cys Tyr Gly
    210                 215                 220

Ser Phe Ala Arg Pro Thr Asn Ile Lys Gly Gly Gln Ala Lys Asn Arg
225                 230                 235                 240

Lys Val Lys Pro Thr Thr Glu Gly Gly Val Glu Thr Glu Pro Asp
                245                 250                 255

Ile Asp Met Glu Phe Phe Asp Gly Arg Asp Ala Ala Glu Gly Ala Leu
            260                 265                 270

Ser Pro Glu Ile Val Leu Tyr Thr Glu Asn Val Asn Leu Glu Thr Pro
        275                 280                 285

Asp Thr His Val Val Tyr Lys Pro Gly Thr Ser Asp Asp Asn Ser His
    290                 295                 300

Ala Asn Leu Gly Gln Gln Ala Met Pro Asn Arg Pro Asn Tyr Ile Gly
305                 310                 315                 320

Phe Arg Asp Asn Phe Val Gly Leu Leu Tyr Tyr Asn Ser Thr Gly Asn
                325                 330                 335

Met Gly Val Leu Ala Gly Gln Ala Ser Gln Leu Asn Ala Val Val Asp
            340                 345                 350

Leu Gln Asp Arg Asn Thr Glu Leu Ser Tyr Gln Leu Leu Leu Asp Ser
        355                 360                 365

Leu Gly Asp Arg Thr Arg Tyr Phe Ser Met Trp Asn Gln Ala Val Asp
    370                 375                 380
```

```
Ser Tyr Asp Pro Asp Val Arg Ile Ile Glu Asn His Gly Ile Glu Asp
385                 390                 395                 400

Glu Leu Pro Asn Tyr Cys Phe Pro Leu Asp Gly Ile Gly Pro Gly Asn
            405                 410                 415

Ser Tyr Gln Gly Ile Lys Ala Lys Asn Gly Asp Asn Asn Gly Trp Glu
        420                 425                 430

Lys Asp Thr Asn Ala Ser Thr Ala Asn Glu Ile Ala Ile Gly Asn Asn
            435                 440                 445

Leu Ala Met Glu Ile Asn Ile Gln Ala Asn Leu Trp Arg Ser Phe Leu
        450                 455                 460

Tyr Ser Asn Val Ala Leu Tyr Leu Pro Asp Ala Tyr Lys Tyr Thr Pro
465                 470                 475                 480

Ala Asn Ile Thr Leu Pro Ala Asn Thr Asn Thr Tyr Glu Tyr Met Asn
            485                 490                 495

Gly Arg Val Val Ala Pro Ser Leu Val Asp Ser Tyr Ile Asn Ile Gly
        500                 505                 510

Ala Arg Trp Ser Leu Asp Pro Met Asp Asn Val Asn Pro Phe Asn His
            515                 520                 525

His Arg Asn Ala Gly Leu Arg Tyr Arg Ser Met Leu Leu Gly Asn Gly
        530                 535                 540

Arg Tyr Val Pro Phe His Ile Gln Val Pro Gln Lys Phe Phe Ala Ile
545                 550                 555                 560

Lys Asn Leu Leu Leu Leu Pro Gly Ser Tyr Thr Tyr Glu Trp Asn Phe
            565                 570                 575

Arg Lys Asp Val Asn Met Val Leu Gln Ser Ser Leu Gly Asn Asp Leu
        580                 585                 590

Arg Thr Asp Gly Ala Ser Ile Ser Phe Thr Ser Ile Asn Leu Tyr Ala
            595                 600                 605

Thr Phe Phe Pro Met Ala His Asn Thr Ala Ser Thr Leu Glu Ala Met
        610                 615                 620

Leu Arg Asn Asp Thr Asn Asp Gln Ser Phe Asn Asp Tyr Leu Ser Ala
625                 630                 635                 640

Ala Asn Met Leu Tyr Pro Ile Pro Ala Asn Ala Thr Asn Ile Pro Ile
            645                 650                 655

Ser Ile Pro Ser Arg Asn Trp Ala Ala Phe Arg Gly Trp Ser Phe Thr
        660                 665                 670

Arg Leu Lys Thr Lys Glu Thr Pro Ser Leu Gly Ser Gly Phe Asp Pro
            675                 680                 685

Tyr Phe Val Tyr Ser Gly Ser Ile Pro Tyr Leu Asp Gly Thr Phe Tyr
        690                 695                 700

Leu Asn His Thr Phe Lys Lys Val Ser Ile Met Phe Asp Ser Ser Val
705                 710                 715                 720

Ser Trp Pro Gly Asn Asp Arg Leu Leu Thr Pro Asn Glu Phe Glu Ile
            725                 730                 735

Lys Arg Thr Val Asp Gly Glu Gly Tyr Asn Val Ala Gln Cys Asn Met
            740                 745                 750

Thr Lys Asp Trp Phe Leu Val Gln Met Leu Ala Asn Tyr Asn Ile Gly
        755                 760                 765

Tyr Gln Gly Phe Tyr Ile Pro Glu Gly Tyr Lys Asp Arg Met Tyr Ser
        770                 775                 780

Phe Phe Arg Asn Phe Gln Pro Met Ser Arg Gln Val Val Asp Glu Val
785                 790                 795                 800
```

```
Asn Tyr Thr Asp Tyr Lys Ala Val Thr Leu Ala Tyr Gln His Asn Asn
                    805                 810                 815
Ser Gly Phe Val Gly Tyr Leu Ala Pro Thr Met Arg Gln Gly Glu Pro
            820                 825                 830
Tyr Pro Ala Asn Tyr Pro Tyr Pro Leu Ile Gly Thr Thr Ala Val Lys
            835                 840                 845
Ser Val Thr Gln Lys Lys Phe Leu Cys Asp Arg Thr Met Trp Arg Ile
    850                 855                 860
Pro Phe Ser Ser Asn Phe Met Ser Met Gly Ala Leu Thr Asp Leu Gly
865                 870                 875                 880
Gln Asn Met Leu Tyr Ala Asn Ser Ala His Ala Leu Asp Met Thr Phe
                885                 890                 895
Glu Val Asp Pro Met Asp Glu Pro Thr Leu Leu Tyr Val Leu Phe Glu
            900                 905                 910
Val Phe Asp Val Val Arg Val His Gln Pro His Arg Gly Val Ile Glu
            915                 920                 925
Ala Val Tyr Leu Arg Thr Pro Phe Ser Ala Gly Asn Ala Thr Thr
            930                 935                 940
```

<210> SEQ ID NO 45
<211> LENGTH: 205
<212> TYPE: PRT
<213> ORGANISM: Unknown
<220> FEATURE:
<223> OTHER INFORMATION: Synthetic Construct

<400> SEQUENCE: 45

```
Met Ser Gln Arg Arg Gly Ser Lys Lys Leu Lys Val Gln Leu Pro Pro
1               5                   10                  15
Pro Glu Asp Met Glu Glu Asp Trp Asp Ser Gln Ala Glu Glu Glu Glu
            20                  25                  30
Met Glu Asp Trp Asp Ser Gln Ala Glu Glu Ala Asp Ser Leu Glu Glu
            35                  40                  45
Asp Ser Leu Glu Glu Glu Asp Glu Glu Ala Glu Val Glu Glu Glu Ala
    50                  55                  60
Ala Ala Ala Lys Gln Leu Ser Ser Ala Ala Glu Thr Ser Lys Ala Pro
65                  70                  75                  80
Asp Ser Ser Ser Ser Thr Ala Thr Ile Ser Ala Pro Gly Arg Gly Ala
                85                  90                  95
Gln Gln Arg Pro Asn Ser Arg Trp Asp Glu Thr Gly Arg Phe Pro Asn
            100                 105                 110
Pro Thr Thr Ala Ser Lys Thr Gly Lys Lys Glu Arg Gln Gly Tyr Lys
            115                 120                 125
Ser Trp Arg Gly His Lys Asn Ala Ile Ile Ser Cys Leu His Glu Cys
    130                 135                 140
Gly Gly Asn Ile Ser Phe Thr Arg Arg Tyr Leu Leu Phe His His Gly
145                 150                 155                 160
Val Asn Phe Pro Arg Asn Val Leu His Tyr Arg His Leu His Ser
                165                 170                 175
Pro Tyr Tyr Ser Gln Gln Val Pro Thr Ala Ser Ala Glu Lys Asp Ser
            180                 185                 190
Ser Ser Gly Asp Leu Gln Gln Lys Thr Ser Ser Ser Ser
            195                 200                 205
```

<210> SEQ ID NO 46
<211> LENGTH: 227

```
<212> TYPE: PRT
<213> ORGANISM: Unknown
<220> FEATURE:
<223> OTHER INFORMATION: Synthetic Construct

<400> SEQUENCE: 46

Met Ser Lys Glu Ile Pro Thr Pro Tyr Met Trp Ser Tyr Gln Pro Gln
1               5                   10                  15

Met Gly Leu Ala Ala Gly Ala Ser Gln Asp Tyr Ser Thr Arg Met Asn
            20                  25                  30

Trp Leu Ser Ala Gly Pro Ser Met Ile Ser Arg Val Asn Asp Ile Arg
        35                  40                  45

Ala Tyr Arg Asn Gln Leu Leu Leu Glu Gln Ser Ala Leu Thr Thr Thr
    50                  55                  60

Pro Arg Gln His Leu Asn Pro Arg Asn Trp Pro Ala Ala Leu Val Tyr
65                  70                  75                  80

Gln Glu Thr Pro Ala Pro Thr Thr Val Leu Leu Pro Arg Asp Ala Gln
                85                  90                  95

Ala Glu Val Gln Met Thr Asn Ala Gly Val Gln Leu Ala Gly Gly Ser
            100                 105                 110

Ala Leu Cys Arg His Arg Pro Gln Gln Ser Ile Lys Arg Leu Val Ile
        115                 120                 125

Arg Gly Arg Gly Ile Gln Leu Asn Asp Glu Ser Val Ser Ser Ser Leu
130                 135                 140

Gly Leu Arg Pro Asp Gly Val Phe Gln Ile Ala Gly Cys Gly Arg Ser
145                 150                 155                 160

Ser Phe Thr Pro Arg Gln Ala Val Leu Thr Leu Glu Ser Ser Ser Ser
                165                 170                 175

Gln Pro Arg Ser Gly Gly Ile Gly Thr Leu Gln Phe Val Glu Glu Phe
            180                 185                 190

Thr Pro Ser Val Tyr Phe Asn Pro Phe Ser Gly Ser Pro Gly Gln Tyr
        195                 200                 205

Pro Asp Glu Phe Ile Pro Asn Phe Asp Ala Ile Ser Glu Ser Val Asp
    210                 215                 220

Gly Tyr Asp
225

<210> SEQ ID NO 47
<211> LENGTH: 105
<212> TYPE: PRT
<213> ORGANISM: Unknown
<220> FEATURE:
<223> OTHER INFORMATION: Synthetic Construct

<400> SEQUENCE: 47

Met Ser Gly Gly Ala Ala Glu Leu Ala Arg Leu Arg His Leu Asp His
1               5                   10                  15

Cys Arg Arg Phe Arg Cys Phe Ala Arg Glu Leu Thr Glu Phe Ile Tyr
            20                  25                  30

Phe Glu Leu Pro Glu Glu His Pro Gln Gly Pro Ala His Gly Val Arg
        35                  40                  45

Ile Thr Ile Glu Gly Gly Ile Asp Ser Arg Leu His Arg Ile Phe Cys
    50                  55                  60

Gln Arg Pro Val Leu Ile Glu Arg Asp Gln Gly Thr Thr Thr Val Ser
65                  70                  75                  80

Ile Tyr Cys Ile Cys Asn His Pro Gly Leu His Glu Ser Leu Cys Cys
                85                  90                  95
```

```
                        Leu Ile Cys Ala Glu Phe Asn Lys Asn
                                100                 105

<210> SEQ ID NO 48
<211> LENGTH: 172
<212> TYPE: PRT
<213> ORGANISM: Unknown
<220> FEATURE:
<223> OTHER INFORMATION: Synthetic Construct

<400> SEQUENCE: 48

Met Gly Val Val Leu Val Ala Leu Ala Leu Leu Ser Leu Leu Gly Leu
1               5                   10                  15

Gly Ser Ala Asn Leu Ile Pro Pro Asp His Asp Pro Cys Leu Asp Phe
                20                  25                  30

Asn Pro Glu Asn Cys Thr Ile Thr Phe Ala Pro Glu Thr Ser Arg Phe
            35                  40                  45

Cys Gly Val Val Ile Arg Cys Gly Phe Glu Cys Arg Pro Ile Glu Ile
    50                  55                  60

Thr His Asn Asn Lys Thr Trp Asn Asn Thr Leu Phe Thr Ile Trp Gln
65                  70                  75                  80

Pro Gly Asp Pro Gln Trp Tyr Thr Val Ser Val Arg Gly Pro Asp Gly
                85                  90                  95

Ser Val Arg Met Ala Asn Asn Thr Phe Ile Phe Ala Glu Met Cys Asp
                100                 105                 110

Met Ala Met Phe Met Ser Arg Gln Tyr Asp Leu Trp Pro Pro Ser Lys
            115                 120                 125

Glu Asn Ile Val Ala Phe Ser Ile Ala Tyr Cys Phe Cys Thr Cys Leu
    130                 135                 140

Ile Thr Ala Thr Leu Cys Ile Cys Leu His Leu Leu Ile Ala Phe Arg
145                 150                 155                 160

Pro Lys Asn Ser Asn Glu Glu Lys Glu Lys Val Pro
                165                 170

<210> SEQ ID NO 49
<211> LENGTH: 201
<212> TYPE: PRT
<213> ORGANISM: Unknown
<220> FEATURE:
<223> OTHER INFORMATION: Synthetic Construct

<400> SEQUENCE: 49

Met Ala Ser Val Ala Val Leu Ile Phe Ile Ile Thr Ser Val His Thr
1               5                   10                  15

Phe Gly Leu Lys Phe Asn Asp Gln Ile Val His Val Gly Ser Asn His
                20                  25                  30

Thr Leu Arg Gly Pro Ile Gly Asn Ser Glu Val Thr Trp Tyr Trp Tyr
            35                  40                  45

Tyr Ala Asp Asp Ser Trp Pro Glu Lys Leu Cys Asp Asp Ile Asn Leu
    50                  55                  60

His Asn Ile Leu Thr Lys Thr Leu Asn Ser Lys Thr Ile Lys Tyr Asn
65                  70                  75                  80

Cys Thr Asp Tyr Asp Leu Ile Leu Val Asn Val Thr Thr Asn Tyr Ser
                85                  90                  95

Gly Phe Tyr Tyr Gly Thr Asn Phe Glu Asn Val Ala Tyr Tyr Asn Ile
                100                 105                 110

Leu Val Lys Phe Arg Pro Thr Thr Thr Lys Thr Ser Ser Ser Ser Thr
```

```
                115                 120                 125
Ile Thr Ser Thr Thr Leu Pro Ile Arg Thr Ala Met Phe Gln Leu Asn
            130                 135                 140

Lys Ile Glu Asn Thr Thr Asn Ser Asn Tyr Thr Leu Phe Asn Asp Gln
145                 150                 155                 160

Asn Val Gln Gly Ser Leu Thr Thr Ile Ile Leu Leu Ile Val Gly
                165                 170                 175

Leu Ile Ile Ile Ile Cys Met Ile Val Tyr Thr Cys Arg Tyr Arg
            180                 185                 190

Lys Leu His Asn Lys Val Asp Pro Tyr
        195                 200

<210> SEQ ID NO 50
<211> LENGTH: 215
<212> TYPE: PRT
<213> ORGANISM: Unknown
<220> FEATURE:
<223> OTHER INFORMATION: Synthetic Construct

<400> SEQUENCE: 50

Met Ile Ser Ile Thr Thr Leu Leu Tyr Ile Thr Ala Ile Thr Thr Val
1               5                   10                  15

Gln Gly Phe Thr Asn Ile Lys Lys Thr Ile His Val Gly Ser Ser Ser
            20                  25                  30

Thr Leu Glu Gly Tyr Gln Ser Gln Ser Arg Val Ser Trp Tyr Trp Tyr
        35                  40                  45

Tyr Arg Asn Gln Pro Ala Ile Thr Leu Cys Lys Gly Ser Gln Glu Thr
    50                  55                  60

Thr Ile Arg Thr Ile Lys Tyr Lys Cys Asn Asn Asn Asn Leu Thr Leu
65                  70                  75                  80

Ile Asp Val Thr Ala Gln Tyr Ala Gly Thr Tyr Tyr Gly Thr Asn Phe
                85                  90                  95

Asn Ile Gly Gln Asp Thr Tyr Tyr Thr Ile Thr Val Ile Asn Ser Thr
            100                 105                 110

Thr Pro Val Thr Thr Thr Ile Lys Pro Thr Lys Thr Lys Ser Thr Lys
        115                 120                 125

Thr His Ile Phe Pro Ser Ser Lys Pro Thr Ser Ile Tyr Thr Thr Ser
    130                 135                 140

Leu Leu Gln Leu Leu Gln Lys Ala Asn Val Thr Asp Asn Tyr Thr Ile
145                 150                 155                 160

Asn Pro Thr Leu Pro Ser Glu Glu Ile Pro Lys Ser Met Ile Gly Ile
                165                 170                 175

Ile Ala Ala Val Val Ala Gly Met Leu Ile Ile Ile Leu Cys Met Ile
            180                 185                 190

Tyr Tyr Ala Cys Cys Tyr Arg Lys Tyr Glu His Glu Gln Lys Ile Asp
        195                 200                 205

Pro Leu Leu Ser Phe Asp Ile
    210                 215

<210> SEQ ID NO 51
<211> LENGTH: 102
<212> TYPE: PRT
<213> ORGANISM: Unknown
<220> FEATURE:
<223> OTHER INFORMATION: Synthetic Construct

<400> SEQUENCE: 51
```

```
Met Lys Gly Pro Val Ile Leu Leu Phe Ile Ser Thr Phe Trp Cys Cys
1               5                   10                  15

Asp Thr Phe Ser Ile Thr Thr Asn Val Gln Thr Thr Leu Asn Asn Ile
            20                  25                  30

Met Thr Thr Ser Asn Thr Gln Leu Ser Pro Gln Ser Glu Asp Asp Ile
        35                  40                  45

Lys Leu Gln Ile Thr Ile Leu Ile Val Ile Gly Leu Ile Ile Leu Ala
    50                  55                  60

Val Leu Leu Tyr Phe Ile Phe Cys Arg Gln Ile Pro Asn Val Val Lys
65                  70                  75                  80

Lys Pro Thr Arg Arg Pro Ile Tyr Arg Ser Ile Ser Lys Pro His
                85                  90                  95

Met Ala Leu Asn Glu Ile
            100
```

<210> SEQ ID NO 52
<211> LENGTH: 91
<212> TYPE: PRT
<213> ORGANISM: Unknown
<220> FEATURE:
<223> OTHER INFORMATION: Synthetic Construct

<400> SEQUENCE: 52

```
Met Ile Pro Arg Asn Phe Phe Thr Ile Leu Ile Cys Ala Phe Asn
1               5                   10                  15

Val Cys Ala Thr Phe Ala Thr Val Ala Asn Val Thr Pro Asp Cys Ile
            20                  25                  30

Gly Ala Phe Ala Ser Tyr Val Leu Phe Ala Phe Ile Thr Cys Ile Cys
        35                  40                  45

Val Cys Ser Ile Val Cys Leu Val Ile Asn Phe Phe Gln Leu Val Asp
    50                  55                  60

Trp Val Phe Val Arg Ile Ala Tyr Leu Gln His His Pro Glu Tyr Arg
65                  70                  75                  80

Asn Gln Asn Val Ala Ala Ile Leu Arg Leu Ile
            85                  90
```

<210> SEQ ID NO 53
<211> LENGTH: 132
<212> TYPE: PRT
<213> ORGANISM: Unknown
<220> FEATURE:
<223> OTHER INFORMATION: Synthetic Construct

<400> SEQUENCE: 53

```
Met Thr Asp Pro His Ala Ala Glu Glu Leu Leu Asp Met Asp Gly
1               5                   10                  15

Arg Ala Ser Glu Gln Arg Leu Ala Gln Leu Arg Ile Arg Gln Gln Gln
            20                  25                  30

Glu Arg Ala Ala Lys Glu Leu Arg Asp Ala Ile Gln Ile His Gln Cys
        35                  40                  45

Lys Lys Gly Ile Phe Cys Leu Val Lys Gln Ala Lys Ile Ser Tyr Glu
    50                  55                  60

Ile Thr Ala Asn Asp His Arg Leu Ser Tyr Glu Leu Gly Pro Gln Arg
65                  70                  75                  80

Gln Lys Phe Thr Cys Met Val Gly Ile Asn Pro Ile Val Ile Thr Gln
            85                  90                  95

Gln Ala Gly Asp Thr Lys Gly Cys Ile His Cys Ser Cys Glu Ser Thr
        100                 105                 110
```

```
Glu Cys Ile Tyr Thr Leu Leu Lys Thr Leu Cys Gly Leu Arg Asp Leu
        115                 120                 125

Leu Pro Met Asn
    130

<210> SEQ ID NO 54
<211> LENGTH: 325
<212> TYPE: PRT
<213> ORGANISM: Unknown
<220> FEATURE:
<223> OTHER INFORMATION: Synthetic Construct

<400> SEQUENCE: 54

Met Ala Lys Arg Ala Arg Leu Ser Ser Ser Phe Asn Pro Val Tyr Pro
1               5                   10                  15

Tyr Glu Asp Glu Ser Thr Thr His Pro Phe Ile Asn Pro Gly Phe Ile
            20                  25                  30

Ser Pro Asp Gly Phe Ala Gln Ser Pro Asp Gly Val Leu Thr Leu Lys
        35                  40                  45

Cys Ile Ser Pro Leu Asn Thr Thr Gly Gly Ser Leu Gln Leu Lys Val
    50                  55                  60

Gly Gly Gly Leu Lys Val Asp Ser Thr Asp Gly Ser Leu Glu Glu Asn
65                  70                  75                  80

Ile Asn Thr Thr Ala Pro Leu Thr Lys Thr Asn His Ser Ile Ser Met
                85                  90                  95

Leu Val Gly Asn Gly Leu His Thr Glu Glu Asn Lys Leu Cys Ala Lys
            100                 105                 110

Leu Gly Gln Gly Leu Glu Phe Asn Ser Gly Ser Ile Cys Ile Asp His
        115                 120                 125

Asn Thr Asn Thr Leu Trp Thr Gly Val Pro Thr Glu Ala Asn Cys His
    130                 135                 140

Met Leu Glu Tyr Thr Asp Asp Lys Asp Cys Lys Leu Thr Leu Val Leu
145                 150                 155                 160

Val Lys Asn Gly Ala Met Val Asn Gly Tyr Val Ser Leu Met Gly Ala
                165                 170                 175

Thr Asp Glu Phe Asn Ala Ile Thr Thr Val Lys Ile Ala Gln Leu Thr
            180                 185                 190

Ala Asp Ile Tyr Phe Asp Thr Asn Gly Lys Val Leu Thr Asp Ile Ser
        195                 200                 205

Ala Leu Lys Thr Glu Leu Lys Tyr Lys Ser Gly Gln Asn Met Ala Thr
    210                 215                 220

Gly Glu Pro Ser Asn Ser Lys Ser Phe Met Pro Ser Leu Thr Ala Tyr
225                 230                 235                 240

Pro Leu Arg Asn Pro Thr Ile Lys Pro Val Arg Gly Asn Glu Asp Tyr
                245                 250                 255

Ile Tyr Gly Thr Thr Tyr Phe Arg Ser Ser Asp Asp Ala Leu Leu Pro
            260                 265                 270

Leu Asp Thr Tyr Val Met Leu Asn Tyr Lys Leu Ser Asn Ala Gln Cys
        275                 280                 285

Ala Tyr Ala Met His Phe Met Trp Ser Trp Asn Thr Ser Ile Lys Pro
    290                 295                 300

Glu Glu Thr Ala Thr Thr Phe Ile Ala Ser Pro Phe Thr Phe Ser Tyr
305                 310                 315                 320

Ile Arg Glu Asp Asp
                325
```

<210> SEQ ID NO 55
<211> LENGTH: 560
<212> TYPE: DNA
<213> ORGANISM: Unknown
<220> FEATURE:
<223> OTHER INFORMATION: Simian adenovirus 41.2
<220> FEATURE:
<221> NAME/KEY: CDS
<222> LOCATION: (9)..(551)
<223> OTHER INFORMATION: E1b\19K

<400> SEQUENCE: 55

```
tgccatcc atg gag gtt tgg gct atc ttg gaa gat ctc aga cag act agg      50
         Met Glu Val Trp Ala Ile Leu Glu Asp Leu Arg Gln Thr Arg
         1               5                   10 caa ctg cta gaa aac gcc tcg gac gga gtc tct agt ctt tgg aga ttc       98
Gln Leu Leu Glu Asn Ala Ser Asp Gly Val Ser Ser Leu Trp Arg Phe
15                  20                  25                  30 tgg ttc ggt ggt gat cta gct agg cta gtc ttt agg gta aaa cgg gag      146
Trp Phe Gly Gly Asp Leu Ala Arg Leu Val Phe Arg Val Lys Arg Glu
                35                  40                  45 tat agt gaa gaa ttt gaa aag tta ttg gaa gac agt cca gga ctt ttt      194
Tyr Ser Glu Glu Phe Glu Lys Leu Leu Glu Asp Ser Pro Gly Leu Phe
            50                  55                  60 gaa gcc ctt aac ttg ggc cac cag gct cat ttt aag gag aag gtt tta      242
Glu Ala Leu Asn Leu Gly His Gln Ala His Phe Lys Glu Lys Val Leu
65                  70                  75 tca gtt tta gat ttt tct acc cct ggt aga act gct gct gct gta gca      290
Ser Val Leu Asp Phe Ser Thr Pro Gly Arg Thr Ala Ala Ala Val Ala
        80                  85                  90 ttt ctt act ttt ata ttg gat aaa tgg atc cca caa acc cac ttc agc      338
Phe Leu Thr Phe Ile Leu Asp Lys Trp Ile Pro Gln Thr His Phe Ser
95                  100                 105                 110 aag gga tac gtc ttg gat ttc ata gca gca gct ttg tgg aga aca tgg      386
Lys Gly Tyr Val Leu Asp Phe Ile Ala Ala Ala Leu Trp Arg Thr Trp
                115                 120                 125 aag gcc cgc agg ctg agg ata atc tta gat tac tgg cca gtg cag cct      434
Lys Ala Arg Arg Leu Arg Ile Ile Leu Asp Tyr Trp Pro Val Gln Pro
            130                 135                 140 ctg ggc gta gcg gca atc ctg aga cac cca cca gtc atg cca gcg gtt      482
Leu Gly Val Ala Ala Ile Leu Arg His Pro Pro Val Met Pro Ala Val
        145                 150                 155 ttg gag gag gag cag cag gag gac aac ccg aga gcc ggc ctg gac cct      530
Leu Glu Glu Glu Gln Gln Glu Asp Asn Pro Arg Ala Gly Leu Asp Pro
160                 165                 170 ccg gtg gag gag gcg gag gag tagctgacc                                560
Pro Val Glu Glu Ala Glu Glu
175                 180
```

<210> SEQ ID NO 56
<211> LENGTH: 181
<212> TYPE: PRT
<213> ORGANISM: Unknown
<220> FEATURE:
<223> OTHER INFORMATION: Synthetic Construct

<400> SEQUENCE: 56

```
Met Glu Val Trp Ala Ile Leu Glu Asp Leu Arg Gln Thr Arg Gln Leu
1               5                   10                  15

Leu Glu Asn Ala Ser Asp Gly Val Ser Ser Leu Trp Arg Phe Trp Phe
            20                  25                  30
```

```
Gly Gly Asp Leu Ala Arg Leu Val Phe Arg Val Lys Arg Glu Tyr Ser
            35                  40                  45

Glu Glu Phe Glu Lys Leu Leu Glu Asp Ser Pro Gly Leu Phe Glu Ala
 50                  55                  60

Leu Asn Leu Gly His Gln Ala His Phe Lys Glu Lys Val Leu Ser Val
 65                  70                  75                  80

Leu Asp Phe Ser Thr Pro Gly Arg Thr Ala Ala Val Ala Phe Leu
                 85                  90                  95

Thr Phe Ile Leu Asp Lys Trp Ile Pro Gln Thr His Phe Ser Lys Gly
            100                 105                 110

Tyr Val Leu Asp Phe Ile Ala Ala Ala Leu Trp Arg Thr Trp Lys Ala
            115                 120                 125

Arg Arg Leu Arg Ile Ile Leu Asp Tyr Trp Pro Val Gln Pro Leu Gly
130                 135                 140

Val Ala Ala Ile Leu Arg His Pro Pro Val Met Pro Ala Val Leu Glu
145                 150                 155                 160

Glu Glu Gln Gln Glu Asp Asn Pro Arg Ala Gly Leu Asp Pro Pro Val
                165                 170                 175

Glu Glu Ala Glu Glu
            180

<210> SEQ ID NO 57
<211> LENGTH: 9860
<212> TYPE: DNA
<213> ORGANISM: Unknown
<220> FEATURE:
<223> OTHER INFORMATION: Simian adenovirus 41.2
<220> FEATURE:
<221> NAME/KEY: CDS
<222> LOCATION: (6)..(791)
<223> OTHER INFORMATION: protease
<220> FEATURE:
<221> NAME/KEY: CDS
<222> LOCATION: (2472)..(4964)
<223> OTHER INFORMATION: 100K
<220> FEATURE:
<221> NAME/KEY: CDS
<222> LOCATION: (6569)..(6994)
<223> OTHER INFORMATION: E3\CR1\alpha
<220> FEATURE:
<221> NAME/KEY: CDS
<222> LOCATION: (9433)..(9852)
<223> OTHER INFORMATION: E3\RID\beta

<400> SEQUENCE: 57 catgg atg agc cca ccc tgc ttt atg ttc ttt tcg aag tct tcg acg tgg      50
      Met Ser Pro Pro Cys Phe Met Phe Phe Ser Lys Ser Ser Thr Trp
       1               5                  10                  15 tca gag tgc acc agc cac acc gcg gcg tca tcg agg ctg tct acc tgc       98
Ser Glu Cys Thr Ser His Thr Ala Ala Ser Ser Arg Leu Ser Thr Cys
                 20                  25                  30 gta ccc cgt tct cag ctg gta acg cca cca cat aaa gaa gct tct tgc      146
Val Pro Arg Ser Gln Leu Val Thr Pro Pro His Lys Glu Ala Ser Cys
             35                  40                  45 ttc ttg caa gca gct gcc atg gcc tgt ggg tcc ggc aac gga tcc agc      194
Phe Leu Gln Ala Ala Ala Met Ala Cys Gly Ser Gly Asn Gly Ser Ser
         50                  55                  60 gag caa gag ctc agg gcc att gct aga gac ctg ggc tgc gga ccc tat      242
Glu Gln Glu Leu Arg Ala Ile Ala Arg Asp Leu Gly Cys Gly Pro Tyr
 65                  70                  75 ttc ctg gga acc ttt gat aaa cgc ttc ccg ggg ttc atg gcc ccc gac      290
Phe Leu Gly Thr Phe Asp Lys Arg Phe Pro Gly Phe Met Ala Pro Asp
 80                  85                  90                  95
```

```
aag ctc gcc tgc gcc att gtt aac acg gcc ggt cgc gag acg ggg ggt      338
Lys Leu Ala Cys Ala Ile Val Asn Thr Ala Gly Arg Glu Thr Gly Gly
            100                 105                 110 gag cac tgg ctg gct ttt ggt tgg aat ccg cgc tcc aac acc tgc tac      386
Glu His Trp Leu Ala Phe Gly Trp Asn Pro Arg Ser Asn Thr Cys Tyr
            115                 120                 125 ctt ttt gat ccc ttt ggc ttc tct gac gag cgc ctc aag caa atc tac      434
Leu Phe Asp Pro Phe Gly Phe Ser Asp Glu Arg Leu Lys Gln Ile Tyr
            130                 135                 140 cag ttt gag tat gag ggg ctt ctg cgc cgc agt gcc cta gct acc aag      482
Gln Phe Glu Tyr Glu Gly Leu Leu Arg Arg Ser Ala Leu Ala Thr Lys
        145                 150                 155 gac cgc tgt atc acc ctg gaa aag tca acc cag acc gtg cag ggc ccg      530
Asp Arg Cys Ile Thr Leu Glu Lys Ser Thr Gln Thr Val Gln Gly Pro
160                 165                 170                 175 cgc tcc gca gcc tgt gga ctg ttt tgc tgc atg ttc ctc cac gct ttt      578
Arg Ser Ala Ala Cys Gly Leu Phe Cys Cys Met Phe Leu His Ala Phe
                180                 185                 190 gtg cac tgg cca gac cgc ccc atg gac gga aac ccc acc atg aag ttg      626
Val His Trp Pro Asp Arg Pro Met Asp Gly Asn Pro Thr Met Lys Leu
            195                 200                 205 ctg act ggg gtg ccc aac agc atg ctc caa tca ccc caa gtc cag ccc      674
Leu Thr Gly Val Pro Asn Ser Met Leu Gln Ser Pro Gln Val Gln Pro
            210                 215                 220 acc ctg cgc cac aac cag gag gcg ctc tac cgc ttc cta aac tcc cac      722
Thr Leu Arg His Asn Gln Glu Ala Leu Tyr Arg Phe Leu Asn Ser His
            225                 230                 235 tca tct tac ttt cgt tct cac cgc gcg cgc atc gaa aag gcc acc gcg      770
Ser Ser Tyr Phe Arg Ser His Arg Ala Arg Ile Glu Lys Ala Thr Ala
240                 245                 250                 255 ttt aat cga atg gat atg caa taataagtca tgtaaaccgt gttcaaataa         821
Phe Asn Arg Met Asp Met Gln
                260 acagcacttt attttttaca tgcactgtgg ctctgggttg ctcattcatt catcattcac    881 tcagaagtcg aagggttct ggcgggaatc agcgtgaccc gctggcaggg atacgttgcg     941 gaactggaac ctgttctgcc acttgaactc ggggatcacc agcttgggaa ctgggatctc    1001 ggggaaggtg tcttgccaca gctttctggt tagttgcaga gcaccaagca ggtcaggagc    1061 agagatcttg aaatcacagt ggggccagc attctgggca cgggagttgc ggtacactgg    1121 gttgcagcac tggaacacca tcagggcggg gtgtctcacg ctcgccagca cggtcgggtc    1181 actgatggta gtcacatcca agtcttcagc attggccatt ccaaaggggg tcatcttaca    1241 ggtctgcctg cccatcacgg gagcgcagcc gggcttgtgg ttgcaatcgc agcgaatggg    1301 gatcagcatc atcctggcct ggtcgggggt tatccctgga tacaccgcct tcataaaggc    1361 ttcgtactgc ttgaaagctt cctgagcctt acttccctcg gtgtagaaca tcccacagga    1421 cttgctggaa aattgattag tagcacagtt ggcatcattc acacagcagc gggcatcgtt    1481 gttggccagc tggaccacat tcctgcccca gcggttctgg gtgatcttgg ctcggtctgg    1541 gttctccttc atcgcgcgct gcccgttctc gctcgccaca tccatctcga tgatgtgatc    1601 cttctggatc atgatagtgc catgcaggca tttcaccttg ccttcataat cggtgcagcc    1661 atgagcccac agagcgcacc cggtgcactc ccaattgttg tgggcgatct cagaataaga    1721 atgcaccaat ccctgcatga atcttcccat catgctggtg agggtcttta tgctggtaaa    1781 tgtcagcggg atgccacggt gctcctcgtt cacatactgg tggcagatac gcctgtactg    1841
```

```
ctcgtgctgc tcgggcatca gcttgaaaga ggttctcagg tcattatcca gcctgtacct    1901
ctccattagc acggccatta cttccatgcc cttctcccag gcagagacca agggcaggct    1961
catgggattc ctaacagcaa tagcagcaga cgcagctcct ttagccagag ggtcattctt    2021
gtcaatcttc tcaacacttc tcttgccatc cttctcagtg atgcgcactg gggggtagct    2081
gaagcccacg gccaccagct ccgcctgttc tctttcttct tcgctgtcct ggctgatgtc    2141
ttgcaaaggg acatgcttgg tcttcctggg cttcttcttg ggaggatcg ggggagggct     2201
gttgctccgc tccggagaca gggaggaccg cgaagtttcg ctcaccagta ccacctggct    2261
ctcggtagaa gaaccggacc ccacgcggcg gtaggtgttc ctcttcgggg gcagaggtgg    2321
aggcgactgc gatggactgc ggtccggcct gggaggcgga tggctggcag agcctcttcc    2381
gcgttcgggg gtgtgctccc ggtggcggtc gcttgactga tttcctccgc ggctggccat    2441
tgtgttctcc taggcagaga acaacagac atg gag act cag cca tcg ctg cca      2495
                                  Met Glu Thr Gln Pro Ser Leu Pro
                                                  265         270 aca ccg ctg caa gcg cca tca cac ctc gcc ccc agc agc gac gag gag      2543
Thr Pro Leu Gln Ala Pro Ser His Leu Ala Pro Ser Ser Asp Glu Glu
            275                 280                 285 gag agc tta acc acc cca cca ccc agt ccc gcc acc acc acc tct acc      2591
Glu Ser Leu Thr Thr Pro Pro Pro Ser Pro Ala Thr Thr Thr Ser Thr
        290                 295                 300 cta gag gat gag gag gag gtc gac gca ccc cag gag atg cag gat atg      2639
Leu Glu Asp Glu Glu Glu Val Asp Ala Pro Gln Glu Met Gln Asp Met
    305                 310                 315 gag gat gag aaa gcg gaa gag att gag gca gat gtc gag cag gac ccg      2687
Glu Asp Glu Lys Ala Glu Glu Ile Glu Ala Asp Val Glu Gln Asp Pro
320                 325                 330 ggc tat gtg aca ccg gcg gag cac gag gag gag ctg aga cgc ttt cta     2735
Gly Tyr Val Thr Pro Ala Glu His Glu Glu Glu Leu Arg Arg Phe Leu
335                 340                 345                 350 gac aga gag gat gac aac cgc cca gag cag aaa gca gat ggc gat cac     2783
Asp Arg Glu Asp Asp Asn Arg Pro Glu Gln Lys Ala Asp Gly Asp His
            355                 360                 365 cag gag gct ggg ctc ggg gat cat gtc gcc gac tac ctc acc ggg ctt     2831
Gln Glu Ala Gly Leu Gly Asp His Val Ala Asp Tyr Leu Thr Gly Leu
        370                 375                 380 ggc ggg gag gac gtg ctc ctc aaa cat cta gca agg cag tcg atc ata     2879
Gly Gly Glu Asp Val Leu Leu Lys His Leu Ala Arg Gln Ser Ile Ile
    385                 390                 395 gtt aaa gac gca ctg ctc gac cgc acc gaa gtg ccc atc agt gtg gaa     2927
Val Lys Asp Ala Leu Leu Asp Arg Thr Glu Val Pro Ile Ser Val Glu
400                 405                 410 gag ctc agc cgc gcc tac gag ctc aac ctg ttc tcg cct cgg ctg ccc     2975
Glu Leu Ser Arg Ala Tyr Glu Leu Asn Leu Phe Ser Pro Arg Leu Pro
415                 420                 425                 430 ccc aaa cgt cag cca aac ggc acc tgt gag ccc aac cct cgc ctc aac     3023
Pro Lys Arg Gln Pro Asn Gly Thr Cys Glu Pro Asn Pro Arg Leu Asn
            435                 440                 445 ttc tat ccg gcc ttt gct gtc cca gaa gtg ctt gct acc tac cac atc     3071
Phe Tyr Pro Ala Phe Ala Val Pro Glu Val Leu Ala Thr Tyr His Ile
        450                 455                 460 ttt ttc aag aac caa aag att cca gtt tcc tgc cgt gcc aac cgc acc     3119
Phe Phe Lys Asn Gln Lys Ile Pro Val Ser Cys Arg Ala Asn Arg Thr
    465                 470                 475 cgc gcc gat gcc ctg ctc aac ttg ggt ccg gga gct cgc tta cct gat     3167
Arg Ala Asp Ala Leu Leu Asn Leu Gly Pro Gly Ala Arg Leu Pro Asp
480                 485                 490
```

```
ata gct tcc ttg gaa gag gtt cca aag atc ttc gag ggt ctg ggc agt       3215
Ile Ala Ser Leu Glu Glu Val Pro Lys Ile Phe Glu Gly Leu Gly Ser
495             500                 505                 510 gat gag act cgg gcc gca aat gct ctg caa cag gga gag aat ggc atg       3263
Asp Glu Thr Arg Ala Ala Asn Ala Leu Gln Gln Gly Glu Asn Gly Met
                515                 520                 525 gat gaa cat cac agc gct ctg gtg gag ttg gag gga gac aat gcc cgg       3311
Asp Glu His His Ser Ala Leu Val Glu Leu Glu Gly Asp Asn Ala Arg
            530                 535                 540 ctt gca gtg ctc aag cgc agt atc gag gtc acc cat ttt gca tac ccc       3359
Leu Ala Val Leu Lys Arg Ser Ile Glu Val Thr His Phe Ala Tyr Pro
        545                 550                 555 gct gtc aac ctg ccc ccc aaa gtc atg agc gct gtc atg gat cag ctg       3407
Ala Val Asn Leu Pro Pro Lys Val Met Ser Ala Val Met Asp Gln Leu
    560                 565                 570 ctc atc aag cgc gca agc ccc ctt tcc gaa gac cag aac atg cag gat       3455
Leu Ile Lys Arg Ala Ser Pro Leu Ser Glu Asp Gln Asn Met Gln Asp
575                 580                 585                 590 cca gac gcc tct gac gag ggc aag ccg gtg gtc agt gac gag cag ctg       3503
Pro Asp Ala Ser Asp Glu Gly Lys Pro Val Val Ser Asp Glu Gln Leu
                595                 600                 605 tct cgc tgg ctg ggc acc aac tcc ccg cga gac ttg gaa gag agg cgc       3551
Ser Arg Trp Leu Gly Thr Asn Ser Pro Arg Asp Leu Glu Glu Arg Arg
            610                 615                 620 aag ctt atg atg gct gta gtg cta gtc act gtg gag ctg gag tgt ctc       3599
Lys Leu Met Met Ala Val Val Leu Val Thr Val Glu Leu Glu Cys Leu
        625                 630                 635 cgc cgc ttt ttc acc gac cct gag acc ctg cgc aag ctc gag gag aac       3647
Arg Arg Phe Phe Thr Asp Pro Glu Thr Leu Arg Lys Leu Glu Glu Asn
    640                 645                 650 ctg cac tat act ttc aga cat ggt ttc gtg cgc cag gca tgc aag atc       3695
Leu His Tyr Thr Phe Arg His Gly Phe Val Arg Gln Ala Cys Lys Ile
655                 660                 665                 670 tcc aac gtg gag ctc acc aac ctg gtc tcc tac atg ggc att ttg cat       3743
Ser Asn Val Glu Leu Thr Asn Leu Val Ser Tyr Met Gly Ile Leu His
                675                 680                 685 gag aac cgc ctg ggg cag agc gtg ttg cat acc acc ctg aaa ggg gag       3791
Glu Asn Arg Leu Gly Gln Ser Val Leu His Thr Thr Leu Lys Gly Glu
            690                 695                 700 gcc cgc cgc gac tac atc cgc gac tgt gtc tac ctc tac ctc tgc cat       3839
Ala Arg Arg Asp Tyr Ile Arg Asp Cys Val Tyr Leu Tyr Leu Cys His
        705                 710                 715 acc tgg cag act ggc atg ggt gta tgg cag cag tgt ttg gaa gag cag       3887
Thr Trp Gln Thr Gly Met Gly Val Trp Gln Gln Cys Leu Glu Glu Gln
    720                 725                 730 aac ctg aaa gag ctg gac aag ctc ttg cag aga tcc ctc aaa gcc ctg       3935
Asn Leu Lys Glu Leu Asp Lys Leu Leu Gln Arg Ser Leu Lys Ala Leu
735                 740                 745                 750 tgg aca ggt ttt gac gag cgc acc gtc gcc tca gac ctg gca gac atc       3983
Trp Thr Gly Phe Asp Glu Arg Thr Val Ala Ser Asp Leu Ala Asp Ile
                755                 760                 765 atc ttc ccc gag cgt ctc agg gtt act ctg cgc aac ggc ctg cct gac       4031
Ile Phe Pro Glu Arg Leu Arg Val Thr Leu Arg Asn Gly Leu Pro Asp
            770                 775                 780 ttc atg agc cag agc atg ctt aac aac ttt cgc tct ttc atc ctg gaa       4079
Phe Met Ser Gln Ser Met Leu Asn Asn Phe Arg Ser Phe Ile Leu Glu
        785                 790                 795 cgc tcc ggt atc ctg ccc gcc acc tgc tgc gcg ctg ccc tcc gac ttt       4127
Arg Ser Gly Ile Leu Pro Ala Thr Cys Cys Ala Leu Pro Ser Asp Phe
```

-continued

```
            800                 805                 810
gtg cct ctc acc tac cgc gag tgc ccc ccg ccg cta tgg agc cac tgc   4175
Val Pro Leu Thr Tyr Arg Glu Cys Pro Pro Pro Leu Trp Ser His Cys
815                 820                 825                 830 tac ctg ttc cgc ctg gcc aac tac ctc tcc tac cac tcg gat gtg atc   4223
Tyr Leu Phe Arg Leu Ala Asn Tyr Leu Ser Tyr His Ser Asp Val Ile
                835                 840                 845 gag gat gtg agc gga gac ggt ctg ctg gag tgc cac tgc cgc tgc aat   4271
Glu Asp Val Ser Gly Asp Gly Leu Leu Glu Cys His Cys Arg Cys Asn
            850                 855                 860 ctt tgc aca ccc cac cgt tcc ctc gcc tgc aac ccc cag ttg ctg agc   4319
Leu Cys Thr Pro His Arg Ser Leu Ala Cys Asn Pro Gln Leu Leu Ser
        865                 870                 875 gag act cag atc atc ggc acc ttc gag ttg cag ggt ccc agc agt gaa   4367
Glu Thr Gln Ile Ile Gly Thr Phe Glu Leu Gln Gly Pro Ser Ser Glu
880                 885                 890 ggc gag ggg tct tct ccg ggg cag agt ctg aaa ctg act ccg ggg cta   4415
Gly Glu Gly Ser Ser Pro Gly Gln Ser Leu Lys Leu Thr Pro Gly Leu
895                 900                 905                 910 tgg acc tcc gcc tac ctg cgc aag ttc gcc ccc gaa gac tac cac ccc   4463
Trp Thr Ser Ala Tyr Leu Arg Lys Phe Ala Pro Glu Asp Tyr His Pro
                915                 920                 925 tat gag atc agg ttc tat gag gac caa tca cag ccg ccc aaa acc gag   4511
Tyr Glu Ile Arg Phe Tyr Glu Asp Gln Ser Gln Pro Pro Lys Thr Glu
            930                 935                 940 ctc tca gcc tgc gtc atc act cag ggg gca att ctc gcc caa ttg caa   4559
Leu Ser Ala Cys Val Ile Thr Gln Gly Ala Ile Leu Ala Gln Leu Gln
        945                 950                 955 gcc atc caa aaa tcc cgc caa gaa ttt ctg ctg aaa aag ggg aac ggg   4607
Ala Ile Gln Lys Ser Arg Gln Glu Phe Leu Leu Lys Lys Gly Asn Gly
960                 965                 970 gtc tac ctc gac ccc cag acc ggt gag gag ctc aac aca agg ttc cct   4655
Val Tyr Leu Asp Pro Gln Thr Gly Glu Glu Leu Asn Thr Arg Phe Pro
975                 980                 985                 990 cag gat gtc cca gcg ccg agg aag caa gaa gtt gaa ggt gca gct gcc   4703
Gln Asp Val Pro Ala Pro Arg Lys Gln Glu Val Glu Gly Ala Ala Ala
                995                1000                1005 gcc ccc aga gga tat gga gga aga ctg gga cag tca ggc aga    gga   4748
Ala Pro Arg Gly Tyr Gly Gly Arg Leu Gly Gln Ser Gly Arg    Gly
            1010                1015                1020 gga gga gat gga aga ttg gga cag cca ggc aga gga ggc gga    cag   4793
Gly Gly Asp Gly Arg Leu Gly Gln Pro Gly Arg Gly Gly Gly    Gln
            1025                1030                1035 cct gga gga aga cag ttt gga gga gga aga cga gga ggc aga    gga   4838
Pro Gly Gly Arg Gln Phe Gly Gly Gly Arg Arg Gly Gly Arg    Gly
            1040                1045                1050 ggt gga aga agc agc cgc cgc caa aca gtt gtc ctc ggc agc    gga   4883
Gly Gly Arg Ser Ser Arg Arg Gln Thr Val Val Leu Gly Ser    Gly
            1055                1060                1065 gac aag caa ggc ccc aga cag cag cag cag cac ggc tac aat    ctc   4928
Asp Lys Gln Gly Pro Arg Gln Gln Gln Gln His Gly Tyr Asn    Leu
            1070                1075                1080 cgc tcc ggg tcg ggg ggc cca gca gcg tcc caa cag tagatgggac        4974
Arg Ser Gly Ser Gly Gly Pro Ala Ala Ser Gln Gln
            1085                1090 gagaccgggc gattcccgaa cccgaccacc gcttccaaga ccggtaagaa ggagcggcag   5034
ggatacaagt cctggcgggg gcataagaat gccatcatct cctgcttgca tgaatgcggg   5094
ggcaacatat ccttcacccg gcgctacctg ctcttccacc acggggtgaa cttccccgc    5154
```

```
aatgtcttgc attactaccg tcacctccac agccctact acagccagca agtcccgaca    5214
gcctcggcag agaagacag cagcagcggg gacctccagc agaaaaccag cagcagcagt    5274
tagaaaatcc agtgcagcag gaggaggact gaggatcaca gcgaacgagc cagcgcagac    5334
ccgagagctg agaaacagga tctttccaac cctctatgcc atcttccagc agagtcgggg    5394
gcaagagcag gaactgaaag taaaaaaccg atctctgcgc tcgctcaccc gaagttgttt    5454
gtatcacaag agcgaagacc aacttcagcg cactctcgag gacgccgagg ctctcttcaa    5514
caagtactgc gcgctgactc ttaaagagta gcccgcgccc gcgctcgctc gaaaaaggcg    5574
ggaattacgt caccccttggc acctgtcctt tgccctcgtc atgagtaaag aaattcccac    5634
gccttacatg tggagctatc agccccaaat gggactggca gcaggcgcct cccaggacta    5694
ctccacccgc atgaattggc tcagcgccgg cccctcgatg atctcacggg ttaatgatat    5754
acgagcttac cgaaaccagt tactcctaga acagtcagct ctcaccacca caccccgcca    5814
acaccttaat ccccggaatt ggcccgccgc cctggtgtac caggaaactc ccgctcccac    5874
caccgtacta cttcctcgag acgcccaggc cgaagttcag atgactaacg caggtgtaca    5934
gctggcgggg ggttccgccc tgtgtcgtca ccggcctcag cagagtataa acgcctggt    5994 gatcagaggc cgaggtatcc agctcaacga cgagtcggtg agctcttcgc ttggtctgcg    6054
accagacgga gtcttccaaa tcgccggctg tgggagatct tccttcactc ctcgtcaggc    6114
tgtcctgact ttggagagtt cgtcctcgca accccgctcg ggcggcatcg ggactctcca    6174
gtttgtggag gagtttactc cctctgtcta cttcaacccc ttctccggct ctcctggcca    6234
gtacccggac gagttcatac cgaacttcga cgcaatcagc gagtcagtgg atggctatga    6294
ttgatgtctg gtggcgcggc tgagttagct cgactcgcgac atctagacca ctgccgccgc    6354
tttcgctgtt tcgcccggga actcaccgag ttcatctact tcgaactccc cgaggagcac    6414
cctcagggac cggcccacgg agtgcggatt accatcgaag ggggaataga ctctcgcctg    6474
catcggatct tctgccagcg acccgtgctg atcgagcgcg accagggaac tacaacagtc    6534
tccatctact gcatctgtaa ccaccccgga ttgc atg aaa gcc ttt gct gtc       6586
                                     Met Lys Ala Phe Ala Val
                                         1095 tta ttt gtg ctg agt tta ata aaa act gag ttc aga ccc tcc tac         6631
Leu Phe Val Leu Ser Leu Ile Lys Thr Glu Phe Arg Pro Ser Tyr
1100                1105                1110 gga cta ccg ctt ctt caa ccc gga ctt tac aac acc agc cag aag         6676
Gly Leu Pro Leu Leu Gln Pro Gly Leu Tyr Asn Thr Ser Gln Lys
1115                1120                1125 acc cag acc ctt cct ctg atc cag gac tct aat tct acc tcc cca         6721
Thr Gln Thr Leu Pro Leu Ile Gln Asp Ser Asn Ser Thr Ser Pro
1130                1135                1140 gca cct ttt cct act aac ctt ccc gtt act aac aac ctc gaa gct         6766
Ala Pro Phe Pro Thr Asn Leu Pro Val Thr Asn Asn Leu Glu Ala
1145                1150                1155 cag ctg caa cac cgc ttc tcc aga agc ctc ctt tct gcc aat act         6811
Gln Leu Gln His Arg Phe Ser Arg Ser Leu Leu Ser Ala Asn Thr
1160                1165                1170 act act ccc aga acc gga ggt gag ctc cgt ggt ctc cct act aac         6856
Thr Thr Pro Arg Thr Gly Gly Glu Leu Arg Gly Leu Pro Thr Asn
1175                1180                1185 aac ccc tgg gtg gta gcg ggt ttt gta gcg cta gga gta gtt gcg         6901
Asn Pro Trp Val Val Ala Gly Phe Val Ala Leu Gly Val Val Ala
1190                1195                1200
```

| | | |
|---|---|---|
| ggt ggg ctg gtg ctt ata ctc tgc tac cta tac aca cct tgc tgt<br>Gly Gly Leu Val Leu Ile Leu Cys Tyr Leu Tyr Thr Pro Cys Cys<br>1205                      1210                      1215 | | 6946 |
| gct tat tta gta gta ttg tgt tgc tgg ttt aag aaa tgg ggg tcg<br>Ala Tyr Leu Val Val Leu Cys Cys Trp Phe Lys Lys Trp Gly Ser<br>1220                      1225                      1230 | | 6991 |
| tac   tagtagcgct tgctttactt tcgcttttgg gtctgggctc tgctaatctc<br>Tyr<br>1235 | | 7044 |
| attcctcccg atcacgatcc atgtctggac tttaatccag agaactgcac aatcactttt | | 7104 |
| gcacctgaaa caagtcgctt ctgtggagtt gttattaggt gcggatttga atgcaggccc | | 7164 |
| attgagatta cacacaataa caaaacttgg aacaatacct tattcacaat atggcaacca | | 7224 |
| ggagaccctc agtggtatac tgtctctgtc cggggtcctg acggttccgt ccgcatggct | | 7284 |
| aataacactt ttattttttgc tgaaatgtgc gatatggcca tgttcatgag cagacagtat | | 7344 |
| gacctatggc ctcccagcaa agagaacatt gtggcattct ccattgctta ttgcttctgt | | 7404 |
| acttgcctta tcactgctac tttgtgtatt tgcttacact tacttatagc atttcgccca | | 7464 |
| aaaaacagca acgaggaaaa agaaaaagtg ccttaatctt ttcctcacct ttttttgttta | | 7524 |
| cagcatggct tctgttgctg ttctaatctt tataattaca tcagttcata catttgggct | | 7584 |
| aaaatttaat gatcaaatag tccatgtagg ttccaaccat acactgcgtg gaccaatagg | | 7644 |
| caattcagaa gtaacctggt actggtatta tgcagatgat agctggcctg aaaaactttg | | 7704 |
| tgatgacatt aatttacata acattcttac aaaaactctt aatagtaaga ctattaaata | | 7764 |
| taactgtact gattatgatt taattctagt taatgtcact acaaactatt caggttttta | | 7824 |
| ttacggaact aattttgaaa atgttgcata ttataatatt ctagtaaagt ttagacctac | | 7884 |
| aacaactaaa acgtctagca gcagtactat aaccagcacc acgcttccaa ttagaacagc | | 7944 |
| aatgtttcaa ttgaacaaaa tagaaaatac caccaatagc aattacactc tattcaacga | | 8004 |
| tcaaaatgtt caagggtcat taactacaat tatcattcta ctaattgtgg ggttaataat | | 8064 |
| tataataatt tgcatgatag tctataccctg ccgctacaga aaactacaca ataaagtaga | | 8124 |
| cccctattag attccatact tagacatcta acttttttta aaacacttta ttttcagcca | | 8184 |
| tgatttctat tacaacccctt ctctatatca ctgccattac tactgtacag gggttcacaa | | 8244 |
| acatcaaaaa aacaatacat gtgggatcca gttctacact agaaggttac caatcccaat | | 8304 |
| cacgtgtttc ttggtattgg tattaccgta atcagccagc tattcacactt tgcaaaggat | | 8364 |
| ctcaggaaac cacaatacgc acaatcaaat acaaatgcaa taacaataat ttaaccctaa | | 8424 |
| ttgatgttac agctcaatat gcaggaactt actatggaac aaattttaac ataggacaag | | 8484 |
| acacatacta taccattaca gtaattaact ctactactcc tgtaacaact accataaaac | | 8544 |
| ctacaaaaac taaaagcaca aaaactcaca ttttccctag cagcaagccc acctcaatct | | 8604 |
| atacaacttc acttttgcaa ctacttcaaa aggctaacgt tacagacaat tatactatta | | 8664 |
| accccactct tcctagcgaa gagatacccca aatcaatgat aggaattatt gctgctgtgg | | 8724 |
| tagcgggaat gctaattata attctatgta tgatttatta tgcttgctgc tatagaaaat | | 8784 |
| atgaacatga acaaaaaata gacccactac tgagctttga tatttaattt tttttagagc | | 8844 |
| accatgaaag gtccagttat cctattgttt atttccactt tttggtgttg tgatacttttt | | 8904 |
| tcaattacca ccaatgtgca gactacttta ataacatca tgactacctc taacacacaa | | 8964 |
| cttttcacctc aatctgaaga tgacataaaa ctacaaatca ctatccttat tgtaattggt | | 9024 |
| ttaattatcc ttgctgttct cctttacttt atcttttgcc gtcaaatacc caatgtagtt | | 9084 |

```
aagaaaccta ccagacgtcc catctatcga tcaataatca gcaaacccca catggctcta    9144
aatgaaattt aatctttctc ttcacagtat ggtgatcaac tatgatccct agaaatttct    9204
tcttcaccat acttatctgc gctttcaatg tctgtgctac attcgccaca gtcgccaatg    9264
tgacaccaga ttgtataggg gcatttgctt cctacgtact atttgccttc attacctgca    9324
tctgcgtttg tagcatagtc tgcctggtta tcaacttctt tcaactagta gactgggttt    9384
ttgtacgcat tgcctaccta caacatcacc ctgaataccg caaccaaa atg ttg cag     9441
                                                  Met Leu Gln caa ttc tta ggc tca ttt aaa acc atg caa act ctg cta ctg ctt         9486
Gln Phe Leu Gly Ser Phe Lys Thr Met Gln Thr Leu Leu Leu Leu
    1240            1245                1250 ctg cta gtt ata cac cca tgt gcc tca aac ccc aca agc ccc aca         9531
Leu Leu Val Ile His Pro Cys Ala Ser Asn Pro Thr Ser Pro Thr
    1255            1260                1265 aaa tta gat cta aga aaa tgt aaa ttt caa gaa cca tgg aaa ttc         9576
Lys Leu Asp Leu Arg Lys Cys Lys Phe Gln Glu Pro Trp Lys Phe
    1270            1275                1280 ctt gat tgc tat cat gaa aca tct gat ttc ccc aca tac tgg att         9621
Leu Asp Cys Tyr His Glu Thr Ser Asp Phe Pro Thr Tyr Trp Ile
    1285            1290                1295 aca atc att ggg gtt gtt aat cta gtc tct tgc aca cta ttc tct         9666
Thr Ile Ile Gly Val Val Asn Leu Val Ser Cys Thr Leu Phe Ser
    1300            1305                1310 ttc ctt gtt tac cac tta ttt gat ttt gga tgg aac tcc ctc aat         9711
Phe Leu Val Tyr His Leu Phe Asp Phe Gly Trp Asn Ser Leu Asn
    1315            1320                1325 gca ctc act tac cca caa gaa cca gag gaa cat ata cca cta cag         9756
Ala Leu Thr Tyr Pro Gln Glu Pro Glu Glu His Ile Pro Leu Gln
    1330            1335                1340 aac ata caa cca tta gca cta gta gaa tat gaa aat gag cca cag         9801
Asn Ile Gln Pro Leu Ala Leu Val Glu Tyr Glu Asn Glu Pro Gln
    1345            1350                1355 cct cca cta ctc cct gcc att agc tac ttc aac tta acc ggt gga         9846
Pro Pro Leu Leu Pro Ala Ile Ser Tyr Phe Asn Leu Thr Gly Gly
    1360            1365                1370 gat gac      tgacccac                                                9860
Asp Asp
    1375
```

<210> SEQ ID NO 58
<211> LENGTH: 262
<212> TYPE: PRT
<213> ORGANISM: Unknown
<220> FEATURE:
<223> OTHER INFORMATION: Synthetic Construct

<400> SEQUENCE: 58

```
Met Ser Pro Pro Cys Phe Met Phe Phe Ser Lys Ser Ser Thr Trp Ser
1               5                   10                  15

Glu Cys Thr Ser His Thr Ala Ala Ser Ser Arg Leu Ser Thr Cys Val
                20                  25                  30

Pro Arg Ser Gln Leu Val Thr Pro His Lys Glu Ala Ser Cys Phe
            35                  40                  45

Leu Gln Ala Ala Ala Met Ala Cys Gly Ser Gly Asn Gly Ser Ser Glu
        50                  55                  60

Gln Glu Leu Arg Ala Ile Ala Arg Asp Leu Gly Cys Gly Pro Tyr Phe
65                  70                  75                  80
```

Leu Gly Thr Phe Asp Lys Arg Phe Pro Gly Phe Met Ala Pro Asp Lys
                85                  90                  95

Leu Ala Cys Ala Ile Val Asn Thr Ala Gly Arg Glu Thr Gly Gly Glu
            100                 105                 110

His Trp Leu Ala Phe Gly Trp Asn Pro Arg Ser Asn Thr Cys Tyr Leu
        115                 120                 125

Phe Asp Pro Phe Gly Phe Ser Asp Glu Arg Leu Lys Gln Ile Tyr Gln
    130                 135                 140

Phe Glu Tyr Glu Gly Leu Leu Arg Arg Ser Ala Leu Ala Thr Lys Asp
145                 150                 155                 160

Arg Cys Ile Thr Leu Glu Lys Ser Thr Gln Thr Val Gln Gly Pro Arg
                165                 170                 175

Ser Ala Ala Cys Gly Leu Phe Cys Cys Met Phe Leu His Ala Phe Val
            180                 185                 190

His Trp Pro Asp Arg Pro Met Asp Gly Asn Pro Thr Met Lys Leu Leu
        195                 200                 205

Thr Gly Val Pro Asn Ser Met Leu Gln Ser Pro Gln Val Gln Pro Thr
    210                 215                 220

Leu Arg His Asn Gln Glu Ala Leu Tyr Arg Phe Leu Asn Ser His Ser
225                 230                 235                 240

Ser Tyr Phe Arg Ser His Arg Ala Arg Ile Glu Lys Ala Thr Ala Phe
                245                 250                 255

Asn Arg Met Asp Met Gln
            260

<210> SEQ ID NO 59
<211> LENGTH: 831
<212> TYPE: PRT
<213> ORGANISM: Unknown
<220> FEATURE:
<223> OTHER INFORMATION: Synthetic Construct

<400> SEQUENCE: 59

Met Glu Thr Gln Pro Ser Leu Pro Thr Pro Leu Gln Ala Pro Ser His
1               5                   10                  15

Leu Ala Pro Ser Ser Asp Glu Glu Ser Leu Thr Pro Pro Pro Pro Pro
            20                  25                  30

Ser Pro Ala Thr Thr Thr Ser Thr Leu Glu Asp Glu Glu Glu Val Asp
        35                  40                  45

Ala Pro Gln Glu Met Gln Asp Met Glu Asp Glu Lys Ala Glu Glu Ile
    50                  55                  60

Glu Ala Asp Val Glu Gln Asp Pro Gly Tyr Val Thr Pro Ala Glu His
65                  70                  75                  80

Glu Glu Glu Leu Arg Arg Phe Leu Asp Arg Glu Asp Asp Asn Arg Pro
                85                  90                  95

Glu Gln Lys Ala Asp Gly Asp His Gln Glu Ala Gly Leu Gly Asp His
            100                 105                 110

Val Ala Asp Tyr Leu Thr Gly Leu Gly Gly Glu Asp Val Leu Leu Lys
        115                 120                 125

His Leu Ala Arg Gln Ser Ile Ile Val Lys Asp Ala Leu Leu Asp Arg
    130                 135                 140

Thr Glu Val Pro Ile Ser Val Glu Glu Leu Ser Arg Ala Tyr Glu Leu
145                 150                 155                 160

Asn Leu Phe Ser Pro Arg Leu Pro Pro Lys Arg Gln Pro Asn Gly Thr
                165                 170                 175

```
Cys Glu Pro Asn Pro Arg Leu Asn Phe Tyr Pro Ala Phe Ala Val Pro
            180                 185                 190
Glu Val Leu Ala Thr Tyr His Ile Phe Phe Lys Asn Gln Lys Ile Pro
        195                 200                 205
Val Ser Cys Arg Ala Asn Arg Thr Arg Ala Asp Ala Leu Leu Asn Leu
    210                 215                 220
Gly Pro Gly Ala Arg Leu Pro Asp Ile Ala Ser Leu Glu Glu Val Pro
225                 230                 235                 240
Lys Ile Phe Glu Gly Leu Gly Ser Asp Glu Thr Arg Ala Ala Asn Ala
                245                 250                 255
Leu Gln Gln Gly Glu Asn Gly Met Asp Glu His His Ser Ala Leu Val
            260                 265                 270
Glu Leu Glu Gly Asp Asn Ala Arg Leu Ala Val Leu Lys Arg Ser Ile
        275                 280                 285
Glu Val Thr His Phe Ala Tyr Pro Ala Val Asn Leu Pro Pro Lys Val
    290                 295                 300
Met Ser Ala Val Met Asp Gln Leu Leu Ile Lys Arg Ala Ser Pro Leu
305                 310                 315                 320
Ser Glu Asp Gln Asn Met Gln Asp Pro Asp Ala Ser Asp Gly Lys
                325                 330                 335
Pro Val Val Ser Asp Glu Gln Leu Ser Arg Trp Leu Gly Thr Asn Ser
            340                 345                 350
Pro Arg Asp Leu Glu Glu Arg Lys Leu Met Met Ala Val Val Leu
        355                 360                 365
Val Thr Val Glu Leu Glu Cys Leu Arg Arg Phe Phe Thr Asp Pro Glu
    370                 375                 380
Thr Leu Arg Lys Leu Glu Glu Asn Leu His Tyr Thr Phe Arg His Gly
385                 390                 395                 400
Phe Val Arg Gln Ala Cys Lys Ile Ser Asn Val Glu Leu Thr Asn Leu
                405                 410                 415
Val Ser Tyr Met Gly Ile Leu His Glu Asn Arg Leu Gly Gln Ser Val
            420                 425                 430
Leu His Thr Thr Leu Lys Gly Glu Ala Arg Arg Asp Tyr Ile Arg Asp
        435                 440                 445
Cys Val Tyr Leu Tyr Leu Cys His Thr Trp Gln Thr Gly Met Gly Val
    450                 455                 460
Trp Gln Gln Cys Leu Glu Glu Gln Asn Leu Lys Glu Leu Asp Lys Leu
465                 470                 475                 480
Leu Gln Arg Ser Leu Lys Ala Leu Trp Thr Gly Phe Asp Glu Arg Thr
                485                 490                 495
Val Ala Ser Asp Leu Ala Asp Ile Ile Phe Pro Glu Arg Leu Arg Val
            500                 505                 510
Thr Leu Arg Asn Gly Leu Pro Asp Phe Met Ser Gln Ser Met Leu Asn
        515                 520                 525
Asn Phe Arg Ser Phe Ile Leu Glu Arg Ser Gly Ile Leu Pro Ala Thr
    530                 535                 540
Cys Cys Ala Leu Pro Ser Asp Phe Val Pro Leu Thr Tyr Arg Glu Cys
545                 550                 555                 560
Pro Pro Pro Leu Trp Ser His Cys Tyr Leu Phe Arg Leu Ala Asn Tyr
                565                 570                 575
Leu Ser Tyr His Ser Asp Val Ile Glu Asp Val Ser Gly Asp Gly Leu
            580                 585                 590
Leu Glu Cys His Cys Arg Cys Asn Leu Cys Thr Pro His Arg Ser Leu
```

```
                    595                 600                 605
Ala Cys Asn Pro Gln Leu Leu Ser Glu Thr Gln Ile Ile Gly Thr Phe
            610                 615                 620
Glu Leu Gln Gly Pro Ser Ser Glu Gly Glu Gly Ser Ser Pro Gly Gln
625                 630                 635                 640
Ser Leu Lys Leu Thr Pro Gly Leu Trp Thr Ser Ala Tyr Leu Arg Lys
                645                 650                 655
Phe Ala Pro Glu Asp Tyr His Pro Tyr Glu Ile Arg Phe Tyr Glu Asp
            660                 665                 670
Gln Ser Gln Pro Pro Lys Thr Glu Leu Ser Ala Cys Val Ile Thr Gln
        675                 680                 685
Gly Ala Ile Leu Ala Gln Leu Gln Ala Ile Gln Lys Ser Arg Gln Glu
    690                 695                 700
Phe Leu Leu Lys Lys Gly Asn Gly Val Tyr Leu Asp Pro Gln Thr Gly
705                 710                 715                 720
Glu Glu Leu Asn Thr Arg Phe Pro Gln Asp Val Pro Ala Pro Arg Lys
                725                 730                 735
Gln Glu Val Glu Gly Ala Ala Ala Pro Arg Gly Tyr Gly Gly Arg
            740                 745                 750
Leu Gly Gln Ser Gly Arg Gly Gly Asp Gly Arg Leu Gly Gln Pro
        755                 760                 765
Gly Arg Gly Gly Gln Pro Gly Gly Arg Gln Phe Gly Gly Arg
    770                 775                 780
Arg Gly Gly Arg Gly Gly Arg Ser Ser Arg Arg Gln Thr Val Val
785                 790                 795                 800
Leu Gly Ser Gly Asp Lys Gln Gly Pro Arg Gln Gln Gln His Gly
                805                 810                 815
Tyr Asn Leu Arg Ser Gly Ser Gly Pro Ala Ala Ser Gln Gln
            820                 825                 830

<210> SEQ ID NO 60
<211> LENGTH: 142
<212> TYPE: PRT
<213> ORGANISM: Unknown
<220> FEATURE:
<223> OTHER INFORMATION: Synthetic Construct

<400> SEQUENCE: 60

Met Lys Ala Phe Ala Val Leu Phe Val Leu Ser Leu Ile Lys Thr Glu
1               5                   10                  15
Phe Arg Pro Ser Tyr Gly Leu Pro Leu Leu Gln Pro Gly Leu Tyr Asn
            20                  25                  30
Thr Ser Gln Lys Thr Gln Thr Leu Pro Leu Ile Gln Asp Ser Asn Ser
        35                  40                  45
Thr Ser Pro Ala Pro Phe Pro Thr Asn Leu Pro Val Thr Asn Asn Leu
    50                  55                  60
Glu Ala Gln Leu Gln His Arg Phe Ser Arg Ser Leu Leu Ser Ala Asn
65                  70                  75                  80
Thr Thr Thr Pro Arg Thr Gly Gly Glu Leu Arg Gly Leu Pro Thr Asn
                85                  90                  95
Asn Pro Trp Val Val Ala Gly Phe Val Ala Leu Gly Val Ala Leu Gly
            100                 105                 110
Gly Leu Val Leu Ile Leu Cys Tyr Leu Tyr Thr Pro Cys Cys Ala Tyr
        115                 120                 125
Leu Val Val Leu Cys Cys Trp Phe Lys Lys Trp Gly Ser Tyr
```

130          135          140

<210> SEQ ID NO 61
<211> LENGTH: 140
<212> TYPE: PRT
<213> ORGANISM: Unknown
<220> FEATURE:
<223> OTHER INFORMATION: Synthetic Construct

<400> SEQUENCE: 61

Met Leu Gln Gln Phe Leu Gly Ser Phe Lys Thr Met Gln Thr Leu Leu
1               5                   10                  15

Leu Leu Leu Leu Val Ile His Pro Cys Ala Ser Asn Pro Thr Ser Pro
            20                  25                  30

Thr Lys Leu Asp Leu Arg Lys Cys Lys Phe Gln Glu Pro Trp Lys Phe
        35                  40                  45

Leu Asp Cys Tyr His Glu Thr Ser Asp Phe Pro Thr Tyr Trp Ile Thr
    50                  55                  60

Ile Ile Gly Val Val Asn Leu Val Ser Cys Thr Leu Phe Ser Phe Leu
65                  70                  75                  80

Val Tyr His Leu Phe Asp Phe Gly Trp Asn Ser Leu Asn Ala Leu Thr
                85                  90                  95

Tyr Pro Gln Glu Pro Glu Glu His Ile Pro Leu Gln Asn Ile Gln Pro
            100                 105                 110

Leu Ala Leu Val Glu Tyr Glu Asn Glu Pro Gln Pro Pro Leu Leu Pro
        115                 120                 125

Ala Ile Ser Tyr Phe Asn Leu Thr Gly Gly Asp Asp
    130                 135                 140

<210> SEQ ID NO 62
<211> LENGTH: 1500
<212> TYPE: DNA
<213> ORGANISM: Unknown
<220> FEATURE:
<223> OTHER INFORMATION: Simian adenovirus 41.2
<220> FEATURE:
<221> NAME/KEY: CDS
<222> LOCATION: (573)..(1149)
<223> OTHER INFORMATION: E1a
<220> FEATURE:
<221> NAME/KEY: CDS
<222> LOCATION: (1243)..(1448)
<223> OTHER INFORMATION: E1a

<400> SEQUENCE: 62
catcatcaat aatataccct ataaatggaa cggtgccaac atgcaaatga gcttttgaaa        60
atggagggcg gaaggggatt ggccagcggg ttcaacggtc aaaagggggcg ggccggcgcg      120 gggaggtgac gtggttagtg tgggaggagt tatgttgcaa gttctcgcgg taaatgtgac       180
gtaaaacgag gtgtggtttg aacacggaag tacacagttt tcccgcgctg actgacagga      240
tatgaggtag ttttgggcgg atgcaagtga aaattctcca ttttcgcgcg aaaactgaat      300
gaggaagtga atttctgagt aatttcgagt ttatgacagg gcggagtatt taccgagggc      360
cgagtagact ttgaccgatt acgtggaggt ttcgattacc gtgttttca cctaaatttc       420 cgcgtacggt gtcaaagtcc tgtgtttta cgtaggcgtc agctgatcgc tagggtattt      480
aaacctgacg agttccgtca gaggccact cttgagtgcc agcgagaaga gatttctcct      540
ccgcgccgcg agtcagatct ccactttgaa aa atg aga cac ctg cga ttc ctg       593
                                    Met Arg His Leu Arg Phe Leu
                                    1               5

| | | |
|---|---|---|
| cct cag gaa atc tcc att gcg acc ggg aat gaa ata ctg cag ttt gtg<br>Pro Gln Glu Ile Ser Ile Ala Thr Gly Asn Glu Ile Leu Gln Phe Val<br>10                       15                     20 | | 641 |
| gta gat gcc ctg atg gga gac gat ccg gag ccg cct gcg cag cct ttc<br>Val Asp Ala Leu Met Gly Asp Asp Pro Glu Pro Pro Ala Gln Pro Phe<br>    25                    30                    35 | | 689 |
| gat cct cct acg ctt cat gaa ctg tat gat tta gag gta gac ggg ccg<br>Asp Pro Pro Thr Leu His Glu Leu Tyr Asp Leu Glu Val Asp Gly Pro<br>40                       45                     50                     55 | | 737 |
| gag gat cct aac gag gaa gct gtg aat ggt ttt ttc agc gat tct atg<br>Glu Asp Pro Asn Glu Glu Ala Val Asn Gly Phe Phe Ser Asp Ser Met<br>                  60                          65                         70 | | 785 |
| cta tta gct gct agt gaa gga gtg gac tta gac cca cct tct gag acc<br>Leu Leu Ala Ala Ser Glu Gly Val Asp Leu Asp Pro Pro Ser Glu Thr<br>                75                         80                         85 | | 833 |
| ctt gat acc cca ggg gtg gtg gtg gaa agc ggc aga ggt ggg aaa aaa<br>Leu Asp Thr Pro Gly Val Val Val Glu Ser Gly Arg Gly Gly Lys Lys<br>90                       95                    100 | | 881 |
| ttg cct gaa ctt ggt gct gct gaa atg gat ttg cac tgt tat gaa gag<br>Leu Pro Glu Leu Gly Ala Ala Glu Met Asp Leu His Cys Tyr Glu Glu<br>105                      110                    115 | | 929 |
| ggc ttt cct ccg agt gat gat gaa gat gag gaa aat gtg cag tcg atc<br>Gly Phe Pro Pro Ser Asp Asp Glu Asp Glu Glu Asn Val Gln Ser Ile<br>120                    125                    130                    135 | | 977 |
| cag acc gca gct ggt gag gga atg aaa gct gcc aat gat ggt ttt aag<br>Gln Thr Ala Ala Gly Glu Gly Met Lys Ala Ala Asn Asp Gly Phe Lys<br>                  140                    145                    150 | | 1025 |
| ttg gac tac ccg gag ctg cct gga cat ggc tgt aag tct tgt gaa ttt<br>Leu Asp Tyr Pro Glu Leu Pro Gly His Gly Cys Lys Ser Cys Glu Phe<br>155                      160                    165 | | 1073 |
| cac agg aat agt act gga cta aaa gaa ctg ttg tgc tcg ctt tgc tat<br>His Arg Asn Ser Thr Gly Leu Lys Glu Leu Leu Cys Ser Leu Cys Tyr<br>170                      175                    180 | | 1121 |
| atg aga acg cac tgc cat ttt att tac a gtaagtgtgt ttaagttaaa<br>Met Arg Thr His Cys His Phe Ile Tyr<br>    185                    190 | | 1169 |
| tttaaggga cagtgtagca gtgttaataa ctgtgaatgt gggatttatg ttttttgctt | | 1229 |
| gtgattttta tag gt cct gtg tct gat gct gat gaa tcg cct tct cct<br>                        Ser Pro Val Ser Asp Ala Asp Glu Ser Pro Ser Pro<br>                                             195                    200 | | 1277 |
| gat tca act acc tca cct cct gaa att cag gcg cca gtc cct gca aac<br>Asp Ser Thr Thr Ser Pro Pro Glu Ile Gln Ala Pro Val Pro Ala Asn<br>205                      210                    215                    220 | | 1325 |
| gta tgc aag ccc att cct gtg aag gct aag cct ggg aaa cgc cct gct<br>Val Cys Lys Pro Ile Pro Val Lys Ala Lys Pro Gly Lys Arg Pro Ala<br>                  225                    230                    235 | | 1373 |
| gtg gat aag ctg gag gac ttg ctt gag ggt ggg gat gga cct ttg gac<br>Val Asp Lys Leu Glu Asp Leu Leu Glu Gly Gly Asp Gly Pro Leu Asp<br>240                      245                    250 | | 1421 |
| ttg agt acc cgg aaa ctg cca agg caa tgagtaccct gcacctgtgt<br>Leu Ser Thr Arg Lys Leu Pro Arg Gln<br>        255                    260 | | 1468 |
| ttatttaatg tgacgtcagt atttatgtga ga | | 1500 |

<210> SEQ ID NO 63
<211> LENGTH: 261
<212> TYPE: PRT
<213> ORGANISM: Unknown
<220> FEATURE:
<223> OTHER INFORMATION: Synthetic Construct

<400> SEQUENCE: 63

Met Arg His Leu Arg Phe Leu Pro Gln Glu Ile Ser Ile Ala Thr Gly
1               5                   10                  15

Asn Glu Ile Leu Gln Phe Val Val Asp Ala Leu Met Gly Asp Asp Pro
            20                  25                  30

Glu Pro Pro Ala Gln Pro Phe Asp Pro Pro Thr Leu His Glu Leu Tyr
        35                  40                  45

Asp Leu Glu Val Asp Gly Pro Glu Asp Pro Asn Glu Ala Val Asn
    50                  55                  60

Gly Phe Phe Ser Asp Ser Met Leu Leu Ala Ala Ser Glu Gly Val Asp
65              70                  75                  80

Leu Asp Pro Pro Ser Glu Thr Leu Asp Thr Pro Gly Val Val Val Glu
                85                  90                  95

Ser Gly Arg Gly Gly Lys Lys Leu Pro Glu Leu Gly Ala Ala Glu Met
            100                 105                 110

Asp Leu His Cys Tyr Glu Glu Gly Phe Pro Pro Ser Asp Asp Glu Asp
            115                 120                 125

Glu Glu Asn Val Gln Ser Ile Gln Thr Ala Ala Gly Glu Gly Met Lys
    130                 135                 140

Ala Ala Asn Asp Gly Phe Lys Leu Asp Tyr Pro Glu Leu Pro Gly His
145                 150                 155                 160

Gly Cys Lys Ser Cys Glu Phe His Arg Asn Ser Thr Gly Leu Lys Glu
                165                 170                 175

Leu Leu Cys Ser Leu Cys Tyr Met Arg Thr His Cys His Phe Ile Tyr
            180                 185                 190

Ser Pro Val Ser Asp Ala Asp Glu Ser Pro Ser Pro Asp Ser Thr Thr
            195                 200                 205

Ser Pro Pro Glu Ile Gln Ala Pro Val Pro Ala Asn Val Cys Lys Pro
    210                 215                 220

Ile Pro Val Lys Ala Lys Pro Gly Lys Arg Pro Ala Val Asp Lys Leu
225                 230                 235                 240

Glu Asp Leu Leu Glu Gly Gly Asp Gly Pro Leu Asp Leu Ser Thr Arg
                245                 250                 255

Lys Leu Pro Arg Gln
            260

<210> SEQ ID NO 64
<211> LENGTH: 900
<212> TYPE: DNA
<213> ORGANISM: Unknown
<220> FEATURE:
<223> OTHER INFORMATION: Simian adenovirus 41.2
<220> FEATURE:
<221> NAME/KEY: CDS
<222> LOCATION: (10)..(367)
<223> OTHER INFORMATION: 33K
<220> FEATURE:
<221> NAME/KEY: CDS
<222> LOCATION: (537)..(892)
<223> OTHER INFORMATION: 33K

<400> SEQUENCE: 64 tccctcagg atg tcc cag cgc cga gga agc aag aag ttg aag gtg cag ctg      51
          Met Ser Gln Arg Arg Gly Ser Lys Lys Leu Lys Val Gln Leu
          1               5                   10 ccg ccc cca gag gat atg gag gaa gac tgg gac agt cag gca gag gag      99
Pro Pro Pro Glu Asp Met Glu Glu Asp Trp Asp Ser Gln Ala Glu Glu
15                  20                  25                  30

```
gag gag atg gaa gat tgg gac agc cag gca gag gag gcg gac agc ctg      147
Glu Glu Met Glu Asp Trp Asp Ser Gln Ala Glu Glu Ala Asp Ser Leu
             35                  40                  45 gag gaa gac agt ttg gag gag gaa gac gag gag gca gag gag gtg gaa      195
Glu Glu Asp Ser Leu Glu Glu Glu Asp Glu Glu Ala Glu Glu Val Glu
         50                  55                  60 gaa gca gcc gcc gcc aaa cag ttg tcc tcg gca gcg gag aca agc aag      243
Glu Ala Ala Ala Ala Lys Gln Leu Ser Ser Ala Ala Glu Thr Ser Lys
 65                  70                  75 gcc cca gac agc agc agc agc acg gct aca atc tcc gct ccg ggt cgg      291
Ala Pro Asp Ser Ser Ser Ser Thr Ala Thr Ile Ser Ala Pro Gly Arg
             80                  85                  90 ggg gcc cag cag cgt ccc aac agt aga tgg gac gag acc ggg cga ttc      339
Gly Ala Gln Gln Arg Pro Asn Ser Arg Trp Asp Glu Thr Gly Arg Phe
 95                 100                 105                 110 ccg aac ccg acc acc gct tcc aag acc g gtaagaagga gcggcaggga          387
Pro Asn Pro Thr Thr Ala Ser Lys Thr
                 115 tacaagtcct ggcgggggca taagaatgcc atcatctcct gcttgcatga atgcgggggc    447 aacatatcct tcaccggcg ctacctgctc ttccaccacg gggtgaactt ccccgcaat      507 gtcttgcatt actaccgtca cctccacag cc  cct act aca gcc agc aag tcc      559
                                    Ala Pro Thr Thr Ala Ser Lys Ser
                                                         125 cga cag cct cgg cag aga aag aca gca gca gcg ggg acc tcc agc aga      607
Arg Gln Pro Arg Gln Arg Lys Thr Ala Ala Ala Gly Thr Ser Ser Arg
            130                 135                 140 aaa cca gca gca gca gtt aga aaa tcc agt gca gca gga gga gga ctg      655
Lys Pro Ala Ala Ala Val Arg Lys Ser Ser Ala Ala Gly Gly Gly Leu
145                 150                 155 agg atc aca gcg aac gag cca gcg cag acc cga gag ctg aga aac agg      703
Arg Ile Thr Ala Asn Glu Pro Ala Gln Thr Arg Glu Leu Arg Asn Arg
160                 165                 170                 175 atc ttt cca acc ctc tat gcc atc ttc cag cag agt cgg ggg caa gag      751
Ile Phe Pro Thr Leu Tyr Ala Ile Phe Gln Gln Ser Arg Gly Gln Glu
                180                 185                 190 cag gaa ctg aaa gta aaa aac cga tct ctg cgc tcg ctc acc cga agt      799
Gln Glu Leu Lys Val Lys Asn Arg Ser Leu Arg Ser Leu Thr Arg Ser
            195                 200                 205 tgt ttg tat cac aag agc gaa gac caa ctt cag cgc act ctc gag gac      847
Cys Leu Tyr His Lys Ser Glu Asp Gln Leu Gln Arg Thr Leu Glu Asp
210                 215                 220 gcc gag gct ctc ttc aac aag tac tgc gcg ctg act ctt aaa gag          892
Ala Glu Ala Leu Phe Asn Lys Tyr Cys Ala Leu Thr Leu Lys Glu
                225                 230                 235 tagcccgc                                                             900

<210> SEQ ID NO 65
<211> LENGTH: 238
<212> TYPE: PRT
<213> ORGANISM: Unknown
<220> FEATURE:
<223> OTHER INFORMATION: Synthetic Construct

<400> SEQUENCE: 65

Met Ser Gln Arg Arg Gly Ser Lys Lys Leu Lys Val Gln Leu Pro Pro
1               5                   10                  15

Pro Glu Asp Met Glu Glu Asp Trp Asp Ser Gln Ala Glu Glu Glu
            20                  25                  30
```

Met Glu Asp Trp Asp Ser Gln Ala Glu Glu Ala Asp Ser Leu Glu Glu
 35                  40                  45

Asp Ser Leu Glu Glu Asp Glu Glu Ala Glu Val Glu Glu Ala
 50                  55                  60

Ala Ala Ala Lys Gln Leu Ser Ser Ala Ala Glu Thr Ser Lys Ala Pro
 65                  70                  75                  80

Asp Ser Ser Ser Ser Thr Ala Thr Ile Ser Ala Pro Gly Arg Gly Ala
                 85                  90                  95

Gln Gln Arg Pro Asn Ser Arg Trp Asp Glu Thr Gly Arg Phe Pro Asn
            100                 105                 110

Pro Thr Thr Ala Ser Lys Thr Ala Pro Thr Thr Ala Ser Lys Ser Arg
        115                 120                 125

Gln Pro Arg Gln Arg Lys Thr Ala Ala Ala Gly Thr Ser Ser Arg Lys
    130                 135                 140

Pro Ala Ala Val Arg Lys Ser Ser Ala Ala Gly Gly Gly Leu Arg
145                 150                 155                 160

Ile Thr Ala Asn Glu Pro Ala Gln Thr Arg Glu Leu Arg Asn Arg Ile
                165                 170                 175

Phe Pro Thr Leu Tyr Ala Ile Phe Gln Gln Ser Arg Gly Gln Glu Gln
            180                 185                 190

Glu Leu Lys Val Lys Asn Arg Ser Leu Arg Ser Leu Thr Arg Ser Cys
        195                 200                 205

Leu Tyr His Lys Ser Glu Asp Gln Leu Gln Arg Thr Leu Glu Asp Ala
    210                 215                 220

Glu Ala Leu Phe Asn Lys Tyr Cys Ala Leu Thr Leu Lys Glu
225                 230                 235

<210> SEQ ID NO 66
<211> LENGTH: 48
<212> TYPE: DNA
<213> ORGANISM: Unknown
<220> FEATURE:
<223> OTHER INFORMATION: based on Simian adenovirus 41.2

<400> SEQUENCE: 66
gatcggcgcg ccacgcgtgc ggccgcttac aggattcgag cagttatt         48

<210> SEQ ID NO 67
<211> LENGTH: 20
<212> TYPE: DNA
<213> ORGANISM: Unknown
<220> FEATURE:
<223> OTHER INFORMATION: Simian adenovirus 41.2

<400> SEQUENCE: 67
ctggccctgt ggttccgcag                                         20

<210> SEQ ID NO 68
<211> LENGTH: 30
<212> TYPE: DNA
<213> ORGANISM: Unknown
<220> FEATURE:
<223> OTHER INFORMATION: Simian adenovirus 41.2

<400> SEQUENCE: 68
gatcacgcgt taacgcaggt gtacagctgg                              30

<210> SEQ ID NO 69
<211> LENGTH: 50
<212> TYPE: DNA

```
<213> ORGANISM: Unknown
<220> FEATURE:
<223> OTHER INFORMATION: Simian adenovirus 41.2

<400> SEQUENCE: 69
catgacgcgt actgattttt caataaaaag ttaaatttat ttttgttgtc          50
```